United States Patent
Marcusson et al.

(10) Patent No.: US 7,618,947 B2
(45) Date of Patent: Nov. 17, 2009

(54) MODULATION OF HIF-1 BETA EXPRESSION

(75) Inventors: Eric G. Marcusson, San Francisco, CA (US); Scott W. Henry, Cardiff, CA (US); Youngsoo Kim, San Diego, CA (US); Kenneth W. Dobie, Del Mar, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 149 days.

(21) Appl. No.: 11/213,593

(22) Filed: Aug. 25, 2005

(65) Prior Publication Data

US 2006/0252720 A1 Nov. 9, 2006

Related U.S. Application Data

(60) Provisional application No. 60/604,190, filed on Aug. 25, 2004, provisional application No. 60/649,586, filed on Feb. 2, 2005.

(51) Int. Cl.
*A61K 31/70* (2006.01)
*C07H 21/02* (2006.01)
*C07H 21/04* (2006.01)
*C12Q 1/68* (2006.01)

(52) U.S. Cl. .............................. 514/44; 435/6; 435/375; 435/377; 536/23.1; 536/24.1; 536/24.5

(58) Field of Classification Search ....................... None
See application file for complete search history.

(56) References Cited

U.S. PATENT DOCUMENTS

| | | | |
|---|---|---|---|
| 5,801,154 A | 9/1998 | Baracchini et al. | |
| 5,998,148 A * | 12/1999 | Bennett et al. | ................. 435/6 |
| 6,352,829 B1 | 3/2002 | Chenchik et al. | |
| 6,582,908 B2 | 6/2003 | Fodor et al. | |
| 6,627,619 B2 * | 9/2003 | Cech et al. | ..................... 514/44 |
| 7,030,236 B2 * | 4/2006 | Jhaveri et al. | .............. 536/24.5 |
| 2001/0053519 A1 | 12/2001 | Fodor et al. | |
| 2003/0228597 A1 | 12/2003 | Cowsert et al. | |
| 2004/0086498 A9 | 5/2004 | Krissansen et al. | |
| 2004/0096848 A1 | 5/2004 | Thrue et al. | |
| 2004/0101858 A1 | 5/2004 | Ward et al. | |
| 2004/0152655 A1 | 8/2004 | Yoon et al. | |
| 2004/0180357 A1 | 9/2004 | Reich et al. | |
| 2004/0220393 A1 | 11/2004 | Ward et al. | |
| 2005/0070474 A1 | 3/2005 | Krissansen et al. | |
| 2005/0148496 A1 | 7/2005 | Defranoux et al. | |
| 2005/0163781 A1 | 7/2005 | Koninckx et al. | |

FOREIGN PATENT DOCUMENTS

| | | |
|---|---|---|
| WO | WO 99/48916 | 9/1999 |
| WO | WO 9950403 A2 * | 10/1999 |
| WO | WO 02/053735 | 7/2002 |
| WO | WO 2004/048526 | 6/2004 |

OTHER PUBLICATIONS

Weintraub, H. Scientific American, pp. 40-46, Jan. 1990.*
Furuta et al., Hypoxia-Induced Factor Dependent Induction of Intestinal Trefoil factor Protects Barrier Function During Hypoxia, J.Exp. Med. May 7, 2001, vol. 193, No. 9, pp. 1027-1034.
Gunton et al., Loss or ARNT/HIF1.beta. Mediates Altered Gene Expression and Pancreatic-Islet Dysfunction in Human Type 2 Diabetes, Aug. 12, 2005, vol. 122, pp. 337-349.
Sun et al., Gene transfer of antisense hypoxia inducible factor-1 α enhances the therapeutic efficacy of cancer immunotheraphy, Gene Therapy, 2001, vol. 8, pp. 638-645.
Aplin, J. D., "Hypoxia and human placental development," *J. Clin. Investig.* (2000) 105(5):559-560.
Carmeliet, P. et al., "Angiogenesis in cancer and other diseases," *Nature* (2000) 407:249-257.
Ebert, B. L. et al., "Hypoxia and Mitochondrial Inhibitors Regulate Expression of Glucose Transporter-1 via Distinct Cis-acting Sequences," *J. Biol. Chem.* (1995) 270(49): 29083-29089.
Ema, M. et al., "A novel bHLH-PAS factor with close sequence similarity to hypoxia-inducible factor 1α regulates the *VEGF* expression and is potentially involved in lung and vascular development," *Proc. Natl. Acad. Sci. USA* (1997) 94:4273-4278.
Gölach, A. et al., "Efficient translation of mouse hypoxia-inducible factor-1α under normoxic and hypoxic conditions," *Biochim. Biophys. Acta* (2000) 1493:125-134.
Harris, A. L., "Hypoxia—A Key Regulatory Factor in Tumour Growth," *Nature Rev. Cancer* (2002) 2:38-47.
Henry, S. P. et al., "Setting sights on the treatment of ocular angiogenesis using antisense oligonucleotides," *Trends Pharm. Sci.* (2004) 25(10): 523-527.
Hoffman, E. C. et al., "Cloning of a Factor Required for Activity of the Ah (Dioxin) Receptor," *Science* (1991) 252:954-958.
Hogenesch, J. B. et al., "Characterization of a Subset of the Basic-Helix-Loop-Helix-PAS Superfamily that Interacts with Components of the Dioxin Signaling Pathway," *J. Biol. Chem.* (1997) 272(13):8581-8593.
Jewell, U. R. et al., "Induction of HIF-1α in response to hypoxia is instantaneous," *FASEB J.* (2001) 15:1312-1314.
Kallio, P. J. et al., "Signal transduction in hypoxic cells: inducible nuclear translocation and recruitment of the CBP/p300 coactivator by the hypoxia-inducible factor-1α," *EMBO J.* (1998) 17(22):6573-6586.
Lee, S. H. et al., "Early Expression of Angiogenesis Factors in Acute Myocardial Ischemia and Infarction," *N. Eng. J. Med.* (2000) 342:626-633.

(Continued)

*Primary Examiner*—Sean R McGarry
(74) *Attorney, Agent, or Firm*—Knobbe Martens Olson & Bear LLP

(57) ABSTRACT

Compounds, compositions and methods are provided for modulating the expression of HIF1-beta. The compositions comprise oligonucleotides, targeted to nucleic acid encoding HIF1-beta. Methods of using these compounds for modulation of HIF1-beta expression and for diagnosis and treatment of diseases and conditions associated with expression of HIF1-beta are provided.

32 Claims, No Drawings

OTHER PUBLICATIONS

Levy, A. P. et al., "Transcriptional Regulation of the Rat Vascular Endothelial Growth Factor Gene by Hypoxia," *J. Biol. Chem.* (1995) 270(22):13333-13340.

Maxwell, P. H. et al., "Inducible operation of the erythropoietin 3' enhancer in multiple cell lines: Evidence for a widespread oxygen-sensing mechanism," *Proc. Natl. Acad. Sci. USA* (1993) 90:2423-2427.

Moore, A. W. et al., "A genomewide survey of basic helix-loop-helix factors in *Drosophila*," *PNAS* (2000) 97(19):10436-10441.

Ohtake, F. et al., "Modulation of oestrogen receptor signaling by association with the activated dioxin receptor," *Nature* (2003) 423:545-550.

Poland, A. et al., "Evidence that the Binding Species is Receptor for Induction of Aryl Hydrocarbon Hydroxylase," *J. Biol. Chem.* (1976) 251(16):4936-4946.

Reisz-Porszasz, S. et al., "Identification of Functional Domains of the Aryl Hydrocarbon Receptor Nuclear Translocator Protein (ARNT)," *Mol. Cell. Biol.* (1994) 14(9):6075-6086.

Rolfs, A. et al., "Oxygen-regulated Transferrin Expression is Mediated by Hypoxia-inducible Factor-1," *J. Biol. Chem.* (1997) 272(32):20055-20062.

Safe, S., "Molecular biology of the Ah receptor and its role in carcinogenesis," *Toxicol. Lett.* (2001) 120:1-7.

Safran, M. et al., "HIF hydroxylation and the mammalian oxygen-sensing pathway," *J. Clin. Investig.* (2003) 111(6):779-783.

Semenza, G. L., "Hypoxia-inducible factor 1: oxygen homeostasis and disease pathophysiology," *Trends Mol. Med.* (2001) 7(8):345-350.

Semenza, G. L. et al., "Transcriptional Regulation of Genes Encoding Glycolytic Enzymes by Hypoxia-inducible Factor 1," *J. Biol. Chem.* (1994) 269(38):23757-23763.

Wang, G. L. et al., "General involvement of hypoxia-inducible factor 1 in transcriptional response to hypoxia," *Proc. Natl. Acad. Sci. USA* (1993) 90:4304-4308.

Wang, G. L. et al., "Effect of Protein Kinase and Phosphatase Inhibitors on Expression of Hypoxia-Inducible Factor 1," *Biochem. Biophys. Res. Commun.* (1995) 216(2):669-675.

Wang, G. L. et al., "Purification and Characterization of Hypoxia-inducible Factor 1," *J. Biol. Chem.* (1995) 270(3):1230-1237.

Wang, G. L. et al., "Characterization of Hypoxia-inducible Factor 1 and Regulation of DNA Binding Activity of Hypoxia," *J. Biol. Chem.* (1993) 268(29):21513-21518.

Wiesener, M. S. et al., "Induction of Endothelial PAS Domain Protein-1 by Hypoxia: Characterization and Comparison with Hypoxia-Inducible Factor-1α," *Blood* (1998) 92(1):2260-2268.

Wood, S. M. et al., "The Role of the Aryl Hydrocarbon Receptor Nuclear Translocator (ARNT) in Hypoxic Induction of Gene Expression," *J. Biol. Chem.* (1996) 271(25):15117-15123.

Zhang, L. et al., "Combined Anti-Fetal Liver Kinase 1 Monoclonal Antibody and Continuous Low-Dose Doxorubicin Inhibits Angiogenesis and Growth of Human Soft Tissue Sarcoma Xenografts by Induction of Endothelial Cell Apoptosis," *Cancer Res.* (2002) 62:2034-2042.

Branch, "A good antisense molecule is hard to find" TIBS (1998) 23:45-50.

Chin, Andrew "On the Preparation and Utilization of isolated and Purified Oligonucleotides." Document purportedly located on a CD-ROM and contributed to the public collection of the Katherine R. Everett Law Library of the University of North Carolina on Mar. 14, 2002.

Crooke, S, "Basic Principles of Antisense Therapeutics," Antisense Research and Applications, Chapter 1, Springer-Verlag Press, Berlin, Heidelberg, New York, p. 3, Jun. 1998.

New England BioLabs, Inc. Catalogue (1998): 121, 284.

Reynolds et al., Rational siRNA design for RNA interference, Mar. 2004, Nature Biotechnology, vol. 22, pp. 326-330.

Sanghvi, Y. Antisense Research & Applications, Ch 15, pp. 274-286, CRC Press, 1993.

International Search Report from PCT/US2005/030513 dated Apr. 19, 2006.

\* cited by examiner

MODULATION OF HIF-1 BETA EXPRESSION

CROSS-REFERENCE TO RELATED APPLICATIONS

This application claims the benefit of priority to U.S. provisional patent application Ser. No. 60/604,190, filed Aug. 25, 2004, and U.S. provisional patent application Ser. No. 60/649,586, filed Feb. 2, 2005, both of which are incorporated herein by reference in their entirety.

FIELD OF THE INVENTION

The present invention provides compositions and methods for modulating the expression of HIF1-beta. In particular, this invention relates to antisense compounds, particularly oligonucleotide compounds, which, in preferred- embodiments, hybridize with nucleic acid molecules encoding HIF1-beta. Such compounds are shown herein to modulate the expression of HIF1-beta.

BACKGROUND OF THE INVENTION

Oxygen homeostasis in mammals is tightly regulated, necessitated by the need to maintain sufficient levels for critical oxygen-dependent processes while minimizing the production of oxygen reactive species that are capable of causing oxidative damage to DNA, lipids, and proteins. In a state of hypoxia, where oxygen demand exceeds supply, a physiological response is mounted that increases the capacity of blood to carry oxygen to tissues and alters cellular metabolism, such as facilitating ATP production by anaerobic glycolysis. The hypoxia-inducible factors (HIFs) are key transcriptional regulators of this hypoxic response. These factors have also been implicated in the pathology of many major human diseases, including cancer, myocardial infarction, ischemia and preeclampsia (Harris, *Nat. Rev. Cancer*, 2002, 2, 38-47); (Lee et al., *N Engl J Med*, 2000, 342, 626-633); (Aplin, *J Clin Invest*, 2000, 105, 559-560)). Cells are typically cultured in the laboratory at an ambient oxygen concentration of 21%, but cells in the human body are exposed to much lower oxygen concentrations ranging from 16% in the lungs to less than 6% in most other organs of the body and often significantly less in tumors (Semenza, *Trends Mol Med*, 2001, 7, 345-350).

The HIF proteins are heterodimers consisting of HIF1-beta and one of three alpha subunits, HIF1-alpha, HIF2-alpha and HIF3-alpha (Safran and Kaelin, *J Clin. Invest.*, 2003, 111, 779-783). The discovery of the HIF proteins was enabled by the identification of a minimal hypoxia-responsive element (HRE) in the 3' enhancer of the erythropoietin gene (Wang and Semenza, *Proc Natl Acad Sci USA*, 1993, 90, 4304-4308). Subsequent analysis identified the HIF protein as a phosphorylation-dependent protein that binds DNA under hypoxic conditions (Wang and Semenza, *J Biol Chem*, 1993, 268, 21513-21518). Purification of this DNA-binding factor revealed HIF was a heterodimeric complex consisting of a novel protein, HIF1-alpha, and the aryl hydrocarbon nuclear translocator (ARNT, also termed HIF1-beta), previously identified as a binding partner of the dioxin/aryl hydrocarbon receptor (Wang and Semenza, *J. Biol. Chem.*, 1995, 270, 1230-1237.); (Hoffman et al., *Science*, 1991, 252, 954-958). HIF proteins belong to a class of transcription factors termed basic helix-loop-helix proteins, grouped by two conserved domains. The basic region consists of approximately 15 predominantly basic amino acids responsible for direct DNA binding. This region is adjacent to two amphipathic alpha helices, separated by a loop of variable length, which forms the primary dimerization interface between family members (Moore et al., *Proc Natl Acad Sci USA*, 2000, 97, 10436-10441).

HIF1-beta is a key player in two major signaling pathways, the hypoxic-response pathway and the aryl hydrocarbon receptor (AHR) pathway. Since the discovery of HIF1-alpha/HIF1-beta involvement in erythropoietin transcription, HIF activity has been detected in various non-erythropoietin-producing cell lines cultured under hypoxic conditions (Wang and Semenza, *Proc Natl Acad Sci USA*, 1993, 90, 4304-4308); (Maxwell et al., *Proc Natl Acad Sci USA*, 1993, 90, 2423-2427), providing the first evidence that the HIF1 dimer not only activates the erythropoietin gene, but is part of a widespread oxygen-sensing and signal transduction mechanism. Under normoxic conditions, HIF1-alpha is rapidly degraded due to the oxygen-dependent hydroxylation of specific proline residues that mark the protein for proteasomal degradation (Jewell et al., *Faseb J*, 2001, 15, 1312-1314); (Gorlach et al., *Biochim Biophys Acta*, 2000, 1493, 125-134). Under hypoxic conditions, this hydroxylation is reversed, and the protein is further stabilized by phosphorylation (Wang et al., *Biochem Biophys Res Commun*, 1995, 216, 669-675). Subsequently, the protein is translocated to the nucleus, where it interacts with HIF1-beta to form a heterodimeric transcription factor (Kallio et al., *Embo J*, 1998, 17, 6573-6586). Studies in HIF1-beta deficient cells revealed an absolute requirement for this dimerization step for the transcriptional activation of hypoxia response element genes (Wood et al., *J Biol Chem*, 1996, 271, 15117-15123). Categories of genes that are activated by the HIF1 dimer include oxygen transport genes, such as erythropoietin (Semenza et al., *J Biol Chem*, 1994, 269, 23757-23763) and transferrin (Rolfs et al., *J Biol Chem*, 1997, 272, 20055-20062); genes involved in angiogenesis, such as VEGF (Levy et al., *J Biol Chem*, 1995, 270, 13333-13340); and genes involved in anaerobic metabolism, such as glucose transporter 1 (Ebert et al., *J Biol Chem*, 1995, 270, 29083-29089). Hypoxia-induced genes such as VEGF are thought to play a role in promoting angiogenesis and subsequent tumor growth (Harris, *Nat. Rev. Cancer*, 2002, 2, 38-47).

HIF transcriptional activity is precisely regulated by cellular oxygen concentration. Whereas changes in oxygen levels do no affect HIF1-beta protein levels, the abundance of the HIF-alpha subunits is markedly increased upon exposure of cells to hypoxia, primarily due to stabilization of the alpha subunits (Safran and Kaelin, *J. Clin. Invest.*, 2003, 111, 779-783). HIF2-alpha mRNA and protein is expressed at low levels in tissue culture cells, but protein expression is markedly induced by exposure to 1% oxygen, a hypoxic state (Wiesener et al., *Blood*, 1998, 92, 2260-2268). The HIF2-alpha/HIF1-beta heterodimer protein binds to the hypoxic response element, which contains the core recognition sequence 5'-TACGTG-3' and is found in the cis-regulatory regions of hypoxia-regulated genes (Ema et al., *Proc. Natl. Acad. Sci. U.S.A.*, 1997, 94, 4273-4278); (Hogenesch et al., *J. Biol. Chem.*, 1997, 272, 8581-8593). Binding of the heterodimer to the HRE induces gene expression (Wiesener et al., *Blood*, 1998, 92, 2260-2268).

In contrast to the HIF-alpha subunits, HIF1beta is stable under both hypoxic and normoxic conditions, and also participates in the aryl hydrocarbon receptor (AHR) signaling pathway. AHR is a cytoplasmic receptor protein that translocates to the nucleus after ligand binding. Ligands of AHR include 2,3,7,8-tetrachlorodibenzo-p-dioxin (TCDD), an environmental toxin that is a by-product of industrial processes (Poland et al., *J Biol Chem*, 1976, 251, 4936-4946);

polycylic aromatic hydrocarbons, found in cigarette smoke and smog (Reisz-Porszasz et al., *Mol Cell Biol*, 1994, 14, 6075-6086); and heterocyclic amines, found in some cooked meats (Reisz-Porszasz et al., *Mol Cell Biol*, 1994, 14, 6075-6086). After ligand-binding and nuclear translocation, AHR forms a dimer with HIF1-beta, resulting in the activation of a number of genes involved in drug metabolism, such as the cytochromes P450, CYP1A1, CYP1A2, and CYP1B1. AHR/HIF1-beta dimers are capable of activating a range of other genes regulated by the dioxin response element (DRE), resulting in some of the toxic and carcinogenic effects associated with many of the AHR ligands, such as immunotoxicity, developmental and reproductive toxicity, disruption of endocrine pathways, a wasting syndrome, and tumor promotion (Safe, *Toxicol Lett*, 2001, 120, 1-7). Ohtake and colleagues (Ohtake et al., *Nature*, 2003, 423, 545-550) demonstrated that the AHR/HIF1-beta heterodimer directly associates with the estrogen receptors ER-alpha and ER-beta. They showed that this association results in the recruitment of unliganded estrogen receptor and coactivator p300 to estrogen-responsive gene promoters, leading to activation of transcription and estrogenic effects and giving rise to the adverse estrogen-related actions of dioxin-type environmental contaminants.

The role of HIF1-beta in both hypoxia-induced and AHR signaling pathways makes it an attractive therapeutic candidate, as both of these pathways have been linked to various forms of malignancies (Harris, *Nat. Rev. Cancer*, 2002, 2, 38-47); (Safe, *Toxicol Lett*, 2001, 120, 1-7). The angiogenic promoting capabilities of HIF1-beta also mark this gene as a potential therapeutic target for a variety of angiogenic disorders, such as arthritis, cardiovascular diseases, skin conditions, aberrant wound healing and ocular conditions (e.g., macular degeneration, diabetic retinopathy, diabetic macular edema and retinopathy of prematurity).

PCT publication WO 02/053735 discloses the use of an oligonucleotide 35 nucleotides in length as a PCR primer for amplification of the HIF1-beta sequence.

U.S. Pat. No. 6,352,829 discloses the use of an oligonucleotide 26 nucleotides in length as a PCR primer for amplification of the HIF1-beta sequence.

U.S. pre-grant publication 2004-0152655 discloses antisense oligonucleotide compounds for inhibiting HIF1-alpha.

U.S. pre-grant publication 2004-0096848 discloses oligomeric compounds directed against HIF1-alpha.

U.S. pre-grant publication 2005-0163781 discloses compounds for use as inhibitors of hypoxia-induced genes, such as HIF1-alpha and HIF2-alpha, to treat adhesion formation.

U.S. pre-grant publication 2004-0180357 discloses HIF1-alpha siRNA compounds for downregulating expression of HIF1-alpha and VEGF and inhibiting angiogenesis.

U.S. pre-grant publication 2005-0148496 discloses methods of treating inflammatory disorders such as rheumatoid arthritis using compounds that inhibit HIF1-alpha activity.

U.S. pre-grant publication 2004-0086498 discloses methods for treating animals with advanced or large tumor burdens by administration of an immunotherapeutic agent and a tumor growth restricting agent, such as an expression vector encoding an antisense version of HIF1-alpha.

U.S. pre-grant publication 2005-0070474 discloses methods of treating tumors using an agent to increase B7-H3 in combination with an agent to inhibit HIF1-alpha, HIF2-alpha or HIF3-alpha.

Currently, there are no known therapeutic agents which effectively inhibit the synthesis of HIF1-beta and to date, investigative strategies aimed at modulating the function of HIF1-beta have involved the use of antibodies and inactive mutants. Consequently, there remains a long felt need for additional agents capable of effectively inhibiting HIF1-beta function.

Antisense technology is an effective means for reducing the expression of specific gene products and may therefore prove to be uniquely useful in a number of therapeutic, diagnostic, and research applications for the modulation of HIF1-beta expression. Provided herein are antisense compounds for inhibition of HIF1-beta expression. The disclosed compounds can used for treating or preventing conditions associated with HIF1-beta, such as cancer and angiogenic disorders.

SUMMARY OF THE INVENTION

The present invention is directed to antisense compounds, especially nucleic acid and nucleic acid-like oligomers, which are targeted to a nucleic acid encoding HIF1-beta, and which modulate the expression of HIF1-beta. Pharmaceutical and other compositions comprising the compounds of the invention and methods of treating an animal, particularly a human, suspected of having or being prone to a disease or condition associated with expression of HIF1-beta are also set forth herein.

Provided herein are antisense oligonucleotides which are specifically hybridizable with a nucleic acid molecule encoding human HIF1-beta. The HIF1-beta antisense oligonucleotides comprise at least one internucleoside, sugar or nucleobase modification. Contemplated are oligonucleotides 13 to 80, 13 to 50, 13 to 30, 20 to 30, 15 to 25 or 20 nucleobases in length. In one embodiment, the internucleoside modification is a phosphorothioate. In one embodiment, the modified sugar moiety is a 2'-O-(2-methoxyethyl). In one embodiment, the modified nucleobase in a 5-methyl cytosine. In some embodiments, the HIF1-beta antisense oligonucleotides further comprise a complementary strand. Also provided are antisense oligonucleotides which specifically hybridize to a splice variant of human HIF1-beta.

In one embodiment, the antisense oligonucleotides comprise at least an 8-nucleobase portion of one of the illustrative antisense oligonucleotides provided herein. In one embodiment, the antisense oligonucleotide is specifically hybridizable with at least a portion of a start codon region of human HIF1-beta. In another embodiment, the antisense oligonucleotide comprises at least an 8-nucleobase portion of SEQ ID NO: 30. In one embodiment, the antisense oligonucleotide is specifically hybridizable with at least of portion of nucleotides 1876-1895 of a coding region of human HIF1-beta. In another embodiment, the antisense oligonucleotide comprises at least an 8-nucleobase portion of SEQ ID NO: 77.

Further provided are chimeric antisense oligonucleotides which are specifically hybridizable with a nucleic acid molecule encoding human HIF1-beta. In one embodiment, the chimeric antisense oligonucleotides have a first region comprising deoxynucleotides and second and third regions flanking the first region comprising at least one 2'-O-(2-methoxyethyl) nucleotide. In some embodiments, the first region is 10 deoxynucleotides in length and the second and third regions are each 5 nucleotides in length. The chimeric antisense oligonucleotides provided herein may further comprise a phosphorothioate linkage at each position.

Also provided are pharmaceutical compositions comprising the antisense oligonucleotides of the invention and a pharmaceutically acceptable carrier or diluent. Pharmaceutical compositions further comprising a colloidal dispersion system are also provided.

The present invention also provides methods of inhibiting expression of human HIF1-beta in cells or tissues by contacting the cells or tissues with one or more of the compounds provided herein such that expression is inhibited. In one embodiment, HIF1-beta expression is inhibited by 20%. In another embodiment, HIF1-beta expression is inhibited by 40%. In another embodiment, HIF1beta expression is inhibited by 50%. In another embodiment, HIF1-beta expression is inhibited by 60%. In another embodiment, HIF1-beta expression is inhibited by 70%. In another embodiment, HIF1-beta expression is inhibited by 80%. In one embodiment, the compounds used to inhibit expression of human HIF1-beta comprise at least an 8-nucleobase portion of SEQ ID NO: 30. In another embodiment, the compounds used to inhibit expression of human HIF1-beta comprise at least an 8-nucleobase portion of SEQ ID NO: 77.

Also provided are methods of inhibiting expression of HIF1-beta regulated genes in cells or tissues by contacting the cells or tissues with one or more of the compounds provided herein. In one embodiment, the HIF1-beta regulated gene is VEGF. In another embodiment, the HIF1-beta regulated gene is GLUT-1. In another embodiment, the HIF1-beta regulated gene is PGK-1. In another embodiment, the HIF1-beta regulated gene is PAI-1. In yet another embodiment, the HIF1-beta regulated gene is Epo.

Further provided are methods of treating an animal having a disease or condition associated with HIF1-beta comprising administrating to the animal a therapeutically or prophylactically effective amount of a composition comprising one of more of the antisense oligonucleotides provided herein. In one embodiment, the disease or condition associated with HIF1-beta is a hyperproliferative disorder. In one aspect, the hyperproliferative disorder is cancer. In another aspect, the hyperproliferative disorder is an angiogenic disorder. In further embodiments, the angiogenic disorder is an ocular disorder. Ocular disorders contemplated herein, include, but are not limited to macular degeneration, diabetic retinopathy, macular edema and retinopathy of prematurity. In one embodiment, the compounds used to treat the disease or disorder comprise at least an 8-nucleobase portion of SEQ ID NO: 30. In another embodiment, the compounds used to treat the disease or disorder comprise at least an 8-nucleobase portion of SEQ ID NO: 77.

Also provided are methods of treating an animal having a disease or condition associated with a HIF1-beta regulated gene by administrating to the animal a therapeutically or prophylactically effective amount of a composition comprising one or more of the HIF1-beta antisense oligonucleotides provided herein. In one embodiment, the disease or condition is a hyperproliferative disorder. In a further embodiment, the hyperproliferative disorder is an angiogenic disorder.

The present invention also provides methods of preventing or inhibiting aberrant angiogenesis in an animal, methods of inhibiting tumor growth in an animal and methods of preventing or inhibiting ocular neovascularization in an animal, comprising administering to said animal one or more of the antisense oligonucleotides provided herein.

In one embodiment of the methods, the antisense oligonucleotides comprise at least an 8-nucleobase portion of one of the illustrative antisense oligonucleotides provided herein.

DETAILED DESCRIPTION OF ILLUSTRATIVE EMBODIMENTS

HIF1-beta is known to play an important role in cellular signaling pathways that can contribute to a number of medically-important pathologic conditions such as cancer and disorders arising from aberrant angiogenesis. To date, there are no effective means for inhibition of HIF1-beta expression. Thus, disclosed herein are antisense compounds for modulation of HIF1-beta expression. The compounds of the invention can be used, for example, to inhibit or prevent aberrant angiogenesis, inhibit tumor growth, or inhibit expression of HIF1-beta regulated genes.

As used herein, "aberrant angiogenesis" refers to unwanted or uncontrolled angiogenesis.

As used herein, "targeting" or "targeted to" refer to the process of designing an oligomeric compound such that the compound hybridizes with a selected nucleic acid molecule or region of a nucleic acid molecule.

As used herein, "hybridization" means the pairing of complementary strands of oligomeric compounds. In the context of the present invention, an oligomeric compound is "specifically hybridizable" when there is a sufficient degree of complementarity to avoid non-specific binding of the oligomeric compound to non-target nucleic acid sequences. One of skill in the art will be able to determine when an oligomeric compound is specifically hybridizable.

As used herein, a "HIF1-beta regulated gene" is a gene whose expression is modulated by HIF1-beta gene products.

The present invention employs antisense compounds, preferably oligonucleotides and similar species for use in modulating the function or effect of nucleic acid molecules encoding HIF1-beta. This is accomplished by providing oligonucleotides which specifically hybridize with one or more nucleic acid molecules encoding HIF1-beta. As used herein, the terms "target nucleic acid" and "nucleic acid molecule encoding HIF1-beta" have been used for convenience to encompass DNA encoding HIF1-beta, RNA (including pre-mRNA and mRNA or portions thereof) transcribed from such DNA, and also cDNA derived from such RNA. The hybridization of a compound of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of HIF1-beta. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch, or hairpin structure). It is preferred that the antisense compounds of the present invention comprise at least 70%, or at least 75%, or at least 80%, or at least 85% sequence complementarity to a target region within the target nucleic acid, more preferably that they comprise at least 90% sequence complementarity and even more preferably comprise at least 95% or at least 99% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

Percent homology, sequence identity or complementarity, can be determined by, for example, using default settings of the Gap program (Wisconsin Sequence Analysis Package, Version 8 for Unix, Genetics Computer Group, University Research Park, Madison Wis.), which uses the algorithm of Smith and Waterman (Adv. Appl. Math., 1981, 2, 482-489). In some embodiments, homology, sequence identity or complementarity, between the oligomeric compound and target is between about 50% to about 60%. In some embodiments, homology, sequence identity or complementarity, is between about 60% to about 70%. In further embodiments, homology, sequence identity or complementarity, is between about 70% and about 80%. In further embodiments, homology, sequence identity or complementarity, is between about 80% and about 90%. In some preferred embodiments, homology, sequence identity or complementarity, is about 90%, about 92%, about 94%, about 95%, about 96%, about 97%, about 98%, about 99% or about 100%.

B. Compounds of the Invention

According to the present invention, antisense compounds include antisense oligomeric compounds, antisense oligonucleotides, siRNAs, ribozymes, external guide sequence (EGS) oligonucleotides, alternate splicers and other oligomeric compounds which hybridize to at least a portion of the target nucleic acid. As such, these compounds may be introduced in the form of single-stranded, double-stranded, circular or hairpin oligomeric compounds and may contain structural elements such as internal or terminal bulges or loops. Once introduced to a system, the compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the one form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The term "oligomeric compound" refers to a polymeric structure capable of hybridizing to a region of a nucleic acid molecule. This term includes oligonucleotides, oligonucleosides, oligonucleotide analogs, oligonucleotide mimetics and chimeric combinations of these. Oligomeric compounds are routinely prepared linearly but can be joined or otherwise prepared to be circular. Moreover, branched structures are known in the art. An "antisense compound" or "antisense oligomeric compound" refers to an oligomeric compound that is at least partially complementary to the region of a nucleic acid molecule to which it hybridizes and which modulates (increases or decreases) its expression. Consequently, while all antisense compounds can be said to be oligomeric compounds, not all oligomeric compounds are antisense compounds. An "antisense oligonucleotide" is an antisense compound that is a nucleic acid-based oligomer. An antisense oligonucleotide can be chemically modified. Non-limiting examples of oligomeric compounds include primers, probes, antisense compounds, antisense oligonucleotides, external guide sequence (EGS) oligonucleotides and alternate splicers. In one embodiment, the oligomeric compound comprises an antisense strand hybridized to a sense strand. Oligomeric compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self complementarity to allow for hybridization and formation of a fully or partially double-stranded compound.

The oligomeric compounds in accordance with this invention comprise compounds from about 8 to about 80 nucleobases (i.e. from about 8 to about 80 linked nucleosides). One of ordinary skill in the art will appreciate that this comprehends antisense compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the antisense compounds of the invention comprise 13 to 80 nucleobases. One having ordinary skill in the art will appreciate that this embodies antisense compounds of 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases.

In one embodiment, the antisense compounds of the invention comprise 13 to 50 nucleobases. One having ordinary skill in the art will appreciate that this embodies antisense compounds of 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases.

In one embodiment, the antisense compounds of the invention comprise 13 to 30 nucleobases. One having ordinary skill in the art will appreciate that this embodies antisense compounds of 13, 14, 15, 16, 17, 18, 19, 20, 21, 22, 23, 24, 25, 26, 27, 28, 29 or 30 nucleobases.

In one embodiment, the antisense compounds of the invention comprise 20 to 30 nucleobases. One having ordinary skill in the art will appreciate that this embodies antisense compounds of 20, 21, 22, 23, 24, 25, 26, 27, 28, 29, or 30 nucleobases.

In one embodiment, the antisense compounds of the invention comprise 15 to 25 nucleobases. One having ordinary skill in the art will appreciate that this embodies antisense compounds of 15, 16, 17, 18, 19, 20, 21, 22, 23, 24 or 25.

In one embodiment, the antisense compounds of the invention comprise 20 nucleobases.

In one embodiment, the antisense compounds of the invention comprise 19 nucleobases.

In one embodiment, the antisense compounds of the invention comprise 18 nucleobases.

In one embodiment, the antisense compounds of the invention comprise 17 nucleobases.

In one embodiment, the antisense compounds of the invention comprise 16 nucleobases.

In one embodiment, the antisense compounds of the invention comprise 15 nucleobases.

In one embodiment, the antisense compounds of the invention comprise 14 nucleobases.

In one embodiment, the antisense compounds of the invention comprise 13 nucleobases.

Antisense compounds 13-80 nucleobases in length comprising a stretch of at least eight (8) consecutive nucleobases selected from within the illustrative antisense compounds are considered to be suitable antisense compounds. Antisense compounds 13-80 nucleobases in length comprising a stretch of at least eight (8) consecutive nucleobases selected from within the illustrative antisense compounds are considered to be suitable antisense compounds as well.

Compounds of the invention include oligonucleotide sequences that comprise at least the 8 consecutive nucleobases from the 5'-terminus of one of the illustrative antisense compounds (the remaining nucleobases being a consecutive stretch of the same oligonucleotide beginning immediately upstream of the 5'-terminus of the antisense compound which is specifically hybridizable to the target nucleic acid and continuing until the oligonucleotide contains about 13 to about 80 nucleobases). Other compounds are represented by oligonucleotide sequences that comprise at least the 8 consecutive nucleobases from the 3'-terminus of one of the illustrative antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 13 to about 80 nucleobases). It is also understood that compounds may be represented by oligonucleotide sequences that comprise at least 8 consecutive nucleobases from an internal portion of the sequence of an illustrative compound, and may extend in either or both directions until the oligonucleotide contains about 13 to about 80 nucleobases.

One having skill in the art armed with the antisense compounds illustrated herein will be able, without undue experimentation, to identify further antisense compounds.

C. Targets of the Invention

"Targeting" an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes HIF1-beta.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

Suitable target regions include, for example, 3' untranslated region (3'UTR), start codon region, coding region, stop codon region, 5'untranslated region (5'UTR), 5' cap region, exons, introns, intron-exon junctions and exon-exon junctions.

In the context of the invention, "start codon" and "translation initiation codon" refer to the codon or codons that are used in vivo to initiate translation of an mRNA transcribed from a gene, regardless of the sequence(s) of such codons. The terms "start codon region" and "translation initiation codon region" refer to a portion of an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. The open reading frame (ORF) or "coding region" is known in the art to refer to the region between the translation initiation codon and the translation termination codon. The 5'UTR refers to the portion of an mRNA in the 5' direction from the translation initiation codon, and thus including nucleotides between the 5' cap site and the translation initiation codon of an mRNA (or corresponding nucleotides on the gene), and the 3'UTR refers to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence, resulting in exon-exon junctions at the sites where exons are joined. Targeting exon-exon junctions can be useful in situations where the overproduction of a normal splice product is implicated in disease, or where the overproduction of an aberrant splice product is implicated in disease. Targeting splice sites, i.e., intron-exon junctions or exon-intron junctions, may also be particularly useful in situations where aberrant splicing is implicated in disease, or where an overproduction of a particular splice product is implicated in disease. It is also known that introns can be effectively targeted using antisense compounds targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred antisense compounds hybridize are referred to as "preferred target segments." As used herein the term "preferred target segment" is defined as at least an 8-nucleobase portion of a target region to which an active antisense compound is targeted. While not wishing to be bound by theory, it is presently believed that these target segments represent portions of the target nucleic acid which are accessible for hybridization.

Target segments 13-80 nucleobases in length comprising a stretch of at least eight (8) consecutive nucleobases selected from within a preferred target segment are considered to be suitable for targeting as well.

Target segments can include DNA or RNA sequences that comprise at least the 8 consecutive nucleobases from the 5'-terminus of one of the illustrative preferred target segments (the remaining nucleobases being a consecutive stretch of the same DNA or RNA beginning immediately upstream of the 5'-terminus of the target segment and continuing until the DNA or RNA contains about 13 to about 80 nucleobases). Similarly preferred target segments are represented by DNA or RNA sequences that comprise at least the 8 consecutive nucleobases from the 3'-terminus of one of the illustrative preferred target segments (the remaining nucleobases being a consecutive stretch of the same DNA or RNA beginning immediately downstream of the 3'-terminus of the target segment and continuing until the DNA or RNA contains about 13 to about 80 nucleobases). It is also understood that preferred antisense target segments may be represented by DNA or RNA sequences that comprise at least 8 consecutive nucleobases from an internal portion of the sequence of an illustrative preferred target segment, and may extend in either or both directions until the oligonucleotide contains about 13 to about 80 nucleobases. One having skill in the art armed with the preferred target segments illustrated herein will be able, without undue experimentation, to identify further preferred target segments.

Once one or more target regions, segments or sites have been identified, antisense compounds are chosen which are sufficiently complementary to the target, i.e., hybridize sufficiently well and with sufficient specificity, to give the desired effect.

The oligomeric antisense compounds can also be targeted to regions of a target nucleobase sequence, such as those disclosed herein.

D. Kits, Research Reagents, Diagnostics, and Therapeutics

The antisense compounds of the present invention can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics, the compounds of the present invention, either alone or in combination with other compounds or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.,* 2000, 480, 17-24; Celis, et al., *FEBS Lett.,* 2000, 480, 2-16), SAGE (serial analysis of gene expression) (Madden, et al., *Drug Discov. Today,* 2000, 5, 415-425), READS (restriction enzyme amplification of digested cDNAs) (Prashar and Weissman, *Methods Enzymol.,* 1999, 303, 258-72), TOGA (total gene expression analysis) (Sutcliffe, et al., *Proc. Natl. Acad. Sci. U.S.A.,* 2000, 97, 1976-81), protein arrays and proteomics (Celis, et al., *FEBS Lett.,* 2000, 480, 2-16; Jungblut, et al., *Electrophoresis,* 1999, 20, 2100-10), expressed sequence tag (EST) sequencing (Celis, et al., *FEBS. Lett.,* 2000, 480, 2-16; Larsson, et al., *J Biotechnol.,* 2000, 80, 143-57), subtractive RNA fingerprinting (SuRF) (Fuchs, et al., *Anal. Biochem.,* 2000, 286, 91-98; Larson, et al., *Cytometry,* 2000, 41, 203-208), subtractive cloning, differential display (DD) (Jurecic and Belmont, *Curr. Opin. Microbiol.,* 2000, 3, 316-21), comparative genomic hybridization (Carulli, et al., *J. Cell Biochem. Suppl.,* 1998, 31, 286-96), FISH (fluorescent in situ hybridization) techniques (Going and Gusterson, *Eur. J. Cancer,* 1999, 35, 1895-904) and mass spectrometry methods (To, *Comb. Chem. High Throughput Screen,* 2000, 3, 235-41).

The antisense compounds of the invention are useful for research and diagnostics, because these compounds hybridize to nucleic acids encoding HIF1-beta and inhibit their function. The primers and probes disclosed herein are useful in methods requiring the specific detection of nucleic acid molecules encoding HIF1-beta and in the amplification of said nucleic acid molecules for detection or for use in further studies of HIF1-beta. Hybridization of the primers and probes with a nucleic acid encoding HIF1-beta can be detected by means known in the art. Such means may include conjugation of an enzyme to the primer or probe, radiolabeling of the primer or probe or any other suitable detection means. Kits using such detection means for detecting the level of HIF1-beta in a sample may also be prepared.

The specificity and sensitivity of antisense is also harnessed by those of skill in the art for therapeutic uses. Antisense compounds are employed as therapeutic moieties in the treatment of disease states in animals, including humans. Antisense oligonucleotide drugs, including ribozymes, have been safely and effectively administered to humans and numerous clinical trials are presently underway. It is thus established that antisense compounds are useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of HIF1-beta is treated by administering antisense compounds in accordance with this invention. For example, in one non-limiting embodiment, the methods comprise the step of administering to the animal in need of treatment, a therapeutically effective amount of a HIF1-beta inhibitor. The HIF1-beta inhibitors of the present invention effectively inhibit the activity of the HIF1-beta protein or inhibit the expression of the HIF1-beta protein. In one embodiment, the activity or expression of HIF1-beta in an animal is inhibited by about 10%. Preferably, the activity or expression of HIF1-beta in an animal is inhibited by about 25%. More preferably, the activity or expression of HIF1-beta in an animal is inhibited by 40% or more. Thus, the oligomeric antisense compounds modulate expression of HIF1-beta mRNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of HIF1beta may be measured in serum, adipose tissue, liver or any other body fluid, tissue or organ of the animal. Preferably, the cells contained within said fluids, tissues or organs being analyzed contain a nucleic acid molecule encoding HIF1-beta protein and/or the HIF1-beta protein itself.

The antisense compounds of the invention can be utilized in pharmaceutical compositions by adding an effective amount of a compound to a suitable pharmaceutically acceptable diluent or carrier. Use of the compounds and methods of the invention may also be useful prophylactically.

E. Modifications

As is known in the art, a nucleoside is a base-sugar combination. The base portion of the-nucleoside is normally a heterocyclic base sometimes referred to as a "nucleobase" or simply a "base". The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Modified Internucleoside Linkages (Backbones)

Specific examples of oligomeric antisense compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

Oligomeric compounds of the invention can have one or more modified internucleoside linkages. One phosphorus-containing modified internucleoside linkage is the phosphorothioate internucleoside linkage. Other modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkyl-phosphoramidates, thionophosphoramidates, thionoalkylphosphonates, thionoalkylphosphotriesters, phosphonoacetate and thiophosphonoacetate (see Sheehan et al., *Nucleic Acids Research*, 2003, 31(14), 4109-4118 and Dellinger et al., *J. Am. Chem. Soc.*, 2003, 125, 940-950), selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

N3'-P5'-phosphoramidates have been reported to exhibit both a high affinity towards a complementary RNA strand and nuclease resistance (Gryaznov et al., *J Am. Chem. Soc.*, 1994, 116, 3143-3144). N3'-P5'-phosphoramidates have been studied with some success in vivo to specifically down regulate the expression of the c-myc gene (Skorski et al., *Proc. Natl. Acad. Sci.*, 1997, 94, 3966-3971; and Faira et al., *Nat. Biotechnol.*, 2001, 19, 40-44).

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, each of which is herein incorporated by reference.

In some embodiments of the invention, oligomeric compounds may have one or more phosphorothioate and/or heteroatom internucleoside linkages, in particular —CH$_2$—NH—O—CH$_2$—, —CH$_2$—N(CH$_3$)—O—CH$_2$— (known as a methylene (methylimino) or MMI backbone), —CH$_2$—O—N(CH$_3$)—CH$_2$—, —CH$_2$—N(CH$_3$)—N(CH$_3$)—CH$_2$— and —O—N(CH$_3$)—CH$_2$—CH$_2$— (wherein the native phosphodiester internucleotide linkage is represented as —O—P(=O)(OH)—O—CH$_2$—). The MMI type internucleoside linkages are disclosed in the above referenced U.S. Pat. No. 5,489,677. Amide internucleoside linkages are disclosed in the above referenced U.S. Pat. No. 5,602,240.

Some oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Modified Sugar and Internucleoside Linkages (Mimetics)

Another group of oligomeric compounds amenable to the present invention includes oligonucleotide mimetics. The term mimetic as it is applied to oligonucleotides is intended to include oligomeric compounds wherein the furanose ring or the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid.

One such oligomeric compound, an oligonucleotide mimetic that has been shown to have excellent hybridization properties, is referred to as a peptide nucleic acid (PNA). Nielsen et al., *Science*, 1991, 254, 1497-1500. PNAs have favorable hybridization properties, high biological stability and are electrostatically neutral molecules. In one recent study PNA compounds were used to correct aberrant splicing in a transgenic mouse model (Sazani et al., *Nat. Biotechnol.*, 2002, 20, 1228-1233). In PNA oligomeric compounds, the sugar-backbone of an oligonucleotide is replaced with an amide containing backbone, in particular an aminoethylglycine backbone. The nucleobases are bound directly or indirectly (—C(=O)—CH$_2$— as shown below) to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262, each of which is herein incorporated by reference. PNA compounds can be obtained commercially from Applied Biosystems (Foster City, Calif., USA). Numerous modifications to the basic PNA backbone are known in the art; particularly useful are PNA compounds with one or more amino acids conjugated to one or both termini. In particular, 1-8 lysine or arginine residues are useful when conjugated to the end of a PNA molecule.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. One class of linking groups have been selected to give a non-ionic oligomeric compound. The non-ionic morpholino-based oligomeric compounds are less likely to have undesired interactions with cellular proteins. Morpholino-based oligomeric compounds are non-ionic mimics of oligonucleotides which are less likely to form undesired interactions with cellular proteins (Dwaine A. Braasch and David R. Corey, *Biochemistry*, 2002, 41(14), 4503-4510). Morpholino-based oligomeric compounds have been studied in zebrafish embryos (see: *Genesis, volume* 30, issue 3, 2001 and Heasman, J., Dev. Biol., 2002, 243, 209-214). Further studies of morpholino-based oligomeric compounds have also been reported (see: Nasevicius et al., Nat. Genet., 2000, 26, 216-220; and Lacerra et al., Proc. Natl. Acad. Sci., 2000, 97, 9591-9596). Morpholino-based oligomeric compounds are disclosed in U.S. Pat. No. 5,034,506, issued Jul. 23, 1991. The morpholino class of oligomeric compounds have been prepared having a variety of different linking groups joining the monomeric subunits. Linking groups can be varied from chiral to achiral, and from charged to neutral. U.S. Pat. No. 5,166,315 discloses linkages including —O—P(=O)(N $(CH_3)_2$)—O—; U.S. Pat. No. 5,034,506 discloses achiral intermorpholino linkages; and US Pat. No. 5,185,444 discloses phosphorus containing chiral intermorpholino linkages.

A further class of oligonucleotide mimetic is referred to as cyclohexenyl nucleic acids (CeNA). The furanose ring normally present in a DNA or RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., J. Am. Chem. Soc., 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate E. coli RNase resulting in cleavage of the target RNA strand.

A further modification includes bicyclic sugar moieties such as "Locked Nucleic Acids" (LNAs) in which the 2'-hydroxyl group of the ribosyl sugar ring is linked to the 4' carbon atom of the sugar ring thereby forming a 2'-C,4'-C-oxymethylene linkage to form the bicyclic sugar moiety (reviewed in Elayadi et al., Curr. Opinion Invens. Drugs, 2001, 2, 558-561; Braasch et al., Chem. Biol., 2001, 8 1-7; and Orum et al., Curr. Opinion Mol. Ther., 2001, 3, 239-243; see also U.S. Pat. Nos. 6,268,490 and 6,670,461). The linkage can be a methylene (—$CH_2$—) group bridging the 2' oxygen atom and the 4' carbon atom, for which the term LNA is used for the bicyclic moiety; in the case of an ethylene group in this position, the term ENA™ is used (Singh et al., Chem. Commun., 1998, 4, 455-456; ENA™: Morita et al., Bioorganic Medicinal Chemistry, 2003, 11, 2211-2226). LNA and other bicyclic sugar analogs display very high duplex thermal stabilities with complementary DNA and RNA (Tm=+3 to +10 C), stability towards 3'-exonucleolytic degradation and good solubility properties. LNAs are commercially available from ProLigo (Paris, France and Boulder, Colo., USA).

An isomer of LNA that has also been studied is α-L-LNA which has been shown to have superior stability against a 3'-exonuclease (Frieden et al., Nucleic Acids Research, 2003, 21, 6365-6372). The α-L-LNA's were incorporated into antisense gapmers and chimeras that showed potent antisense activity.

Another similar bicyclic sugar moiety that has been prepared and studied has the bridge going from the 3'-hydroxyl group via a single methylene group to the 4' carbon atom of the sugar ring thereby forming a 3'-C,4'-C-oxymethylene linkage (see U.S. Pat. No. 6,043,060).

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000, 13, 44-53). These conformations are associated with improved stacking of the nucleobases (Wengel et al., Nucleosides Nucleotides, 1999, 18, 1365-1370).

LNA has been shown to form exceedingly stable LNA: LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving filly modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands. DNA LNA chimeras have been shown to efficiently inhibit gene expression when targeted to a variety of regions (5'-untranslated region, region of the start codon or coding region) within the luciferase mRNA (Braasch et al., Nucleic Acids Research, 2002, 30, 5160-5167).

Potent and nontoxic antisense oligonucleotides containing LNAs have been described (Wahlestedt et al., Proc. Natl. Acad. Sci. U.S.A., 2000, 97, 5633-5638.) The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in Escherichia coli. Lipofectin-mediated efficient delivery of LNA into living human breast cancer cells has also been accomplished. Further successful in vivo studies involving LNA's have shown knock-down of the rat delta opioid receptor without toxicity (Wahlestedt et al., Proc. Nat. Acad. Sci., 2000, 97, 5633-5638) and in another study showed a blockage of the translation of the large subunit of RNA polymerase II (Fluiter et al., Nucleic Acids Res., 2003, 31, 953-962).

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., WO 99/14226). Furthermore, synthesis of 2'-amino-LNA, a novel conformationally restricted high-affinity oligonucleotide analog has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Another oligonucleotide mimetic amenable to the present invention that has been prepared and studied is threose nucleic acid. This oligonucleotide mimetic is based on threose nucleosides instead of ribose nucleosides. Initial interest in (3',2')-α-L-threose nucleic acid (TNA) was directed to the question of whether a DNA polymerase existed that would copy the TNA. It was found that certain DNA polymerases are able to copy limited stretches of a TNA template (reported in C&EN/Jan. 13, 2003). In another study it was determined that TNA is capable of antiparallel Watson-Crick base pairing with complementary DNA, RNA and TNA oligonucleotides (Chaput et al., J. Am. Chem. Soc., 2003, 125, 856-857).

In one study (3',2')-α-L-threose nucleic acid was prepared and compared to the 2' and 3' amidate analogs (Wu et al., Organic Letters, 2002, 4(8), 1279-1282). The amidate analogs were shown to bind to RNA and DNA with comparable strength to that of RNA/DNA.

Further oligonucleotide mimetics have been prepared to include bicyclic and tricyclic nucleoside analogs (see Steffens et al., Helv. Chim. Acta, 1997, 80, 2426-2439; Steffens et al., J. Am. Chem. Soc., 1999, 121, 3249-3255; Renneberg et al., J. Am. Chem. Soc., 2002, 124, 5993-6002; and Renneberg et al., Nucleic acids res., 2002, 30, 2751-2757). These modified nucleoside analogs have been oligomerized using the phosphoramidite approach and the resulting oligomeric compounds containing tricyclic nucleoside analogs have shown increased thermal stabilities (Tms) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids which incorporate a phosphorus group in the backbone. This class of oligonucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology. Further oligonucleotide mimetics amenable to the present invention have been prepared wherein a cyclobutyl ring replaces the naturally occurring furanosyl ring.

Modified sugars

Oligomeric compounds may also contain one or more substituted sugar moieties. Suitable compounds can comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly suitable are $O((CH_2)_nO)_mCH_3$, $O(CH_2)_nOCH_3$, $O(CH_2)_nNH_2$, $O(CH_2)_nCH_3$, $O(CH_2)_nONH_2$, and $O(CH_2)_nON((CH_2)_nCH_3)_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. One modification includes 2'-methoxyethoxy (2'-O—$CH_2CH_2OCH_3$, also known as 2'-O-(2-methoxyethyl) or 2'-MOE) (Martin et al., Helv. Chim. Acta, 1995, 78, 486-504) i.e., an alkoxyalkoxy group. A further modification includes 2'-dimethylaminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$, also described in examples herein below.

Other modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. One 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Antisense compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the C. elegans system. Properties that are enhanced by using more stable 3'-endo nucleosides include but are not limited to: modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric triggers of RNAi having one or more nucleosides modified in such a way as to favor a C3'-endo type conformation.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer- Verlag.) Modification of the 2' position to favor the 3'-endo conformation can be achieved while maintaining the 2'-OH as a recognition element, as illustrated in FIG. 2, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'-F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, oligomeric triggers of RNAi response might be composed of one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA, Morita et al, Bioorganic & Medicinal Chemistry Letters (2002), 12, 73-76.)

One conformation of modified nucleosides and their oligomers can be estimated by various methods such as molecular dynamics calculations, nuclear magnetic resonance spectroscopy and CD measurements. Hence, modifications predicted to induce RNA like conformations, A-form duplex geometry in an oligomeric context, are selected for use in the modified oligonucleotides of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum press., and the examples section below.)

The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, Biochem. Biophys. Res. Comm., 1970, 47, 1504.) In general, RNA:RNA duplexes are more stable and have higher melting temperatures (Tms) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., Nucleic Acids. Research, 1998, 26, 2473-2480, who pointed out that in considering the furanose conformations which give rise to B-form duplexes consideration should also be given to a O4'-endo pucker contribution. DNA:RNA hybrid duplexes, however, are usually less stable than pure RNA:RNA duplexes, and depending on their sequence may be either more or less stable than DNA:DNA duplexes (Searle et al., Nucleic Acids Res., 1993, 21, 2051-2056). The structure of a hybrid duplex is intermediate between A- and B-form geometries, which may result in poor stacking interactions (Lane et al., Eur. J. Biochem., 1993, 215, 297-306; Fedoroff et al., J. Mol. Biol., 1993, 233, 509-523; Gonzalez et al., Biochemistry, 1995, 34, 4969-4982; Horton et al., J. Mol. Biol., 1996, 264, 521-533). The stability of the duplex formed between a target RNA and a synthetic sequence is central to therapies such as but not limited to antisense and RNA interference as these mechanisms require the binding of a synthetic oligomer strand to an RNA target strand. In the case of antisense, effective inhibition of the mRNA requires that the antisense DNA have a very high binding affinity with the mRNA. Otherwise the desired interaction between the synthetic oligomer strand and target mRNA strand will occur infrequently, resulting in decreased efficacy.

One routinely used method of modifying the sugar puckering is the substitution of the sugar at the 2'-position with a substituent group that influences the sugar geometry. The influence on ring conformation is dependant on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

Increasing the percentage of C3'-endo sugars in a modified oligonucleotide targeted to an RNA target strand should pre-organize this strand for binding to RNA. Of the several sugar modifications that have been reported and studied in the literature, the incorporation of electronegative substituents such as 2'-fluoro or 2'-alkoxy shift the sugar conformation towards the 3' endo (northern) pucker conformation. This preorganizes an oligonucleotide that incorporates such modifications to have an A-form conformational geometry. This A-form conformation results in increased binding affinity of the oligonucleotide to a target RNA strand.

Representative 2'-substituent groups amenable to the present invention that give A-form conformational properties (3'-endo) to the resultant duplexes include 2'-O-alkyl, 2'-O-substituted alkyl and 2'-fluoro substituent groups. Suitable for the substituent groups are various alkyl and aryl ethers and thioethers, amines and monoalkyl and dialkyl substituted amines. It is further intended that multiple modifications can be made to one or more of the oligomeric compounds of the invention at multiple sites of one or more monomeric subunits (nucleosides are suitable) and or internucleoside linkages to enhance properties such as but not limited to activity in a selected application.

Natural and Modified Nucleobases

Antisense compounds may also include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750, 692, which is commonly owned with the instant application and also herein incorporated by reference.

Conjugates

Another modification of the antisense compounds of the invention involves chemically linking to the antisense compound one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Antisense compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodo-benzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270, incorporated by reference herein). These terminal modifications protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or can be present on both termini. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, incorporated by reference herein).

Particularly preferred 3'-cap structures of the present invention include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925; incorporated by reference herein).

Further 3' and 5'-stabilizing groups that can be used to cap one or both ends of an oligomeric compound to impart nuclease stability include those disclosed in WO 03/004602 published on Jan. 16, 2003.

Chimeric Compounds

It is not necessary for all positions in a given compound to be uniformly modified, and in fact more than one of the aforementioned modifications may be incorporated in a single compound or even at a single nucleoside within an oligonucleotide.

The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. Chimeric antisense oligonucleotides are thus a form of antisense compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Chimeric antisense compounds can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers". Such compounds have also been referred to in the art as hybrids. In a gapmer that is 20 nucleotides in length, a gap or wing can be 1, 2, 3, 4, 5, 6, 7, 8, 9, 10, 11, 12, 13, 14, 15, 16, 17 or 18 nucleotides in length. In one embodiment, a 20-nucleotide gapmer is comprised of a gap 8 nucleotides in length, flanked on both the 5' and 3' sides by wings 6 nucleotides in length. In another embodiment, a 20-nucleotide gapmer is comprised of a gap 10 nucleotides in length, flanked on both the 5' and 3' sides by wings 5 nucleotides in length. In another embodiment, a 20-nucleotide gapmer is comprised of a gap 12 nucleotides in length flanked on both the 5' and 3' sides by wings 4 nucleotides in length. In a further embodiment, a 20-nucleotide gapmer is comprised of a gap 14 nucleotides in length flanked on both the 5' and 3' sides by wings 3 nucleotides in length. In another embodiment, a 20-nucleotide gapmer is comprised of a gap 16 nucleotides in length flanked on both the 5' and 3' sides by wings 2 nucleotides in length. In a further embodiment, a 20-nucleotide gapmer is comprised of a gap 18 nucleotides in length flanked on both the 5' and 3' ends by wings 1 nucleotide in length. Alternatively, the wings are of different lengths, for example, a 20-nucleotide gapmer may be comprised of a gap 10 nucleotides in length, flanked by a 6-nucleotide wing on one side (5' or 3') and a 4-nucleotide wing on the other side (5' or 3').

In a hemimer, an "open end" chimeric antisense compound, 20 nucleotides in length, a gap segment, located at either the 5' or 3' terminus of the oligomeric compound, can be 1, 2, 3, 4, 5, 6, 7, 8, 9, 10, 11, 12, 13, 14, 15, 16, 17, 18 or 19 nucleotides in length. For example, a 20-nucleotide hemimer can have a gap segment of 10 nucleotides at the 5' end and a second segment of 10 nucleotides at the 3' end. Alternatively, a 20-nucleotide hemimer can have a gap segment of 10 nucleotides at the 3' end and a second segment of 10 nucleotides at the 5' end.

Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

F. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

G. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Such considerations are well known to those skilled in the art.

While the present invention has been described with specificity in accordance with certain of its preferred embodiments, the following examples serve only to illustrate the invention and are not intended to limit the same. Each of the references, GenBank accession numbers, and the like recited in the present application is incorporated herein by reference in its entirety.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4,4'-Dimethoxytriphenylmethyl)-2'-deoxy-$N^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, [5'-O-(4,4'-Dinethoxytriphenylmethyl)-2'-(2-methoxyethyl)-$N^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylaminooxy-ethyl) nucleoside amidites, 2'-(Dimethylaminooxyethoxy) nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenyl-silyl-2'-O-[(2-formadoximinooxy)ethyl]-5-methyluridine, 5'-O-tert-Butyldiphenylsilyl-2'-O-[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethyl-aminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides

Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.,* 1998, 120, 11820-11821; Matteucci, M. D. and Caruthers, M. H. *J. Am. Chem. Soc.,* 1981, 103, 3185-3191; Beaucage, S. L. and Caruthers, M. H. *Tetrahedron Lett.,* 1981, 22, 1859-1862; Dahl, B. J., et al., *Acta Chem. Scand,.* 1990, 44, 639-641; Reddy, M. P., et al., *Tetrahedrom Lett.,* 1994, 25, 4311-4314; Wincott, F. et al., *Nucleic Acids Res.,* 1995, 23, 2677-2684; Griffin, B. E., et al., *Tetrahedron,* 1967, 23, 2301-2313; Griffin, B. E., et al., *Tetrahedron,* 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 µl of each of the complementary strands of RNA oligonucleotides (50 µM RNA oligonucleotide solution) and 15 µl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid, or for diagnostic or therapeutic purposes.

Example 4

Synthesis of Chimeric Compounds

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me]Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligo is then recovered by an appropriate method (precipitation, column chromatography, volume reduced in vacuo and analyzed spectrophotometrically for yield and for purity by capillary electrophoresis and by mass spectrometry.

[2'-O-(2-Methoxyethyl)]-[2'-deoxy]-[2'-O-(Methoxyethyl)]Chimeric Phosphorothioate Oligonucleotides

[2'-O-(2-methoxyethyl)]-[2'-deoxy]-[-2'-O-(methoxyethyl)]chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester]Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Design and Screening of Duplexed Antisense Compounds Targeting HIF1-beta

In accordance with the present invention, a series of nucleic acid duplexes comprising the antisense compounds of the present invention and their complements can be designed to target HIF1-beta. The nucleobase sequence of the antisense strand of the duplex comprises at least an 8-nucleobase portion of an oligonucleotide in Table 1 or Table 2. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini. The antisense and sense strands of the duplex comprise from about 17 to 25 nucleotides, or from about 19 to 23 nucleotides. Alternatively, the antisense and sense strands comprise 20, 21 or 22 nucleotides.

For example, a duplex comprising an antisense strand having the sequence CGAGAGGCGGACGGGACCG (SEQ ID NO: 187) and having a two-nucleobase overhang of deoxythymidine(dT) would have the following structure:

```
cgagaggcggacgggaccgTT  Antisense Strand   (SEQ ID NO: 188)
|||||||||||||||||||
                 TTgctctccgcctgccctggc  Sense Strand       (SEQ ID NO: 189)
```

Overhangs can range from 2 to 6 nucleobases and these nucleobases may or may not be complementary to the target nucleic acid. In another embodiment, the duplexes may have an overhang on only one terminus.

In another embodiment, a duplex comprising an antisense strand having the same sequence CGAGAGGCGGACGG-GACCG may be prepared with blunt ends (no single stranded overhang) as shown:

```
cgagaggcggacgggaccg  Antisense Strand  (SEQ ID NO: 187)
|||||||||||||||||||
gctctccgcctgccctggc  Sense Strand      (SEQ ID NO: 190)
```

The RNA duplex can be unimolecular or bimolecular; i.e., the two strands can be part of a single molecule or may be separate molecules.

RNA strands of the duplex can be synthesized by methods disclosed herein or purchased from Dharmacon Research Inc., (Lafayette, Colo.). Once synthesized, the complementary strands are annealed. The single strands are aliquotted and diluted to a concentration of 50 μM. Once diluted, 30 μL of each strand is combined with 15 μL of a 5× solution of annealing buffer. The final concentration of said buffer is 100 mM potassium acetate, 30 mM HEPES-KOH pH 7.4, and 2mM magnesium acetate. The final volume is 75 μL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 µM. This solution can be stored frozen (−20° C.) and freeze-thawed up to 5 times.

Once prepared, the duplexed antisense compounds are evaluated for their ability to modulate HIF1-beta expression.

When cells reach 80% confluency, they are treated with duplexed antisense compounds of the invention. For cells grown in 96-well plates, wells are washed once with 200 µL OPTI-MEM-1 reduced-serum medium (Gibco BRL) and then treated with 130 µL of OPTI-MEM-1 containing 12 µg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

Example 6

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M $NH_4OAc$ with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., *J Biol. Chem.* 1991, 266, 18162-18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated $NH_4OH$ at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal bovine serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal bovine serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

b.END Cells:

The mouse brain endothelial cell line b.END was obtained from Dr. Werner Risau at the Max Plank Institute (Bad Nauheim, Germany). b.END cells were routinely cultured in DMEM, high glucose (Invitrogen Corporation, Carlsbad, Calif.) supplemented with 10% fetal bovine serum (Invitrogen Corporation, Carlsbad, Calif.). Cells were routinely passaged by trypsinization and dilution when they reached 90% confluence. Cells were seeded into 96-well plates (Falcon-Primaria #3872) at a density of 3000 cells/well for use in RT-PCR analysis.

MCF7 Cells:

The human breast carcinoma cell line MCF-7 was obtained from the American Type Culture Collection (Manassas, Va.). MCF-7 cells were routinely cultured in DMEM low glucose supplemented with 10% fetal bovine serum (Invitrogen Life Technologies, Carlsbad, Calif.). Cells were routinely passaged by trypsinization and dilution when they reached 90% confluence. Cells were seeded into poly-D-lysine coated 96-well plates (Falcon-Primaria #3872) at a density of 8000 cells/well for use in antisense oligonucleotide transfection.

PC3 Cells:

The human prostatic carcinoma cell line PC3 was obtained from the American Type Culture Collection (ATCC) (Manassas, Va.). PC3 cells were routinely cultured in Ham's F12K medium with 2 mM L-glutamine adjusted to contain 1.5 g/L sodium bicarbonate supplemented with 10% fetal bovine serum (Invitrogen Life Technologies, Carlsbad, Calif.) and antibiotics (Invitrogen Life Technologies, Carlsbad, Calif.). Cells were routinely passaged by trypsinization and dilution when they reached approximately 90% confluence. Cells were seeded into 96-well plates (Falcon-Primaria #353872) at a density of approximately 6000 cells/well for use in antisense oligonucleotide transfection.

Hep3B Cells:

The human hepatoma cell line Hep3B (Hep3B2.1-7) was obtained from the American Type Culture Collection (ATCC-ATCC Catalog # HB-8064) (Manassas, Va.). This cell line was initially derived from a hepatocellular carcinoma of an 8-yr-old black male. The cells are epithelial in morphology and are tumorigenic in nude mice. Hep3B cells are routinely cultured in Minimum Essential Medium (MEM) with Earle's Balanced Salt Solution, 2 mM L-glutamine, 1.5 g/L sodium bicarbonate, 0.1 mM nonessential amino acids, 1.0 mM sodium pyruvate (ATCC #20-2003, Manassas, Va.) and with 10% heat-inactivated fetal bovine serum (Invitrogen Life Technologies, Carlsbad, Calif.). Cells are routinely passaged by trypsinization and dilution when they reach 90% confluence.

HeLa Cells:

The human epithelioid carcinoma cell line HeLa was obtained from the American Tissue Type Culture Collection (Manassas, Va.). HeLa cells were routinely cultured in DMEM, high glucose (Invitrogen Corporation, Carlsbad, Calif.) supplemented with 10% fetal bovine serum (Invitrogen Corporation, Carlsbad, Calif.). Cells were routinely passaged by trypsinization and dilution when they reached 90% confluence. Cells were seeded into 24-well plates (Falcon-Primaria #3846) at a density of 50,000 cells/well or in 96-well plates at a density of 5,000 cells/well for use in RT-PCR analysis. For Northern blotting or other analyses, cells were harvested when they reached 90% confluence.

HuVEC Cells:

The human umbilical vein endothelial cell line HuVEC is obtained from Cascade Biologics (Portland, Oreg.). HuVEC cells are routinely cultured in EBM (Clonetics Corporation Walkersville, Md.) supplemented with SingleQuots supplements (Clonetics Corporation, Walkersville, Md.). Cells are routinely passaged by trypsinization and dilution when they reach 90% confluence and are maintained for up to 15 passages.

Treatment with Antisense Compounds:

When cells reached 65-75% confluency, they were treated with oligonucleotide. For cells grown in 96-well plates, wells were washed once with 100 μL OPTI-MEM™-1 reduced-serum medium (Invitrogen Corporation, Carlsbad, Calif.) and then treated with 130 μL of OPTI-MEM™-1 containing 3.75 μg/mL LIPOFECTIN™ (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCTCAGGG, SEQ ID NO: 1) which is targeted to human H-ras, or ISIS 18078, (GTGCGCGCGAGCCCGAAATC, SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770 (ATGCATTCTGCCCCCAAGGA, SEQ ID NO: 3), a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

For Northern blotting or other analyses, cells may be seeded onto 100 mm or other standard tissue culture plates and treated similarly, using appropriate volumes of medium and oligonucleotide.

Example 10

Analysis of Oligonucleotide Inhibition of HIF1-Beta Expression

Antisense modulation of HIF1-beta expression can be assayed in a variety of ways known in the art. For example, HIF1-beta mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of HIF1-beta can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to HIF1-beta can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 11

Design of Phenotypic Assays for the Use of HIF1-Beta Inhibitors

Phenotypic Assays

Once HIF1-beta inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of HIF1-beta in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with HIF1-beta inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the HIF1-beta inhibitors. Hallmark genes, or those genes suspected to be associated with a specific disease state, condition, or phenotype, are measured in both treated and untreated cells.

Example 12

RNA Isolation

Poly(A)+ mRNA Isolation

Poly(A)+ mRNA was isolated according to Miura et al., (*Clin. Chem.*, 1996, 42, 1758-1764). Other methods for poly (A)+ mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIA-VAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-time Quantitative PCR Analysis of HIF1-Beta mRNA Levels

Quantitation of HIF1-beta mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

Gene target quantities are obtained by real-time PCR. Prior to the real-time PCR, isolated RNA is subjected to a reverse transcriptase (RT) reaction, for the purpose of generating complementary DNA (cDNA). Reverse transcriptase and PCR reagents were obtained from Invitrogen Corporation, (Carlsbad, Calif.). RT, real-time PCR reactions were carried out by adding 20 µL PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µL total RNA solution (20-200 ng). The RT reaction was carried out by incubation for 30 minutes at 48° C. Following a 10 minute incubation at 95° C. to activate the PLATINUM Taq, 40 cycles of a two-step PCR protocol were carried out: 95° C. for 15 seconds (denaturation) followed by 60° C. for 1.5 minutes (annealing/extension). The method of obtaining gene target quantities by RT, real-time PCR is herein referred to as real-time PCR.

Gene target quantities obtained by real-time PCR were normalized using either the expression level of GAPDH, a gene whose expression is constant, or by quantifying total RNA using RiboGreen™ (Molecular Probes, Inc. Eugene, Oreg.). GAPDH expression is quantified by real-time PCR by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 µL of RiboGreen™ working reagent (RiboGreen™ reagent diluted 1:350 in 10 mM Tris-HCl, 1 mM EDTA, pH 7.5) was pipetted into a 96-well plate containing 30 µL purified, cellular RNA. The plate was read in a CytoFluor 4000 (PE Applied Biosystems) with excitation at 485 nm and emission at 530 nm.

Probes and primers to human HIF1-beta were designed to hybridize to a human HIF1-beta sequence, using published sequence information (Genbank accession number BC028362.1, incorporated herein as SEQ ID NO: 4). For human HIF1-beta the PCR primers were: forward primer: AGCAGAGGGTGTGGGTGTCT (SEQ ID NO: 5) reverse primer: TGGCGGTTGTTGAACATGTT (SEQ ID NO: 6) and the PCR probe was: FAM-CCAGCAGCCTCAT-CATCGTTCA-TAMRA (SEQ ID NO: 7) where FAM is the fluorescent dye and TAMRA is the quencher dye. For human GAPDH the PCR primers were: forward primer: GAAGGTGAAGGTCGGAGTC(SEQ ID NO: 8) reverse primer: GAAGATGGTGATGGGATTTC (SEQ ID NO: 9) and the PCR probe was: 5' JOE-CAAGCTTCCCGTTCTCAGCC-TAMRA 3' (SEQ ID NO: 10) where JOE is the fluorescent reporter dye and TAMRA is the quencher dye.

Probes and primers to mouse HIF1-beta were designed to hybridize to a mouse HIF1-beta sequence, using published sequence information (GenBank accession number BC012870.1, incorporated herein as SEQ ID NO: 11). For mouse HIF1-beta the PCR primers were: forward primer: GGCATCTCCTCCAGCACTGT (SEQ ID NO: 12) reverse primer: GGTAAGACCACTATTCCTGAAATTCTCT (SEQ ID NO: 13) and the PCR probe was: FAM-TCCCTCCTAAC-CCCCGGCCG-TAMRA (SEQ ID NO: 14) where FAM is the fluorescent reporter dye and TAMRA is the quencher dye. For mouse GAPDH the PCR primers were: forward primer: GGCAAATTCAACGGCACAGT(SEQ ID NO: 15) reverse primer: GGGTCTCGCTCCTGGAAGAT(SEQ ID NO: 16) and the PCR probe was: 5' JOE-AAGGCCGAGAATGG-GAAGCTTGTCATC- TAMRA 3' (SEQ ID NO: 17) where JOE is the fluorescent reporter dye and TAMRA is the quencher dye.

Example 14

Northern Blot Analysis of HIF1-Beta mRNA Levels

Eighteen hours after antisense treatment, cell monolayers were washed twice with cold PBS and lysed in 1 mL RNA-ZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AM-RESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ WV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human HIF1-beta, a human HIF1-beta specific probe was prepared by PCR using the forward primer AGCA-GAGGGTGTGGGTGTCT (SEQ ID NO: 5) and the reverse primer TGGCGGTTGTTGAACATGTT (SEQ ID NO: 6). To normalize for variations in loading and transfer efficiency membranes were stripped and probed for human glyceralde-hyde-3-phosphate dehydrogenase (GAPDH) RNA (Clontech, Palo Alto, Calif.).

To detect mouse HIF1-beta, a mouse HIF1-beta specific probe was prepared by PCR using the forward primer GGCATCTCCTCCAGCACTGT (SEQ ID NO: 12) and the reverse primer GGTAAGACCACTATTCCTGAAAT-TCTCT (SEQ ID NO: 13). To normalize for variations in loading and transfer efficiency membranes were stripped and probed for mouse glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human HIF1Beta Expression by Chimeric Phosphorothioate Oligonucleotides Having 2'-MOE Wings and a Deoxy Gap In accordance with the present invention, a series of antisense compounds was designed to target different regions of the human HIF1-beta RNA, using published sequences (GenBank accession number BC028362.1, incorporated herein as SEQ ID NO: 4, nucleotides 336578 to 404364 of Genbank accession number NT_021907.12, the complement of which is incorporated herein as SEQ ID NO: 18, GenBank accession number N72808. 1, incorporated herein as SEQ ID NO: 19, and GenBank accession number AL834279.1, incorporated herein as SEQ ID NO: 20). The compounds are shown in Table 1. "Target site" indicates the first (5'-most) nucleotide number on the particular target sequence to which the compound binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl nucleotides, also known as 2'-MOE nucleotides. The internucleoside (backbone) linkages are phosphorothioate (P=S) throughout the oligonucleotide. All cytidine residues are 5-methylcytidines. The compounds were analyzed for their effect on human HIF1-beta mRNA levels by quantitative real-time PCR as described in other examples herein. Data are averages from two experiments in which T-24 cells were treated with 100 nM of antisense oligonucleotides of the present invention. The positive control for each datapoint is identified in the table by sequence ID number. If present, "N.D." indicates "no data".

TABLE 1

Inhibition of human HIF1-beta mRNA levels by chimeric phosphorothioate oligonucleotides having 2'-MOE wings and a deoxy gap

| ISIS # | REGION | TARGET SEQ ID NO | TARGET SITE | SEQUENCE (5' to 3') | % INHIB | SEQ ID NO | CONTROL SEQ ID NO |
|---|---|---|---|---|---|---|---|
| 311073 | Intron 1 | 18 | 1578 | acacacatatctcaaggccc | 65 | 21 | 2 |
| 311074 | Intron 1 | 18 | 10523 | aagggagcagaggactccct | 6 | 22 | 2 |
| 311075 | Intron 1 | 18 | 15791 | caagatcaggctgggaaaca | 25 | 23 | 2 |
| 311076 | Intron 2 | 18 | 23071 | cccctaatctggtcacctgt | 71 | 24 | 2 |

TABLE 1-continued

Inhibition of human HIF1-beta mRNA levels by chimeric phosphorothioate oligonucleotides having 2'-MOE wings and a deoxy gap

| ISIS # | REGION | TARGET SEQ ID NO | TARGET SITE | SEQUENCE (5' to 3') | % INHIB | SEQ ID NO | CONTROL SEQ ID NO |
|---|---|---|---|---|---|---|---|
| 311077 | Intron 8: Exon 9 junction | 18 | 44694 | actgccacacctgtttcaag | 51 | 25 | 2 |
| 311078 | Intron 13 | 18 | 52827 | taggaataataacttatttc | 0 | 26 | 2 |
| 311079 | Exon 21: Intron 21 junction | 18 | 63922 | actctcttacctggaagacc | 4 | 27 | 2 |
| 311080 | 5'UTR | 4 | 19 | caagatggcggcttcagcag | 3 | 28 | 2 |
| 311081 | 5'UTR | 4 | 80 | ggaaaagaaaggccactccc | 0 | 29 | 2 |
| 311082 | Start Codon | 4 | 163 | gccgccatggccgcagatgc | 87 | 30 | 2 |
| 311083 | Coding | 4 | 199 | ggtacatctgatgtcatttc | 38 | 31 | 2 |
| 311084 | Coding | 4 | 281 | cttaatagccctctggacaa | 29 | 32 | 2 |
| 311085 | Coding | 4 | 308 | atcatcaaaatccagccctg | 42 | 33 | 2 |
| 311086 | Coding | 4 | 388 | tccgacctggcaaaccgctc | 52 | 34 | 2 |
| 311087 | Coding | 4 | 393 | catcatccgacctggcaaac | 17 | 35 | 2 |
| 311088 | Coding | 4 | 432 | attttccctggcaagtctct | 55 | 36 | 2 |
| 311089 | Coding | 4 | 472 | ctgtcatcttgttccgtcgc | 69 | 37 | 2 |
| 311090 | Coding | 4 | 494 | tctgacagttctgtgatgta | 82 | 38 | 2 |
| 311091 | Coding | 4 | 527 | tttcgagccagggcactaca | 83 | 39 | 2 |
| 311092 | Coding | 4 | 532 | ctggttttcgagccagggca | 76 | 40 | 2 |
| 311093 | Coding | 4 | 652 | aatgtttcagttcctgatca | 56 | 41 | 2 |
| 311094 | Coding | 4 | 658 | agatcaaatgtttcagttcc | 66 | 42 | 2 |
| 311095 | Coding | 4 | 663 | ctccaagatcaaatgtttca | 43 | 43 | 2 |
| 311096 | Coding | 4 | 668 | gctgcctccaagatcaaatg | 55 | 44 | 2 |
| 311097 | Coding | 4 | 673 | catctgctgcctccaagatc | 73 | 45 | 2 |
| 311098 | Coding | 4 | 678 | aaagccatctgctgcctcca | 80 | 46 | 2 |
| 311099 | Coding | 4 | 804 | atcatctgggtgcacctgat | 76 | 47 | 2 |
| 311100 | Coding | 4 | 810 | atccacatcatctgggtgca | 80 | 48 | 2 |
| 311101 | Coding | 4 | 815 | agtttatccacatcatctgg | 43 | 49 | 2 |
| 311102 | Coding | 4 | 892 | ccttttcactgttccagtc | 81 | 50 | 2 |
| 311103 | Coding | 4 | 900 | ctgaccttcctttttcactg | 68 | 51 | 2 |
| 311104 | Coding | 4 | 906 | agactgctgaccttccttt | 63 | 52 | 2 |
| 311105 | Coding | 4 | 1029 | tccattcctgcatctgttcc | 53 | 53 | 2 |
| 311106 | Coding | 4 | 1036 | agccaagtccattcctgcat | 84 | 54 | 2 |
| 311107 | Coding | 4 | 1139 | gcctctgggtcatcatctgg | 79 | 55 | 2 |
| 311108 | Coding | 4 | 1200 | gggagaactagttacctgca | 48 | 56 | 2 |
| 311109 | Coding | 4 | 1205 | cagttgggagaactagttac | 43 | 57 | 2 |

TABLE 1-continued

Inhibition of human HIF1-beta mRNA levels by chimeric phosphorothioate oligonucleotides having 2'-MOE wings and a deoxy gap

| ISIS # | REGION | TARGET SEQ ID NO | TARGET SITE | SEQUENCE (5' to 3') | % INHIB | SEQ ID NO | CONTROL SEQ ID NO |
|---|---|---|---|---|---|---|---|
| 311110 | Coding | 4 | 1210 | ctgtacagttgggagaacta | 74 | 58 | 2 |
| 311111 | Coding | 4 | 1215 | catgtctgtacagttgggag | 34 | 59 | 2 |
| 311112 | Coding | 4 | 1220 | ttactcatgtctgtacagtt | 84 | 60 | 2 |
| 311113 | Coding | 4 | 1251 | tcgggagatgaactctgttg | 65 | 61 | 2 |
| 311114 | Coding | 4 | 1256 | ttgtgtcgggagatgaactc | 49 | 62 | 2 |
| 311115 | Coding | 4 | 1261 | caatgttgtgtcgggagatg | 57 | 63 | 2 |
| 311116 | Coding | 4 | 1310 | tagccaacagtagccacaca | 48 | 64 | 2 |
| 311117 | Coding | 4 | 1315 | gctggtagccaacagtagcc | 51 | 65 | 2 |
| 311118 | Coding | 4 | 1320 | ctgtggctggtagccaacag | 52 | 66 | 2 |
| 311119 | Coding | 4 | 1343 | acaatattctttcctaagag | 27 | 67 | 2 |
| 311120 | Coding | 4 | 1405 | atttcactacctgttggaag | 67 | 68 | 2 |
| 311121 | Coding | 4 | 1418 | acttggccttttaatttcac | 55 | 69 | 2 |
| 311122 | Coding | 4 | 1423 | acagcacttggccttttaat | 63 | 70 | 2 |
| 311123 | Coding | 4 | 1434 | gaacatgacagacagcactt | 62 | 71 | 2 |
| 311124 | Coding | 4 | 1551 | gttcttcacattggtgttgg | 68 | 72 | 2 |
| 311125 | Coding | 4 | 1556 | ctagagttcttcacattggt | 56 | 73 | 2 |
| 311126 | Coding | 4 | 1706 | ccatctcttcctggtaccat | 77 | 74 | 2 |
| 311127 | Coding | 4 | 1862 | ttactctgatccgcattgat | 49 | 75 | 2 |
| 311128 | Coding | 4 | 1871 | gagatgcctttactctgatc | 67 | 76 | 2 |
| 311129 | Coding | 4 | 1876 | tggaggagatgcctttactc | 84 | 77 | 2 |
| 311130 | Coding | 4 | 1881 | agtgctggaggagatgcctt | 75 | 78 | 2 |
| 311131 | Coding | 4 | 1953 | gaaattctctgccggccggg | 70 | 79 | 2 |
| 311132 | Coding | 4 | 1958 | ttcctgaaattctctgccgg | 67 | 80 | 2 |
| 311133 | Coding | 4 | 1967 | agaccactattcctgaaatt | 15 | 81 | 2 |
| 311134 | Coding | 4 | 1990 | ggacaatggttacaggaggg | 68 | 82 | 2 |
| 311135 | Coding | 4 | 1995 | tggctggacaatggttacag | 80 | 83 | 2 |
| 311136 | Coding | 4 | 2276 | gtctcaggagcaaagttaga | 48 | 84 | 2 |
| 311137 | Coding | 4 | 2339 | cactgtggccagacacccac | 65 | 85 | 2 |
| 311138 | Coding | 4 | 2349 | ctggccctgccactgtggcc | 42 | 86 | 2 |
| 311139 | Coding | 4 | 2354 | ggctgctggccctgccactg | 85 | 87 | 2 |
| 311140 | Coding | 4 | 2507 | ggaaacatagttagatcagg | 66 | 88 | 2 |
| 311141 | Stop Codon | 4 | 2531 | caatagttctattctgaaaa | 21 | 89 | 2 |
| 311142 | Stop Codon | 4 | 2537 | tcaccccaatagttctattc | 27 | 90 | 2 |
| 311143 | Stop Codon | 4 | 2542 | tatcctcaccccaatagttc | 24 | 91 | 2 |
| 311144 | 3'UTR | 4 | 2616 | agaggaacttttattctgtt | 51 | 92 | 2 |
| 311145 | 3'UTR | 4 | 2621 | aagggagaggaacttttatt | 0 | 93 | 2 |

TABLE 1-continued

Inhibition of human HIF1-beta mRNA levels by chimeric phosphorothioate oligonucleotides having 2'-MOE wings and a deoxy gap

| ISIS # | REGION | TARGET SEQ ID NO | TARGET SITE | SEQUENCE (5' to 3') | % INHIB | SEQ ID NO | CONTROL SEQ ID NO |
|---|---|---|---|---|---|---|---|
| 311146 | 3'UTR | 4 | 2873 | atccaaggcaaacagtggat | 66 | 94 | 2 |
| 311147 | 3'UTR | 4 | 3791 | gtccaggccccatctatcat | 57 | 95 | 2 |
| 311148 | 3'UTR | 4 | 4429 | tgaaaatctttgctacatgt | 72 | 96 | 2 |
| 311149 | 5'UTR | 19 | 231 | ccaggtggtcacatctggtc | 33 | 97 | 2 |
| 311150 | Exon1: Exon1A junction | 20 | 162 | tgagtccaagatcaggcggg | 18 | 98 | 2 |

As shown in Table 1, the majority of antisense compounds targeting human HIF1-beta resulted in inhibition of HIF1-beta mRNA levels. Treatment of cells with antisense compounds represented by SEQ ID NOs: 21, 23-25, 30-34, 36-80, 82-92 and 94-97 resulted in at least 20% inhibition of HIF1-beta mRNA; SEQ ID NOs: 21, 24, 25, 30, 33, 34, 36-58, 60-66, 68-80, 82-88, 92 and 94-96 resulted in at least 40% inhibition of HIF1-beta mRNA; SEQ ID NOs: 21, 24, 25, 30, 34, 36-42, 44-48, 50-55, 58, 60, 61, 63, 65, 66, 68-74, 76-80, 82, 83, 85, 87, 88, 92 and 94-96 resulted in at least 50% inhibition of HIF1-beta mRNA; SEQ ID NOs: 21, 24, 30, 37-40, 42, 45-48, 50-52, 54, 55, 58, 60, 61, 68, 70-72, 74, 76-80, 82, 83, 85, 87, 88, 94 and 96 resulted in at least 60% inhibition of HIF1-beta mRNA; SEQ ID NOs: 24, 30, 38-40, 45-48, 50, 54, 55, 58, 60, 74, 77-79, 83, 87 and 96 resulted in at least 70% inhibition of HIF1-beta mRNA; and SEQ ID NOs: 30, 38, 39, 46, 48, 50, 54, 60, 77, 83 and 87 resulted in at least 80% inhibition of HIF1-beta mRNA.

Example 16

Antisense Inhibition of Mouse HIF1-Beta Expression by Chimeric Phosphorothioate Oligonucleotides Having 2'-MOE Wings and a Deoxy Gap In accordance with the present invention, a second series of antisense compounds was designed to target different regions of the mouse HIF1-beta RNA, using published sequences (GenBank accession number BC012870.1, incorporated herein as SEQ ID NO: 11, nucleotides 1145000 to 1210000 of GenBank accession number NW_000199.1, incorporated herein as SEQ ID NO: 99, GenBank accession number AK040475.1, incorporated herein as SEQ ID NO: 100, GenBank accession number AK028546.1, incorporated herein as SEQ ID NO: 101, GenBank accession number BG083773.1, incorporated herein as SEQ ID NO: 102, and GenBank accession number AK049738.1, incorporated herein as SEQ ID NO: 103). The compounds are shown in Table 2. "Target site" indicates the first (5'-most) nucleotide number on the particular target nucleic acid to which the compound binds. All compounds in Table 2 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl nucleotides, also known as 2'-MOE nucleotides. The internucleoside (backbone) linkages are phosphorothioate (P=S) throughout the oligonucleotide. All cytidine residues are 5-methylcytidines. The compounds were analyzed for their effect on mouse HIF1-beta mRNA levels by quantitative real-time PCR as described in other examples herein. Data are averages from two experiments in which b.END cells were treated with 40 nM of antisense oligonucleotides of the present invention. The positive control for each datapoint is identified in the table by sequence ID number. If present, "N.D." indicates "no data".

TABLE 2

Inhibition of mouse HIF1-beta mRNA levels by chimeric phosphorothioate oligonucleotides having 2'-MOE wings and a deoxy gap

| ISIS # | REGION | TARGET SEQ ID NO | TARGET SITE | SEQUENCE (5' to 3') | % INHIB | SEQ ID NO | CONTROL SEQ ID NO |
|---|---|---|---|---|---|---|---|
| 347985 | Intron 1 | 99 | 12686 | gattccagcagaaacaagat | 76 | 104 | 2 |
| 347986 | Intron 2 | 99 | 20208 | agtaccataaccaggaagag | 82 | 105 | 2 |
| 347987 | Intron 3: Exon 4 junction | 99 | 28425 | atcatcgcatctgaaaagaa | 51 | 106 | 2 |

TABLE 2-continued

Inhibition of mouse HIF1-beta mRNA levels by chimeric phosphorothioate oligonucleotides having 2'-MOE wings and a deoxy gap

| ISIS # | REGION | TARGET SEQ ID NO | TARGET SITE | SEQUENCE (5' to 3') | % INHIB | SEQ ID NO | CONTROL SEQ ID NO |
|---|---|---|---|---|---|---|---|
| 347988 | Exon 11: Intron 11 junction | 99 | 51989 | tcatacttgcctgcagcctg | 59 | 107 | 2 |
| 347989 | 5'UTR | 11 | 3 | agattaggcaccttaccgcc | 80 | 108 | 2 |
| 347990 | Start Codon | 11 | 98 | gccgccatggtcgagatggc | 73 | 109 | 2 |
| 347991 | Start Codon | 11 | 111 | gttagctgtagtcgccgcca | 88 | 110 | 2 |
| 347992 | Coding | 11 | 121 | tcatttctgggttagctgta | 75 | 111 | 2 |
| 347993 | Coding | 11 | 131 | acatctgatgtcatttctgg | 79 | 112 | 2 |
| 347994 | Coding | 11 | 163 | ttccagaagcaatggtggga | 69 | 113 | 2 |
| 347995 | Coding | 11 | 195 | agctcctccaccttgaatcc | 41 | 114 | 2 |
| 347996 | Coding | 11 | 221 | cgtcgcttaatagccctctg | 81 | 115 | 2 |
| 347997 | Coding | 11 | 231 | cagccctgaccgtcgcttaa | 83 | 116 | 2 |
| 347998 | Coding | 11 | 241 | catcaaaatccagccctgac | 29 | 117 | 2 |
| 347999 | Coding | 11 | 317 | ctggcaaaccgctctttgtc | 47 | 118 | 2 |
| 348000 | Coding | 11 | 327 | atcatccgacctggcaaacc | 85 | 119 | 2 |
| 348001 | Coding | 11 | 337 | agctctgctcatcatccgac | 41 | 120 | 2 |
| 348002 | Coding | 11 | 355 | gtctctctttatccgcagag | 89 | 121 | 2 |
| 348003 | Coding | 11 | 362 | ctggcaagtctctctttatc | 66 | 122 | 2 |
| 348004 | Coding | 11 | 367 | tttccctggcaagtctctct | 56 | 123 | 2 |
| 348005 | Coding | 11 | 372 | atgattttccctggcaagtc | 75 | 124 | 2 |
| 348006 | Coding | 11 | 414 | gtaagctgtcatcttgttcc | 73 | 125 | 2 |
| 348007 | Coding | 11 | 424 | gttctgtgatgtaagctgtc | 49 | 126 | 2 |
| 348008 | Coding | 11 | 477 | tagcttgtctggttttcgag | 63 | 127 | 2 |
| 348009 | Coding | 11 | 591 | caaatgtttcagttcctgat | 82 | 128 | 2 |
| 348010 | Coding | 11 | 622 | taaacagaaagccatctgct | 83 | 129 | 2 |
| 348011 | Coding | 11 | 686 | tggttcaaaacgggagtcac | 39 | 130 | 2 |
| 348012 | Coding | 11 | 763 | gctgctctcgaagtttatcc | 58 | 131 | 2 |
| 348013 | Coding | 11 | 858 | gcacatcctcatggaagact | 90 | 132 | 2 |
| 348014 | Coding | 11 | 929 | ttcatggaaacagggtccac | 84 | 133 | 2 |
| 348015 | Coding | 11 | 939 | gctcagtctattcatggaaa | 76 | 134 | 2 |
| 348016 | Coding | 11 | 949 | tcctcaaaaagctcagtcta | 56 | 135 | 2 |
| 348017 | Coding | 11 | 959 | ctgcatctgttcctcaaaaa | 86 | 136 | 2 |
| 348018 | Coding | 11 | 1015 | tgcagtggactaccacaaag | 68 | 137 | 2 |
| 348019 | Coding | 11 | 1081 | ggccagcctctgggtcatca | 89 | 138 | 2 |
| 348020 | Coding | 11 | 1097 | cagaatttgctcccctggcc | 73 | 139 | 2 |
| 348021 | Coding | 11 | 1107 | ggccactaggcagaatttgc | 79 | 140 | 2 |
| 348022 | Coding | 11 | 1119 | cagcctgccaatggccacta | 70 | 141 | 2 |

TABLE 2-continued

Inhibition of mouse HIF1-beta mRNA levels by chimeric phosphorothioate oligonucleotides having 2'-MOE wings and a deoxy gap

| ISIS # | REGION | TARGET SEQ ID NO | TARGET SITE | SEQUENCE (5' to 3') | % INHIB | SEQ ID NO | CONTROL SEQ ID NO |
|---|---|---|---|---|---|---|---|
| 348023 | Coding | 11 | 1211 | gtgaatatcccttcaatgtt | 74 | 142 | 2 |
| 348024 | Coding | 11 | 1241 | acagtagccacacaacgatg | 79 | 143 | 2 |
| 348025 | Coding | 11 | 1291 | gacaaaattctacaatattc | 53 | 144 | 2 |
| 348026 | Coding | 11 | 1302 | gtcttcaggatgacaaaatt | 79 | 145 | 2 |
| 348027 | Coding | 11 | 1312 | gaagttgttggtcttcagga | 65 | 146 | 2 |
| 348028 | Coding | 11 | 1323 | gctgtctcttagaagttgtt | 25 | 147 | 2 |
| 348029 | Coding | 11 | 1333 | cctgctgaaagctgtctctt | 76 | 148 | 2 |
| 348030 | Coding | 11 | 1343 | aatttcaccacctgctgaaa | 56 | 149 | 2 |
| 348031 | Coding | 11 | 1408 | tcatccacagccattctcgg | 75 | 150 | 2 |
| 348032 | Coding | 11 | 1504 | gtggttcctggctagagttc | 58 | 151 | 2 |
| 348033 | Coding | 11 | 1550 | gtcggacctagctgtgacct | 80 | 152 | 2 |
| 348034 | Coding | 11 | 1579 | ctgtacccatctctagggat | 79 | 153 | 2 |
| 348035 | Coding | 11 | 1651 | ccagcccatctcttcctggt | 23 | 154 | 2 |
| 348036 | Coding | 11 | 1681 | ggacagaaacctgggaatga | 76 | 155 | 2 |
| 348037 | Coding | 11 | 1719 | gggcttgctgtgttctgatc | 70 | 156 | 2 |
| 348038 | Coding | 11 | 1742 | aagagaccttctgacttctc | 57 | 157 | 2 |
| 348039 | Coding | 11 | 1855 | cctgggagaacagctgttgg | 84 | 158 | 2 |
| 348040 | Coding | 11 | 1865 | aatgagctgccctgggagaa | 83 | 159 | 2 |
| 348041 | Coding | 11 | 1875 | gttaggagggaatgagctgc | 69 | 160 | 2 |
| 348042 | Coding | 11 | 1906 | cactattcctgaaattctct | 65 | 161 | 2 |
| 348043 | Coding | 11 | 1958 | atctgccctgcagaagatga | 58 | 162 | 2 |
| 348044 | Coding | 11 | 2083 | aagaacgagtcttggctgta | 70 | 163 | 2 |
| 348045 | Coding | 11 | 2110 | tctgaaagttgttcacacca | 51 | 164 | 2 |
| 348046 | Coding | 11 | 2219 | gtctcaggaggaaagttgga | 88 | 165 | 2 |
| 348047 | Coding | 11 | 2287 | cctgccactgtggccagaca | 77 | 166 | 2 |
| 348048 | Coding | 11 | 2379 | ttcttgaaagacctcaggct | 52 | 167 | 2 |
| 348049 | Coding | 11 | 2399 | tctcccagcatggacagcat | 68 | 168 | 2 |
| 348050 | Stop Codon | 11 | 2475 | ccaatagttctattcggaaa | 87 | 169 | 2 |
| 348051 | 3'UTR | 11 | 2538 | tctgtttacaaaagatttgc | 78 | 170 | 2 |
| 348052 | 5'UTR | 100 | 10 | cggaatccaagatggcggac | 88 | 171 | 2 |
| 348053 | 3'UTR | 100 | 2358 | ctccaaacaagcctgagacc | 87 | 172 | 2 |
| 348054 | Coding | 101 | 352 | atgattttccctggcaaacc | 79 | 173 | 2 |
| 348055 | Coding | 101 | 2031 | ggcacctgggcggcaaagcc | 60 | 174 | 2 |
| 348056 | Coding | 102 | 608 | agacttttcccccacatatc | 67 | 175 | 2 |
| 348057 | 5'UTR | 103 | 50 | taacctatgtattcagtgat | 34 | 176 | 2 |

TABLE 2-continued

Inhibition of mouse HIF1-beta mRNA levels by chimeric phosphorothioate oligonucleotides having 2'-MOE wings and a deoxy gap

| ISIS # | REGION | TARGET SEQ ID NO | TARGET SITE | SEQUENCE (5' to 3') | % INHIB | SEQ ID NO | CONTROL SEQ ID NO |
|---|---|---|---|---|---|---|---|
| 311090 | Coding | 11 | 431 | tctgacagttctgtgatgta | 75 | 38 | 2 |
| 311091 | Coding | 11 | 464 | tttcgagccagggcactaca | 82 | 39 | 2 |
| 311112 | Coding | 11 | 1157 | ttactcatgtctgtacagtt | 82 | 60 | 2 |
| 311129 | Coding | 11 | 2819 | tggaggagatgcctttactc | 75 | 77 | 2 |
| 311130 | Coding | 11 | 1824 | agtgctggaggagatgcctt | 78 | 78 | 2 |

As shown in Table 1, the majority of antisense compounds targeting mouse HIF1-beta resulted in inhibition of HIF1-beta mRNA levels. Treatment of cells with antisense compounds represented by SEQ ID NOs: 38, 39, 60, 77,78, 104-153 and 155-176 resulted in at least 25% inhibition of HIF1-beta mRNA; SEQ ID NOs: 38, 39, 60, 77, 78, 104-113, 115, 116, 119, 121-125, 127-129, 131-146, 148-153 and 155-175 resulted in at least 50% inhibition of HIF1-beta mRNA; 38, 39, 60, 77, 78, 104, 105, 108-113, 115, 116, 119, 121, 122, 124, 125, 127-129, 132-134, 136-143, 145, 146, 148, 150, 152, 153, 155, 156, 158-161, 163, 165, 166 and 168-175 resulted in at least 60% inhibition of HIF1-beta mRNA; SEQ ID NOs: 38, 39, 60, 77, 78, 104, 105, 108-112, 115, 116, 119, 121, 124, 125, 128, 129, 132-134, 136, 138-143, 145, 148, 150, 152, 153, 155, 156, 158, 159, 163, 165, 166 and 169-173 resulted in at least 70% inhibition of HIF1-beta mRNA; and SEQ ID NOs: 39, 60, 105, 108, 110, 115, 116, 119, 121, 128, 129, 132, 133, 136, 138, 152, 158, 159, 165, 169, 171 and 172 resulted in at least 80% inhibition of HIF1-beta mRNA.

Example 17

Targeting of Individual Oligonucleotides to Specific Variants of Human HIF1-Beta A search of the National Center for Biotechnology Information database revealed alternative mRNA variants of human HIF1-beta which are the result of alternative splicing. The sequence identified as Genbank accession number N72808.1 represents a variant of HIF1-beta designated herein as HIF1-beta-l (incorporated herein as SEQ ID NO: 19). The sequence identified as Genbank accession number AL834279.1 represents a variant of HIF1-beta designated herein as HIF1-beta-2 (incorporated herein as SEQ ID NO: 20).

It is advantageous to selectively inhibit the expression of one or more variants of HIF1-beta. Consequently, in one embodiment of the present invention are oligonucleotides that selectively target, hybridize to, and specifically inhibit one or more, but fewer than all the variants of HIF1-beta. The oligonucleotides of the present invention that selectively target human HIF1-beta variants are presented in Table 4.

TABLE 4

Targeting of individual oligonucleotides to specific variants of human HIF1-beta

| ISIS # | SEQ ID NO | Target Site | Target Variant | Target SEQ ID NO |
|---|---|---|---|---|
| 311149 | 97 | 231 | HIF1-beta-1 | 19 |
| 331150 | 98 | 162 | HIF1-beta-2 | 20 |

Example 18

Targeting of Individual Oligonucleotides to Specific Variants of Mouse HIF1-Beta A search of the National Center for Biotechnology Information database revealed alternative mRNA variants of mouse HIF1-beta which are the result of alternative splicing. The sequence identified as Genbank accession number AK040475.1 represents a variant of HIF1-beta designated herein as HIF1-beta-3 (incorporated herein as SEQ ID NO: 100). The sequence identified as Genbank accession number AK028546.1 represents a variant of HIF1-beta designated herein as HIF1-beta-4 (incorporated herein as SEQ ID NO: 101). The sequence identified as Genbank accession number BG083773.1 represents a variant of HIF1-beta designated herein as HIF1-beta-5 (incorporated herein as SEQ ID NO: 102). The sequence identified as Genbank accession number AK049738.1 represents a variant of HIF1-beta designated herein as HIF1-beta-6 (incorporated herein as SEQ ID NO: 103).

It is advantageous to selectively inhibit the expression of one or more variants of HIF1. Consequently, in one embodiment of the present invention are oligonucleotides that selectively targe, hybridize to, and specifically inhibit one or more, but fewer than all the variants of mouse HIF1-beta. The oligonucleotides of the present invention that selectively target mouse HIF1-beta variants are presented in Table 5.

TABLE 5

Targeting of individual oligonucleotides to specific variants of mouse HIF1-beta

| ISIS # | SEQ ID NO | Target Site | Target Variant | Target SEQ ID NO |
|---|---|---|---|---|
| 348052 | 171 | 10 | HIF1-beta-3 | 100 |
| 348053 | 172 | 2358 | HIF1-beta-3 | 100 |
| 348053 | 172 | 1543 | HIF1-beta-6 | 103 |
| 348054 | 173 | 352 | HIF1-beta-4 | 101 |
| 348054 | 173 | 149 | HIF1-beta-5 | 102 |
| 348055 | 174 | 2031 | HIF1-beta-4 | 101 |
| 348056 | 175 | 608 | HIF1-beta-5 | 102 |
| 348057 | 176 | 50 | HIF1-beta-6 | 103 |

Example 19

Expression of HIF1-Beta in Various Human Cell Lines

U84-MG human glioblastoma, PC-3 human prostate cancer, JEG-3 human choriocarcinoma, HeLa human cervical cancer, SK-N-BE(2) neuroblastoma, MCF-7 human breast cancer, 786-O human clear-cell renal cell carcinoma, Calu-1 human lung cancer, and Hep3B human hepatocellular carcinoma cells were purchased from American Type Culture Collection (ATCC; Manassas, Va.) and cultured according to ATCC directions. Human umbilical endothelial cells (HU-VEC) were obtained from Cascade Biologics (Portland, Oreg.). Hypoxic treatments cells ($0.5$-$0.8 \times 10^6$/60 mm dish or $1$-$2 \times 10^6$/100 mm dish) were performed at 1% $O_2$ in a chamber controlled by ProOx oxygen sensor (BioSpherix, Redfield, N.Y.) for 18 h. To achieve the optimal hypoxic induction, 2 or 5 ml of medium was used for 60 mm and 100 mm culture dishes, respectively, during incubation. $CoCl_2$ (150 µM) was added to the cells to mimic hypoxic condition in some experiments.

After 18 h of culture at normoxia, hypoxia, or with $CoCl_2$, cells were harvested and whole cell lysates prepared with RIPA buffer containing protease inhibitor cocktails (Roche), 0.5 mM sodium orthovanadate, 10 mM β-glycerophophate, 250 ng/ml ubiquitin aldehyde (Sigma-Aldrich), and 400 nM epoxomicin (Alexis). Lysates were separated on 10% SDS-PAGE and transferred to PVDF membranes (Amersham Biosciences). Immunoblotting was performed with the following antibodies and dilutions: anti-HIF1-beta (BD Transduction Laboratories) at 1:1000; anti-VHL (BD Transduction Laboratories) at 1:500; anti-GLUT-1 (Alpha Diagnostic International) at 1:600, and anti-α-tubulin (Sigma) at 1:2000. Antibodies were diluted in 0.05% Tween-20/Tris-buffered saline (T-TBS) blocking buffer containing 5% nonfat skim milk and incubated with the PVDF membranes at 4° C. overnight, followed by washing with T-TBS for 30 min. Goat anti-mouse or rabbit IgGs coupled with HRP (BioRad) were used as secondary antibodies at 1:3000. Immunospecific bands were detected by enhanced chemiluminescence plus (ECL-Plus) detection kit (Amersham Biosciences).

Expression of HIF1-beta was detected under both normoxic and hypoxic conditions; however, levels of expression of HIF1-beta varied among cell lines. HIF1-beta expression was induced under hypoxic conditions and in the presence of $CoCl_2$ (which mimics hypoxia) in U87-MG human glioblastoma cells and MCF-7 human breast cancer cells. However, expression of HIF1-beta in JEG-3, PC-3, Hep3B, HeLa, 786-O, SK—N—BE(2), Calu-1 and HUVECs was not significantly altered by culturing under hypoxic conditions or in the presence of $CoCl_2$.

Example 20

Antisense Modulation of HIF1-Beta mRNA Expression in Cancer Cells (Dose Response)

Hep3B or U87-MG cells were plated in 96-well plates (8-10,000/well) 16 h prior to transfection. Control oligonucleotide ISIS 129688 (SEQ ID NO: 177) or HIF1-beta antisense oligonucleotides ISIS 311082 (SEQ ID NO: 30) and ISIS 311129 (SEQ ID NO: 77) at a concentration of 0, 6.25 or 25 nM were delivered into cells by lipofectin (3 µg/ml per 100 nM oligonucleotide) in Opti-Mem media (Invitrogen). Both control and HIF1-beta antisense oligonucleotides are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-O-methoxyethyl nucleotides, also known as 2'-MOE nucleotides. The internucleoside (backbone) linkages are phosphorothioate (P=S) throughout the oligonucleotide. All cytidine residues are 5-methylcytidines.

The transfection medium (120 µl/well) was switched to low-serum medium (0.1% FBS) 4 h after transfection. Sixty microliters of medium was removed from the well 3 h after media switch and the cells were further incubated at normoxia or hypoxia for 16-20 h.

Total RNAs were isolated using RNeasy 96 BioRobot 9604 kit (Qiagen) according to the manufacturer's instructions. Quantitative real-time RT-PCR for detection of HIF1-beta mRNA was performed as described in other Examples herein by ABI Prism 7700 Sequence Detector (Applied Biosystems) in 25 or 50 µl reaction volumes. The level of mRNA for each gene was normalized to the amount of total RNA determined by Ribogreen™ (Molecular Probes).

TABLE 6

HIF1-beta mRNA expression in hypoxic Hep3B cells treated with antisense oligonucleotide to HIF1-beta (shown as percent of untreated control cells at normoxia)

| | Percent expression of HIF1-beta mRNA after treatment with oligonucleotide at the concentrations shown: | | |
|---|---|---|---|
| Oligonucleotide | 0 nM | 6.25 nM | 25 nM |
| 129688 | 78 | 78 | 77 |
| 311082 | 79 | 50 | 20 |
| 311129 | 77 | 70 | 30 |

TABLE 7

HIF1-beta mRNA expression in hypoxic U87-MG cells treated with antisense oligonucleotide to HIF1-beta (shown as percent of untreated control cells at normoxia)

| Oligonucleotide | Percent expression of HIF1-beta mRNA after treatment with oligonucleotide at the concentrations shown: | | |
|---|---|---|---|
| | 0 nM | 6.25 nM | 25 nM |
| 129688 | 78 | 78 | 77 |
| 311082 | 79 | 50 | 20 |
| 311129 | 77 | 70 | 20 |

HIF1-beta antisense oligonucleotides ISIS 311082 and ISIS 311129 specifically inhibited mRNA expression of HIF1-beta in both Hep3B and U87-MG cells in a dose-dependent manner.

Example 21

Antisense Modulation of HIF1-Beta Protein Expression

U87-MG cells were plated in 10 cm dishes ($1-2 \times 10^6$ cells/dish) 16 h prior to transfection. 100 nM control oligonucleotide (ISIS 129688, SEQ ID NO: 177) or HIF1-beta antisense oligonucleotide (ISIS 311082, SEQ ID NO: 30) were delivered into cells by lipofectin (3 μg/ml per 100 μM oligonucleotide) in Opti-Mem media (Invitrogen).

The transfection medium (10 ml/dish) was switched to low-serum medium (0.1% FBS) 4 h after transfection. Five ml of medium was removed from the well 3 h after media switch and the cells were further incubated at normoxia or hypoxia for 16-20 h.

Following incubation at normoxia or hypoxia, transfected cells were harvested and whole cell lysates prepared with RIPA buffer containing protease inhibitor cocktails (Roche), 0.5 mM sodium orthovanadate, 10 mM β-glycerophophate, 250 ng/ml ubiquitin aldehyde (Sigma-Aldrich), and 400 nM epoxomicin (Alexis). Lysates were separated on 10% SDS-PAGE and transferred to PVDF membranes (Amersham Biosciences). Immunoblotting was performed with the following antibodies and dilutions: anti-HIF1BETA (BD Transduction Laboratories) at 1:1000; anti-GLUT-1 (Alpha Diagnostic International) at 1:600, and anti-α-tubulin (Sigma) at 1:2000. Antibodies were diluted in 0.05% Tween-20/Tris-buffered saline (T-TBS) blocking buffer containing 5% nonfat skim milk and incubated with the PVDF membranes at 4° C. overnight, followed by washing with T-TBS for 30 min. Goat anti-mouse or rabbit IgGs coupled with HRP (BioRad) were used as secondary antibodies at 1:3000. Immunospecific bands were detected by enhanced chemiluminescence plus (ECL-Plus) detection kit (Amersham Biosciences).

The results demonstrated that transfection with HIF1beta antisense oligonucleotide inhibited HIF1-beta protein expression. Furthermore, protein expression of GLUT-1, a HIF1-beta-responsive gene, was induced under hypoxia in the absence of HIF1-beta antisense oligonucleotide, but was nearly eliminated in hypoxic cells transfected with HIF1-beta antisense oligonucleotide.

Example 22

Expression HIF1-Beta-Regulated Genes in Cells Cultured Under Hypoxic Conditions

Genes whose products are significantly induced by hypoxia (or $CoCl_2$, a mimic of hypoxia) include erythropoietin (Epo), glucose transporter-1 (GLUT-1), vascular endothelial growth factor (VEGF), phosphoglycerate kinase-1 (PGK-1) and plasminogen activator inhibitor-1 (PAI-1). These genes are regulated by HIF1-beta and are induced under hypoxic conditions to varying extents in different cell lines. To determine mRNA expression levels of Epo, GLUT-1, VEGF, PGK-1 and PAI-1 at normoxia (21% $O_2$), hypoxia (1% $O_2$) and in the presence of 150 μM $CoCl_2$, in HeLa, Hep3B, U87-MG, PC-3 and 786-O cells, RT-PCR was performed. Total RNA was isolated after 18 h of culture using the RNeasy 96 BioRobot 9604 (Qiagen) according to the manufacturer's protocol. Quantitative real-time RT-PCR was performed as described in other Examples herein by ABI Prism 7700 Sequence Detector (Applied Biosystems) in 25 or 50 μl reaction volumes. The level of mRNA for each gene was normalized to the amount of total RNA determined by Ribogreen™ (Molecular Probes).

TABLE 8

VEGF, GLUT-1, PGK-1, PAI-1 and Epo mRNA expression levels at normoxia, hypoxia and 150 μM $CoCl_2$ (shown as fold-induction relative to HeLa cells at normoxia)

| Gene | Cell Type | Normoxia | Hypoxia | $CoCl_2$ |
|---|---|---|---|---|
| VEGF | HeLa | 1 | 3 | 2 |
| | Hep3B | 4 | 24 | 11 |
| | U87-MG | 17 | 46 | 28 |
| | PC-3 | 1 | 2 | 2 |
| | 786-O | 6 | 6 | 10 |
| GLUT-1 | HeLa | 1 | 2.1 | 1.5 |
| | Hep3B | 0.2 | 1 | 1 |
| | U87-MG | 2.5 | 3.1 | 5.3 |
| | PC-3 | 1 | 4.1 | 3.7 |
| | 786-O | 2.9 | 3.4 | 5.7 |
| PGK-1 | HeLa | 1 | 3 | 2 |
| | Hep3B | 4 | 24 | 10 |
| | U87-MG | 16 | 46 | 28 |
| | PC-3 | 1 | 2 | 2 |
| | 786-O | 6 | 6 | 9 |
| PAI-1 | HeLa | 1 | 1.5 | 1 |
| | Hep3B | 1.5 | 28 | 2 |
| | U87-MG | 9 | 24 | 32 |
| | PC-3 | 3 | 4 | 3 |
| | 786-O | 2 | 3 | 16 |
| Epo | HeLa | 1 | 1 | 1 |
| | Hep3B | 7 | 260 | 15 |
| | U87-MG | 1 | 1 | 1 |
| | PC-3 | 1 | 1 | 1 |
| | 786-O | 1 | 1 | 1 |

Although expression levels of the five genes under each condition varied widely among cell lines, VEGF, GLUT-1, PGK-1, PAI-1 and Epo exhibited a trend of increased expression when cells were cultured under hypoxia or in the presence of 150 μM $CoCl_2$. As previously reported, hypoxia-induced Epo expression occurred only in Hep3B cells.

Example 23

Antisense Inhibition of HIF1-Beta Target Genes

Hep3B or U87-MG cells were plated in 96-well plates (8-10,000/well) 16 h prior to transfection. Control oligonucleotide ISIS 129688 (SEQ ID NO: 177) or HIF1-beta antisense oligonucleotides ISIS 311082 (SEQ ID NO: 30) and ISIS 311129 (SEQ ID NO: 77) at a concentration of 0, 6.25 or 25 nM were delivered into cells by lipofectin (3 µg/ml per 100 nM oligonucleotide) in Opti-Mem media (Invitrogen).

The transfection medium (120 µl/well) was switched to low-serum medium (0.1% FBS) 4 h after transfection. Sixty microliters of medium was removed from the well 3 h after media switch and the cells were further incubated at normoxia or hypoxia for 16-20 h.

Total RNAs were isolated using RNeasy 96 BioRobot 9604 kit (Qiagen) according to the manufacturer's instructions. Quantitative real-time RT-PCR for detection of GLUT-1, VEGF or Epo mRNA was performed as described in other Examples herein by ABI Prism 7700 Sequence Detector (Applied Biosystems) in 25 or 50 µl reaction volumes. The level of mRNA for each gene was normalized to the amount of total RNA determined by Ribogreen™ (Molecular Probes).

TABLE 9

GLUT-1 mRNA expression in hypoxic Hep3B cells treated with antisense oligonucleotide to HIF1-beta (shown as percent of untreated control cells)

| Oligonucleotide | Percent expression of GLUT-1 mRNA after treatment with oligonucleotide at the concentrations shown: | | |
| --- | --- | --- | --- |
| | 0 nM | 6.25 nM | 25 nM |
| 129688 | 100 | 85 | 83 |
| 311082 | 100 | 72 | 34 |
| 311129 | 100 | 74 | 79 |

TABLE 10

GLUT-1 mRNA expression in hypoxic U87-MG cells treated with antisense oligonucleotide to HIF1-beta (shown as percent of untreated control cells)

| Oligonucleotide | Percent expression of GLUT-1 mRNA after treatment with oligonucleotide at the concentrations shown: | | |
| --- | --- | --- | --- |
| | 0 nM | 6.25 nM | 25 nM |
| 129688 | 100 | 100 | 102 |
| 311082 | 100 | 76 | 28 |
| 311129 | 100 | 83 | 40 |

TABLE 11

VEGF mRNA expression in hypoxic U87-MG cells treated with antisense oligonucleotide to HIF1-beta (shown as percent of untreated control cells)

| Oligonucleotide | Percent expression of VEGF mRNA after treatment with oligonucleotide at the concentrations shown: | | |
| --- | --- | --- | --- |
| | 0 nM | 6.25 nM | 25 nM |
| 129688 | 100 | 101 | 82 |
| 311082 | 100 | 62 | 26 |
| 311129 | 100 | 71 | 28 |

TABLE 12

Epo mRNA expression in hypoxic Hep3B cells treated with antisense oligonucleotide to HIF1-beta (shown as percent of untreated control cells)

| Oligonucleotide | Percent expression of Epo mRNA after treatment with oligonucleotide at the concentrations shown: | | |
| --- | --- | --- | --- |
| | 0 nM | 6.25 nM | 25 nM |
| 129688 | 100 | 107 | 114 |
| 311082 | 100 | 95 | 38 |
| 311129 | 100 | 100 | 74 |

As shown in other Examples herein, GLUT-1, Epo and VEGF mRNA expression was induced under hypoxic conditions. HIF1-beta antisense oligonucleotides ISIS 311082 and ISIS 311129 specifically inhibited mRNA expression of GLUT-1, Epo and VEGF in both Hep3B cells (GLUT-1 and Epo) and U87.-MG cells (GLUT-1 and VEGF).

Example 24

Antisense Inhibition of Protein Expression of HIF1Beta Downstream Targets

U87-MG, HeLa or Hep3B cells were plated in 10 cm dishes (1-2×10$^6$ cells/dish) 16 h prior to transfection. 100 nM control oligonucleotide (ISIS 129688, SEQ ID NO: 177) or HIF1-beta antisense oligonucleotide (ISIS 311082, SEQ ID NO: 30) were delivered into cells by lipofectin (3 µg/ml per 100 nM oligonucleotide) in Opti-Mem media (Invitrogen).

The transfection medium (10 ml/well) was switched to low-serum medium (0.1% FBS) 4 h after transfection. Five ml of medium was removed from the well 3 h after media switch and the cells were further incubated at normoxia or hypoxia.

After incubation at normoxia or hypoxia for 16 h, the media was removed and stored at −80° C. prior to use. Levels of VEGF protein in either U87-MG or HeLa cells was determined by Quantikine ELISA kit (R&D Systems) according to the manufacturer's protocol. To determine levels of Epo protein in Hep3B cells, cell culture media was concentrated up to 10% of the original volume by Amicon Ultra (Millipore) and Epo protein was quantitated by Quantikine IVD human Epo ELISA kit (R&D Systems). The obtained values were normalized to the number of cells (VEGF) or the amount of total protein (Epo) used for the assay.

Under hypoxic conditions, VEGF protein production in U87-MG cells treated with HIF1-beta antisense oligonucleotide was significantly reduced (approximately 4-fold) relative to cells treated with control oligonucleotide. In HeLa cells, VEGF protein levels were slightly reduced by treatment with HIF1-beta antisense oligonucleotide. In Hep3B cells treated with HIF1-beta antisense oligonucleotide, Epo protein levels were significantly reduced (approximately 15-fold) relative to cells treated with control oligonucleotide. Thus, treatment with HIF1-beta antisense oligonucleotides not only inhibits expression of HIF1-beta, but also results in downregulation of HIF1-beta target genes.

Example 25

Hypoxia-Induced Binding of HIF1-Beta to Hypoxia Response Element (HRE) In Vivo

To demonstrate binding of HIF1-beta to the hypoxia response element (HRE) on the promoter region of the VEGF gene under hypoxic conditions, chromatin immunoprecipitation (CHIP) assays were performed. U87-MG cells were plated in 10 cm dishes in complete growth media containing 10% FBS at a density of $1 \times 10^6$ cells/dish. After 24 h, the media was replaced with low serum media (0.1% FBS) and the cells were incubated at either normoxia or hypoxia for 16 h. After incubation, cells were cross-linked with a 1% formaldehyde solution for 10 min at 37° C. After two washes with cold PBS, cells were processed following the ChIP assay kit protocol (Upstate). For immunoprecipitation, protein extracts were incubated with antibodies to HIF1-beta (10 μg) and mouse IgG (10 μg) at 4° C. for 40 h, followed by 2 h incubation with salmon sperm DNA/Protein A agarose slurry. After extensive washing, the immune/DNA complex was eluted in 500 μl of buffer (1% SDS, 0.1 M $NaHCO_3$), reverse-crosslinked at 65° C. for 4 h in the presence of 0.2 M NaCl and subjected to proteinase K (Ambion) digestion at 45° C. for 1 h. Samples were extracted with phenol-chloroform-isoamylalcohol, ethanol-precipitated overnight at −80° C. and the DNA was resuspended in water.

Samples were analyzed by PCR using Accuprime II (Invitrogen) Taq polymerase in the presence of [$^{32}$P-dCTP]. PCR products were separated on 6% Tris-borate-EDTA (TBE)-PAGE, dried and exposed to X-ray film at −80° C. The forward (F) and reverse (R) primers used for PCR are as follows:

```
VEGF I(F):
CCTGGCAACATCTGGGGTTGG      (SEQ ID NO: 178)

VEGF I(R):
CAACAGGCTGGAGTGACTGGGCTCC  (SEQ ID NO: 179)

VEGF II(F):
GTGGAGACAGGACTAGTGCACGAATG (SEQ ID NO: 180)

VEGF II(R):
CTGTGGAGGCATGGACTGAGAATGG  (SEQ ID NO: 181)

Epo (F):
CTGGGAACCTCCAAATCCCCTGGC   (SEQ ID NO: 182)

Epo (R):
CTGGGCAGGGTTGGCAGCTGCCTTAC (SEQ ID NO: 183)
```

VEGF I primers amplify a region that includes the HRE. VEGF II primers amplify a promoter region upstream of the HRE, therefore this region serves as a negative control. The Epo gene also is a negative control since it is not expressed in U87-MG cells.

HIF1-beta was not detected on the VEGF HRE at normoxia. However, hypoxia induced the recruitment of HIF1-beta to the VEGF HRE (VEGF I). No binding of HIF1-beta was detected to the regions amplified by the VEGF II or Epo primers.

Example 26

Inhibition of HIF1-Beta Expression In Vivo

C57Bl/6 mice are maintained on a standard rodent diet and are used as control animals. Seven-week old male C57Bl/6 mice are injected subcutaneously with oligonucleotides at a dose of 25 mg/kg two times per week for 4 weeks. Saline-injected animals serve as a control. After the treatment period, mice are sacrificed and target levels are evaluated in liver, spleen, adipose and other tissues using RNA isolation and target mRNA expression level quantitation (RT-PCR) as described in other examples herein.

Example 27

Tube Formation Assay to determine Effect of HIF1-Beta Antisense Inhibitors on Angiogenesis Angiogenesis is stimulated by numerous factors that promote interaction of endothelial cells with each other and with extracellular matrix molecules, resulting in the formation of capillary tubes. This process can be reproduced in tissue culture by the formation of tube-like structures by endothelial cells. Loss of tube formation in vitro has been correlated with the inhibition of angiogenesis in vivo (Carmeliet et al., (2000) Nature 407:249-257; and Zhang et al., (2002) Cancer Research 62:2034-42), which supports the use of in vitro tube formation as an endpoint for angiogenesis.

Angiogenesis, or neovascularization, is the formation of new capillaries from existing blood vessels. In adult organisms this process is typically controlled and short-lived, for example in wound repair and regeneration. However, aberrant capillary growth can occur and this uncontrolled growth plays a causal and/or supportive role in many pathologic conditions such as tumor growth and metastasis. In the context of this invention "aberrant angiogenesis" refers to unwanted or uncontrolled angiogenesis. Angiogenesis inhibitors are being evaluated for use as antitumor drugs. Other diseases and conditions associated with angiogenesis include arthritis, cardiovascular diseases, skin conditions (e.g., psoriasis), and aberrant wound healing. Aberrant angiogenesis can also occur in the eye, causing loss of vision. Examples of ocular conditions involving aberrant angiogenesis include macular degeneration, diabetic retinopathy, diabetic macular edema and retinopathy of prematurity.

The tube formation assay is performed using an in vitro Angiogenesis Assay Kit. (Chemicon International, Temecula, Calif.), or growth factor reduced Matrigel (BD Biosciences, Bedford, Mass.). HUVECs were plated at 4000 cells/well in 96-well plates. One day later, cells were transfected with antisense and control oligonucleotides according to standard published procedures (Monia et al., (1993) J Biol Chem. Jul. 5, 1993 ;268(19):14514-22) using 75 nM oligonucleotide in lipofectin (Gibco, Grand Island, N.Y.). Approximately fifty hours post-transfection, cells were transferred to 96-well plates coated with ECMatrix™ (Chemicon International) or growth factor depleted Matrigel. Under these conditions, untreated HUVECs form tube-like structures. After an overnight incubation at 37° C., treated and untreated cells were. inspected by light microscopy. Individual wells were assigned discrete scores from 1 to 5 depending on the extent of tube formation. A score of 1 refers to a well with no tube formation while a score of 5 is given to wells where all cells are forming an extensive tubular network.

ISIS 29848 is a control oligonucleotide containing an equal mixture of the bases A, C, G and T at every position. ISIS 175510 (TGAGCTGTCTGTGATCCAGC; SEQ ID NO: 184) is targeted to HIF1α; ISIS 222035 (GCGCTGCTC-CCAAGAACTCT; SEQ ID NO: 185) is targeted to HIF2α. ISIS 298697 (TCCTCATGGTCACATGGATG; SEQ ID NO: 186) is a cross-HIF1α/HIF2α oligonucleotide having perfect complementarity to HIF1α target and imperfect complementarity (and thus less inhibitory effect) for HIF2α; ISIS 311082 (SEQ ID NO: 30) is targeted to HIF1-beta.

TABLE 13

Effect of antisense oligonucleotides on angiogenic tube formation

| ISIS # | Target | Score |
|---|---|---|
| Lipid control | N/A | 4.7 |
| 29848 | Control | 4.7 |
| 175510 | HIF1α | 2.0 |
| 222035 | HIF2α | 1.0 |
| 298697 | HIF1α/2α | 3.0 |
| 311082 | HIF1-beta | 2.0 |

As calculated from the assigned discrete scores, the results demonstrate that HUVEC tube formation is inhibited by treatment with antisense oligonucleotides targeting the Hif family. Thus, a reduction in HIF1-beta expression results in inhibition of angiogenic processes.

Example 28

HIF1-Beta Antisense Compounds in an Animal Model of Ocular Neovascularization

A pig model of ocular neovascularization, the branch retinal vein occlusion (BVO) model, is used to study ocular neovascularization. Male farm pigs (8-10 kg) are subjected to branch retinal vein occlusions (BVO) by laser treatment in both eyes. The extent of BVO is determined by indirect opthalmoscopy after a 2 week period. Intravitreous injections (10 μM) of HIF1-beta antisense oligonucleotides and control oligonucleotides are started on the day of BVO induction and are repeated at weeks 2, 6 and 10 after BVO (Right eye=vehicle, Left eye=antisense oligonucleotide). Stereo fundus photography and fluorescein angiography are performed at baseline BVO and at weeks 1, 6 and 12 following intravitreous injections to measure the neovascular response. In addition, capillary gel electrophoresis analysis of the eye sections containing sclera, choroid, and the retina are performed to determine antisense concentrations, and gross and microscopic evaluations are performed to determine eye histopathology.

Example 29

Matrix Metalloproteinase Activity Assay

During angiogenesis, endothelial cells need to be able to degrade the extracellular matrix (ECM). Endothelial cells secrete matrix metalloproteinases (MMPs) in order to accomplish this degradation. HIF1-beta antisense compounds of the invention are evaluated for their effects on MMP activity in HUVECs. MMP activity is measured using the EnzChek Gelatinase/Collagenase Assay Kit (Molecular Probes, Eugene, Oreg.). In this assay, HUVECs are plated at approximately 4000 cells per well in 96-well plates and transfected one day later. A 20-nucleotide oligomeric compound with a randomized sequence is used a negative control. An oligomeric compound targeted to integrin β3 is known to inhibit MMP activity and is used as a positive control.

Cells are transfected as described herein. Antisense compounds are mixed with LIPOFECTIN™ in Opti-MEM to achieve a final concentration of 75 nM of antisense compound and 2.25 μg/mL LIPOFECTIN™. Antisense compounds of the invention and the positive control are tested in triplicate, and the negative control is tested in up to six replicates. Untreated control cells received LIPOFECTIN™ in Opti-MEM only.

Approximately 50 hours after transfection, a p-aminophenylmercuric acetate (APMA, Sigma-Aldrich, St. Louis, Mo.) solution is added to each well of a Corning-Costar 96-well clear bottom plate (VWR International, Brisbane, Calif.). The APMA solution is used to promote cleavage of inactive MMP precursor proteins. Medium above the HUVECs is then transferred to the wells in the 96-well plate. After approximately 30 minutes, the quenched, fluorogenic MMP cleavage substrate is added, and baseline fluorescence is read immediately at 485 nm excitation/530 nm emission. Following an overnight incubation at 37° C. in the dark, plates are read again to determine the amount of fluorescence, which corresponds to MMP activity. Total protein from HUVEC lysates is used to normalize the readings, and MMP activity from cells treated with antisense compounds is normalized to that of untreated control cells. MMP activities above or below 100% are considered to indicate a stimulation or inhibition of MMP activity, respectively. HIF1-beta antisense compounds resulting in a decrease in MMP activity are candidate therapeutic agents for the inhibition of angiogenesis where such activity is desired, for example, in the treatment of cancer, diabetic retinopathy, cardiovascular disease, rheumatoid arthritis and psoriasis.

Various modifications of the invention, in addition to those described herein, will be apparent to those skilled in the art from the foregoing description. Such modifications are also intended to fall within the scope of the appended claims. Each of the patents, applications, printed publications, and other published documents mentioned or referred to in this specification are herein incorporated by reference in their entirety. Those skilled in the art will appreciate that numerous changes and modifications may be made to the embodiments of the invention and that such changes and modifications may be made without departing from the spirit of the invention. It is therefore intended that the appended claims cover all such equivalent variations as fall within the true spirit and scope of the invention.

What is claimed:

1. A compound comprising a modified oligonucleotide consisting of 13 to 30 linked nucleosides, wherein said modified oligonucleotide has a nucleobase sequence comprising at least 8 consecutive nucleobases complementary to nucleotides 1200-1239 of SEQ ID NO:4, wherein said nucleobase sequence of said modified oligonucleotide is at least 90% complementary to SEQ ID NO:4 as measured over the entirety of said nucleobase sequence of said modified oligonucleotide, wherein said compound inhibits expression of human HIF-1beta.

2. A composition comprising the compound of claim 1, or a salt thereof, and a pharmaceutically acceptable carrier or diluent.

3. A method of inhibiting expression of human HIF-1 beta in cells or tissues, comprising contacting said cells or tissues with the compound of claim 1, such that expression of human HIF-1 beta is inhibited.

4. A method of inhibiting expression of a HIF-1 beta regulated gene in a cell or tissue comprising contacting said cells or tissues with the compound of claim 1, such that expression of the HIF-1 beta regulated gene is inhibited.

5. The method of claim 4, wherein the HIF-1 beta regulated gene is selected from the group consisting of VEGF, GLUT-1, PGK-1, PAI-1 and Epo.

6. A method of treating an animal having a disease or condition associated with HIF-1 beta comprising administrating to said animal a therapeutically or prophylactically effective amount of the composition of claim 2 so that expression of HIF-1 beta is inhibited.

7. The method of claim 6, wherein the disease or condition is a hyperproliferative disorder.

8. The method of claim 7, wherein the hyperproliferative disorder is cancer.

9. The method of claim 7, wherein the hyperproliferative disorder is an angiogenic disorder.

10. The method of claim 9, wherein the angiogenic disorder is an ocular disorder.

11. The method of claim 10, wherein the ocular disorder is selected from the group consisting of macular degeneration, diabetic retinopathy, macular edema and retinopathy of prematurity.

12. A method of inhibiting aberrant angiogenesis in an animal, comprising administering to said animal the compound of claim 1 such that aberrant angiogenesis is inhibited.

13. The compound of claim 1, wherein said modified oligonucleotide has a nucleobase sequence comprising at least 8 consecutive nucleobases of a nucleobase sequence selected from the group consisting of SEQ ID NOs: 56, 57, 58, 59, and 60.

14. The compound of claim 1, wherein said modified oligonucleotide has a nucleobase sequence comprising at least 8 consecutive nucleobases of the nucleobase sequence of SEQ ID NO: 60.

15. The compound of claim 1, wherein said modified oligonucleotide has a nucleobase sequence comprising the nucleobase sequence of SEQ ID NO:60.

16. The compound of claim 1, consisting of a single-stranded modified oligonucleotide.

17. The compound of claim 16, wherein the nucleobase sequence of the modified oligonucleotide is 100% complementary to SEQ ID NO: 4.

18. The compound of claim 16, wherein at least one internucleoside linkage is a modified internucleoside linkage.

19. The compound of claim 18, wherein each internucleoside linkage is a phosphorothioate internucleoside linkage.

20. The compound of claim 16, wherein at least one nucleoside comprises a modified sugar.

21. The compound of claim 20, wherein at least one modified sugar is a bicyclic sugar.

22. The compound of claim 20, wherein at least one modified sugar comprises a 2'-O-methoxyethyl.

23. The compound of claim 20, wherein at least one modified sugar comprises a 4'-$(CH_2)_n$—O-2' bridge, wherein n is 1 or 2.

24. The compound of claim 16, wherein at least one nucleoside comprises a modified nucleobase.

25. The compound of claim 24, wherein the modified nucleobase is a 5-methylcytosine.

26. The compound of claim 1, wherein the modified oligonucleotide comprises:
a gap segment consisting of linked deoxynucleosides;
a 5' wing segment consisting of linked nucleosides;
a 3' wing segment consisting of linked nucleosides;
wherein the gap segment is positioned between the 5' wing segment and the 3' wing segment and wherein each nucleoside of each wing segment comprises a modified sugar.

27. The compound of claim 26, wherein the modified oligonucleotide comprises:

a gap segment consisting of ten linked deoxynucleosides;
a 5' wing segment consisting of five linked nucleosides;
a 3' wing segment consisting of five linked nucleosides;
wherein the gap segment is positioned between the 5' wing segment and the 3' wing segment, wherein each nucleoside of each wing segment comprises a 2'-O-methoxyethyl sugar; and wherein each internucleoside linkage of said modified oligonucleotide is a phosphorothioate linkage.

28. The compound of claim 16, wherein the modified oligonucleotide consists of 20 linked nucleosides.

29. The composition of claim 2, consisting of a single-stranded oligonucleotide.

30. The composition of claim 2, wherein the modified oligonucleotide consists of 20 linked nucleosides.

31. The compound of claim 15, wherein the modified oligonucleotide comprises:
a gap segment consisting of ten linked deoxynucleosides;
a 5' wing segment consisting of five linked nucleosides;
a 3' wing segment consisting of five linked nucleosides;
wherein the gap segment is positioned between the 5' wing segment and the 3' wing segment, wherein each nucleoside of each wing segment comprises a 2'-O-methoxyethyl sugar; and wherein each internucleoside linkage of said modified oligonucleotide is a phosphorothioate linkage.

32. The compound of claim 31, wherein the modified oligonucleotide consists of 20 linked nucleosides.

\* \* \* \* \*

SEQUENCE LISTING

<160> NUMBER OF SEQ ID NOS: 190

<210> SEQ ID NO 1
<211> LENGTH: 20
<212> TYPE: DNA
<213> ORGANISM: Artificial Sequence
<220> FEATURE:
<223> OTHER INFORMATION: Antisense Compound

<400> SEQUENCE: 1
tccgtcatcg ctcctcaggg                                                    20

<210> SEQ ID NO 2
<211> LENGTH: 20
<212> TYPE: DNA
<213> ORGANISM: Artificial Sequence
<220> FEATURE:
<223> OTHER INFORMATION: Antisense Compound

<400> SEQUENCE: 2
gtgcgcgcga gcccgaaatc                                                    20

<210> SEQ ID NO 3
<211> LENGTH: 20
<212> TYPE: DNA
<213> ORGANISM: Artificial Sequence
<220> FEATURE:
<223> OTHER INFORMATION: Antisense Compound

<400> SEQUENCE: 3
atgcattctg cccccaagga                                                    20

<210> SEQ ID NO 4
<211> LENGTH: 4504
<212> TYPE: DNA
<213> ORGANISM: H. sapiens
<220> FEATURE:
<221> NAME/KEY: CDS
<222> LOCATION: (175)...(2542)

<400> SEQUENCE: 4
agcgggggat gctgggggct gctgaagccg ccatcttgga ttccgcggta gcggaggcgg         60
cggtcaggcg ccgcttctgg ggagtggcct ttcttttccc ctccctcccg gttcggtggc        120
ggcggctcct cccactgggg gggggtggc gcggcggcgg tggcatctgc ggcc atg         177
                                                                Met
                                                                  1 gcg gcg act act gcc aac ccc gaa atg aca tca gat gta cca tca ctg        225
Ala Ala Thr Thr Ala Asn Pro Glu Met Thr Ser Asp Val Pro Ser Leu
          5                  10                  15 ggt cca gcc att gcc tct gga aac tct gga cct gga att caa ggt gga        273
Gly Pro Ala Ile Ala Ser Gly Asn Ser Gly Pro Gly Ile Gln Gly Gly
     20                  25                  30 gga gcc att gtc cag agg gct att aag cgg cga cca ggg ctg gat ttt        321
Gly Ala Ile Val Gln Arg Ala Ile Lys Arg Arg Pro Gly Leu Asp Phe
 35                  40                  45 gat gat gat gga gaa ggg aac agt aaa ttt ttg agg tgt gat gat gat        369
Asp Asp Asp Gly Glu Gly Asn Ser Lys Phe Leu Arg Cys Asp Asp Asp
 50                  55                  60                  65 cag atg tct aac gat aag gag cgg ttt gcc agg tcg gat gat gag cac        417
Gln Met Ser Asn Asp Lys Glu Arg Phe Ala Arg Ser Asp Asp Glu His
                 70                  75                  80

| | | |
|---|---|---|
| ctc tgc gga taa aga gag act tgc cag gga aaa tca cag tga aat tga<br>Leu Cys Gly * Arg Glu Thr Cys Gln Gly Lys Ser Gln * Asn *<br>               85                           90 | 465 |
| acg gcg gcg acg gaa caa gat gac agc cta cat cac aga act gtc aga<br>Thr Ala Ala Thr Glu Gln Asp Asp Ser Leu His His Arg Thr Val Arg<br>95                      100                  105               110 | 513 |
| tat ggt acc cac ctg tag tgc cct ggc tcg aaa acc aga caa gct aac<br>Tyr Gly Thr His Leu * Cys Pro Gly Ser Lys Thr Arg Gln Ala Asn<br>               115                      120                  125 | 561 |
| cat ctt acg cat ggc agt ttc tca cat gaa gtc ctt gcg ggg aac tgg<br>His Leu Thr His Gly Ser Phe Ser His Glu Val Leu Ala Gly Asn Trp<br>                    130                    135                 140 | 609 |
| caa cac atc cac tga tgg ctc cta taa gcc gtc ttt cct cac tga tca<br>Gln His Ile His * Trp Leu Leu * Ala Val Phe Pro His * Ser<br>               145                              150 | 657 |
| gga act gaa aca ttt gat ctt gga ggc agc aga tgg ctt tct gtt tat<br>Gly Thr Glu Thr Phe Asp Leu Gly Gly Ser Arg Trp Leu Ser Val Tyr<br>155                      160                  165               170 | 705 |
| tgt ctc atg tga gac agg cag ggt ggt gta tgt gtc tga ctc cgt gac<br>Cys Leu Met * Asp Arg Gln Gly Gly Val Cys Val * Leu Arg Asp<br>                    175                    180 | 753 |
| tcc tgt ttt gaa cca gcc aca gtc tga atg gtt tgg cag cac act cta<br>Ser Cys Phe Glu Pro Ala Thr Val * Met Val Trp Gln His Thr Leu<br>185                      190                  195 | 801 |
| tga tca ggt gca ccc aga tga tgt gga taa act tcg tga gca gct ttc<br>* Ser Gly Ala Pro Arg * Cys Gly * Thr Ser * Ala Ala Phe<br>    200                            205                      210 | 849 |
| cac ttc aga aaa tgc cct gac agg gcg tat cct gga tct aaa gac tgg<br>His Phe Arg Lys Cys Pro Asp Arg Ala Tyr Pro Gly Ser Lys Asp Trp<br>               215                      220                 225 | 897 |
| aac agt gaa aaa gga agg tca gca gtc ttc cat gag aat gtg tat ggg<br>Asn Ser Glu Lys Gly Arg Ser Ala Val Phe His Glu Asn Val Tyr Gly<br>                    230                    235                 240 | 945 |
| ctc aag gag atc gtt tat ttg ccg aat gag gtg tgg cag tag ctc tgt<br>Leu Lys Glu Ile Val Tyr Leu Pro Asn Glu Val Trp Gln * Leu Cys<br>     245                      250                  255 | 993 |
| gga ccc agt ttc tgt gaa tag gct gag ctt tgt gag gaa cag atg cag<br>Gly Pro Ser Phe Cys Glu * Ala Glu Leu Cys Glu Glu Gln Met Gln<br>260                      265                  270 | 1041 |
| gaa tgg act tgg ctc tgt aaa gga tgg gga acc tca ctt cgt ggt ggt<br>Glu Trp Thr Trp Leu Cys Lys Gly Trp Gly Thr Ser Leu Arg Gly Gly<br>        275                  280                285 | 1089 |
| cca ctg cac agg cta cat caa ggc ctg gcc ccc agc agg tgt ttc cct<br>Pro Leu His Arg Leu His Gln Gly Leu Ala Pro Ser Arg Cys Phe Pro<br>290                      295                  300               305 | 1137 |
| ccc aga tga tga ccc aga ggc tgg cca ggg aag caa gtt tgc cct agt<br>Pro Arg * * Pro Arg Gly Trp Pro Gly Lys Gln Val Leu Pro Ser<br>                    310                    315 | 1185 |
| ggc cat tgg cag att gca ggt aac tag ttc tcc caa ctg tac aga cat<br>Gly His Trp Gln Ile Ala Gly Asn * Phe Ser Gln Leu Tyr Arg His<br>320                      325                  330 | 1233 |
| gag taa tgt ttg tca acc aac aga gtt cat ctc ccg aca caa cat tga<br>Glu * Cys Leu Ser Thr Asn Arg Val His Leu Pro Thr Gln His *<br>335                      340                  345 | 1281 |
| ggg tat ctt cac ttt tgt gga tca ccg ctg tgt ggc tac tgt tgg cta<br>Gly Tyr Leu His Phe Cys Gly Ser Pro Leu Cys Gly Tyr Cys Trp Leu<br>                    350                    355               360 | 1329 |
| cca gcc aca gga act ctt agg aaa gaa tat tgt aga att ctg tca tcc<br>Pro Ala Thr Gly Thr Leu Arg Lys Glu Tyr Cys Arg Ile Leu Ser Ser<br>365                      370                  375               380 | 1377 |

-continued

| | |
|---|---|
| tga aga cca gca gct tct aag aga cag ctt cca aca ggt agt gaa att<br>\*  Arg Pro Ala Ala Ser Lys Arg Gln Leu Pro Thr Gly Ser Glu Ile<br>                385                     390                     395 | 1425 |
| aaa agg cca agt gct gtc tgt cat gtt ccg gtt ccg gtc taa gaa cca<br>Lys Arg Pro Ser Ala Val Cys His Val Pro Val Pro Val  \*  Glu Pro<br>                400                     405                     410 | 1473 |
| aga atg gct ctg gat gag aac cag ctc ctt tac ttt cca gaa ccc tta<br>Arg Met Ala Leu Asp Glu Asn Gln Leu Leu Tyr Phe Pro Glu Pro Leu<br>                415                     420                     425 | 1521 |
| ctc aga tga aat tga gta cat cat ctg tac caa cac caa tgt gaa gaa<br>Leu Arg  \*  Asn  \*  Val His His Leu Tyr Gln His Gln Cys Glu Glu<br>                430                     435                     440 | 1569 |
| ctc tag cca aga acc acg gcc tac act ctc caa cac aat cca gag gcc<br>Leu  \*  Pro Arg Thr Thr Ala Tyr Thr Leu Gln His Asn Pro Glu Ala<br>                445                     450                     455 | 1617 |
| aca act agg tcc cac agc taa ttt acc cct gga gat ggg ctc agg aca<br>Thr Thr Arg Ser His Ser  \*  Phe Thr Pro Gly Asp Gly Leu Arg Thr<br>                460                     465                     470 | 1665 |
| gct ggc acc cag gca gca gca aca gca aac aga att gga cat ggt acc<br>Ala Gly Thr Gln Ala Ala Ala Thr Ala Asn Arg Ile Gly His Gly Thr<br>                475                     480                     485 | 1713 |
| agg aag aga tgg act ggc cag cta caa tca ttc cca ggt ggt tca gcc<br>Arg Lys Arg Trp Thr Gly Gln Leu Gln Ser Phe Pro Gly Gly Ser Ala<br>                490                     495                     500 | 1761 |
| tgt gac aac cac agg acc aga aca cag caa gcc cct tga gaa gtc aga<br>Cys Asp Asn His Arg Thr Arg Thr Gln Gln Ala Pro  \*  Glu Val Arg<br>                505                     510                     515 | 1809 |
| tgg ttt att tgc cca gga tag aga tcc aag att ttc aga aat cta tca<br>Trp Phe Ile Cys Pro Gly  \*  Arg Ser Lys Ile Phe Arg Asn Leu Ser<br>                520                     525                     530 | 1857 |
| caa cat caa tgc gga tca gag taa agg cat ctc ctc cag cac tgt ccc<br>Gln His Gln Cys Gly Ser Glu  \*  Arg His Leu Leu Gln His Cys Pro<br>                535                     540                     545 | 1905 |
| tgc cac cca aca gct att ctc cca ggg caa cac att ccc tcc tac ccc<br>Cys His Pro Thr Ala Ile Leu Pro Gly Gln His Ile Pro Ser Tyr Pro<br>                550                     555                     560 | 1953 |
| ccg gcc ggc aga gaa ttt cag gaa tag tgg tct agc ccc tcc tgt aac<br>Pro Ala Gly Arg Glu Phe Gln Glu  \*  Trp Ser Ser Pro Ser Cys Asn<br>                565                     570                     575 | 2001 |
| cat tgt cca gcc atc agc ttc tgc agg aca gat gtt ggc cca gat ttc<br>His Cys Pro Ala Ile Ser Phe Cys Arg Thr Asp Val Gly Pro Asp Phe<br>                580                     585                     590 | 2049 |
| ccg cca ctc caa ccc cac cca agg agc aac ccc aac ttg gac ccc tac<br>Pro Pro Leu Gln Pro His Pro Arg Ser Asn Pro Asn Leu Asp Pro Tyr<br>595                     600                     605                     610 | 2097 |
| tac ccg ctc agg ctt ttc tgc cca gca ggt ggc tac cca ggc tac tgc<br>Tyr Pro Leu Arg Leu Phe Cys Pro Ala Gly Gly Tyr Pro Gly Tyr Cys<br>                615                     620                     625 | 2145 |
| taa gac tcg tac ttc cca gtt tgg tgt ggg cag ctt tca gac tcc atc<br> \*  Asp Ser Tyr Phe Pro Val Trp Cys Gly Gln Leu Ser Asp Ser Ile<br>                630                     635                     640 | 2193 |
| ctc ctt cag ctc cat gtc cct ccc tgg tgc ccc aac tgc atc gcc tgg<br>Leu Leu Gln Leu His Val Pro Pro Trp Cys Pro Asn Cys Ile Ala Trp<br>                645                     650                     655 | 2241 |
| tgc tgc tgc cta ccc tag tct cac caa tcg tgg atc taa ctt tgc tcc<br>Cys Cys Cys Leu Pro  \*  Ser His Gln Ser Trp Ile  \*  Leu Cys Ser<br>                660                     665                     670 | 2289 |
| tga gac tgg aca gac tgc agg aca att cca gac acg gac agc aga ggg<br> \*  Asp Trp Thr Asp Cys Arg Thr Ile Pro Asp Thr Asp Ser Arg Gly | 2337 |

-continued

|  |  |  | 675 |  |  |  | 680 |  |  |  | 685 |  |  |  |  |
|---|---|---|---|---|---|---|---|---|---|---|---|---|---|---|---|
| tgt | ggg | tgt | ctg | gcc | aca | gtg | gca | ggg | cca | gca | gcc | tca | tca | tcg | ttc | 2385 |
| Cys | Gly | Cys | Leu | Ala | Thr | Val | Ala | Gly | Pro | Ala | Ala | Ser | Ser | Ser | Phe |
|  |  |  | 690 |  |  |  | 695 |  |  |  | 700 |  |  |  |  |
| aag | ttc | tag | tga | gca | aca | tgt | tca | aca | acc | gcc | agc | aca | gca | acc | tgg | 2433 |
| Lys | Phe | * | * | Ala | Thr | Cys | Ser | Thr | Thr | Ala | Ser | Thr | Ala | Thr | Trp |
|  |  |  |  | 705 |  |  |  | 710 |  |  |  | 715 |  |  |
| cca | gcc | tga | ggt | ctt | cca | gga | gat | gct | gtc | cat | gct | ggg | aga | tca | gag | 2481 |
| Pro | Ala | * | Gly | Leu | Pro | Gly | Asp | Ala | Val | His | Ala | Gly | Arg | Ser | Glu |
|  |  |  | 720 |  |  |  | 725 |  |  |  | 730 |  |  |  |  |
| caa | cag | cta | caa | caa | tga | aga | att | ccc | tga | tct | aac | tat | gtt | tcc | ccc | 2529 |
| Gln | Gln | Leu | Gln | Gln | * | Arg | Ile | Pro | * | Ser | Asn | Tyr | Val | Ser | Pro |
|  |  |  | 735 |  |  |  |  | 740 |  |  |  |  | 745 |  |  | ctt ttc aga ata g aactattggg gtgaggataa ggggtggggg agaaaaaatc 2582
Leu Phe Arg Ile actgtttgtt tttaaaaagc aaatctttct gtaaacagaa taaaagttcc tctcccttcc 2642 cttccctcac ccctgacatg tacccccttt cccttctggc tgttcccctg ctctgttgcc 2702 tctctaaggt aacatttata gaagaaatgg aatgaatctc caaggctttt aggactgtct 2762 gaaaatttga ggctgggtga agttaaaaca cctttcctta tgtctcctga cctgaaattg 2822 tatagtgttg atttgtgctg agatcaagag gcaggttaga agaacctgac atccactgtt 2882 tgccttggat agtatggctt gttttttggaa aggaattctg aagagagtgg aggagaggag 2942 aaatgtcctc atatttgagg accatgaaac attgtaggta tatgtgggc tttagcaagt 3002 ttgagcctag gctcttttg ctgcctgtga gcagtccctc tggaaagaaa catgtgagta 3062 agtgagagag agtgtgtgtg tatgtgtgtg tgtgtgtgtg tgtgtgtgcg cacacatgct 3122 tctgtatttc actcttctc cctattaggg agttatgcaa aatttgtccc cgattttacc 3182 tttgtctttc tgtgtacttt tcaaagagtc ctaaggagtt aaatcttcca ggtattttcc 3242 acttagtatt gcagccaaag aatatttaaa taaacgtctt tgctgcgctt gcatccatgc 3302 ccagccaata tacaactgta aagcaaatat agaaagtcgg ctgttgatac gattgtctgt 3362 tatcgaacac attcagtgat aaagctgggt tactgctgct tttggtgctc tcaccttatc 3422 tggaagatct gcaaacatta cctaaatagg ctggcaagat aaacactttc tggaacccga 3482 gacttggcca taaagataat gctgcatttt tctgtcagaa tcacatatga tgtgtgttct 3542 gtagaggtta tttctgcatg gaaactcaac ttcttggatt agccgtccca gtgaaaatcc 3602 tcattgttgg agtgtaaacc aaatacgaag ccctcttgca aagtagcctc tttcatccca 3662 tactcaaaat acccagtttα gcaagcaact gagatttaag tctctctggc cctaagaggt 3722 ttttcctctt tgctccctcc aatcttgaga ttgggttttg ctttagagtg caagtatcat 3782 aattccgtat gatagatggg gcctggacac ccatctcaac agggtcactt ggtaattaac 3842 aatagccata taaatgcgga tacaggttac taccctcacc ctttaccttc ctcaggtaac 3902 agtcgtagat accagctttt ttttttttt ttttaaattg gctttggcca gtagctaaag 3962 tgcaagactg agttaatgag aagatatatt aaatgtagtc ataggggact gaggagcaag 4022 ggtggccttg aagaggccaa aggaatgtcc atttgctgag tttcccttcc ttatgtctcc 4082 agtctggtgc caggtagtgg agtaaaaaag gagacagttt atttttttat tctatgtgca 4142 cacttacagt atacatatat atttatatca caatttacga aaccaaaaag ttgagtttcc 4202 aatggaaccc ttgttttta ataatcgact ttttaaatgt gatcaagact ataatattgt 4262 acagttatta tagggctttt ggggaagggg aggatagcga gaagatgctc tgggggtttt 4322

-continued

```
gtttttgctt ttccttcagg gttttatttt tgactgtttt gttttcttgt tggccatttc    4382
tgtattgctg gcatctgtgc taagctttac agtggcaaaa ataatgacat gtagcaaaga    4442
ttttcaaaca aaatatttt tccttttgta aaaaaaaaaa aaaagaaaaa aaaaaaaaa      4502 aa                                                                   4504
```

```
<210> SEQ ID NO 5
<211> LENGTH: 20
<212> TYPE: DNA
<213> ORGANISM: Artificial Sequence
<220> FEATURE:
<223> OTHER INFORMATION: PCR Primer

<400> SEQUENCE: 5
agcagagggt gtgggtgtct                                                  20

<210> SEQ ID NO 6
<211> LENGTH: 20
<212> TYPE: DNA
<213> ORGANISM: Artificial Sequence
<220> FEATURE:
<223> OTHER INFORMATION: PCR Primer

<400> SEQUENCE: 6
tggcggttgt tgaacatgtt                                                  20

<210> SEQ ID NO 7
<211> LENGTH: 22
<212> TYPE: DNA
<213> ORGANISM: Artificial Sequence
<220> FEATURE:
<223> OTHER INFORMATION: PCR Probe

<400> SEQUENCE: 7
ccagcagcct catcatcgtt ca                                               22

<210> SEQ ID NO 8
<211> LENGTH: 19
<212> TYPE: DNA
<213> ORGANISM: Artificial Sequence
<220> FEATURE:
<223> OTHER INFORMATION: PCR Primer

<400> SEQUENCE: 8
gaaggtgaag gtcggagtc                                                   19

<210> SEQ ID NO 9
<211> LENGTH: 20
<212> TYPE: DNA
<213> ORGANISM: Artificial Sequence
<220> FEATURE:
<223> OTHER INFORMATION: PCR Primer

<400> SEQUENCE: 9
gaagatggtg atgggatttc                                                  20

<210> SEQ ID NO 10
<211> LENGTH: 20
<212> TYPE: DNA
<213> ORGANISM: Artificial Sequence
<220> FEATURE:
<223> OTHER INFORMATION: PCR Probe

<400> SEQUENCE: 10
caagcttccc gttctcagcc                                                  20
```

<210> SEQ ID NO 11
<211> LENGTH: 2691
<212> TYPE: DNA
<213> ORGANISM: M. musculus
<220> FEATURE:
<220> FEATURE:
<221> NAME/KEY: CDS
<222> LOCATION: (110)...(2485)

<400> SEQUENCE: 11

```
gcggcggtaa ggtgcctaat ctgcggagtg gctcttccct cccctccccc agctcggtgg       60
cggctgcccc tcccaccgag ggtggcgcag ggacggtgcc atctcgacc atg gcg gcg     118
                                                     Met Ala Ala
                                                       1 act aca gct aac cca gaa atg aca tca gat gta cca tcg ctg ggt ccc       166
Thr Thr Ala Asn Pro Glu Met Thr Ser Asp Val Pro Ser Leu Gly Pro
      5                  10                  15 acc att gct tct gga aac cct gga cct ggg att caa ggt gga gga gct       214
Thr Ile Ala Ser Gly Asn Pro Gly Pro Gly Ile Gln Gly Gly Gly Ala
 20                  25                  30                  35 gtt gta cag agg gct att aag cga cgg tca ggg ctg gat ttt gat gat       262
Val Val Gln Arg Ala Ile Lys Arg Arg Ser Gly Leu Asp Phe Asp Asp
                 40                  45                  50 gaa gta gaa gtg aac act aaa ttt ttg aga tgc gat gat gac cag atg       310
Glu Val Glu Val Asn Thr Lys Phe Leu Arg Cys Asp Asp Asp Gln Met
             55                  60                  65 tgt aat gac aaa gag cgg ttt gcc agg tcg gat gat gag cag agc tct       358
Cys Asn Asp Lys Glu Arg Phe Ala Arg Ser Asp Asp Glu Gln Ser Ser
         70                  75                  80 gcg gat aaa gag aga ctt gcc agg gaa aat cat agt gaa ata gaa cgg       406
Ala Asp Lys Glu Arg Leu Ala Arg Glu Asn His Ser Glu Ile Glu Arg
     85                  90                  95 cgg cga cgg aac aag atg aca gct tac atc aca gaa ctg tca gac atg       454
Arg Arg Arg Asn Lys Met Thr Ala Tyr Ile Thr Glu Leu Ser Asp Met
100                 105                 110                 115 gta cct aca tgt agt gcc ctg gct cga aaa cca gac aag cta acc atc       502
Val Pro Thr Cys Ser Ala Leu Ala Arg Lys Pro Asp Lys Leu Thr Ile
                120                 125                 130 tta cgc atg gcc gtt tct cac atg aag tcc ttg agg gga act ggc aac       550
Leu Arg Met Ala Val Ser His Met Lys Ser Leu Arg Gly Thr Gly Asn
            135                 140                 145 aca tct act gat ggc tcc tac aag cca tct ttc ctc act gat cag gaa       598
Thr Ser Thr Asp Gly Ser Tyr Lys Pro Ser Phe Leu Thr Asp Gln Glu
        150                 155                 160 ctg aaa cat ttg atc ttg gag gca gca gat ggc ttt ctg ttt att gtc       646
Leu Lys His Leu Ile Leu Glu Ala Ala Asp Gly Phe Leu Phe Ile Val
    165                 170                 175 tcc tgt gag act gga cgg gtg gtg tat gtc tct gac tca gtg act ccc       694
Ser Cys Glu Thr Gly Arg Val Val Tyr Val Ser Asp Ser Val Thr Pro
180                 185                 190                 195 gtt ttg aac cag cca cag tct gaa tgg ttc ggg agc aca ctg tat gat       742
Val Leu Asn Gln Pro Gln Ser Glu Trp Phe Gly Ser Thr Leu Tyr Asp
                200                 205                 210 cag gtg cac cca gat gat gtg gat aaa ctt cga gag cag ctc tct aca       790
Gln Val His Pro Asp Asp Val Asp Lys Leu Arg Glu Gln Leu Ser Thr
            215                 220                 225 tca gaa aat gcc cta aca ggg cgg gtc ctg gat ctg aag act gga aca       838
Ser Glu Asn Ala Leu Thr Gly Arg Val Leu Asp Leu Lys Thr Gly Thr
        230                 235                 240
```

```
gtg aaa aag gaa ggc cag cag tct tcc atg agg atg tgc atg ggc tca      886
Val Lys Lys Glu Gly Gln Gln Ser Ser Met Arg Met Cys Met Gly Ser
245                 250                 255 cga agg tcg ttc atc tgc cgc atg agg tgt ggt act agc tcc gtg gac      934
Arg Arg Ser Phe Ile Cys Arg Met Arg Cys Gly Thr Ser Ser Val Asp
260                 265                 270                 275 cct gtt tcc atg aat aga ctg agc ttt ttg agg aac aga tgc agg aat      982
Pro Val Ser Met Asn Arg Leu Ser Phe Leu Arg Asn Arg Cys Arg Asn
                280                 285                 290 ggg ctt ggc tct gtg aag gaa gga gaa cct cac ttt gtg gta gtc cac     1030
Gly Leu Gly Ser Val Lys Glu Gly Glu Pro His Phe Val Val Val His
            295                 300                 305 tgc aca ggc tac atc aag gcc tgg cca cca gca ggt gtc tcc ctc cca     1078
Cys Thr Gly Tyr Ile Lys Ala Trp Pro Pro Ala Gly Val Ser Leu Pro
        310                 315                 320 gat gat gac cca gag gct ggc cag ggg agc aaa ttc tgc cta gtg gcc     1126
Asp Asp Asp Pro Glu Ala Gly Gln Gly Ser Lys Phe Cys Leu Val Ala
    325                 330                 335 att ggc agg ctg cag gta act agt tct ccc aac tgt aca gac atg agt     1174
Ile Gly Arg Leu Gln Val Thr Ser Ser Pro Asn Cys Thr Asp Met Ser
340                 345                 350                 355 aac att tgt cag cca aca gag ttc atc tcc cga cac aac att gaa ggg     1222
Asn Ile Cys Gln Pro Thr Glu Phe Ile Ser Arg His Asn Ile Glu Gly
                360                 365                 370 ata ttc act ttt gta gac cat cgt tgt gtg gct act gtt ggc tac cag     1270
Ile Phe Thr Phe Val Asp His Arg Cys Val Ala Thr Val Gly Tyr Gln
            375                 380                 385 cca cag gag ctc tta ggg aag aat att gta gaa ttt tgt cat cct gaa     1318
Pro Gln Glu Leu Leu Gly Lys Asn Ile Val Glu Phe Cys His Pro Glu
        390                 395                 400 gac caa caa ctt cta aga gac agc ttt cag cag gtg gtg aaa tta aaa     1366
Asp Gln Gln Leu Leu Arg Asp Ser Phe Gln Gln Val Val Lys Leu Lys
    405                 410                 415 ggt cag gtg ctg tcc gtc atg ttc cga ttc cga tct aag acc cga gaa     1414
Gly Gln Val Leu Ser Val Met Phe Arg Phe Arg Ser Lys Thr Arg Glu
420                 425                 430                 435 tgg ctg tgg atg aga acg agc tcc ttt acc ttc caa aac cct tat tca     1462
Trp Leu Trp Met Arg Thr Ser Ser Phe Thr Phe Gln Asn Pro Tyr Ser
                440                 445                 450 gat gaa att gag tat att atc tgc acc aac acc aat gtg aag aac tct     1510
Asp Glu Ile Glu Tyr Ile Ile Cys Thr Asn Thr Asn Val Lys Asn Ser
            455                 460                 465 agc cag gaa cca cgg cct aca ctg tcc aac acc atc cca agg tca cag     1558
Ser Gln Glu Pro Arg Pro Thr Leu Ser Asn Thr Ile Pro Arg Ser Gln
        470                 475                 480 cta ggt ccg aca gcc aat tta tcc cta gag atg ggt aca ggg cag ctg     1606
Leu Gly Pro Thr Ala Asn Leu Ser Leu Glu Met Gly Thr Gly Gln Leu
    485                 490                 495 cca tcc agg cag cag cag cag cag cac aca gaa ctg gat atg gta cca     1654
Pro Ser Arg Gln Gln Gln Gln Gln His Thr Glu Leu Asp Met Val Pro
500                 505                 510                 515 gga aga gat ggg ctg gcc agc tat aat cat tcc cag gtt tct gtc cag     1702
Gly Arg Asp Gly Leu Ala Ser Tyr Asn His Ser Gln Val Ser Val Gln
                520                 525                 530 cct gtg gca agt gca gga tca gaa cac agc aag ccc ctt gag aag tca     1750
Pro Val Ala Ser Ala Gly Ser Glu His Ser Lys Pro Leu Glu Lys Ser
            535                 540                 545 gaa ggt ctc ttt gca cag gac aga gat cca agg ttt cca gaa atc tat     1798
Glu Gly Leu Phe Ala Gln Asp Arg Asp Pro Arg Phe Pro Glu Ile Tyr
        550                 555                 560
```

```
ccc agc atc act gca gat cag agt aaa ggc atc tcc tcc agc act gtc      1846
Pro Ser Ile Thr Ala Asp Gln Ser Lys Gly Ile Ser Ser Ser Thr Val
565                 570                 575 cct gcc acc caa cag ctg ttc tcc cag ggc agc tca ttc cct cct aac      1894
Pro Ala Thr Gln Gln Leu Phe Ser Gln Gly Ser Ser Phe Pro Pro Asn
580                 585                 590                 595 ccc cgg ccg gca gag aat ttc agg aat agt ggt ctt acc cct cct gta      1942
Pro Arg Pro Ala Glu Asn Phe Arg Asn Ser Gly Leu Thr Pro Pro Val
                600                 605                 610 acc att gtc cag cca tca tct tct gca ggg cag ata ctg gcc cag att      1990
Thr Ile Val Gln Pro Ser Ser Ser Ala Gly Gln Ile Leu Ala Gln Ile
615                 620                 625 tca cgt cac tcc aac cct gcc cag gga tca gcg ccg acc tgg acc tct      2038
Ser Arg His Ser Asn Pro Ala Gln Gly Ser Ala Pro Thr Trp Thr Ser
            630                 635                 640 agc tcc cgc cca ggc ttt gcc gcc cag cag gtg ccc acc cag gct aca      2086
Ser Ser Arg Pro Gly Phe Ala Ala Gln Gln Val Pro Thr Gln Ala Thr
645                 650                 655 gcc aag act cgt tct tcc caa ttt ggt gtg aac aac ttt cag act tct      2134
Ala Lys Thr Arg Ser Ser Gln Phe Gly Val Asn Asn Phe Gln Thr Ser
660                 665                 670                 675 tcc tcc ttc agt gct atg tct ctt ccg ggt gct ccc act gcc tca tct      2182
Ser Ser Phe Ser Ala Met Ser Leu Pro Gly Ala Pro Thr Ala Ser Ser
                680                 685                 690 ggt act gct gcc tac cct gct ctc ccc aac cgt ggc tcc aac ttt cct      2230
Gly Thr Ala Ala Tyr Pro Ala Leu Pro Asn Arg Gly Ser Asn Phe Pro
            695                 700                 705 cct gag act gga cag acc aca gga cag ttc cag gcc cgg aca gca gag      2278
Pro Glu Thr Gly Gln Thr Thr Gly Gln Phe Gln Ala Arg Thr Ala Glu
710                 715                 720 ggc gtg ggt gtc tgg cca cag tgg cag ggc cag cag ccc cat cat cgg      2326
Gly Val Gly Val Trp Pro Gln Trp Gln Gly Gln Gln Pro His His Arg
    725                 730                 735 tct agt tcc agt gag cag cat gtt cag cag aca caa gca caa gca cct      2374
Ser Ser Ser Ser Glu Gln His Val Gln Gln Thr Gln Ala Gln Ala Pro
740                 745                 750                 755 agc cag cct gag gtc ttt caa gaa atg ctg tcc atg ctg gga gac caa      2422
Ser Gln Pro Glu Val Phe Gln Glu Met Leu Ser Met Leu Gly Asp Gln
                760                 765                 770 agc aac acc tac aac aat gaa gaa ttt cct gat cta act atg ttt ccc      2470
Ser Asn Thr Tyr Asn Asn Glu Glu Phe Pro Asp Leu Thr Met Phe Pro
            775                 780                 785 ccc ttt tcc gaa tag aactattggg gtgaggataa gggtgggggg aaatcactgt      2525
Pro Phe Ser Glu
        790 ttgttttaa aagcaaatct tttgtaaaca gaataaaagt tcctctccct tcccttccct      2585 caccctgat atgtaccctt tccaccccctt gacttgctga agaaacgtta tagaagaaat     2645
taaatgaatt tcccaggcaa aaaaaaaaaa aaaaaaaaaa aaaaa                     2691

<210> SEQ ID NO 12
<211> LENGTH: 20
<212> TYPE: DNA
<213> ORGANISM: Artificial Sequence
<220> FEATURE:
<223> OTHER INFORMATION: PCR Primer

<400> SEQUENCE: 12
ggcatctcct ccagcactgt                                                   20
```

```
<210> SEQ ID NO 13
<211> LENGTH: 28
<212> TYPE: DNA
<213> ORGANISM: Artificial Sequence
<220> FEATURE:
<223> OTHER INFORMATION: PCR Primer

<400> SEQUENCE: 13
ggtaagacca ctattcctga aattctct                                             28

<210> SEQ ID NO 14
<211> LENGTH: 20
<212> TYPE: DNA
<213> ORGANISM: Artificial Sequence
<220> FEATURE:
<223> OTHER INFORMATION: PCR Probe

<400> SEQUENCE: 14
tccctcctaa ccccggccg                                                       20

<210> SEQ ID NO 15
<211> LENGTH: 20
<212> TYPE: DNA
<213> ORGANISM: Artificial Sequence
<220> FEATURE:
<223> OTHER INFORMATION: PCR Primer

<400> SEQUENCE: 15
ggcaaattca acggcacagt                                                      20

<210> SEQ ID NO 16
<211> LENGTH: 20
<212> TYPE: DNA
<213> ORGANISM: Artificial Sequence
<220> FEATURE:
<223> OTHER INFORMATION: PCR Primer

<400> SEQUENCE: 16
gggtctcgct cctggaagat                                                      20

<210> SEQ ID NO 17
<211> LENGTH: 27
<212> TYPE: DNA
<213> ORGANISM: Artificial Sequence
<220> FEATURE:
<223> OTHER INFORMATION: PCR Probe

<400> SEQUENCE: 17
aaggccgaga atgggaagct tgtcatc                                              27

<210> SEQ ID NO 18
<211> LENGTH: 67787
<212> TYPE: DNA
<213> ORGANISM: H. sapiens

<400> SEQUENCE: 18
ttagtagaga cggggtttcg ccatgttggc caggctggtt tcgaacccct ggccacaggt      60
gatccggccg cctcggcctc ccaaagtgct gggattacag acgcgagcca ccgcgcccag     120
cctaaaatac ccattttaat tgcatttcaa tgacgttact cggtcattga cctcttacgc     180
aaggagggcg agattaggga gacagctgga cttcttcctc gccctccctt cactggactg     240
gctggcgcag tgagtagccc tgcccttgga cgatttggca ttttcattgg tcaattttc      300 ttaggaggct ggccgtgtgt tgactccgcc tactatatag gcggggtctc cccgccgcag     360
```

```
gggctgggat gctggggget gctgaagccg ccatcttgga ttccgcggta gcggaggcgg      420
cggtcaggcg ccgcttctgg ggagtggcct ttcttttccc ctccctcccg gttcggtggc      480
ggcggctcct cccactgggg ggggggggtgg cgcggcggcg gtggcatctg cggccatggc    540
ggcgactact gccaaccccg gtgaggagac ggaggactgg ggcgcctcta aggggaggg      600 gccgaagggg ctgacaacta aggagaccca gggctgaggg gacgcagctg gagctgaagg     660
cgccggggcg gggcggggc cgcgagagac ggtgggggag cggtgacctg ggaggggcc       720 cgatcccggg gacttgggta gactcgagta tacccaaggg agcgagggg caggtgggag      780 ttgagggggg ctccctgtcc tgacctccgt tggagcggca gccagtgcgg ggctggcccg    840
ccctcactcc tcggtcggcg tctggtctgt gatgtggtcc tcttttaacc ctctgcccgc     900
tggagccgct tgatgccgaa aactgtaggc agagtgtctc ggtttacttt aagagtagtt    960
tggattcata aaccctggac cacactgctc tttagttgag gcgttgcttc caaacattta     1020
aaggtttaga ttttaattta aaaaataaaa aatggacatt ctttgatata tacgacgttt    1080
ctttaggctg ttacctccca cccgcaaccc ccgtccccgt ctccgtcccc ggactatact   1140
ttgaaactta gatcttgtgt taagagggcc tgtaggtctt tgcctgctga gggcaggggt   1200
ttgtgtaatg gttatggttc cggacaggtc tttagttcca cagccccagg tttaaatctt   1260
gttaggccta cgtcgaggca atttccaaac tctttcagaa aagtttgatt ccacaccatt   1320
tctcaatttc aaaaaataat caaatatcaa aaaggtttgg tctgttttgt ctaagagatg   1380
gagtagggtg tagtgcagtt ctagagagat cagatcttca aattactagt cccagccctc   1440
tttcctctat gttacagtta ttcctctta gaaggcattt catttaggg gtctagttta    1500 tcttggagac cttggttatt cttgccaaat aaagtctatc cttttccaaa aaccaatata  1560
tttgatagcc ttaaaagggg ccttgagata tgtgtgtgtg ttgcgtgggg cggagaattt  1620
cttgaaaata aaacagtagg agtgattacc cccatcccca cgttgaaatt taaattagat  1680 ttttttcat gttactgaaa ggcagtatga ttttgcaata tccagatttt gataggacag    1740
ttgaatcact gaaatttctt ttctaccgtg tttctgggaa tagctatttt aagaaatggt  1800
taatttgtca cgtcattttt ttttaatctt ttaaatttt tttgaaggaa agggaggtaa   1860
aattaatcgc aaaaattaca ttgcaggaag tgctgagtga tagaataaaa ctataaaaca    1920
ggaaaaatgc cgttatgtca aacctgacct tgtagtaata taacctatct gtgaactatg   1980
gaataaataa acaagatttt taactgatca cacattgcaa aatacttata taaccctagt    2040
taaattgcaa agcatttctc ttattaagaa gtggcctggg taaacaagtt ttagttcata   2100
tgtcagaagc ttttttccag ctgtgtgggt ggggttgctt tattttgttt tgttttttga   2160
acaacagcaa ccagaatgac agcctcttga ccatattttc ataagctgat caatatcagc   2220
ttaaatctta gcagaaaata gcatatgtta gtgtgtatgt gtgtgtgcag aatccttgtt   2280
aatgaaacag cttgtttac tatgctttgg ctgcttgctt ctgcaatttt tagatttcct   2340 ttttctttt ctttgttttc ctttctcctc tccctctct cctgtcccct ctccctcttt   2400 tttctttgc tacagggtct tgctccttgc tctgtcgccc agtctggagt gcagtggcaa   2460
gatcactgct cacggcagcc tccacctcag gggctcaagt gatcctctca cgatcagcct   2520
cccgaatagc tgggactaca ggtgccttgc caccatgcgc ggttaatttt taatttttt   2580 tgtagagaca gatgccttgc tatgttgccc atgctgatct tgatctcctg gtctcaagca   2640
agccttgcct cagtctctcc aagttgggaa tacagatgtg agacactttg accagattc    2700
```

```
tttttttgatg ttgaaaaatt attccatctc ttctgactta ttgatcccat gttcagttca    2760
atcaaatcag aagatatatt ttctttttc ttttctccct ttgctcttgt atatcatgag      2820
gaagagatca gagatacatt gtggattttt tcagtagcct gttgctttt gggaaatgag      2880 attaatgaat ggagggacat aggtggaaat gtactgtgct tagtgaaagt aaatgttttc    2940
aggtcagaat tctttgctac actgtccatac cttctttcct tagagccatt ttaaggacta   3000
gggacaccat gcctatttct ttgagttttt tctactttgt attttgctg gagtactaat      3060 tttttttttt tttttttttt tttacaatt cttgttagtt ttgtcaagat tttaaaaaat      3120
atttcactct ttaaccttca cttcagttaa tccttttaa aaataatact tatttttatt       3180
tttcagacag gttcttgctc tgtctcccag actgtagtgc aatggtgtaa tcacagctca    3240
ctgtagcctt gaactcctga gctcaagtga tcttcccacc tcagcctcct gagtatctgg    3300
gtctacagac acacaccacc acacctggat acattttta acttttgta gaaatgggat       3360 cttgctatgt tgcccaggct gatcttgaac tcctgtcctc aagcaatcct cccaccttag    3420
cctcctaaac tgctgggatt ataggtgtga gccactgacc cggccaagtt aatccttagg    3480
gttagtaata tgcttgaac atgttaattg tgctggtggc cctgcagtgt ttttcaaggg      3540
gaccacgttc ttctgcattt ttcactgtgg tgctgcatta aagaagagt aaaatatggt      3600 tggtactctc taagagttgt gttgaagtaa tagttctgtg atgattttt ttctcgaatt      3660 gataattctt catattctat cattttcac tagttctact tatcactggc aagtagaact       3720
cggtgggtag gtggtccatg aaactttagg ctgtttctta tctatggact agacaagttt    3780
tgttttgttt ttttttttgtt tgtttgtttg ttttgagaca gagtctcact ctgtcgccca    3840
ggctggagtg cagtggtgct atcttggctc actgcaagct ccgcctccca ggttcacgcc    3900
attctcctgc ctcagcctcc cgagtagctg ggactacagg tacccgccac cacgcccggc    3960 taatttttt ttttgtattt ttagtagaga cagggtttca ccctgttagc cagggtggtc      4020
tcgatctcct gaccttgtga tccgcctgcc tcggcctccc aaagtgctgg gattacaggc    4080
ttgagtcacc gtgcccggcc cggactagac aagttttgag gaacacattt ttttccccca    4140
taggagaggg tcttgctctg tcactgaggc tggagtgcag tgacacaatc atggctcact    4200
gcagccttga ccttctggga gcatgtgatc ctcccacttc agcctcctga gtaggtggga    4260
ccacaggtgt gcaccaccgt ggctggctaa ttttaaattt tttttagaga caggtcttg     4320 ctatgttgcc caggctggtc tttaactcct ggcctcaagt gatcttcctg cgttgggcac    4380
tccccaagag ctgggattat aggcatgacc accatgccca gccaaggtgg aacactttt    4440 aaattgaatg tgtcatttgt aatgcattgg ctgagggaac agttgggagg agattaggta    4500
tttgatttac aattccaaat tcaaactaga gatgttgaat gagtttgtag taagtgtagg    4560 ttttatctc tcttgattct ggtattctca ttagcagaga attcttttg tgctattatg       4620 tacaagttac tgtggatgaa gaatgtagaa ggaaaagggt aataccgttt gggtttgtaa    4680
ggctgtcatt taggaagaaa attttttta gctaatttc acctatataa cttagtttta      4740
actgcgtcaa ttaacacaat tcttacctgt taccttatt taccttttc agatatggga      4800 aaataggaat tcatgcaatg taaagttaag atgtcaagat attctttat ggccaggtgt     4860 ggtggctcgt gcctctaatc cctttgggag gccgaggcag gccgattgct tgagcccagg    4920
aatttgagac cagcccggac aacgtgacga aaccccttta ctacaaaaaa tacaaaaaat    4980
tttccgggca ctgtggtgca cttctatagt cccagctact tggaggctg agatgggagt     5040 atcacctgag cctggaaagt tgaagctgca gtgagctgtg atcatgccac tgtactccag    5100
```

```
cctgggtgtt ggagtgagac cctgtccccc aacaaaaaaa gagatagtat tttattatat    5160
tgcaaaggcc tttttttttt tttttttttt ttttttgagac agggtcttac tgtgtcgccc    5220
aggctggagt gcaatggcgt gatcttggct cactgcaacc tccgcctcct gggttcaagc    5280
tattctcccg cctcagcctc ccgagtagct gggattacag gcacctgcca tcacgccggc    5340
taatttttta ttttaatag agacaggggt tctccatgtt ggccaggctg gtcttgaact    5400
cctcacctca ggtgatccgc ccaccttggc ctcccaaagt gctgggatta caggcgtgag    5460
ccgccatgct ccgccgccat ctgttttaa aatgctgcc ttggccgggc atggtggctc    5520
atgcctgtaa tcctagcatt tgggaggcc gaagtgggca gatcacctga ggtcaggagt    5580
tcaagaccag cctggccaac atggagaaac cctgtctcta ctaaaaatac aaaaattagc    5640
caggcatggt ggcaggtgcc tgtaatccca gctactcggg aggctgaggc gggagaatcg    5700
cttgaacctg gaaggtggtg gttgcagtga gctgagatcg taccactgca ctctagcctg    5760
ggcgacagag tgagactccg tctaaaaaaa aaaaaaaaaa aaaaaaaacc acgactgcct    5820
aatatgccat aatgacttta gtaagtagac atcagtgaat cttcaggttg gaaatatgac    5880
aacacctatc attttacact taaggagaca aacccaggga aaggagtgga taattaagtt    5940
ccttctatat gccaggctgc actttcctat tttgttgcta atctttatgt ctagtctgta    6000
gcaactgtct ccaactttc acataaactc ttcaaattta tgtcactttt cataatttcg    6060
tcaatgtatt ttcttgtttt aaagttttta ttatttaga tagtgaccgg gtctcactat    6120
attgccccgg ctggtctcaa actcctgggc tcaagcaatc ctcctgcctc ggcctcccag    6180
agtgccgggg ttacaggtgt gagccaccct ctgaggccca ttttatattt tccctccacg    6240
ttttcattgt agttgaatgg acaagtaagt ttatggattc aacagtatac ttagggctgg    6300
acatggtggc tcatacctgt aatcctagca ctttgggagg ctgatgtagg tggattgctt    6360
gagcccaaaa gtttgagacc agcctgggca acgtggtgaa accccatctg tacaaaaaaa    6420
tacaaaaaat tagcagggtg tggtagcatt ccctgtagtc ccagctacgt gggagactga    6480
gatgcgagga tgacctgagc ctgggaggtt gaggctgcag tgagccatga ttgtgccact    6540
gcattcctgt ctgggtgact aggagacaga gtgagaccct gtctcaaaaa acacaacaaa    6600
accagcatac ttaggatata agttccatga gagcagaact tttgctttcc ttgtttacca    6660
gagcattgca gtgcttacag tgggtgccta gtatgttgga ttagagttca atgtatgttt    6720
gtggaataaa aatgaatgta aaacccactg ttaatatgaa ataccttga agggataaaa    6780 ctaattaagc cattgacatc atgaatttgt actaactata ataatatcta atatttatta    6840
gtaatactta ccagctgttc tcatttaatt tttataacaa tcgtattagg taagtattat    6900
tattcttgtt ttacagatga ggaaactaag gcacagagag tgaataagta acttgtctga    6960
agtcacatag ctactagaag ttagagacag aatttattg ttggcagtcc atctacacag    7020
tcatcattct taatctccaa gttatgattt tttccattgt gacttagagt caccttccta    7080
ctgaaatata gtacaatgga tatctttga aaggaggta ggtggagtat tgtctttttt    7140
gtagatgaaa agggtgaaat accacattag gcagcctggg ggcaaggcat tgcttggttg    7200
gagaaccaag tgcaaggtgc taaaaaaagg agctagaaca gtagtttcca ggctgagtgt    7260
ggtggctcat acctgtaatc tcagcacttt gagaggccag ggtgagagga ttgtttaagc    7320
ccaggagttg gagaccagcc tgagcaatat agggagacct tgtctccaca aaatatata    7380 taaaaaaatt agctagatgt ggtggtggat gcctatagtc ccaactactt gggaggctga    7440
```

-continued

```
ggtggtggga ggatctctga gcttgctagg tcagggctgc agtgagccat gatcatgcca      7500
ctggactcta atctggttga cagagtgagc ccctgtctct aggaaaaaaa aaaaaaaagg      7560
agtagtttcc taaaatcttt tctgtaacat tctataattc ttcattttgt tttgttttgt      7620
tttttttgaga ctgagtgtcc ttctgtcacc caggctgggg tgcagtggca cgatctcagc    7680
tcactgcaag ctccgcctcc caggttcacg ccattctcct gcctcatcct cgcgagtagc      7740
tgggactaca ggcatccacc accatgccct gctaattttt tgtgttttta gtggagatgg      7800
ggtttcactg tgttagccag gatggcctcg atctcctgac cttgtgatcc gcccacctca      7860
gcctcccaaa gtgctgggat tataggcttg agctagcgcg cccagcctaa cattctatat      7920
ttctttctcc tagttctatg tttcaattct ttaaatactt ttaagggttt ttttgagaca      7980
aggtcctgtt gtgtcagcca ggctggagtg cagtagcgtg accatagctt cctgcaacac      8040
ctccaattcc taggctcaag cgattctcac tcctcagttt cctgaatagt tgggaccata      8100
ggtatgcacc atcatgccca gctaattttt taattttgta gagacaggat ctcgctatgt      8160
tgcccaggct ggtccttttt tttttaaatt ttattattat tttttgagac ggagtcttgc      8220
tttgtcaccc aggctggagt gcagtggcgt gatctcggct cactgcaacc tctgcctccc      8280
gggtttaagc gattctcctg cctcagcctc ctgtagctgg gactacaggc acgtgccacc      8340
gcgcctggct aattttttgtg tttttagtag agacggggtt tcaccatgtt ggccaggatg     8400
gtctcgatct cctgacctcg tgatctgccc acctcggcct cccaaagtgc tgggattaca      8460
ggcgtgagcc accgcgcccg gcctgcccag gctggtcttg aactactgtc ctcgagtgat      8520
cctcctgctg ttggcctccc agattgctga gattacaggc atgaatcatg cactgcagct      8580
tttaggatta ttattagaat cctctacaag ttccttgatac tccataattg agcctctcct     8640
agaaacttgg tttcagagac actgttgcta ggtctttatc actgattgtt ccttctttgt      8700
cctttttgct tatctttctg cttgtttctt tctcttgttc agtatgcttc tacttttctc      8760
ttctcaccct tgaggctagg actcttcttt gagacagggt cttgactctt ttttgagaca      8820
gggtcttgct atgttgccca cgttggtctt ggattcctga gctcaaatga tcctcccacc      8880
tctgcttcct gagtagctgg gattacaagt gtacaccaca gtgcccggct tgggctaga      8940
actaaatagt aaaccaagca gtttccttca tttcttccca tttgcccacc tacctgcctt      9000
tctagctgct tgccttccta cttcaatttg acattcactt ggtacctacc atagtcctct      9060
tcccttttgta ttagtccatt ctcacactgc tataaataac tacctgagac tgggtaattt    9120
atgaagaaaa gaggtttaat tgactcatag ttccgcaggc tgtatgggag cagggctgg      9180
ggaggcctca ggaaacttgg aatcatggcg gaaggcgaag gggaagcaag catgtcttca     9240
catggctggc aggatagagg gagagaaggg gaaggtgcta cacactttca aacaaccaga     9300
tctcttgaga actctatcat gagagagcat taggggaatg gtgctaaacc tttggaaacc     9360
accccctatga tccaataacc tcccaccaga ctgcaccttc aacactgggg attacaattt    9420
gacatgatat ttgggtggag acacacagag ccaaaccata tcacccttta tttatctttt    9480
atgtataaaa gactccaaaa atttcattcc tggcttctca cataaactac tttcctatat     9540
ttttatctat ttaaaagata tctctctctt tttcttttaa agttgagaca gggttttact     9600
atgttgccca ggctggtctt gaatcctgg gctcaagcat tcctcccact tcagcaacct      9660
gagtagctgg actacaggtg tgtgccattg tgcctggctg catctctgtt tgaatagttt     9720
tttttttttt taatttatag aaatgaggtc tcactgtatt gcccagactg gtcttgaact     9780
gctgagctca agtagtcccc ccatcttggt ctccctagta gctgggatta taggtgtatg     9840
```

```
acacgatgcc cagctctatt tgagtaatct gttttttttt gttgttgttg tttttttaa      9900
agacagagtc tttctgtgtt gcccaggctg gagtgcagtg gtgcgatctt ggctcaccgc     9960
agcctccgcc tcctaggttc aaatgatttt tgtgcctcag cctctcgagt agctgggact   10020
acagtgtgcc accacgcctg gctaatttt tgtatcttta gtagagatgg ggtttcacca    10080
tgttggccag gctggtcttg aactcccgtc ctcaagtgat ccacctgcct tggcctccca   10140
cagtgctggg attacaagtg tgagccattg cgcccagcct ctatttgaat aatctttaac   10200
atcctatata tgtatgtact caccagtatt tcctttaaat ctgctgttct tcctacctt    10260
ctgtatcttt catcactatc acaattcagt ttttcatttc cccaggctaa ggaactataa   10320
gtgtttggat tttatttttt atgtgtttat ctgggttatt aactcttctc aggtcttttg   10380
ccaaatatac gtgtgtgtgt gtgtatatgt atgtgtgtat acatacatat ataaaagtta   10440
tttaaatcaa aactatacat ccatatatta atatttaaag acttagatag ttttataaaa   10500
tgtttgttac aaaaaaatta taagggagtc ctctgctccc tttctctcat ttccttctct   10560
ccagtggcat cattttttatt tcttttaaca gaattctttg tttctgttta aataaagtgt   10620
cccagtgaaa gacattagtt tccagatcaa aggggctgtg cacacatcaa ggcccattat   10680
gctgaaattt cagcatcaga tagagaatat cctataagct tcagagagaa taagattatt   10740
cacattcaaa agattcaggt atcagattgg tcttttttct cagtagtcat gctggaaagt   10800
agaagacctt ggaacaggct gactgaccct ggtggctcac gcctgtaatc ccagcatttt   10860
gggaggctga ggcaggtgga tcacctgagg tcaggagttt gggaccagcc tggccaacat   10920
ggtgaaaccc cgtctctact aaaaatacaa agattagttg gacgtggtgg tgtgtgcctg   10980
tagtaccagc tacttgggag gctgaggcag gagaattgct tgaacctggg aagcagaggt   11040
tgcagtgagc cgagatcacg ccactgcaca ccagcctggg caaaagagcg aagactctgt   11100
ctcaaaaaaa aaaaaaaaaa ctttggagta atgccttcaa aattctgagg gaaaataaat   11160
tctaatttag aattccatag ctaggcaaac tatcaattag tgaaatagaa gaaatatttt   11220
catacatcca aggcatttct tacacccttt caggaatcca ctagaagata ggctctacca   11280
gtaggagata gtaaaccaag aaagtggaga tacgaaatat aggaaatagg cagtataaca   11340
cagaagaaaa atgaagcatg tagtatgcat acattggtgt tagttttcct gttttcagta   11400
cgggtccctc actttcacct ttacgtcgtg ttcactagac tgtaagacct ttgatttata   11460
ctctccagag agtaaatctg tcttttgaca gaatggagag gggtagttgc cttggttaga   11520
aggaatagag aaaaggatct aggaatccat ctctgtagta aacagatgct gaactaattc   11580
tccttatttt cacttcattc accctaccct gcatacccag agttacctgg actcaccagc   11640
ttctgagact ttggggaatt ccatagcgta aattgagttg gttttctgct ttttcccttg   11700
tcagtttagg atttagttct tgtcgatctc ccaaggcaat agtccatttt atctctagtt   11760
tcaaaaaaat tattgctctt cttctcttat tctttccatc cttgtggttt tatgtcttgt   11820
gtaaaaattt ttgctttaa aaattttttt cctgtgtgtg agtgaagaga aagagagta    11880
gaaatagata gatacattta attcactatc cttactcaga agttgcatag tttaaaattt   11940
tagaagtaac tacctttcg ttgtgccatc ctcatttagg cctttatcac cttgttttt    12000
ttattaatct tgtcttccta cttctattac ttcaaacttt aaatctgtca gattaatttt   12060
aatttatatt ttcatcttgt tactcagact taaagttata tgtttgtctt tgttgaatct   12120
gatccaggtg tttcatcgtg gcattcaaag ctttctcttg gttagcactt gacatcttac   12180
```

```
cttttatagg tcttttttctt tctttttttt ttttttttttg atttaaagaa aaccattttg    12240
ttttcttcag gggcaatttt ttttttacat tccaccacat attatttata tgtttatcat    12300
atttctttta tttatttatt tatttattta tttatttttt attatacttt aagttttagg    12360
gtacatgtgc acattgtgca ggttagttac atatgtatac atgtgccatg ctggtgcgct    12420
gcacccacta actggtcatc tagcattagg tatatctccc aatgctatcc ctcccccctc    12480
cccccacccc accacagtcc ccagagtgtg atattcccct tcctgtgtcc atgtgatctc    12540
attgttcagt tcccacctat gagtgagaat atgcggtgtt tggttttttg atcttgcgat    12600
agtttactga gaatgatgat ttccaatttc gtccatgtcc ctacaaagga catgaactca    12660
tcatttttta tggctgcata gtattccatg gtgtatatgt gccacatttt cttaatccag    12720
tctatcattg ttggacattt gggttggttc caataggtct ttttctttac agctcttcac    12780
agttgctgtt atgtgtcacc taatgacact ttggtcatca aaggactgca tgtatgatgg    12840
tggtcccata agattataat ggagatgaaa aattcctatt gcccagtgac atcatagttg    12900
tcataaggtc ttagcacaac acattacttt ttctatgttt agatacataa atagttacca    12960
ctgagttata gttgcctaca gtattcagta tagtaacatg ttgtacaggt tgggagtaat    13020
aggctgttac tgggagtaat aggctacata taggtatgta ggctatacac ctacatacct    13080
aggtgtgtag tggctgtacc atctagattt gtgtaagtat actcaatgat attcacacaa    13140
tgttgaaatc tcctaatgac acatttctca gaacatatcc ctgttgttaa gtgatacata    13200
actgtatttt catatctccc tttagacttg ctcatgtact tttatctatg tggaatgcct    13260
ttttcttctt ctttactttt tttttttgag acggagtttt gctcttgttg cccaggctgg    13320
agttcagtgg ctcgattggc tcactgcaac ctctgcctcc tgggttcaag caattctcct    13380
atctcagcct cctgagtagc tgggattaca ggcgcctggt aattttttat attttttagta    13440 gagacggggt ttcaccatgt tggtcaggct ggtctcgaac tcctgacctt aggtgatcca    13500
cccacctcgg cctcccaaag tgttgggatt acaggcgtga gccactgtgc ctggtctcct    13560 ttacttttt taaggcccag tttgatttac ctttttgaaa cttccccatg gctggttgc    13620 ctgccttctt tatttccttt agtttcctct tcatattgag catcttctct gcaagtacta    13680
tgccaggcct taatttaaac caggattatc ttctctgaat ttacctggca ctcttttttt    13740 ttttttttgag acagagtctc attctgttgc ccaggctgga gtgcagtggc atgatctcgg    13800
ctcactgcag cctttgcctc ccaggcgatt ctcatgcctc agtctcccaa gtagctggga    13860
ttatagacgt gtaccaccac acctgactaa ttttttgtatt tttagtagag acggattttt    13920
gccgtgttgg tcaggctggt ctcaaacttg accttaagtg atctaccac ctcagcctcc    13980 taaagtgctg gggttacagg catcagccac cgtgcctggc ctccatggta atctttttt    14040 tttttttttt ttgagacgga atcttgctct gtcacccagg ctagagtgca gtggcacgat    14100
cttggctcat tgcaacctcc gccttttgtg ttcaagcgat tcttctgcct cagcctcccg    14160
agtagctggg actacaggtg tgcgccacca tgcctggcta atttttgtat ttttagtaga    14220
cacggagttt caccatattg gccaggctgg tctcgaactc ctgatgtcgt gatctgcctg    14280
cctcggcctc tcaaagtgct aggattacag gtttgactcc atggtactct tatatcctat    14340
ataaacgtat tactaaaagt atgaactttt ttttttttt tttttttttt acagaggcag    14400
gatctcacta tgttgctcag gctagttttg aactcctgag ctcaagcaat cctcatgcct    14460
tgacctccca aagtgctggg attataggca tgagccactg cacttggccc tgaacttttt    14520
tttttaatgg aaaaagtgtt ttttcttagg aaagtaacat atgcttacta tttcaaattt    14580
```

```
ataggctgaa ataqaaaaat tagcagtaac ataaaaatat actcagcctt aatgtatgtt   14640
aaactaacag tggtaattgt tttttaccaa gaaaatgacc acaaatttga aggattccca   14700
aaacacagtg ctgttggagg tatggctaaa ttgatgcagt ggatgaggct ttaaattggt   14760
ataacctcct tggcaggtaa tgggcaatca gagttttaaa tgtgtctacc cttaggccca   14820
gggagtcatt ttcagaaata atatggaagt actggcacct gtgcatgaag atacacaatg   14880
atgttccttg aaacattatt tataatagtg aaggtttgaa tgtcataact atacatttat   14940
agtacagagt actatgtaac tgttaaaaag aatgatctac gtgtgtattt attgccatag   15000
caatatattg ttacgtggaa gggaaaaagt tcagaataag tacatctgta cttatggtgg   15060
ggttatggct tgataaaccc attgtaaatt gaaaacatcc taagtcaaaa atacatttaa   15120
tacacttaac ctattcttag cctagactac cttaaatgtg tgtggaatac ttacattagc   15180
ctgcagtggg caaataatc taacttaaat tctactttat aataaagtac tggatattat    15240
gtaatttaca gaacactgta cattacactg aaattgtaat ggtttcccac tatcataaag   15300
gtgaaaagcc ctacatggaa ccattataag tcaggactgt ttgtatagta tgacccttt   15360 tttgggtaa aaattaccga aaccctggct gggcgtggtg actcatgcct gtaatcaggc    15420
acataccaca tgtatggcca attttgttca ttttttttag ataggggtc tcactgtgtt   15480 gcccagggtg gtcttgaact tctggactca aatgatcctc ctccctcggc cttttaaagt   15540
gctagcctta caggtgtaag ccaccatgtt cagccccaca gtttctttat ccgttaacct   15600
gtagatagac acttgggttg ccctcaccct tgactactgt tgaatagtac ttctgtgaac   15660
gtgggtatac aaatgtttct ttgagaccct gctttcaatt cttt caggta tatcccaga    15720 ggtggaattg ctggatcatg tggtaattct attttttaatt taattttttt tttgcgatgt   15780
tgtcttgctg tgtttcccag cctgatcttg gactcaagat tctcctgcct cagaccccga   15840
gtagctggga ctacaggtgc gcaccactgc acccagtttt attttaatt tttggaggca   15900 tctccatact gttttctatt gctgttacgc cattttacat ttccactagc agtgcataag   15960
ggttttaatt tctccacatc cttgccaacc ctttatttat ttatatattt ttggataata   16020
gtcatcttaa tgagtagcaa atgctttctc attgtggttt tgatttgcat ttccctagcg   16080
attggttatg ttgagcactt tacatgtatt tattggccat tagtatatct tctttgtaga   16140
aatgcttgtt caagttcttt gcccatttta aaattgggtt tgcttttgt tgagttgtag    16200 gagctcttta tatattttgt tttatttttt atttgtttat ttttttgagg cagagtcttt   16260
ctctgtcgct caggctggag tgcagtggtg cgatcttggt tcactgcagt ctccgcctcc   16320
tgggttcaat taattctccc tgcctcagct tcccgagtag ctgggattac aggtgcccac   16380
caccattcct ggctaattgt tgtatttta gtagagatgg gattt cacca tgttgatcag   16440 gctggtctcg aactgctgac ctcaggtgat atgcccgcct tggcctccca aagtgctggg   16500
attacaggtg tgagccaccg tgcctggcca ctctttatat attttggata ttctgtgttg   16560
catatatgat tcgaaaattt ttttttctgc tgggcacggt ggctcatgcc tgtaatccta   16620
gcattttggg aggctgaggt gggcggatca cttgaggtca ggagttaaag accagcctgg   16680
ccaacatggt gaaaccccat ctctaataaa aatacaaaaa ttagccaggc gtggtggtgc   16740
gtgcctgtaa tcccagctat tgggaggct gaggctcgag aatcacttga acccgagagt    16800
tggaggttgc agggagccaa gattgcgcca ctgcactcca gcctgggcga cagagtgaga   16860
ctctaactca aaaaaaaaaa aaagaatttt ttttttttct attccatggg ttgccttttc   16920
```

```
actctgttgg tagtgttatt tgatgcacaa aatattgtac actatacagt atgaactaac    16980
aaaaaacaat gagatgtgtg tagatagata ttcatgatgt atattgaaat gacgagcaag    17040
ttgaagatca ggcctccatt ttttactaag agaaaaatgc accctttttt ttttttttaga   17100
caggatcttg ctctgttgcc cagggtggag tgcagtggtg caatcacgac tcactgcagc    17160
ctcgacttcc caggctcaag tgatcctccc acatcaacct cttgagtagc tgggactaca    17220
ggcatgggcc accatgctgg ctaacttgta ttttttgtac agatgaggtt tcactgtgtt    17280
gcaaaggcta gtctcgaact cctgggctca agtgatctgc ccaccttggt ctcccaaagc    17340
tctaggattc caggcatccg ccactgtgcc cagcctgcac ctcttttgta ttacagagtt    17400
aggtatatat aaactgagat tgaaaaataa gagaaaatat actcagggct gggctcagtg    17460
gctcaaacct gtaattccag tgctctggga agctgaggtg ggagtattgc ttgagctcag    17520
gagtttgaga ccagcctggg aacacagtg agaccctatc tctacaaaga aaaaaaaga     17580
aaaaaaaat caccgaggtg tggtggtacc catctgtagt cccagctact taggaagctg    17640
agacaggagg atcactggag cccgggaggt tgaggctgca gtaagccatg atcatgccac    17700
tgtactccag cctgggctgg acaaagtgag accctgtctt aaaaaaaaaa aaaaaaagt    17760
actcagctgt tactaatggt tactgctggg ggatgagatt gaattggaag gagagaggag    17820
aggtacgggg ggcaggaaag ggagacaata atgagggact ttcagtttta ctttacataa    17880
ttttctttta agtattggaa tttaggtgat ttttcctttg gggttttctg tattttccaa    17940
tcacaataaa taaataagt tataaatatt tgttgcatga atgaaatgta taaacccatt    18000
tatgtatgta ttttttttaaa attagtatat tattaagtct atacaatatt agtatattgt    18060
tatgtatgta taagcttttt aacatgaagt ttgcagaata tagtacttct tccaaactct    18120
atgacatggg gggaactgaa gtatggggat atcttgtacc agtgtaagaa ttcaagaaga    18180
gaccgtgtgt ggtggctcat gcctataatc ccagcacttt gggatgccaa agcaggatga    18240
tctcttggag ctaggcgttc aagaccagcc tgggcaacat atcaagaccc catctctaaa    18300
aaaaaaaaa aaaattaact gggtgtggta gtgcgggcct atagtcctag ctattccaga    18360
agctgaggtg ggaggattgc ttgagcccag gagtttgagg ctgtagtgac ctataccagt    18420
gattatacca gtgcactcta gcccaggcaa cagagtgaga cctggtctca aaaaaaaaa    18480
aaaaaatcaa gaagagcaat ctggatatga gcatttggga ttttttagcaa actgctgaga    18540
ttttgtctat agcttgaacc tttcttttag ctaacttgat gatactgatg ataagcaagg    18600
actgtctttt taaaatgtt tacttcatta ttttcctgac agaaatgaca tcagatgtac    18660
catcactggg tccagccatt gcctctgaa actctggacc tggaattcaa ggtggaggag    18720
ccattgtcca gagggctatt aagcggcgac cagggtgagt ttgagtgtag tgtgttatga    18780
atatctctcc tataaaccaa ctttagttgc tgaatttatt tagttgctga actcacttcg    18840
ctattcctga ccatctcact tcaacttgat tacttactac actactgtca tataagtctc    18900
cttagtccct gtattttgt ttatgaagaa tttgttttta tccaagtttc ccgtaagcag    18960
ttcttttttt aaaccaaaat ttccgtaaga taaaggactg tagctaagcc cagagattt    19020
actatgcctg agaaaactgt ttgctgcttt cattaagctt tgtttctgtt ttcccaaaat    19080
cattttggta ggctgctttt ctgaatttag agaatgctga gctctagaat agctgtcttc    19140
taagttattg atatgttgct tggtttggaa tgcagagtcc attcagctcc aaaagtatt    19200
attaaattcc taattagtgt tatggcattg tgctgattcc aagtaggata caaagatgaa    19260
taagacacag tccttgtttc taagttggtt gtgttctgat agaaataatt attatacaca    19320
```

-continued

```
tgaatatatg atagaatatg cctagttttg ttaggaacaa atttgatact atgtttttct    19380
gtgtatggaa atatgcattt gttggtaaag actgagaaaa gcttcagaaa ggaggttgcc    19440
ttagagggc  ctggaagaat gggcactatt ttatttactt tttggtatta aattttcctt    19500
tttccttctt tttcttttta aaaattgtgc agctaattat aaccagtctt taagttttgt    19560
cccaccaata gtaatggaag agtgatgctt gggttcagtg gtaacatgag taacatatta    19620
agacttgtta tatgttcagt agctttacag attttaacca tttgctgaag cataagctga    19680
ataagtaact ttctaagatt gtaaagctag taagtgtcag atataggata tgaaccttag    19740
gggtttagct ttgtagctta ctctttaaac actgtgttat gtttatgtac agtaacaaac    19800
aaaagtatta taaatatcaa aattagggca tcacttgaga aagtcatagt atatttaaaa    19860
tggaatgcta tgtagttata agcgacaaat atgtttcagt gtagaaagat gttcacaatc    19920
tattaagaaa ggttacagta ttatagtatt tcactgtcaa aagatatgta taacatgtac    19980
ataggaaaaa actgaaagaa tatataccac atttctgggt aatagtatta tgggtgactt    20040
acggtttctt ttgttttga  tttttcagat ttttgaaatg aacatgtatg attggtaatc    20100
agaaaaatat attaaaggaa gtctttaaaa attttctttt tggttttttt agagacaggg    20160
tcttgtaccc tggctggagt gcagaggcac aatcatggcc cactgcagcc tcaaactcct    20220
gctcaagcag tcctcctgcc ttggcctccc aaagtactgg gattacaggc gtgagccact    20280
tcacctgtcc taaaagaagt cttttaatat ttcttttatt tttatttact tatttatttt    20340
cgaggcagag tcttgctctt ttgccaggct ggagtgcagt ggtgtgatct tggctcactg    20400
caatctccac ctctctggtt caagggattc tcctgcctca gcctcccaag cagctgggac    20460
tacaggcgtg cgccaccacg cccagctaat tttgtatttt ttagtagaga tgggatttca    20520
ccacgttggc caggctggtc tcgaactcct gacctcaggt gatatgccca ccttggcctc    20580
ccaaagtgct gggattacag gcatgagcca ccatgcccgg cctaatattt ctttatttta    20640
tttattttat ttttattttt ttgagatgg agtctcgctc tgtcgcccag gctggagtgc    20700
agtagtgtga tctcagctca ctgtaacctc cacctcccag gttcacgcca ttctcctgtc    20760
tcagcctccc gagtagctgg gactacaggc gcccgccatg atgcccgact aattttttg    20820
tattttcagt agagacgggg tttcaccgtg ttagccagga tggtctcgat ctcctgacct    20880
cgtgatccac ccgccttggc ctcccgaagt gcgggattac aggcacgagc cactgcaccc    20940
ggcccatatt tcttttaaag aaagattgga aaatacagaa agttagaaag aacaataaaa    21000
aggccaaaat ctactaccat gttttttagt gcatgtcctt cagtctttat atgtaaattg    21060
tttttaatag ttatgtaatt atatagtttt acatggccta gtcttttcac cttatataaa    21120
taataagcaa tacacacgca cacacacatt ttggcacctt atataaataa taagcaatac    21180
acacacacac acatttcgga gacagagtct tgctctgttg cccaggctgg agtgcagtgg    21240
catgatcatg gctcattgta gcctcaactt cttgggccca ggaagcaatc ctcctacttc    21300
agttctccga gtagctggga ccacaggcac atggcaccat acctggctat tttttttttt    21360
tttttaaag  acatggtctc actacgttga ccaggctggt ctaaaactcc taggctcaag    21420
cagccctccc atctcgacgt cctaaagtgt tgggattaca gacatgacct actgtacctg    21480
gcccttaaa  aaaatattgt tacatattct atataaacat aatttttatt tatttttttt    21540
tgagacggag tctcgctttg ttgtccaggc tggagtgcgg tgatgcgatc ttggctcact    21600
gcaagctccg cctcctgggt tcatgctatt ctcctgcctc agcctcccga gtagctggga    21660
```

```
ctacaggcgt ccaccaccac gtctggctaa tttttttttt ttttgtattt ttagtagaga    21720
cggggttttta ccatattagc caggatggtc tccatctcct gacttcgtga tccgcctgcc   21780
ttggcttctc aaagtgctgg gattacaggc atgagccact gcgcacagcc ataaacataa    21840
tttttaatgg ttgcgtgaaa ggatgtactt aacttcctat tttgggacat ctaaattgtt    21900
ttgaagattt tgctgttaca tatgatgcta aaaagaactt ctttgtacct aaactttttt    21960
ttcctatttc atattatttc tttagattct tagaaataga gttattgggc tgagcacgga    22020
ggctcatacc tgtagtgcca gcactttggg aggctgaggt aggaggatta cttgagccca    22080
ggaattcaag accagcctgg ggaaaatggc gagacttttt tttctttgac ttagcaatta    22140
tctttcttt ccttccttcc ttcatttttt tcctttgact tagcaattac ctttccctcc     22200
ctccttccct ctctttcccc ttcccttttt tttttttttt ttttgagat gtagtttcgc     22260
tcttgttgcc taggctggag tgcagtggcg caattttggc tcactgcaac ctctgcctcc    22320
cgggttcagg caattctcat gcctcagcct cccgagtagc tgggattaca ggtgcccgcc    22380
accacaccca gctaattttt gtatttttag tagagacgag gtttcaccat gttgactggg    22440
ctggtcttga actcctgacc tcaagtgatc cgcctgcctc agcttcccaa agtgctggga    22500
ttgcagatgt gagccacagt ggctggcccc ttttctttt tgagacaggg tcttgccatg     22560
tcactgaggt tggagtgcag tggcccaatc tcagctcact gcagccttga cctcccaggc    22620
tcaaggcctg cagcccctcc cgcccccca acccaagtag ctaggactac acatgcgcca     22680
ccatgcctgg ttagtttttg tatgttttgt agagacggga tttcaccgtg ttgcccaggc    22740
tggtcttaaa ctcctgagtt caagtagtct gctcgccttg gcctcccaaa gtgcgtggac    22800
tacaggtgtg agcaaccatg cctggctgag atttttaaa ataaaaaaat ttagttgagt     22860
gcagtggtgg gctcctatag ttccagctaa ttgggaggcc aagatgggag gatcccttga    22920
gcccaggagc tcaaggtggc agtgagctat gatcatgcca ctgtactcca gcctgagtaa    22980
cagagtgaga gcttgtctct taaaagaaa gaaaggaaga gatagagaga aagaaagaat     23040
ttgagttact gggtagatag ataggatttt acaggtgacc agattagggg attcaggaag    23100
gaggaagagg agcaaacact ttcaggattg atgctgtatg tgtacttcaa atgcgaccca    23160
tctagaggcc cataatatca aggtatccca atagtagaag taaaaagagt gatcactagg    23220
ttaaggtggt aacatgagca atatttagt tcaatagtgt acagagatta taagggggatt    23280
ggtctatttt attgtttata atctttccta atctcccttta aagaaattca cttcttcttt    23340
ccctgaatgt ctgtagcatg ttgattgtac cccttatgtg acactttcct attctcactt    23400
gttttatatt tgtatttctc taggtgaaga gccccttgag ggcaaggttc ttgttttttac   23460
ctcacctagc acagtgtctt gaatgaagta tatattacat gtttattaga tcaatgaagg    23520
aaagaaacat tatctaacaa tcttcgtagg tattaagtca ctcctttatg taagatcact    23580
gctttgaaag atgtttcaga aatttggtaa cacggcttag agcagactct agaaatgaaa    23640
catggacctg aattatttac gttaattttt tcttattttt tctgagtgga ttcctgctcc    23700
ctttacagag gttgtagtct gattgaaaac tctggcaaag attgactgct actctaggaa    23760
agtgttaagg tagcagaagg tacttttgtt tctattgccc agttttgtac tttttttttt    23820
tgagatggag tcttgcagtt gtcgcccagg cttgagtgca atggtgcgat cttggctcac    23880
tgaaacctcc acctcccggg ttccagcaat tctcctgcct cagcctcctg agtagctgag    23940
attacaggca cccgccacca tgcccagcta atttttgtat ttttagtaga gatgggtttt    24000
cagcatgttg gccaggctga tctcgaactc ctgacctcag gtgatccacc cacctcagcc    24060
```

```
ttccaaagtg ctgggattac aggcgtgagc caccactcct ggccccagtt ttgtacttct   24120
ttgcctagtt tgggactatg aacaagagga aatgtagctt tgtttgactt ctgccacttc   24180
ctctttccat tcttccattt gggtgggtgt tccggtagct tgtgttgaga aattttaact   24240
tcttaatgtt ttgtattatc agcaggctta aagtatttat tgttggcttt cctcaggctg   24300
gattttgatt atgatggaga agggaacagt aaattttga ggtaagagac tgaaaaactt   24360
tccttagatg tctgatatta aaaattagtt tatgatcttt atacttctga cttgtaaatt   24420
tttgtcctta ggtctaagga gagtacttca tcctaaaact ataaatattc atatatctca   24480
gaaaattttt aagcattccg ttaatatctc tagagaaagg acctcagtga ggagaggacg   24540
gcatttacaa accctctgta tcagttctct gctacttcat agcctaaaaa gaacaacagt   24600
tcgttatttc tcaattctgt ggattgactg catgtttatt ctgcttatct cacctagact   24660
cactcataag actgcattct cagctggtca gctgagaact ggactcagct gggatggctg   24720
ggtatttctg tctatgtgtt tttttatcct caaggaggcc agactgaatt ttttcatgtg   24780
gtgatggcta caatctacag cacaaatccc agtgtgcaag tgcttatcaa gcctctgctt   24840
atatgacatt tgcttatgtc ccattggcca aagcaagtca tatgttccag gtgtgagtgt   24900 gtgaggggt tacacaagga agtacatact gagaggtgta attcattggt tgaggtgtca   24960
ttaatctgtg actctgtcat accctctgac acctgttgac acctcttata ggtagcagga   25020
attggaattt gtattttttg ttttttgtttt tttttttttt gagacggagt cttgctctgt   25080
cgccaggagt gcagtggtgc aatctcggct cactgcaacc tccgcctcct gggttctagc   25140
gattctcctg cctcagcctc ccaagtagcc gggactacag gtgcgtgcca ccatgcccag   25200 ctaattttg tattttatt tttttatttt ttattaattt tcttttttat tgatcattct   25260
tgggtgtttc tcgcagaggg ggatttggca gggtcatagg acaatagtgg agggaaggtc   25320
agcagataaa caagtgaaca aaggtctctg gttttcctag gcagaggacc ctgcggcctt   25380
ccacagtgtt tgtgtccctg ggtacttgag attagggagt ggtgatgact cttaatgcgc   25440
atgctgcctt caagcatctg tttaacaaag cacatcttgc accgccctta atccatttaa   25500
ccctgagtgg acacagcaca tgtttcagag agcactgggt tgggggtaag gtcatagatc   25560
aacagcatcc caaggcagaa gaatttttct tagtacagaa caaaatagag tctcctatgt   25620
ctacttcttt ctacacagac acagcaacaa tctgatttct ctatcttttc cccacatttc   25680 cccctttttct attcgacaaa accgccatcg tcatcatggc ccgttctcaa tgagctgttg   25740
ggtacacctc ccagacgggg tggcggccgg gcagaggggc tcctcacttc ccagaagggg   25800
tggccgggca gaggcgcccc ccacctcccg gacggggcgg cggctgggcg gaggcgcccc   25860
caccaccctc ccggatgggg cggctggccg ggcgggggct ggccccgcc tctctcctgg   25920 acggggtggc tggccaggcg ggggctgccc cccacctccc ggacggggcg gctgccgggc   25980
ggagatgctc ctcacttccc ggacggggcg gctgcgggc ggagggctc ctcacttctc   26040 agacggggcg gctgccgggc ggaggggctc ctcacttctc agacggggtg gctgccgggc   26100
agaggggctc ctcaattctc agacggggcg gctgccgggc ggaggggctc ctcacctccc   26160
agacggggtc gtggccgggc agaggcgctc ctcacctccc agacggggtg gcggggcaga   26220
ggcgctcccc acatctcaga ggatgggctg cggggcagag accctcctca cttcctagac   26280
gggatggcgg ccgggaagag gcgctcctca gttcccagac tggcagccg ggcagagggg   26340 ctcctcacat cccagacgat gggcggccag gcagagatgc tcctcacttc ccagacgggg   26400
```

```
tggcggccag gcagaggctg caatcctggc actttgggaa gccaaggcag gcggctggga    26460
ggtggaggtt gtagcgagcc gagatcacgc cactgcactc cagcctgggc aacattgagc    26520
actgagtgaa cgagactcag tctgcaatcc cggcacctcg ggaggccgag gctggcggat    26580
cactcacggt taggagctgg agaccagccc ggccaaccca gcgaaacccc gtctccacca    26640
aaaaaatacg aaaaccagtc aggcgtggcg gcgcgcgact gcaatcgcag gcactcggca    26700
ggctgaggca ggagaatcag gcagggaggt tgcagtgagc ggagatggca gcagtacagt    26760
ccagcttcgg ctcggcatca gagggagacc gtggaaagag agggagaggg agaccgtggg    26820
gagagggaga ccgtggggag aggggagatgg agagggagag ggctaatttt tgtattttta    26880
gtagaaacag ggtttcacca tgttgggcag gatggtctcg atctcttgac ctcgtgatcc    26940
gccctcctcg gcctcccaaa gtgctgggat tacaggtgtg aggaatttgt attttgagt     27000 tgttaatatt ctggagcttt taaaatggac tatttatttg tttgtttttt tgagacagag    27060
tcttcctctg ttgcccaggc tggagtgcag tgctgcagtc ttggctcact acaacttctg    27120
ccttccaggt tcaagcgatt ctagtgcctc agcctcctga gtagctggga ctaccacacc    27180
tggctaattt ttgtatttt agtagagacg gggtttcacc atgttagcca gactggtctt     27240
gaactcttgg ccttaagtgg tccacctgcc tcagcttccc aaagggctgg ggttataggc    27300
ataagccacc atgtccagcc tattttcttc ttatttttt gagacagggt cttactctgt      27360
cacccagact ggagtgcagt ggcacagtct cggctcacta cagcctcgaa ctccagggct    27420
caagcgatcc tcccacctca gtctcccaag tagctgggtc tacaggtgtg agccataata    27480
cctggctaat tttaaaatga tgttgcccag gctggtctta aactcctgtg ctcaagcaat    27540
cctcccacct tggccttcca aagtgttggg attacaggca tgagccactg tacccggcct    27600
gaaaatggac cttttaatat attgatgaag gagttctttc agaaagggg gatattcttg     27660 ctgaagacca attgcttgtc ttcttttcaa gtaagaaaaa cagtaagact caaaaggaag    27720
agaactttga ccgcaatctg cttttttct ttccagagtt gaaaatatta cccaggtagt     27780
ctgtacgttg ctgagtaaca gacaatttga taaaggagcc caatgaaaaa aaatgattt     27840 gattgtgtgg gtgcccagat ttaatatcat ttatttattt tctttctttc ttttttttg     27900 agactgattt tcactcttgt tgcccaggct ggagtgcaat ggtatgatct cggctcaccg    27960
caacctctgc ctcccaggtt caagcgattc tcctgcctca gcctcccgag tagctgggat    28020
tacaggcatg cactaccatg cccggctaat tttgtatttt tagtagagat ggggtttctc    28080
catgttggtc aggctggtct tgaactgccg acctcaggtg atccgcccac ctcggcctcc    28140
caaagtgctg ggattatagg catgagccac cacacccggc ccatttcttt ttcttatttg    28200
tttgttttgt taactaagtt ttttctttaa ttgggaaagt aatataagtg tattttatta    28260
cagaaatttc aggctgggcc tggtggctta cacctgtaat cccagcactt taggaggctg    28320
aggtgggtgg atcgcttaag ctctggaatt caggaccagt ctgggcaaca tggcaaaact    28380
ccatctgtac aaaaaatgtt acaaaaatta gctggaagtg ctggtgtgtg cctgtagtct    28440
cagctactcg ggaagctgag gtgggagggt ggtttgagtc ctggaagcag agattgcagt    28500
gagccgaggt tgcgccactg ctctccaacc tgggcgacct tgcctcaaaa aagaaaaaca    28560
acaaaatttc aaacagtgca gagttatata tagtgaaagc acatcttcgt tttactttgg    28620
accttcagaa ctcctttttt ttttttgag aggagtctcg ctcttgttgc ccacgttgga     28680
gtgcagtggt cgatctctg ctcattgcgt cctccgcctc ctgagttcaa gctattctcc     28740
tgcctcagcc tcctgagtag ctgggattac aggcgcctgc caccatgccc ggctaatttt    28800
```

```
tgtactttta gtagcgacaa ggtttcgcca tgttggccag gctggtctca aactcctgat   28860
ccactcggct cggcctccca aagtgctggg attacaagtg tgggccactg ccccagcct    28920 ggaccttcaa aactctttag acaactacag tttccagttt gttgagtatc cttccaaaaa   28980
tagtatatat agaattgtat ataaatgtgt atgtgtgagc atacacacac ttatctcctc   29040 agttttttt  acacaaagga tgtccatatt gtaaattgct tgccattttt tagttttata   29100
ttgcttcata cagttaatag catctatctt cttttttat agtaacattt aaagttaagg    29160
ctcatatttc tggctactca ctagatgaac tttgccaaat actcttgaaa acaacaaccg   29220
tgacttggcc atcataaaga aatagttgca agtggaagta taattctcta agaggtctct   29280
tgagacttaa tgagtctcag taaatgtgaa gaagggaaga gatttcaatt tctggagaag   29340 atagacttt  tcaaacagct ttattgagaa ttcctcctat tgagaatcct gaattataat   29400
gatacatgct attagtggaa cttcactgtg tgtatgaaag atgtgagggt aaccactagt   29460 cttttttat  acccgtgaat tagctctaac cctgagtcat tgcttccata aaatccagta   29520
gtcacaacta catgcagatc caaagagagg ttcgtttgtc cttttcctaa ccataaaaaa   29580
agactatcgt agtttatctt accaagtcgg gttgttgtgc ctgagaaaag cactgccgaa   29640
ttccctttcc cccttctttt tttttttttt tttttttgag acggagtctc gctctgttgc   29700
cacaaatgca gtggtgtgat ctcagctcac tgcaacctcc gcctcccagg ttcaagtggt   29760
tctgctgcct cagcctccga agtagctggg actataagca cgtgccacca cacccagcta   29820 attttttgtat ttttagtaga gacggggttt caccatgttg gccagagtgg tctggatctc   29880
ttgacttcgt gatccgccca gtgttggcct cccaaagtgc tgggattaca ggcgtgagcc   29940
actgcgccca gcctccccct tcttttttctg ggtatatata tacaaaataa tcgaaggcag   30000
aatcttgaag agatatttgc acactcatgt ttattggccc attttgcgca atagataaga   30060
ggtcgaagta accgaaatgt ccactgacag atgaatggtt acagaaaatg tagtatgtac   30120
atacaaggga atattattca gccttaaaaa gaaagaacct gtcatatgct gcaagatgga   30180
tgaatcttaa ggacattata ctgaaagaat aagccaataa caaaaagaca attactgtat   30240
gattccactt acatgaggta tctacaagta gtcaaattca tagacacaga aagtaaaatg   30300
gtggttgcta ggggttgggg tgaaggagaa atgagaaaat ggtgtttgat gagtatagag   30360
tttcagtttt gcaagatgaa aaagttctag atatctgttg cacaacaatg tgaatatggt   30420
tagcactact caactgtaca cttaaaaatg gtatacagta aattttatgt gttttttacc   30480
agaattaaaa aaaaacccaa aactaacccc ttactttaga attgtgctga caggccagtc   30540
agctgtgttg tcattagatc atcatctttt tttggtgtgt ctggtaaggg taatggaaat   30600
accagaaacc tgacaaataa tagttgtggg tcttttaagt tctatggggt gctgctgtta   30660
tttctatcac tttgtgatgc ttttccattg gcttttttc  tattgaatat tttcacccct   30720
ttctagttta cttttcagag tgaaatagat ataacaagtg taatgctttg aaacaatcct   30780
ttttctctcc ttcaggtgtg atgatgatca gatgtctaac gataaggagc ggtttgccag   30840
gtaatattgt agtaggtaat atattgtaat atataatatg atccatgttg tagaaccaga   30900
cagtcctagc atattgactt aattttttct ggatgagacg gaatttctct gtttaatatc   30960
tttcctattt ggaagtatgt gaaacttagt attataacta tcatttatgt tcaggtgaca   31020
tggcttcaaa ctggcggtat attttataca gtgttttttct gtgtatgtga taactaaagc   31080
aatgtgcttg caaggtttcc ataggagcac aaattatgga ttttgtgctt gcatttatta   31140
```

```
ttaaatggat ctacaaaaat aggaatacag ataatggttc tgtaattaat ttatttattt    31200
tgagacagag tcttgctctg ttgcccaggc tggagtgcaa tggcgccatc tcggctcact    31260
gcaaccttca cctcctgggt tcaagcgatt ctcctgcctc agcctcctga gtagctggga    31320
ttataggccc ctgccaccac gcccagctaa tttttgtatt tttagtagag atggggtttc    31380
accatgttgg tcagggtgat cttgaactcc tgaccttgtg atccgcccgc ctcggcctcc    31440
caaagtgctg ggattatagg tgtgagccac cgcacccggc ctatttt att tttttgagac    31500 agagtctcac tccatcaccc atgctgtagt acagtggtgt aatctcggct cactgtaacc    31560
tctgcctcct gggttcaagc tgttcttcca cctcagcctc ctagtagct gggaatatgg     31620 gcatttgcca ccatgcctag ctaattttg taataatttt ttttagcaga atggggttt      31680 caccatgttg gccaggcttg tctcgaactc ctcacctcaa gcgattcacc cacctcagcc    31740
tcccaaagtg ctgggattac aggtgtgagc cattgtgcct ggcctattat tttatttaaa    31800
gatatgtata tttttagag acattgtttt cattgtgttt cccaggctgg agtacagtgg     31860
catgatcata gctcactgca gcctcaaact ctggggtttc agtgatcctc ctacctcagc    31920
ttcccaaata ttgggattat atgcatagcc accatgcctg gttggtcctg ttttttaaa    31980 aatgacagta agaggcgggg agtggtggca tatgcctgta attccagcac tttgggaggc    32040
agatgcaggt ggatcacttg aggtcaggag ttcaaaacca gcctggccaa catggtgaaa    32100
ccccatctct actaaaaata taaaaattag ccgggcatca tggtgggcac tcataatccc    32160
agctactcta gaggctgagg catgagaatt gcatgagccc gggaggtgga ggttgcagtg    32220
agcagagatg gcaccattgc actccagcct gggtgacagc aagattttgt gtcagaaaaa    32280 aaaaaaaag acagtaagga aacagttttt gtgacaagta gagttttgat tgaaaaaaac    32340
ttaaatttgt ttaaattacc tatcaagatg atgaaatata cttttttta ttaaattctt    32400 aaatgtcagt tttcttttta gaagttttt attaaatatt aggcaataaa ttattctttt    32460
tttgaaaatt aagtttgtag ctacctcaga aagatgaata attcgttatt tcaaaatcca    32520
gtgattaact gagcacttag cacttagtat ttgttcgttg ctgatgctcc tggtctcggg    32580
aacatacttt aagaaccgtt gatgtagaga gattagaaat atcaggggaa gtagttaaaa    32640
actattctgg agtggtgaga tgcaatctca ggctttgaat tagagggtat tacataaaat    32700
gcattgtagg gatatttctc tggtagcagt tatagaattg attaaaggga tggactgtta    32760
gactgtaggg aggtagatag gaagctgttg aaataataag acagctataa aatcatgagg    32820
gcctgggtta cagtggcagt ggtaacagga aaggagtgaa gttaagaggt ttttgaagaa    32880
taatttgttt atcgaaacta attgaaataa atatttgtaa agtctttagg atgtgaacca    32940
tctctaaaat gagaagttaa tcatagatat ttggaggata gttttt caag cttcattgaa   33000 aagtcaggcc atcagttatt attggcagta tcttgatgaa atttcaaaaa gccatgaaaa    33060
catcgcatga atgatttgg ttttcatttg tcctgcttaa tgtgcatata tttcattcag    33120
aaatactgag gtggattagg gattgtggat ctgtagtagt agtagtagta gaaataggaa    33180
ttttagatgc ttaacttttt tttaaataac agaattcatt catatgatgt gttaaggtag    33240
tgcccctcac atatcctcct tgggatatag agggtcttaa aagctgaaaa cttcttgaaa    33300 aactttggg attatatgca tagccaccat gcctggttag tcctgttctt ttaaaaatga    33360
cagtaagagg ccgggagtgg tggcttatgc ctgtaattcc agcactttgg gaggcagagg    33420
caaaagttgc tcaactttt gaaaaaaag aagtttgtag tttgttaagg aactatctag    33480
aagaaataac ccaaggaatg taaaactcta aactgctgaa tatcactcag ttctccttct    33540
```

```
cttgtcatca gaatatatgc gtaaatttt  acattcttct tcattgttac tgtgttattt  33600
tctgcctatt gaccatttta taaaaacatt cccatatatt gataaggtta ttgtatttgt  33660
cattttaat  agctaaataa tcttttagct tgttaacctg tcatacttag acattttatt  33720
cagggcctct ttatctatat aaatatattt aaaatggaat tgacacattc ctgacacaat  33780
ggcctgccaa caccttgcta tttcctcagt tgccacccat cattacagta tctcagtttt  33840
ctagaaaaat ttagtgatgg ttctttgtat ccttctccag tggagaggga attgttactt  33900
ttgatccatt cctgtgtggc tatactgcag agaaatggca aaaggaccga atcaaagtta  33960
ataattattt taggaacaaa tcaataatag aagatatgcc agaaacctac ctcttagagt  34020
tatttatata atttctccag tgaaatctgg ttggttattt tgtcattgtg tggcacgtgc  34080
atgtgttgtt tgtgtgagag ggagagagat tatatttgtc atcacttgtt tgatagtatc  34140
atctttaatg tactctgtct ttaatttctt cattatagaa tagcacatgt ggatatcatt  34200
ttctttccag attgggagca gtgcatgaaa atggtattcc tgaattccct tggttggttc  34260
ttgttcagac tctgtatatc tttggtccct acagagatcg attggcaaaa tgctttctgt  34320
gtttagatca tgttaatttta ctatatattg gctttgcttt tatgttgacc tttatcttgt  34380
aagttacttt ttcttatcc taacagatgg ctttgtagag ttacaggcaa ggttcctgcc  34440
tataattcca tttcctcct  ctcttctctg catctgttta gttctatatc ctttctctc   34500
ttctttctcc ttttcttttt tttctccct  ccatttcctc tccctccctc cttccttttt  34560
tcccttcctc cctcccccct tccttccttc ttttttattt taattttagc ttagttcatt  34620
aattctattt ttaggtcgga tgatgagcag agctctgcgg ataaagagag acttgccagg  34680
taggagaaca gtgtctttta gcatgatgaa gcagatgatg ctgcttttc  tatccttttt  34740
cttactcttt cttttcttcc cctttctctt tgtattttc  cttatctgtg gcaagagagg  34800
acaagatttt ttagaagttt gagtgtaaca ggaactttgg cttcccccat cagaaagtgg  34860
gtgagttgag ggaactttgc ttagggattt aagaaattgc tattagtttt aagttttttt  34920
ttcttttct  ctttatgtca gtactaagtt tcacagaaca aaaagctctt agaaggaatg  34980
caaccgtgcc agttggtgct ttaacaggga atactctttt ttatcagaaa accaataaat  35040
atatctgtat ttgtgattag ttcccagtat ttaggcctca gcatttactc cacacctcta  35100
ggaaactcac acctattttc ctatgaagac tcacagccta gattattctc acaacagaac  35160
tagtgttgct ttggtgaccg aatcctttct tgcggtagtt ttctagaaaa gttttagttt  35220
ccttgatgtg gctatttaaa agaccaggtt tctgtactta cgtgtcagaa atctgtcaga  35280
tactaggaag atgagtgctt tatgtttgag aatagaattt tatgtcttag gcaaagtgta  35340
actaaatatg ggcctatgtg gtgagaccct ttttgccatt tagaaaggag actctagaat  35400
tctcttggga gactgttgtt tgtaatgtag aaatgctgca gaagaaatat gcatagactt  35460
ttctgttttc tagtatctgt gatttggggg tgacttagga aatagatcat tgatgccaat  35520
acccattttt actatattcc ccctttttc  tactatttcc tctttaatct gggtcacaaa  35580
ctcattttgc tgccagttta actcgagctt cttactaacc ctttcactgt tcagaaaatg  35640
gatttggcat gatgtggtgg agaaaacatt gtattgggaa gagagcagcc tggggaaagt  35700
cacttaccta cttgacctcc ctttgctctt ctcagaaaaa agagatttat gttagatttt  35760
taattttctt actttctttt tttttggac  aaagaacttt tgttcaagta gaattcttaa  35820
gtggtaacag aaataaataa aagagataaa gcaggccggg cgcagtggct catgcttgta  35880
```

```
accctagcac tttgggaggc cgaggcaggc agatcacgag gtcaagagat ggagaatatc    35940
ctggccaact tggtgaaacc gcgtctctac taaaaataaa aaaaaaaaaa actgggcgtg    36000
gtggtgtgcg cctgtagtcc cagctacctg ggaggctgag atagcagaat tgcttgaacc    36060
cagaaggcgg aggttgcagt gagccgagat cccgccactg tactccagcc tgggtgacag    36120
agcaagactc catctcaaaa aaaaaaaaaa aaaaaagaa gagagagat aaggcaaata     36180
tttgagtaga agcagaaatg cagcatgttg catgattatc tccttgaggc atccccatgg    36240
aggacactga gaaacttaat gggcttttaa aaattcctgt tggaaaactg ctggattatt    36300
cctgttaaca gtgatatctt tctgtcttaa ttttgaggaa gtcagtgttg gagctgtggt    36360
ctatttacct gggtgagatt caaattgtct tgtcagacct ttaatcatcc tcctctccat    36420
tccactcctc cagttaactt cgtcccagac tggggaccca tatgggactt ttagtagatg    36480
gtgtatctta agtcttgtaa gaagtttagt gcactggcag cacacccaga taaagaaggt    36540
aggactttgt gcattaatgg gccaaataaa acttcaaaat cttcaaattc tgccttttaa    36600
tgttgcaaat aagagagagg cttaccatat tttatagacc aaggaaatct gtactatcaa    36660
ttcttgtatc agctatggag ccacatactt gagttggcaa aaattggtcc ttttattttc    36720
tggccttaa atagttgaat tagtaagcat gggagttaac caagctgagg ttatatgttc     36780
cataggaact taagtgagta aaatcagcat ttaaaaatac tatcttttt tttctcttgt     36840
tttttgtttt ttgttttttt ttgaaatgga gtcttgctct gccacccagg ctgaagtgca    36900
gtggtgtgat ctcagctcac tgcaacctcc acctcccaga ttcaagtgat tctcctgtct    36960
cagcctccca agtagctggg attacagatg catgccactg tgccctgcta attttttgtat  37020
ttttagtaga gacaggattt caccatgttg gccaggccgg tctcaaactc ctggcctcaa    37080
gtaatccacc tgcctccatc tcccaaagtg ctgggattac aggcatgagc caccatgcct    37140
gacctgtcgt ttcttaaaac agcttttgtt ctgagggagt ggtaatttac aaaggatgtg    37200
aagtttccag gaaatagggg gaagggaatt acattatctt cttgttctct gtctgcctta    37260
ttagttctgt ttcatgcttg ctttgcatga gaaggttggc aaaccttatt ttaactgctg    37320
agacttaagc atcactaaat ctgaatacca cattcttcag cagcacactt ggtatccata    37380
tcactctccc tgctaccaaa tgaccagatg tgaccacctg gatggggctt ctctttcttt    37440
ccatgcaggg aaaatcacag tgaaattgaa cggcggcgac ggaacaagat gacagcctac    37500
atcacagaac tgtcagatat ggtacccacc tgtagtgccc tggctcgaaa accagacaag    37560
ctaaccatct tacgcatggc agtttctcac atgaagtcct tgcggggaac tggcaacaca    37620
tccactgatg gctcctataa gccgtctttc ctcactgatc aggtctctgg gacttatagt    37680
tctgagagag tctggaatct gggtgaatct cttgaaagtt ttcgtttttt ggacaagaat    37740
tcagcttttc aggaagaagt cagacaatgg gaaaacgaat ttcaatcctt ggctataaca    37800
ttaattagca ttgggacaat gagaagtaga gaagagttgt gaaaactatt taataagcta    37860
ataagtatta atatttgaga acttgactca tgaatatagc atataggatg gaagaagaac    37920
agtggaatca cagaggaaat gactatgtcc atggaaccaa ttttctttct tgcctttagg    37980
gttatagaag atggaagaaa tctatttctt atccctgaag cagcttctag ttttagtaat    38040
agaatgaatc tgtcccacct ttggtgatag aagaactgag agtctaattg ttgcttaggg    38100
atgtgctctg ttacatgtga tcactatgaa aaaagaagg cgtaaacatt ttctgccttt     38160
caggaacttc atctgaatat aagtatgtga gtggcaggat atcacagaaa ataacaggaa    38220
aatgcataaa gagaggaatt gtatttttta attagtaatt ttatgtggga ctagatagac    38280
```

```
atactgaagg gatggctaaa gtgaatagaa tggctagact tgagtgagga tggttaggga    38340
agacttctga gggtaaggaa gccatgttct gttttggtta ttaaaataac atgatcattg    38400
cagaaaaatt tggaaaatgt aggaggtata aggaagaaaa aaatttactt cagtatcaat    38460
caagtattcc cttaatgcca ccaatttaat caaatgatta gaaagaagga gagaatatag    38520
tttgagaaaa tggaataaga atttccaaa taggatggtc tacttaaaac tacatacttt     38580
gtagctatat acattgaaat agttaatatg ttctaacagt acatgtgcaa gtattcaaca    38640
gactccagtt atgcaccttt tgtgggcaaa ccaggtgtgt tgtgctgtga gaaatagaaa    38700
gaatggtgag acaaatggtt ttctggtgga aacagacatg taaataaata aattaaacat    38760
agaactagtt ctataataga agtgctgtaa tgaatcctgt aaaatgcaga tatggaaaat    38820
gagttgggga gtagtgttgt ggattttggg aagcacttga gcaaaaacct agaagtgtgg    38880
aataattggg ttatgcaaag aaagtcaagt ggtttagcat gttttttggta gataatagga   38940 aggtaggctg ggatctaatg atggaatgtt taggtgttaa agaatttaga ttttaatttt    39000
tatgcagtgg ggagacataa aaaatgtatt agatctggta gcattttaag gattgattga    39060
aagcagggcg actacttaat tagttttggt aaaagatgac taggacagtg acaaagcatt    39120
ggaaagtaga atcgataaaa ctgaattatc actggaatgt gagagaatag ttagattttg    39180
aggcttctag cttaggagga tgctgttaag aatattggaa gagcacggca ggttttttt     39240 tttaagaggg aaataatgat tcaggttttg ggatgttgat gttgagttgc tggtagaata   39300
tttataaata ttttacagat acttgaaatt caagtctgct gaaagctcag gaaaaaacgt    39360
tagtcatgtc tagggctata gacttggtta ttatttcgta gtggggaaga gtgaatatgg    39420
tttcccagga agaaagtatg gtattaataa agagggctta agatgaactt tggaaatgtc    39480
tacatttaag acttgaacaa aggaaaggaa gtctgaaaca aagaggaag caaaaattgg     39540 agtacagtct catagaagaa ggtagggaaa aataaaattt aaaggataag atggacgaca    39600
ttgtcacatt ctgcagagag gttgaataaa gtgatgaaga cccaggaaaa gggacttgaa    39660
ttggtaatta ggaggacatt agtaacctca ttaaaaatat atgtatgctg ttcctggcag    39720
aacaaaaacc aaaccaaaca ggaaaacagt agtttagagt gagagtgaag tgggattgag    39780
aaataattga aagtaagag gataaagcca gtgaatataa cattattctt agtataagct     39840
tgctgctgaa aaagagagat gaggtgggtc aaactgaggg aagatttatc tagaattgag    39900
aaaacttgat catttttata ggcctgaagg gaaagagaga aagtgggaat atttgtcaag    39960
caagatccta aaagagacc agagaggatg gaattaagaa gtcaattatt gttcatggta     40020 agccttttt ttttttgagac agggtctctt gctctgtcgc tcaggctgga gtgtggtggt     40080
atgatctcgg ctcactgcaa cctctgcttc ccaggctcag gtgatcctcc cacctcagcc    40140
tccggagtag ctgggactac aggcgtgtgc caccacacct ggctagtttt gttttttgttt   40200 ttgttttgtt ttgttttgtt tgtttgtaaa gatggagttt cgccccattg cctaggctgg    40260
tcttgaactc ctggactcag tgaccctccc actttgacct cccaaagtgc tgggattacc    40320
ggcgggagcc gctgtgccta gcccaagcct ttttattctt cttgaatcct gagatagaga    40380
ggaagaggtg gatagtgaca tagagaaagt gaggaaacat gtattagaaa aaactttctt    40440
atcgatgaac tacatttagg gtggaaacct gtggctgtgg atcaggtgtg aaccagcagt    40500
tgcttacgga gagatgcatg tggcctgaag tgtcttactt cttcctgtga atagaaatac    40560
ttgttttttc agagtaaaat attaacttct atttcttttt cttgcgcagg aactgaaaca    40620
```

```
tttgatcttg gaggcagcag atggctttct gtttattgtc tcatgtgaga caggcagggt    40680
ggtgtatgtg tctgactccg tgactcctgt tttgaaccag ccacagtctg aatggtttgg    40740
cagcacactc tatgatcagg tgcacccaga tgatgtggat aaacttcgtg agcagctttc    40800
cacttcagaa aatgccctga caggtgagag ttatgtgtat gggaaatgaa tgagaagtcc    40860
tttcttgttt ttttcctgag acttaagaga tgttttagct gttaaattgg tttgttgact    40920
ctggcaaggc ttcaagaatt ttctacttta atgaatatag tcagttcttt ttatccatat    40980
gagattatct actttgtggc tcagcctag aaaatatttc attggtgata atattttaca    41040
tttatcttaa tattggtata aatagaacag taaaagccaa acctacaata cttttttttt    41100
tccgttctaa aagaattatc catgttttta tctcatttgt atggataatt atctggtatt    41160
ttttctacct cctggtgctt ggctttgtgc taggttcaat gataacagct ttttattcta    41220
tagatatggt tattggtcaa tgtataaggt gttttctgtt gttgttgttg ttgttgtttg    41280
tatctgtact gttgttcttt ttttctcccc tattttatta tgttcagtct tttggccaga    41340
gtttggctag aggaaacaag tcatatctat tcttgagcaa ctctagaaaa aaatttaaag    41400
tggaagcaga taaaaaaact ggtagttaaa atgcaagaaa tttcaatata ctcatattag    41460
tgttgttgat cttagttttt cctccttttt tcccacccaa aaaagagaca gggtctctct    41520
cttgcctagg ctgagtacg gtggcacatc atagcttact gtaatcttga actcttctgg    41580
gctcagtaat ctgcctgctt acagcttctt gagtagctag gagtagttca tgtcaccaca    41640
cttgaccaat ttttaaattt tttgtagaga caggttctgt ctgttgccca gactggtctc    41700
aaactcctgg ccttcagcat tcctcctccc atcttggctt ctcaaagggc tgggattatc    41760
ggcatgagcc accacacttg accagttttc ccctcctta tgtttttatg atttcatttt    41820
tctagttctt cctttccc aaaagttgtt cttcgtttct gtataataaa gagacaaac     41880 agatctatat gtttctataa catataaaat tacttggttt ttttctttt aaaattttt     41940 ctttttattc tttttttttt ttttgagaca aggtcttgct ttattgctga ggctagagta    42000
cagtgactct tcacaggcac agtcatagca cactacagcc tcaaactcct gccctcaagc    42060
agtcctcctg cctcagcctc ctgattagct gggactacag aaaagtactt gttttcaac    42120 caatgacatt tactctgtat gtatgtctgt atgtgtatac agataatcag ctatgagaat    42180
atagccttgc ctcttgtttt ctactactac tttccactcc tacttttcct tgcacaatgt    42240
tattttcaat gctgccttg aacttaagag tgagattcat tgatgataat tgaagtattt     42300
taggcttgaa aaaaattca tctcctgctt ggtcagttct gttataagca aggagattaa    42360
gggcatgaat aggatgctta cttatctttg ccttcagtat ctctcccct cttcccaca     42420 cacaaaaatg cactccagac tgctcttcac atcttcctc agggcgtatc ctggatctaa    42480
agactggaac agtgaaaaag gaaggtcagc agtcttccat gagaatgtgt atgggctcaa    42540
ggagatcgtt tatttgccga atgaggtgag tgtcaagctg aggattgtga tttggtatag    42600
gaaggatcaa gagctgagag tttttattct gtcagagtta agttggatta gctccagtgg    42660
attaaattta actctccata cccagatgga ttgtaacaca gaataaagta tttggaaagg    42720
gaactaacgt ttctgaactt gccagacact atgataggtg ctttatatct gtcatcttat    42780
tttatcctca caattgcctt gtagtgtaag attgatggtt accattttgc agatggaaaa    42840
acagatataa agaaatgaac ttggccaggt gcagtggctc aaggctgtaa tcccagcact    42900
ttaggaggct gaggcgagtg gatcacctga ggtcaggagt tgagaccag cctggccaac      42960 atggtgaaac cccatctcta ctaaaaaaaa acaacaacaa aattagacgg gcgtggtggc    43020
```

-continued

```
gtgcgcccat aatcccagcc acttggaggc tgaggcagga caattgcttg aacccaggag    43080
gtggaggttg cagtgagccg agattgtgcc attacactcc agcctaggca aaaagagtga    43140
aactctgtct caaaaaaaaa aaaagaaaa agaaaaagaa atgaatttcc cactgttaca    43200
tactgtttga tacaggattt tgttttaatt catagtagtc tgactacaaa acctctactt    43260
tttccctgtt acaacacaag gcaatatcca tttactcaga ccatttcttc ttttttttt    43320 tggttagaaa tttgagactt cctatgtctt tcagtaggtg tttagtgttt ataaattata    43380
tactgtacgt tttaggattc tgtagaaaat atggtggtcc tttctataca ggtacaaaag    43440
gcatctcagg gtcacaaagt tcaggctata taatggaaat tgactacatt gtactgagag    43500
gatagttgct agaaattatg ggtaggatat taaaggtttg cttggagagg cacaaaattg    43560
aacattatgt ggtttagtga tttattttta tttttattta tttatttttt tgagacagag    43620
tcttgctctg ttgcccaggc tggagtgcag tggcatgatc ttgggtcatt acaacctcta    43680
cctcctgggt tcaagcgatt ctcatgcctc agtttcctga gtagctggat tgccaccaca    43740
gctggctaat ttttgtattt ttagtaaaac agtgtttcac catgttggcc aggctggcct    43800
caaactcttg acctcaagtg attcgcctgc gtcagcctcc caaagtgctg agattacagg    43860
cctgaaccac tgcacccagc gtgtaattta gagtagcttc tagacccaga ctgctggatt    43920
ttgttttaat ccatattcta tggatttgaa ttctagcttt gatgctatct tctgaaacct    43980
tggatgatta catgactaca ttgtgctttg atttcatcat ctcacattgg cgataatgtt    44040
aatactgact ttataaagtt gttatgaaga ttagatgaat taatatatgt aaagatattt    44100
agaacagagc atgacacata ttaaccctat gtaagtttta tttttgtttt aaaggatagg    44160
gagagggaaa gtagcattgg caggagtatc ccaatatgtg gacatggcta atgcaaagac    44220
ataggcaaga gcaagataat aatgaactgt agcaattaca ttaagttgtg gttaatgtag    44280
agcaggagta agcaaaccac agcccttat ttgtaaataa agttttattg gaacatagcc    44340
atgcccatat ttttacatat tatctatggc tattttcatg ctataatgct agagttgact    44400
agttgcaaca gactttctgg cccgcaaagc tgaaaatatg tactatctgg tccttttacag    44460 aaaaagcttg ccaactcttg atgttgagaa tgtttgcata tgaagaacat atggaacatt    44520
ttgacttcaa attctaaaag ttttagaaat actaaacttg acctatcttt atccttcatt    44580
attagtagca ttaccaattt tctatgtctg gttgtatcca gagcatgtta ttctgctatt    44640
actgtggaaa gttcttttgat agggcagtct gattgctttt aatctcttta ttccttgaaa    44700
caggtgtggc agtagctctg tggacccagt ttctgtgaat aggctgagct ttgtgaggaa    44760
cagatgcagg tgagatccta agtggtgaaa accaaaggga tggccaaata cctgcagaga    44820
tcatcacatt tttacctgtc ttactgtagt cgttccttca gcagctctca cttgcatccc    44880
ttacctccca cttaacatcc cttacctccc acttactttt tttctggcaa tattttccta    44940
aacttctaaa acttctcttg aaaatcctgt ttaaggaagt cgctatgcta ttttacctac    45000
tttcctccta ctgcatacct tttgttact ttacttggc aagggtaaaa atgtggcggt    45060 cattttggg tgggaaagat gattatcctg ttttctaaac tcctaagagc ataaacttaa    45120
aagtactaag gcagcattgc cctttgagtt ttacgggtag attttttttt ttttttcaa    45180 actcctgtaa ctcttctagg aatggacttg gctctgtaaa ggatggggaa cctcacttcg    45240
tggtggtcca ctgcacaggc tacatcaagg cctggccccc agcaggtaag aaagtgaaat    45300
agtaaatatt tccccttggt acagttggtt cctcacagag tccatgaaag ctaatattta    45360
```

```
ttatatacct ggtatatgaa atgtactttt gtgtaagatg aaagaaaata ggaaaagaaa   45420
atgtacaatc cttcccttcc attattgagc ttttattcca gttgaggaga tagataactc   45480
aggctggaaa atgattcagt attggctgtg tcacagaatg tggtttttat gtgaacaaat   45540
ttatactgaa catatgtatt ctaagcattt gttgcaaaga aacttagaca ttgaatgcag   45600
ttaatttgag aaagatttct aaagtaggaa caagactttg agagaaaagg ggaaaatgcc   45660
tttattgtaa taacttatca agaggatatt ctctgcaaag actttaaatc aagctttgag   45720
cagattagct ttaccagaac ttgaggtcaa acaaggaatg tgagaaaggt gattgggttg   45780
caggatcaaa gttttaagtt ggcttgtcag agtttccaaa tcttagcaac tttattactt   45840
ccctgctgcc tgggtattat tggaaagtag gggttttggg gagacagaaa ctaagagaaa   45900
agagaagcaa ggtgatgtgt tttggaaaaa ggttaaactt tggatgtgga gaaacctgga   45960
tgtgattcct gtcattgtta cttattagtg gcatcaccta gggtaagttg cttgaccttt   46020
ataaagctca gttttctcat ctgtaattca gagttagtac atcctgtata gggttttgt    46080 gaggattaga tttaatgtaa ggaaagcatc cagcccagtg cctggcatat ggcaggtaac   46140
ccaataaaag taattaatgt aatttaaaaa aatttaactg aagtagtaat gacatttgaa   46200
ctacttagtc tatatactat ataagccaca cagttaaagt atgtgatctt tcatacctct   46260
atgtagcatc aaggaatact attttttctgg ataaaaagag tataactatg caaaaaacag  46320
gggagaaatg cagtcttctt ccctttctgt gtaaaacatt ggttttctc ttttccaagg    46380 gacatgaata actattgatg gttggtataa cttcattttg ggttgcttgc taactttaaa   46440
agttacagat taggcaaagc ataaattttc tgcctataac atggtcatag aatggatgtc   46500
ttcatatgtg ccatatttgg ccagcatagt tttttagagt actctgggta ggacttgtat   46560
tttccagttt actataatta acatgggtaa aatgtaggaa ttaatatata tgtaaatact   46620
taaaacaatg actggcatat atggtaagtt ttatatactt gtttattctt atttatcatt   46680
ctctattgct ttatgcttag cctcttcata actagatgta ttttgttttg ttttgctttt   46740
tggttttttt tttgagaggg agtctcactc tgtctgtcgc ccaggctgga gtgcagtagt   46800
gcgatctcgg ctcactgcat cctccgcctc ctgggttcaa gtgattctct cacctcagcc   46860
tcccaagtag ctgggattac aggtgcatgc caccatgcct ggctaatttt tgtattttta   46920
gtagagatgg ggtttcactg tgtcggccag gctggtcctc aagtgatccg cccaccttgg   46980
cttcccaaag tgttgggatt acaggcgtca gccacggtgc ctgcccata aataggtcta    47040 ttttgaatct ttacttgtct gagttttgaa ggcatttgag ttggaggtcc ccgttaaacc   47100
ttttaacgtc acgtttctga aggtgttcc ctcccagatg atgacccaga ggctggccag    47160
ggaagcaagt tttgcctagt ggccattggc agattgcagg caagtatgaa ttttccacat   47220
ctatattccc gttcaattag agcagatctt caggactcat tcctgttaat tttcttttac   47280
tttctgaata caaatgaaga attccataaa actctcaaaa tttgaaggaa tatggcattt   47340
atagtgacca ttgctattct tggatttaag taaagttgaa aagtatgaga ggagggagat   47400 cttttttcccc ttgtcttaat tttagcttta ctatgcttaa ttttctattt ccagttaatt   47460
tcctttgccc ctatacaaaa gaagaaagat ccttttcatt gtatcattac ctgactaaca   47520
atagaaaagt ggaattattt tgattttttc ataagtatag ataagtttct ggttacttg    47580 taccatatca acctgagtaa tgagttcagc atagccagta tgtggatttt agattgaata   47640
aactttattc ttacttttact aacttggtaa agtgtaaatg tatgggagca gagctagacc   47700
ttatgccttg tctgattgtg attgtcattt ttttttcctt tttggataaa atgtgaaagt   47760
```

```
ttagaaagtc ctaaaactgg gaatcttatg tctatgcaaa agaccatgag gagataggaa    47820
atacatctgt aaataatggt atcattttac ctcatttta tctcttcact ctcaggtaac    47880
tagttctccc aactgtacag acatgagtaa tgtttgtcaa ccaacagagt tcatctcccg    47940
acacaacatt gagggtatct tcacttttgt ggatcaccgc tgtgtggcta ctgttggcta    48000
ccagccacag gtgaggagct ggagctccat taggcctcca ttttcctttg gctatgttga    48060
cattatgtaa tcatgtagtt cctaagacag ccaaaacata tcaacctcag ttaagaaaaa    48120
gagatcatca tattctgtta gtacctaaca ttattttcag cttcctatta ggactgtcat    48180
ctcatgtaga gaaatatggc ttgtcaaacc aggtgggagc agcaggtaca aatatgtatt    48240
tatttttgt tgttgatatt aatacagatg attcaaaggt actcatatta attagttata    48300
ccagtatagc tacatttaga taattcatgt aattacctaa atgaataatg cccataaaa    48360
catgcagatt tagcaccagt tattataatt tactcatgca acagaccagt tagccatctc    48420
tgaattgacg catcatataa acttttaaaa ctgttgtggg tcggaaggac ttctggctgt    48480
ggctatgtga aagaggttgg tgaaaaagag gtcttgaaaa caagaacaa agagaattta    48540
cactacctga ttcaacacta actataaagc tattaccaag acactgtggt gttggtgtaa    48600
ggatagatat atagatcaat agaccagaat aaggtctatt cttatacttg tcaactaatt    48660
ttcagcaaag gtgacaagac aattcaatgg ataaaataaa tatttctaac aaatggaaca    48720
attggatatc tgtatgcaaa aaaaaaaaa aacaaaaaaa aaaccacacc caaaaatgaa    48780
aacacataga tcttacctca tacaatttac aaaaatcagc ttagaggcct aaatgtgtaa    48840
gagctaaagt tacaaataaa ctcctaggag aaaatctttg tgattttgag ttaggcaaaa    48900
gatttcttac actaaaagca tgattcacag aagaaaaaaa attataaatt ggatttaatt    48960
gtaattaaaa tttgccctct ttaaaggata ttattaagaa aatgaaaaga ccagacataa    49020
atggagagaa aatagttaca agtcatatac ctgaaagagg atttgtacca ggaatatata    49080
aacaactcat taagacaaac agctggtaaa aaagagcata agacttgaca tttgactgaa    49140
gaataaaatat gcatttatgc acatgaaaag atgctcaaca tctttttacc attaggaaag    49200
tgcaaattaa aatcacaatg agataccact atatacccac tagaatggct gtaatcaaaa    49260
agtattggtg aaaatgtgta gaagctggaa ggaaccctca tacattgctg atagacatgt    49320
aaaatggtat agctactagc tttgcaaaag cattttggca gtttcctaca aagttaaaca    49380
tactcttagc ctataaccta gcaatttat tcctgagtat ctacctaaga gaaatgaaaa    49440
catgttcacc catagatttg tacacagttc atatctgtat tattcataat agccaaaaaa    49500
atgaaaacta tttaaacgtc cattaacatt ttgtaaatga atacacaact gtgttgtatc    49560
catgtgagaa tactactgag cataaaaagg aataaactac tgataatgca gccatgtaga    49620
tgaacttcaa aaataccatg ctcaatgaaa gaagccagac ccaaaagacc acatattatg    49680
ttgttttatt tatatgaaat ttgtagaaat agcagaacta gagaggcaga aagcagattt    49740
gtggttggct ggggagttgg agtgggagca gagattgact gcagatggca caagggaaca    49800
tcttggggca gtgaatgtgt tctgaaactg gattgtggta atcattgcac aactataaat    49860
ttagtagaca tcatcaaatc atacacttag aatggctgaa ttatgaatgt aaattttatc    49920
taaaatttat aatctcatta aaataaatgt ataatattct gagaaagaaa aatgtttag    49980
aagccagctc cttaacagat tctgcctttt tttagtagat ttcatctttt gtttattgtc    50040
ttttttttt ctcctcctca cttaactata atcttaggat taaaacagaa gaaataaaat    50100
```

-continued

```
ccaggtcccc agctgatgga ccaggccagt tagatgacca taaaattata tatgttggct   50160
gggcacggtg gctcacacct gtaatcccag cgctttggga ggccgaggcg ggtggatcac   50220
ttgaggtcag gagttcgaga ccagcctgac caacatggtg aaaccctgtc tctatttaaa   50280
aaaatacaaa attagccagg tgtggtagca caccctgta atcccagcta cttgggaggt    50340
tgagacagga aaattgcttg aactcaggag gtggaggttg cagtgagcca agatcgcgcc   50400
atcgtactcc agcctgggca acaagagcga aactccatct aaaaaaaaa aaagtatata    50460
tcttactctt ctttctgtat tctaggaact cttaggaaag aatattgtag aattctgtca   50520
tcctgaagac cagcagcttc taagagacag cttccaacag gtaactttt tcctggtttg    50580
gttctgaata aatatttgtc atattcactc cataaatatt gactactgat taactgaaca   50640
ctgtggcagg cactacagtt ttatgttctt tagtagttaa tctgcatttt taaggaatag   50700
aaaaggacta atactttgaa attatggata atgcccaagg tatttctgtt tggctttggc   50760
tatttactgt cttgtattca attaactgta tccaaggagc tgtctttaag gtatttaaac   50820
tattgcgcca ggcatggtgg ctcatgcgcc caacctctgt agatgctgtg aaaatagatg   50880
ttttcctcgt ctgggcatgg tggctcacgc ctataatccc agcactctgg gaggctgagg   50940
caggtggatc acttgaggcc aggagttcaa gcccagcctg ccaacacag tgaaacccca    51000
tgtctactaa aaatacaaaa aattagcctg tatggtggt gcatgcctgt aatcccaggt    51060
actcggagg ctgaggcacg agaatcactt gaacctggga ggcagaggtt gctgtgaact    51120
gagatcatgc cactgtactc tagcctggat gacagagcta gactctgtct caaaaaaaa    51180
aagataaaaa agaaaattgt atacttcact aagcttgtag tagaaaaatt cattttatat   51240
agttttttt ttttttaga aggagtctag ctctgtcgcc agggtggagt gtagtgtgca    51300
atctcagctc attgtaacct ctgcctctta ggttcaagcg attctcctgt ttcagccccc   51360
cgagtagctg ggattatagg cacatgctgc cacgcccagc taattttgt attttagta    51420
gaggcgggt ttcaccacgt tggccaggat ggtctcgatc tcctgacctc gtgatccacc    51480
cacctcagcc tcccaaggtg ctaggattac aggcatgagc cattgcgccc agcctagact   51540
gttcttttat ggatgagtga gagtcgtaat gaattatata agctgactgt taattgtcat   51600
tctcaggctc cagctcctga aaatatctgg tgaattttat agacatggct tttgataacg   51660
gtttttactt tgtattagac aagttaatta acctctttaa gtctcagtag tgtcgttatt   51720
gatacaatga atatattaat agtacctaaa ttcagacggt tgttgggaag attaaataag   51780
gtaatgaata taaacacat cacccagtat ttgatacgta gtattacaaa ataagtggtt    51840
agcttctaat actgtttatt tttatttttt taattttag gaatatagag ttaaagatt    51900
attttctatt ccatgagact agtatctaaa ataacctaaa attggctggg catggtcgct   51960
catgcctgta atcccagcac ttgggaggc tgaggcaggt gatcacttga agccaggagt    52020
ttgaaccagc ctggccaaca tcttgaaacc ctgtctctac taaaaataca aaaattagcc   52080
gggtatggtg gctcatgcct gtagtcccag ctacttggga ggctgaggca tgagaattgc   52140
ttgaacccag gaggcagagg ttgcagtgac ccaagattgc cccactgcac tccagcctgg   52200
gcgatagagc aagactgtct aaaaataaaa taaaataaaa aataaaataa ctaaaattac   52260
ttttaaaaaa taaagcaaa acaagactaa agccaactta attttattta tggaaacctc    52320
tgtagatgct gtgaaaacag atgctctcat ctgggtgcag tggctcacac ctataatccc   52380
agcactttgg gaggccaagg caggcggatc atttgaggtc aggagtttga gaccagccta   52440
gccaacatgg tgaaacccg tctctactaa aaatacaaaa attagctggg cgtgatggtg    52500
```

```
cacgcctcta gtccccagct actcaggagg ctgaggcagg agaatcactt gaaccctgga    52560
ggcgaggttg cagtgagcca agattgcacc actgcactcc agcctggcga cagagcgaga    52620
ctccatctca aaaaaaaaaa aaaagaaaaa gaaagaaaaa cagatgttct caggtttcgg    52680
ggaaaaaata ggattgaaga gcaatatata agctatattc tgtgtcctta aacttaccaa    52740
atttctggta tagacttgta aagctaggtc agagtatctt taatggattt cccaagggaa    52800
gtagggaaac agtcttttcc ttcctggaaa taagttatta ttcctatttg actagaatag    52860
tattaggttg gtgcaaaaga aattgtgatt ttttgccatt ttttaaatg gcaaaaaatg     52920 caattacttt tgcaccaacc taataagaaa gcttgagtct ctggccgggc tcagtggctc    52980
acgcctgtaa tcctagcact ttgggaggcc gaggcaggcg gatcccgagg tcgggaaatc    53040
gagaccatcc tggccaacat ggtgaaaccc cgtctatact aaaaatacaa aaattagctg    53100
ggcgtggtgg cacgtgccta atctcagc tacttgggag gctgaggcag gagaatcgct     53160
tgaaccaggg agtcggaggt tgtagtgagc cgagattgcg ccactgcact ctagcctggt    53220
gacagagcga gactccgtct caaaaaaaaa aaagtctggg cacggtggct cacacttgta    53280
atcccagcac tttgggaggc cgaggcgggc ggatcacaag gtcaggagat caagaccatc    53340
ctggctaaca tggtgaaacc ccgtctctac taaaaataca aaaaattagc tgggcgtggt    53400
ggcacgcgcc tgtagtccca gccactcggg aggctgaggc aagaaaatcg cttgaacccg    53460
aggggtggtg gttgcagtga gcagagatcg tgccactgca ctccagcctg ggcgacagag    53520
ggagactccg tctcaaaaaa aaaaaaaaaa gcttaagtct ctgaaaggaa gcatgagaaa    53580
tatgcttcca tgtttaatca cttagttttt actctcattt tgttttaata ttgaaaaata    53640
ttggtgcctc aaggacaatg acaagagttt tagggttata gaaattggaa aatttttatt    53700 tattttgta atgaaaattt tctatgagtt ccactgatgg catgaaaact ttttcaggta    53760
gtgaaattaa aaggccaagt gctgtctgtc atgttccggt tccggtctaa gaaccaagaa    53820
tggctctgga tgagaaccag ctcctttact ttccagaacc cttactcaga tgaaattgag    53880
tacatcatct gtaccaacac caatgtgaag tatgtattat acaggagtgt gaaaaaactg    53940
tttttcctct gttctcacaa cagaaaacac ttctgatgcc ctatgtgggg ggtaaacaat    54000
caagcaacaa cacaaaaatt tagccgggcg tggtggcatg tgcctgtagt cccagctact    54060
ctggaggctg agacaggaga atcacttgaa cctgagaggt ggaggttgca gtgagctggg    54120
atcatgccac tgcactccag cctgggctac agagcgagac tccatttcaa aaaagaaaa    54180 agaaaaaaga aatcaagcaa tcagtagtgg acaccagctg ggtgtccttc cattcaattc    54240
agttcactat ctactggag atagcatcag atcccccaat ttgtgtatgc agtaccacaa     54300
gactgctccc acttctgatg ccagttgcaa gccccaggtt gttttacctg tgcatctgac    54360
tgaccagctg tctcccatga cccctactt gggttcagtc aatttgcttg aatggctcag    54420
ggaacattta cctatgttta ccagtttatt ataaggata ttacaaagga tactttgtac     54480
atcagatgaa gagatagata gggcaaggta aggaggaagg agtgcagagc tttcagaccc    54540
tttctgggtg ggctacctc cggggatctc catgtgttta cctatcaaga agctcctcaa     54600
acccagtcct tttgggtttt aatggaaatt tcattatgta gccatgagtg attaaatcat    54660
tggccattgg taatcaactt aaccttaggt accggctccc ctccatgagg ttgagggtta    54720
gggctaaaag tcccagccct ctaattttac cttgatcttt ccagagatga gcccccatct    54780
tgaagctacc taggggttgc cagccctcag tcaactcatt agcagacaaa aagacactta    54840
```

```
tcacactgaa gattccaaag attttaattg gtaaaaatcc aggtccactt atacatggat    54900
ttttttcagt aaatatatta gaaaattctt ttgatatttg tgacaatttg aaaaacccaa    54960
aaataagcta catagcctgg atatattgaa aaaattagaa aaagttagcc atgtcataca    55020
tgaatgtatt aaatatatat aaattctagt ctattttatc atttactacc atacaacata    55080
tacaaatcta ttataaaaag taaaaatgct ggacaggtgc agtggctcac acctgtaatc    55140
ccatcacttt atcactttgg gataccaagt tgggatacca agttgagcag atcacttgag    55200
gtcaggagtt cgagaccagc ctggccaaca tggtgaaacc ctgtctctac tgaaaaaaaa    55260
aaaaaaaaaa aaagaaaat acaaaatta gctgggcatg gtggcacacg cctatagtcc    55320
cagctacttg ggaggttaag gtatgagaat cacttgaacc tgggaggtgg aggttgcagt    55380
gagctgagat cgcaccactg cactccagcc tgggtgacag agggagactc catctcaaaa    55440
aaaataaaaa taaaaatgta tcacaacgta tacatacaca ccgtttgtac aatggcacca    55500
tttgtagttg agagaaatgt aaacaaatgt aaagatgcag ttttaaatca taaccgcgta    55560
aagttaacta tagtatatac tgtactgttg taataatttg gtagccacct attgctcaat    55620
tgttgccagt ttgcttaaaa tgctgtgtga tgctaatcat ctcttcatga gcaattcact    55680
ccagtaaatt gcatattgca gtaaacagtg aaatctcatg gttcttgcat attttttcatc   55740 gtgttgagtg caatactgaa accttgaata acatttggga acagtatgaa gtgccactag    55800
tgatgctgga agtcttccca agaagcaggg aaaagtcatg acattataag aaaaaggtga    55860
attgcttgat atgtactata gaatgaagtc tgcagctgtg gttgcttgcc acttcatata    55920
gatgactcat cttgtaagtc atcttgtaag atgatataag cttatgataa cgataaatac    55980
agtacagtgc tgtaaatgca ttttctcttc cttatgattt tcttaataac attttctctt    56040
tagctttatt gtaagaatac agtacataat acgtacaaca tacaaaacgt gttcaactgc    56100
ttatgttatt ggtaaggctt ctggccaaca gtaggctatt agtagtaacg ttttgggaga    56160
gtcagaagtt tacagtcgaa ttttcgatgg cacagggtc agtgcccta gcctccatgt    56220 tgagcaatca gttgtatttc ataatatcac ataggcattt tccaatgttg ggatttctaa    56280
tgtaccaact cttcttagtc ttatcaagct atcccttct cctctacttt tctagtatta     56340
aacaccatta gtttgaagtt cttcattttc cagcttatag gatttgggat agttgatcag    56400
agtagagtaa ggttttttg ttttgttttg ttttgttttg ttttttcaga cagggtctcg     56460
ctctggcacc caggctggaa tgcagtggtg tgatcatggc tcactgcagc ttgaacctcc    56520
caggctcaag tgatcctccc acctcagtcc cctgagtagc tgggactaca gacatctacc    56580
aagacgcctg gctaatttt gtattttttg tagagatggg attttccat gttgcagagt     56640 ctggtcttaa actcctgggc acaagcagtc catcgtcctc ccaaagtgct aggatcacag    56700
gcgtaagcca ctgcacctgg ccagagtaag attttacaaa caataattca gagactaggt    56760
cctgagatgg aagggttag tttcaattct atgtatcaac tctttctgga aaggactatg     56820
ttttgtacac cagtttattg ctctagtctg gcaggatttt cctctggagc aggggtaggc    56880
aagctctttc tataagtggg gctagatagt aaatatttta ggcttgtgg gccatgtggt     56940 ctttattcca cctactcaac tctgctgtag catgaaaaca gtcatagaca aatgaaagaa    57000
tggggctgtg ttccagtaaa tctttattta gaaaaacagg cagtgggcct gatttggtca    57060 gttttctta gagcatagct acatcctcct ctttcattag ttactgttcc tctcttttgc    57120
acttttctat ttgagttttc tttctcagtt tcttttttaa aaagtttat gagatatatt      57180 tcacatacca tatacctcac tcatttaaag tatacagtgt tttttagtat atcacatagt    57240
```

```
tatgtaactc ttactgcagt ctaatttcag aatattttca ttcccccaaa agaaattcta  57300
gatcagttaa cagtcattcc ctgttctttc ccccggctct gaaattctgt ataactatga  57360
atctgttgtc tttataaatt tgtctattct agacttttcg tataaatgga atcatagact  57420
ttgtaattcc tttgtaactg gcctattttta cttagtataa tgtttacaga ggttatctgt  57480
actgatacat gttgtagcat gtatcagtac ttcatttctt tttattgcca ataagattt   57540
cattgtatgg atataccaca tactgtctgt atgttcgtta atggacattt ggttgtttct  57600
acttcttggt tatcaaaaat gcttccatat gtaaaatagg gataaggaac tgaaaaaatg  57660
cttcatgaa tatttgttta ctagttttta tgtggatata tgttttatt ctcttgaatt    57720
ccacccagga gtggaattgc tggccacata gtaactctgt tttaccttt gaggaactgc   57780
caaactgttt tccaaagctg ccccatcatt ttgcattccc aggagctctg attcctccac  57840
atccttgtta acacttgtta ttgccttttt ttttttattg tagccatcta gtaggtatca  57900
attgtcaggt taccaccttg ccatttaatc ttttctttct gtagaattgg ccttgaatcc  57960
acctcttgaa gatcagatta tgactactta gcaaatatga ataataccta gtgacaagtt  58020
ttgtccaatt cagtctttag aacttgtaaa gtttaattct ttgctaacta acttagtata  58080
acagagtgga ttgagttaga aattttttatt aacttaggac tcaagtggat ggtcatggtc 58140
attgtagttc tttattttttg tctctttgca tctttatatt acacaacagc cttcatttt  58200
gtgtttccat tttgtttaaa ttttttaaaaa tttaagttgt ttgaaggact cgagtttctg  58260
gaaataattg ctttctccat gtttatgtat cattttccct accatgatta attttaatta  58320
gcttttaggg atttgtttgt ttgtttgttt cattgagaca gtgtctcact ctgtcaccca  58380
ggctggagtg cggtggcgct atctcagctc actgcaacct ccgcctccca ggctcaagca  58440
atcctcccat ctgtctcctg agtatctggg actacaggag cccgccacca cgcctgctaa  58500
tttttgtatt ttttgtagag acggagcttc accatgttgc ccaggctggt ctcaaactcc  58560
tgagctcaag caatccaccc tgcctcagcc tcccaaagtg ccaggattac aggtgtaagc  58620
caccgtgcct ggccagtatt ttatttttaa ataaatattc tttatagaaa atgtggaaag  58680
tattgaaaaa tacaaagaga aggaataaaa ttctcacact ccagatagtc tttgttgatg  58740
tacagtgtat gtactttcat ttttttacct atgcttttaa aaaatacctt atatgaatat  58800
atacacacat tcacaataac caggttttga ataccctagaa ggagttagaa cccaacaaga  58860
tgaccctgt gtcatagaac atggtttctg tttgctgaaa ctgacaccct agattaacta   58920
taggatagga ctttaatgaa ggatttattg attgttccac ctacagatga atctatagag  58980
ctttacatac agaatcttat tcttctcttt ctctctctct ccccccttcc tccctctcca  59040
cccccctcttt actgtctact ctggtttcct aggaactcta gccaagaacc acggcctaca  59100
ctctccaaca caatccagag gccacaacta ggtcccacag ctaatttacc cctgagatg   59160
ggctcaggac agctggcacc caggtaaaaa agggtgaaat aatcatctgt tgagcagtca  59220
cccaggggg ggtcatttgc aatcccatat atttttgtt cggttggtta atttttttt     59280
tttttttttg agaaggagtt tgctctcat tgctcaggct ggatggaata caatggcacg   59340
atctaggctc actgtgacct ctgtctcctg ggttcaagtg attcacctgc ctcagcctcc  59400
caaatagctg ggattacagg tgcctgccac cacccccggc taatttttg tatttttagt   59460
agagacgggg ttttgccatg ttggccaggc tggtgtcgaa ctcctgacct caggtgatcc  59520
acctgcttcg gcctcccaaa gtgttgggat tacaggcatg agccaccatg cccggcctgt  59580
```

```
ttaatttgtt ttaaggttct ttctccagat tctttttaa  aaaaaatttt tttttctatt  59640
tgtcttgtca actggccttt gacatatagg cagcagcaac agcaaacaga attggacatg  59700
gtaccaggaa gagatggact ggccagctac aatcattccc aggtgagttg tgtcctcttc  59760
gttgaagagg gtagggagta tttacttagg aagtgttctc cggtactagt tagaatgtac  59820
atatgttgta tatgaatttt agggttattg aattgtcatg ttaaatcttt aatggttatt  59880
tttatcattg tattccacag gtggttcagc ctgtgacaac cacaggacca gaacacagca  59940
agccccttga gaagtcagat ggtttatttg cccaggatag agatccaaga ttttcagaaa  60000
tctatcacaa catcaatgcg ggtatgtttc tttctcatta tccttttaaa ttctcattta  60060
gatcacttac tgatgggcat gccactgccc agtcagtaat cttccagtgt ttttccactt  60120
aatcataata ccacctgagt aaataggaac ttgctgaact aatatactac agcccttga   60180 ctggcccttc cccaactcct tttggtccac agatcagagt aaaggcatct cctccagcac  60240
tgtccctgcc acccaacagc tattctccca gggcaacaca ttccctccta cccccggcc   60300 ggcagagaat tcaggtgag  ccccgtatat atgtgctgct ttacagggcc ctgagggatt  60360
cagctgctga atccaaattt tattcttccc ttgctttctc tggttacttc agaaaaagca  60420
gtgaagcttg tagggcctag cgtgaggcaa acaagctgct tttcttcctc ctatttcttt  60480
gcacctgtcc tattgccatg ttctaggctc catctctgtg tgtcctggtc agtgtgtgac  60540
tgtcagtctt tcttgtcttt tccaaattgt tatcaaattt tccttaacct gcaggaagtc  60600
aaggggatct agggatagca ctagattgtc ctttgattcc tagcttctgt gataaatcta  60660
tccttttaat cttttaccct catttattcac tcctaggaat agtggcctag cccctcctgt  60720
aaccattgtc cagccatcag cttctgcagg acagatgttg gcccagattt cccgccactc  60780 caacccccacc caaggagcaa ccccaacttg gaccectact acccgctcag gcttttctgc  60840
ccaggtaaaa cttatcatct gtgtgttccc tgtgtattat ttttttgtttg tttgggcttt  60900 tttccgtatg taaaatcagt gttttctatt ttaaatacct tctccccaac ccctgttctc  60960
cggtttccaa tttccatctt tgttgagagt agctaattaa aaatcacaga taataaaaaa  61020
aaatctcagt agagtctgtg gttttcacct taaatcagaa ttgctcactt ggaacgtttt  61080
gagcacgtct gattttcaga tttgtttttgg agtaaattct aagatgtttc ctctttgttt  61140
aggactccat aaggcaggag caaaggagaa aattaatgac taacttacag tgatgtctgt  61200
ttacaaaaaa gttgaaaaat tctttttttt tttttttttg agacagagtc ttgctctgtc  61260
gcccaggcta gagtgcagtg gtgcgatctt ggctcactgc aagctctgcc tcccgggttc  61320
acgccattct cctgcctcag ccttccaagt agctgggact tgtacaggcg cccgccactg  61380
cgcctaattt ttttttttg tatttttagt agagatgggg tttcaccatg ttagccagga  61440
tggtctcaac ctcctgacct tgtgatccgc ccacctcagc ctcccaaagt gctgggatta  61500
caggcgtgag ccaccgcgcc tggctgaaaa attctttttt tttttttttc ttgagacaga  61560
ctgtcacttt gttgcccagg ctctggagtg cagtggcgcg atctcggctc actgcaagct  61620
ccgcttcctg ggttcatgcc attcctgcc tcagcctcc cgagtagctg ggactacagg   61680
gtgctcgcca ccacgcctgg ctaatttttt gtatttttag tagagacggc atttcaccgt  61740
gttagccaag atggtcttga tctcttgacc tcgtgatccg ccctcctcgg cctcccaaag  61800
tgctgggatt acaggcatga gccaccgcat ccagccgaaa aattctttta taatattcat  61860
atatataata taacgcacaa taatacact gtctaaagaa agattcttta atattactat   61920
atatttatgt tatacaagta atagttttaa aaagtcaaaa ccaaaagcag gttccagaat  61980
```

```
gttatatgca atacgatctc aattgtgtac aaaatgcatg agaaaataga aactggaaga   62040
aattatccaa acatgttaac catggaatta tgaatgattc ttatttcctt tatattttcc   62100
ttcactttct gaatattcta taatgcatat acagaactct catgagaaaa tagttttat    62160 aaaaaataca tcattaggaa caaatgaatg cagaacagac agaataatgg tgcagagtag   62220
tttttctctg catatggtac ttttttttgtt gtttgttttt ttgagacaga gtctcgctgt  62280
tgcccaggct agagtgcagt ggcgcgatct tggctcactg caacctctgt ctcccgggtt   62340
caagtgattc tcctgcctca gcctcctggg ttgctgggat tacaggcacg tgccaccatg   62400
cccagctaat ttttgtattt ttagtagaga cggggatttc accatgttgg cccggctggt   62460
ctggaactcc tcacctcagg tggtctgcct gccttggcct cccaaagtgc tgggattata   62520
ggcatgagcc atgagccacc ccgcctggcc tgcatataat actttactgt tatgaatgcc   62580
tctagtttta taaacttca cagtttataa gatgcttttca tttaattctt acaattttta   62640
ttaatcccat agttcattgc ttttttgtaa ttttatctca gctgcctaaa aaatagtgtc   62700
aagagagatt gagagttaat tggaagaaat atacaatagg aaataagtga tgagcttggt   62760
tcagaaggat gcagtgattg acagtgttga ctctcatagg catggtatgt gcaatgatgt   62820
taatgctgta tttgttctat atcccctctc catctctctt tagcaggtgg ctacccaggc   62880
tactgctaag actcgtactt cccagtttgg tgtgggcagc tttcagactc catcctcctt   62940
cagctccatg tccctccctg gtgccccaac tgcatcgcct ggtgctgctg cctaccctag   63000
tctcaccaat cgtggatcta actttggtga gtccagacca taaggagagt aacaggaaaa   63060
tcgcaccact aaagagaaag gatttggtag ttaaagttgt ttgcctgtgt tgtgggtaca   63120
ctgacctgat tgtagggaaa tgcaaggtga caatctattt agaatttaaa acctaccagc   63180
tgggtgcggt ggctcacgcc tgtaataccca gcactttggg aggctgaggc aggcggatca   63240
cttgaggttg ggagttcaac cccagcctga ccaacatgga gaaaccctgt ctctaccggg   63300
tgtggtaccg catgcctgta attccagcta ctcgggcggc tgaggcagga gaatcgcttg   63360
aacccaggag gcagaggttg cggtgagctg agatcgcgcc tttgcactcc agcctgggca   63420
acaagagtga aactccgtct caaaaaaata aaaataaaa aaaaaaact acccacatga    63480 aaaatacttt agcacatata acaaaaatca tgtgaatttt tatacattta atagtatgca   63540
catttaacct aaatgagtaa agaactctat ggaaaggctg cctggagaag aagaattaat   63600
ttagggctga gtttttgagat agaaaaggca ttgattggca gagagaagga cagagttatc   63660
ctaggtaaaa ttaatggctt acctatagtt gtttacttgt ggcattagta cacaatggaa   63720
ttgtgtagat tggagttgtt tattcttcct tgctgtattt ctagctcctg agactggaca   63780
gactgcagga caattccaga cacggacagc agagggtgtg ggtgtctggc cacagtggca   63840
gggccagcag cctcatcatc gttcaagttc tagtgagcaa catgttcaac aaccgccagc   63900
acagcaacct ggccagcctg aggtcttcca ggtaagagag tgaaaagact ttcaaaaatt   63960
agaagctggg agagaaaggg tccaggagga ggagagacag tgaaggaagc atgcctggat   64020
tgaggtgttt ggttgggggt atatgtgaga agacagagag ggataaatgt agggatcact   64080
gtcagttatt gaaagattg cagaagctag atgcagtggt gcttgtgtat atgatgtcag    64140 cccttagaa ggctgaagca ggggatcact tgaggccatg agttcaaagc caggctgagc    64200
aactagcctg atcctgtccc tgtcaaacaa acaaaaaagg agtatgaatt gagtgtgata   64260
cataccattt aaccagaaca gacaaattta gcaccatagg aagatgccaa agaaagttac   64320
```

```
tttagctcat tcaaatagct ccatataccc aagtcacagt agctttgggt ttaaaagaga   64380
cagaatgatt aaaataaaa agtagtgctc gcttcagcag catatatact aaaattggaa   64440
tgaatataga gaagattagc atggccctg cgtaaggatg acacacaaat tcatgaagtg    64500
ttccatttaa aaaattataa aaagtaaatg aaatagaaca taatgattat agccataatg   64560
gtctatttac acaagtcctg agggactgca agagtgaatg gagtaatctt aggcaggaca   64620
aaggaagagc tggtttaaag caaagattga agaaagcaa aacaggtctt ggtggaaaac    64680
aaataggata agagactcca tatatgtcta taggggggtta tatgaaatac agcaagcaga  64740 ttttctccc tttgaaaata ttgagaacta ggaaaaggaa aaaggtggaa ctgtaggagg    64800
aagacagaag ggattaggaa aaaaggctgc gatctaaagg agtcaaagtt gttggaagta   64860
aggaaggcta agagctcagc acagcaaaga ctcggggtca gggatggtag tgcagggaa    64920 tggtggagta gaacttggta agtgtaagag atcaaggtgt gtgacccaaa cttaatcttt   64980
ttcttttatc aggagatgct gtccatgctg ggagatcaga gcaacagcta caacaatgaa   65040
gaattccctg atctaactat gttttccccc ttttcagaat agaactattg gggtgaggat   65100 aagggggtggg ggagaaaaaa tcactgtttg ttttttaaaaa gcaaatcttt ctgtaaacag  65160
aataaaagtt cctctccctt cccttccctc acccctgaca tgtaccccct ttccccttctg  65220 gctgttcccc tgctctgttg cctctctaag gtaacattta tagaagaaat ggaatgaatc   65280
tccaaggctt ttaggactgt ctgaaaattt gaggctgggt gaagttaaaa caccttttcct 65340 tatgtctcct gacctgaaat tgtatagtgt tgatttgtgc tgagatcaag aggcaggtta   65400
gaagaacctg acatccactg tttgccttgg atagtatggc ttgttttttgg aaagaaattc  65460 tgaagagagt ggaggagagg agaaatgtcc tcatatttga ggaccatgaa acattgtagg   65520
tatatatggg gctttagcaa gtttgagcat aggctctttt tgctgcctgt gagcagtccc   65580
tctggaaaga aacatgtgag taagtgagag agagtgtgtg tgtatgtgtg tgtgtgtgtg   65640
tgtgcgcaca catgcttctg tatttcactc tttctcccta ttagggagtt atgcaaaatt    65700
tgtccccgat tttaccttg tcttctgtg tacttttcaa agagtcctaa ggagttaaat      65760
cttccaggta ttttccactt agtattgcag ccaaagaata tttaaataaa cgtctttgct    65820
gcgcttgcat ccatgcccag ccaatataca actgtaaagc aaatatagaa agtcggctgt   65880
tgatacgatt gtctgttatc gaacacattc agtgataaag ctgggttact gctgcttttg   65940
gtgctctcac cttatctgga agatctgcaa acattaccta aataggctgg caagataaac    66000
actttctgga acccgagact tggccataaa gataatgctg catttttctg tcagaatcac   66060
atatgatgtg tgttctgtag aggttatttc tgcatggaaa ctcaacttct tggattagcc    66120
gtcccagtga aaatcctcat tgttggagtg taaaccaaat acgaagccct cttgcaaagt   66180
agcctctttc atcccatact caaaatacc agtttagcaa gcaactgaga tttaagtctc     66240 tctggccta agaggttttt cctctttgct ccctccaatc ttgagattgg gttttgctttt  66300 agagtgcaag tatcataatt ccgtatgata gatgggggcct ggacacccat ctcaacaggg 66360
tcacttggta attaacaata gccatataaa tgcggataca ggttactacc ctcaccctttt 66420 accttcctca ggtaacagtc gtagatacca gcttttttttt tttttttttt aaattggctt  66480
tggccagtag ctaaagtgca agactgaatt aatgagaaga tatattaaat gtagtcatag   66540
gggactgagg agcaagggtg gccttgaaga ggccaaagga atgtccattt gctgagtttc   66600
ccttccttat gtctccagtc tggtgccagg tagtggagta aaaaggaga cagtttattt     66660 ttttattcta tgtgcacact tacagtatac atatatattt atatcacaat ttacgaaacc   66720
```

```
aaaaagttga gtttccaatg gaacccttgt tttttaataa tcgactttt  aaatgtgatc   66780 aggactataa tattgtacag ttattatagg gcttttgggg aaggggagga tagcgagaag   66840
atgctctggg ggttttgttt ttgcttttcc ttcagggttt tattttttgac tgttttgttt   66900 tcttgttggc catttctgta ttgctggcat ctgtgctaag ctttacagtg gcaaaaataa   66960
tgacatgtag caaagatttt caaacaaaat attttttcct tttgtaaaat ttcttgtgtt   67020
gtgtgatctt gattgcggct ttatcattcc tttccagttc ataaacaaca ggcacccaca   67080
accagaggaa tctatagttt aagctccaga catacaaaca taaggcacat tgtgtcttta   67140
atttcaggaa tcagaaatca tagggttctg atcacattgc acgcctcccc cctcacttgt   67200
cctcctgatc ctgacacatt ctgagtaaca tcagcaggaa tgctctgacc atgaggtggg   67260
ggttttgggg tgggcgttgc ctgggttctt gggagagagg ggaagagtcg ggacttgaaa   67320
accactaggg cacatctgga tgccttcccc cagtatgtcc ttttctggat taaaatgagt   67380
gaaatttaaa ctgttcaagt ctggacctgg tttccctcta ggagactatg ttggttcatt   67440
agcaactttt tttttttttt tttttttgt gtgtgtgtgt gtgtgtgtgt gtgagagatg   67500
gagtctcgct ctgttaccca ggctggagtg cagtggcacg atcttggctc actgcaacct   67560 ctgcccttg  ggttcaagca attctcctgc ctcagcttcc caagtagctg gcactacagg   67620
tgtgtgccac catgcccagc taattttttgt gtttttttt  tttagtagag atggggtttc   67680
actatatgtt ggccaggcta gtctcgaact cctgacctta ggtgatccac atgctttggc   67740
ctcccaaagg cctgggatta caggcgtgaa ccactgcgcc tagcctg               67787
```

<210> SEQ ID NO 19
<211> LENGTH: 501
<212> TYPE: DNA
<213> ORGANISM: H. sapien
<220> FEATURE:
<221> NAME/KEY: misc_feature
<222> LOCATION: 217, 441, 498
<223> OTHER INFORMATION: n = A,T,C or G
<220> FEATURE:
<221> NAME/KEY: misc_feature
<222> LOCATION: 217, 441, 498
<223> OTHER INFORMATION: n = A,T,C or G

<400> SEQUENCE: 19

```
ggagggagtg gtaatttaca aaggatgtga agtttccagg aaatagggg  aagggaatta    60 cattatcttc ttgttctctg tctgccttat tagttctgtt tcatgcttgc tttgcatgag   120
aaggttggca aaccttattt taactgctga gacttaagca tcactaaatc tgaataccac   180
attcttcagc agcacacttg gtatccatat cactctncct gctaccaaat gaccagatgt   240
gaccacctgg atggggcctt ctctttcttt ccatgcaggg aaaatcacag tgaaaattga   300
acggcggcga cggaacaaag atgacagcct acatcacaga actgtcagat atggtaccca   360
cctgtagttg ccctgggctc ggaaaaccag accaagctaa ccatcttacg catggcaagt   420
ttctcacatg aagtccttgc ngggaactt  ggcaacacat ccactgatgg gtcctataag   480
ccggctttcc tcactganta a                                              501
```

<210> SEQ ID NO 20
<211> LENGTH: 2908
<212> TYPE: DNA
<213> ORGANISM: H. sapiens
<220> FEATURE:

<400> SEQUENCE: 20

```
cttggattcc gcggtagcgg aggcggcggt caggcgccgc ttctggggag tggcctttct    60
tttcccctcc ctcccggttc ggtggcggcg gctcctccca ctggggggg ggtggcgcgg    120
cggcggtggc atctgcggcc atggcggcga ctactgccaa ccccgcctga tcttggactc    180
aagattctcc tgcctcagac cccgagtagc tgggactaca gaaatgacat cagatgtacc    240
atcactgggt ccagccattg cctctggaaa ctctggacct ggaattcaag gtggaggagc    300
cattgtccag agggctatta agcggcgacc agggctggat tttgatgatg atggagaagg    360
gaacagtaaa tttttgaggt gtgatgatga tcagatgtct aacgataagg agcggtttgc    420
caggtcggat gatgagcaga gctctgcgga taaagagaga cttgccaggg aaaatcacag    480
tgaaattgaa cggcggcgac ggaacaagat gacagcctac atcacagaac tgtcagatat    540
ggtacccacc tgtagtgccc tggctcgaaa accagacaag ctaaccatct acgcatggc    600
agtttctcac atgaagtcct gcgggggaac tggcaacaca tccactgatg gctcctataa    660
gccgtctttc ctcactgatc aggaactgaa acatttgatc ttggaggcag cagatggctt    720
tctgtttatt gtctcatgtg agacaggcag ggtggtgtat gtctctgact ccgtgactcc    780
tgttttgaac cagccacagt ctgaatggtt tggcagcaca ctctatgatc aggtgcaccc    840
agatgatgtg ataaacttc gtgagcagct ttccacttca gaaaatgccc tgacagggcg    900
tatcctggat ctaaagactg gaacagtgaa aaaggaaggt cagcagtctt ccatgagaat    960
gtgtatgggc tcaaggagat cgtttatttg ccgaatgagg tgtggcagta gctctgtgga   1020
cccagtttct gtgaataggc tgagcttgt gaggaacaga tgcaggaatg acttggctc    1080
tgtaaaggat ggggaacctc acttcgtggt ggtccactgc acaggctaca tcaaggcctg   1140
gccccagca gatgatgacc cagaggctgg ccagggaagc aagttttgcc tagtggccat   1200
tggcagattg caggtaacta gttctcccaa ctgtacagac atgagtaatg tttgtcaacc   1260
aacagagttc atctcccgac acaacattga gggtatcttc acttttgtgg atcaccgctg   1320
tgtggctact gttggctacc agccacagga actcttagga aagaatattg tagaattctg   1380
tcatcctgaa gaccagcagc ttctaagaga cagcttccaa caggtagtga aattaaaagg   1440
ccaagtgctg tctgtcatgt tccggttccg gtctaagaac caagaatggc tctggatgag   1500
aaccagctcc tttactttcc agaacccta ctcagatgaa attgagtaca tcatctgtac   1560
caacaccaat gtgaagaact ctagccaaga accacggcct acactctcca acacaatcca   1620
gaggccacaa ctaggtccca cagctaattt accctggag atgggctcag acagctggc    1680
acccaggcag cagcaacagc aaacagaatt ggacatggta ccaggaagag atggactggc   1740
cagctacaat cattcccagg tggttcagcc tgtgacaacc acaggaccag aacacagcaa   1800
gccccttgag aagtcagatg gtttatttgc ccaggataga gatccaagat tttcagaaat   1860
ctatcacaac atcaatgcgg atcagagtaa aggcatctcc tccagcactg tccctgccac   1920
ccaacagcta ttctcccagg gcaacacatt ccctcctacc ccccggccgg cagagaattt   1980
caggaatagt ggcctagccc ctcctgtaac cattgtccag ccatcagctt ctgcaggaca   2040
gatgttggcc cagatttccc gccactccaa ccccacccaa ggagcaaccc caacttggac   2100
ccctactacc cgctcaggct tttctgccca gcaggtggct acccaggcta ctgctaagac   2160
tcgtacttcc cagtttggtg tgggcagctt tcagactcca tcctccttca gctccatgtc   2220
cctccctggt gccccaactg catcgcctgg tgctgctgcc tacccctagtc tcaccaatcg   2280
tggatctaac tttgctcctg agactggaca gactgcagga caattccaga cacggacagc   2340
```

```
agagggtgtg ggtgtctggc cacagtggca gggccagcag cctcatcatc gttcaagttc    2400
tagtgagcaa catgttcaac aaccgccagc acagcaacct ggccagcctg aggtcttcca    2460
ggagatgctg tccatgctgg gagatcagag caacagctac aacaatgaag aattccctga    2520
tctaactatg tttcccccct tttcagaata gaactattgg ggtgaggata aggggtgggg    2580
gagaaaaaat cactgtttgt ttttaaaaag caaatctttc tgtaaacaga ataaaagttc    2640
ctctcccttc ccttccctca cccctgacat gtaccccctt tcccttctgg ctgttcccct    2700
gctctgttgc ctctctaagg taacatttat agaagaaatg gaatgaatct ccaaggcttt    2760
taggactgtc tgaaaatttg aggctgggtg aagttaaaac acctttcctt atgtctcctg    2820
acctgaaatt gtatagtgtt gatttgtgct gagatcaaga ggcaggttag aagaacctga    2880
catccactgt taaaaaaaaa aaaaaaa                                        2908
```

```
<210> SEQ ID NO 21
<211> LENGTH: 20
<212> TYPE: DNA
<213> ORGANISM: Artificial Sequence
<220> FEATURE:
<223> OTHER INFORMATION: Antisense Compound

<400> SEQUENCE: 21
acacacatat ctcaaggccc                                                  20

<210> SEQ ID NO 22
<211> LENGTH: 20
<212> TYPE: DNA
<213> ORGANISM: Artificial Sequence
<220> FEATURE:
<223> OTHER INFORMATION: Antisense Compound

<400> SEQUENCE: 22
aagggagcag aggactccct                                                  20

<210> SEQ ID NO 23
<211> LENGTH: 20
<212> TYPE: DNA
<213> ORGANISM: Artificial Sequence
<220> FEATURE:
<223> OTHER INFORMATION: Antisense Compound

<400> SEQUENCE: 23
caagatcagg ctgggaaaca                                                  20

<210> SEQ ID NO 24
<211> LENGTH: 20
<212> TYPE: DNA
<213> ORGANISM: Artificial Sequence
<220> FEATURE:
<223> OTHER INFORMATION: Antisense Compound

<400> SEQUENCE: 24
cccctaatct ggtcacctgt                                                  20

<210> SEQ ID NO 25
<211> LENGTH: 20
<212> TYPE: DNA
<213> ORGANISM: Artificial Sequence
<220> FEATURE:
<223> OTHER INFORMATION: Antisense Compound

<400> SEQUENCE: 25
actgccacac ctgtttcaag                                                  20
```

```
<210> SEQ ID NO 26
<211> LENGTH: 20
<212> TYPE: DNA
<213> ORGANISM: Artificial Sequence
<220> FEATURE:
<223> OTHER INFORMATION: Antisense Compound

<400> SEQUENCE: 26
taggaataat aacttatttc                                                    20

<210> SEQ ID NO 27
<211> LENGTH: 20
<212> TYPE: DNA
<213> ORGANISM: Artificial Sequence
<220> FEATURE:
<223> OTHER INFORMATION: Antisense Compound

<400> SEQUENCE: 27
actctcttac ctggaagacc                                                    20

<210> SEQ ID NO 28
<211> LENGTH: 20
<212> TYPE: DNA
<213> ORGANISM: Artificial Sequence
<220> FEATURE:
<223> OTHER INFORMATION: Antisense Compound

<400> SEQUENCE: 28
caagatggcg gcttcagcag                                                    20

<210> SEQ ID NO 29
<211> LENGTH: 20
<212> TYPE: DNA
<213> ORGANISM: Artificial Sequence
<220> FEATURE:
<223> OTHER INFORMATION: Antisense Compound

<400> SEQUENCE: 29
ggaaaagaaa ggccactccc                                                    20

<210> SEQ ID NO 30
<211> LENGTH: 20
<212> TYPE: DNA
<213> ORGANISM: Artificial Sequence
<220> FEATURE:
<223> OTHER INFORMATION: Antisense Compound

<400> SEQUENCE: 30
gccgccatgg ccgcagatgc                                                    20

<210> SEQ ID NO 31
<211> LENGTH: 20
<212> TYPE: DNA
<213> ORGANISM: Artificial Sequence
<220> FEATURE:
<223> OTHER INFORMATION: Antisense Compound

<400> SEQUENCE: 31
ggtacatctg atgtcatttc                                                    20

<210> SEQ ID NO 32
<211> LENGTH: 20
<212> TYPE: DNA
<213> ORGANISM: Artificial Sequence
<220> FEATURE:
```

```
<223> OTHER INFORMATION: Antisense Compound

<400> SEQUENCE: 32
cttaatagcc ctctggacaa                                               20

<210> SEQ ID NO 33
<211> LENGTH: 20
<212> TYPE: DNA
<213> ORGANISM: Artificial Sequence
<220> FEATURE:
<223> OTHER INFORMATION: Antisense Compound

<400> SEQUENCE: 33
atcatcaaaa tccagccctg                                               20

<210> SEQ ID NO 34
<211> LENGTH: 20
<212> TYPE: DNA
<213> ORGANISM: Artificial Sequence
<220> FEATURE:
<223> OTHER INFORMATION: Antisense Compound

<400> SEQUENCE: 34
tccgacctgg caaaccgctc                                               20

<210> SEQ ID NO 35
<211> LENGTH: 20
<212> TYPE: DNA
<213> ORGANISM: Artificial Sequence
<220> FEATURE:
<223> OTHER INFORMATION: Antisense Compound

<400> SEQUENCE: 35
catcatccga cctggcaaac                                               20

<210> SEQ ID NO 36
<211> LENGTH: 20
<212> TYPE: DNA
<213> ORGANISM: Artificial Sequence
<220> FEATURE:
<223> OTHER INFORMATION: Antisense Compound

<400> SEQUENCE: 36
attttccctg gcaagtctct                                               20

<210> SEQ ID NO 37
<211> LENGTH: 20
<212> TYPE: DNA
<213> ORGANISM: Artificial Sequence
<220> FEATURE:
<223> OTHER INFORMATION: Antisense Compound

<400> SEQUENCE: 37
ctgtcatctt gttccgtcgc                                               20

<210> SEQ ID NO 38
<211> LENGTH: 20
<212> TYPE: DNA
<213> ORGANISM: Artificial Sequence
<220> FEATURE:
<223> OTHER INFORMATION: Antisense Compound

<400> SEQUENCE: 38
tctgacagtt ctgtgatgta                                               20
```

```
<210> SEQ ID NO 39
<211> LENGTH: 20
<212> TYPE: DNA
<213> ORGANISM: Artificial Sequence
<220> FEATURE:
<223> OTHER INFORMATION: Antisense Compound

<400> SEQUENCE: 39
tttcgagcca gggcactaca                                           20

<210> SEQ ID NO 40
<211> LENGTH: 20
<212> TYPE: DNA
<213> ORGANISM: Artificial Sequence
<220> FEATURE:
<223> OTHER INFORMATION: Antisense Compound

<400> SEQUENCE: 40
ctggttttcg agccagggca                                           20

<210> SEQ ID NO 41
<211> LENGTH: 20
<212> TYPE: DNA
<213> ORGANISM: Artificial Sequence
<220> FEATURE:
<223> OTHER INFORMATION: Antisense Compound

<400> SEQUENCE: 41
aatgtttcag ttcctgatca                                           20

<210> SEQ ID NO 42
<211> LENGTH: 20
<212> TYPE: DNA
<213> ORGANISM: Artificial Sequence
<220> FEATURE:
<223> OTHER INFORMATION: Antisense Compound

<400> SEQUENCE: 42
agatcaaatg tttcagttcc                                           20

<210> SEQ ID NO 43
<211> LENGTH: 20
<212> TYPE: DNA
<213> ORGANISM: Artificial Sequence
<220> FEATURE:
<223> OTHER INFORMATION: Antisense Compound

<400> SEQUENCE: 43
ctccaagatc aaatgtttca                                           20

<210> SEQ ID NO 44
<211> LENGTH: 20
<212> TYPE: DNA
<213> ORGANISM: Artificial Sequence
<220> FEATURE:
<223> OTHER INFORMATION: Antisense Compound

<400> SEQUENCE: 44
gctgcctcca agatcaaatg                                           20

<210> SEQ ID NO 45
<211> LENGTH: 20
<212> TYPE: DNA
<213> ORGANISM: Artificial Sequence
<220> FEATURE:
<223> OTHER INFORMATION: Antisense Compound
```

```
<400> SEQUENCE: 45
catctgctgc ctccaagatc                                              20

<210> SEQ ID NO 46
<211> LENGTH: 20
<212> TYPE: DNA
<213> ORGANISM: Artificial Sequence
<220> FEATURE:
<223> OTHER INFORMATION: Antisense Compound

<400> SEQUENCE: 46
aaagccatct gctgcctcca                                              20

<210> SEQ ID NO 47
<211> LENGTH: 20
<212> TYPE: DNA
<213> ORGANISM: Artificial Sequence
<220> FEATURE:
<223> OTHER INFORMATION: Antisense Compound

<400> SEQUENCE: 47
atcatctggg tgcacctgat                                              20

<210> SEQ ID NO 48
<211> LENGTH: 20
<212> TYPE: DNA
<213> ORGANISM: Artificial Sequence
<220> FEATURE:
<223> OTHER INFORMATION: Antisense Compound

<400> SEQUENCE: 48
atccacatca tctgggtgca                                              20

<210> SEQ ID NO 49
<211> LENGTH: 20
<212> TYPE: DNA
<213> ORGANISM: Artificial Sequence
<220> FEATURE:
<223> OTHER INFORMATION: Antisense Compound

<400> SEQUENCE: 49
agtttatcca catcatctgg                                              20

<210> SEQ ID NO 50
<211> LENGTH: 20
<212> TYPE: DNA
<213> ORGANISM: Artificial Sequence
<220> FEATURE:
<223> OTHER INFORMATION: Antisense Compound

<400> SEQUENCE: 50 ccttttcac tgttccagtc                                               20

<210> SEQ ID NO 51
<211> LENGTH: 20
<212> TYPE: DNA
<213> ORGANISM: Artificial Sequence
<220> FEATURE:
<223> OTHER INFORMATION: Antisense Compound

<400> SEQUENCE: 51
ctgaccttcc tttttcactg                                              20

<210> SEQ ID NO 52
<211> LENGTH: 20
```

```
<212> TYPE: DNA
<213> ORGANISM: Artificial Sequence
<220> FEATURE:
<223> OTHER INFORMATION: Antisense Compound

<400> SEQUENCE: 52
agactgctga ccttcctttt                                              20

<210> SEQ ID NO 53
<211> LENGTH: 20
<212> TYPE: DNA
<213> ORGANISM: Artificial Sequence
<220> FEATURE:
<223> OTHER INFORMATION: Antisense Compound

<400> SEQUENCE: 53
tccattcctg catctgttcc                                              20

<210> SEQ ID NO 54
<211> LENGTH: 20
<212> TYPE: DNA
<213> ORGANISM: Artificial Sequence
<220> FEATURE:
<223> OTHER INFORMATION: Antisense Compound

<400> SEQUENCE: 54
agccaagtcc attcctgcat                                              20

<210> SEQ ID NO 55
<211> LENGTH: 20
<212> TYPE: DNA
<213> ORGANISM: Artificial Sequence
<220> FEATURE:
<223> OTHER INFORMATION: Antisense Compound

<400> SEQUENCE: 55
gcctctgggt catcatctgg                                              20

<210> SEQ ID NO 56
<211> LENGTH: 20
<212> TYPE: DNA
<213> ORGANISM: Artificial Sequence
<220> FEATURE:
<223> OTHER INFORMATION: Antisense Compound

<400> SEQUENCE: 56
gggagaacta gttacctgca                                              20

<210> SEQ ID NO 57
<211> LENGTH: 20
<212> TYPE: DNA
<213> ORGANISM: Artificial Sequence
<220> FEATURE:
<223> OTHER INFORMATION: Antisense Compound

<400> SEQUENCE: 57
cagttgggag aactagttac                                              20

<210> SEQ ID NO 58
<211> LENGTH: 20
<212> TYPE: DNA
<213> ORGANISM: Artificial Sequence
<220> FEATURE:
<223> OTHER INFORMATION: Antisense Compound

<400> SEQUENCE: 58
```

```
ctgtacagtt gggagaacta                                                   20

<210> SEQ ID NO 59
<211> LENGTH: 20
<212> TYPE: DNA
<213> ORGANISM: Artificial Sequence
<220> FEATURE:
<223> OTHER INFORMATION: Antisense Compound

<400> SEQUENCE: 59
catgtctgta cagttgggag                                                   20

<210> SEQ ID NO 60
<211> LENGTH: 20
<212> TYPE: DNA
<213> ORGANISM: Artificial Sequence
<220> FEATURE:
<223> OTHER INFORMATION: Antisense Compound

<400> SEQUENCE: 60
ttactcatgt ctgtacagtt                                                   20

<210> SEQ ID NO 61
<211> LENGTH: 20
<212> TYPE: DNA
<213> ORGANISM: Artificial Sequence
<220> FEATURE:
<223> OTHER INFORMATION: Antisense Compound

<400> SEQUENCE: 61
tcgggagatg aactctgttg                                                   20

<210> SEQ ID NO 62
<211> LENGTH: 20
<212> TYPE: DNA
<213> ORGANISM: Artificial Sequence
<220> FEATURE:
<223> OTHER INFORMATION: Antisense Compound

<400> SEQUENCE: 62
ttgtgtcggg agatgaactc                                                   20

<210> SEQ ID NO 63
<211> LENGTH: 20
<212> TYPE: DNA
<213> ORGANISM: Artificial Sequence
<220> FEATURE:
<223> OTHER INFORMATION: Antisense Compound

<400> SEQUENCE: 63
caatgttgtg tcgggagatg                                                   20

<210> SEQ ID NO 64
<211> LENGTH: 20
<212> TYPE: DNA
<213> ORGANISM: Artificial Sequence
<220> FEATURE:
<223> OTHER INFORMATION: Antisense Compound

<400> SEQUENCE: 64
tagccaacag tagccacaca                                                   20

<210> SEQ ID NO 65
<211> LENGTH: 20
<212> TYPE: DNA
<213> ORGANISM: Artificial Sequence
```

```
<220> FEATURE:
<223> OTHER INFORMATION: Antisense Compound

<400> SEQUENCE: 65
gctggtagcc aacagtagcc                                              20

<210> SEQ ID NO 66
<211> LENGTH: 20
<212> TYPE: DNA
<213> ORGANISM: Artificial Sequence
<220> FEATURE:
<223> OTHER INFORMATION: Antisense Compound

<400> SEQUENCE: 66
ctgtggctgg tagccaacag                                              20

<210> SEQ ID NO 67
<211> LENGTH: 20
<212> TYPE: DNA
<213> ORGANISM: Artificial Sequence
<220> FEATURE:
<223> OTHER INFORMATION: Antisense Compound

<400> SEQUENCE: 67
acaatattct ttcctaagag                                              20

<210> SEQ ID NO 68
<211> LENGTH: 20
<212> TYPE: DNA
<213> ORGANISM: Artificial Sequence
<220> FEATURE:
<223> OTHER INFORMATION: Antisense Compound

<400> SEQUENCE: 68
atttcactac ctgttggaag                                              20

<210> SEQ ID NO 69
<211> LENGTH: 20
<212> TYPE: DNA
<213> ORGANISM: Artificial Sequence
<220> FEATURE:
<223> OTHER INFORMATION: Antisense Compound

<400> SEQUENCE: 69
acttggcctt ttaatttcac                                              20

<210> SEQ ID NO 70
<211> LENGTH: 20
<212> TYPE: DNA
<213> ORGANISM: Artificial Sequence
<220> FEATURE:
<223> OTHER INFORMATION: Antisense Compound

<400> SEQUENCE: 70
acagcacttg gccttttaat                                              20

<210> SEQ ID NO 71
<211> LENGTH: 20
<212> TYPE: DNA
<213> ORGANISM: Artificial Sequence
<220> FEATURE:
<223> OTHER INFORMATION: Antisense Compound

<400> SEQUENCE: 71
gaacatgaca gacagcactt                                              20
```

```
<210> SEQ ID NO 72
<211> LENGTH: 20
<212> TYPE: DNA
<213> ORGANISM: Artificial Sequence
<220> FEATURE:
<223> OTHER INFORMATION: Antisense Compound

<400> SEQUENCE: 72
gttcttcaca ttggtgttgg                                               20

<210> SEQ ID NO 73
<211> LENGTH: 20
<212> TYPE: DNA
<213> ORGANISM: Artificial Sequence
<220> FEATURE:
<223> OTHER INFORMATION: Antisense Compound

<400> SEQUENCE: 73
ctagagttct tcacattggt                                               20

<210> SEQ ID NO 74
<211> LENGTH: 20
<212> TYPE: DNA
<213> ORGANISM: Artificial Sequence
<220> FEATURE:
<223> OTHER INFORMATION: Antisense Compound

<400> SEQUENCE: 74
ccatctcttc ctggtaccat                                               20

<210> SEQ ID NO 75
<211> LENGTH: 20
<212> TYPE: DNA
<213> ORGANISM: Artificial Sequence
<220> FEATURE:
<223> OTHER INFORMATION: Antisense Compound

<400> SEQUENCE: 75
ttactctgat ccgcattgat                                               20

<210> SEQ ID NO 76
<211> LENGTH: 20
<212> TYPE: DNA
<213> ORGANISM: Artificial Sequence
<220> FEATURE:
<223> OTHER INFORMATION: Antisense Compound

<400> SEQUENCE: 76
gagatgcctt tactctgatc                                               20

<210> SEQ ID NO 77
<211> LENGTH: 20
<212> TYPE: DNA
<213> ORGANISM: Artificial Sequence
<220> FEATURE:
<223> OTHER INFORMATION: Antisense Compound

<400> SEQUENCE: 77
tggaggagat gcctttactc                                               20

<210> SEQ ID NO 78
<211> LENGTH: 20
<212> TYPE: DNA
<213> ORGANISM: Artificial Sequence
<220> FEATURE:
<223> OTHER INFORMATION: Antisense Compound
```

```
<400> SEQUENCE: 78
agtgctggag gagatgcctt                                            20

<210> SEQ ID NO 79
<211> LENGTH: 20
<212> TYPE: DNA
<213> ORGANISM: Artificial Sequence
<220> FEATURE:
<223> OTHER INFORMATION: Antisense Compound

<400> SEQUENCE: 79
gaaattctct gccggccggg                                            20

<210> SEQ ID NO 80
<211> LENGTH: 20
<212> TYPE: DNA
<213> ORGANISM: Artificial Sequence
<220> FEATURE:
<223> OTHER INFORMATION: Antisense Compound

<400> SEQUENCE: 80
ttcctgaaat tctctgccgg                                            20

<210> SEQ ID NO 81
<211> LENGTH: 20
<212> TYPE: DNA
<213> ORGANISM: Artificial Sequence
<220> FEATURE:
<223> OTHER INFORMATION: Antisense Compound

<400> SEQUENCE: 81
agaccactat tcctgaaatt                                            20

<210> SEQ ID NO 82
<211> LENGTH: 20
<212> TYPE: DNA
<213> ORGANISM: Artificial Sequence
<220> FEATURE:
<223> OTHER INFORMATION: Antisense Compound

<400> SEQUENCE: 82
ggacaatggt tacaggaggg                                            20

<210> SEQ ID NO 83
<211> LENGTH: 20
<212> TYPE: DNA
<213> ORGANISM: Artificial Sequence
<220> FEATURE:
<223> OTHER INFORMATION: Antisense Compound

<400> SEQUENCE: 83
tggctggaca atggttacag                                            20

<210> SEQ ID NO 84
<211> LENGTH: 20
<212> TYPE: DNA
<213> ORGANISM: Artificial Sequence
<220> FEATURE:
<223> OTHER INFORMATION: Antisense Compound

<400> SEQUENCE: 84
gtctcaggag caaagttaga                                            20

<210> SEQ ID NO 85
```

<211> LENGTH: 20
<212> TYPE: DNA
<213> ORGANISM: Artificial Sequence
<220> FEATURE:
<223> OTHER INFORMATION: Antisense Compound

<400> SEQUENCE: 85
cactgtggcc agacacccac                                                20

<210> SEQ ID NO 86
<211> LENGTH: 20
<212> TYPE: DNA
<213> ORGANISM: Artificial Sequence
<220> FEATURE:
<223> OTHER INFORMATION: Antisense Compound

<400> SEQUENCE: 86
ctggccctgc cactgtggcc                                                20

<210> SEQ ID NO 87
<211> LENGTH: 20
<212> TYPE: DNA
<213> ORGANISM: Artificial Sequence
<220> FEATURE:
<223> OTHER INFORMATION: Antisense Compound

<400> SEQUENCE: 87
ggctgctggc cctgccactg                                                20

<210> SEQ ID NO 88
<211> LENGTH: 20
<212> TYPE: DNA
<213> ORGANISM: Artificial Sequence
<220> FEATURE:
<223> OTHER INFORMATION: Antisense Compound

<400> SEQUENCE: 88
ggaaacatag ttagatcagg                                                20

<210> SEQ ID NO 89
<211> LENGTH: 20
<212> TYPE: DNA
<213> ORGANISM: Artificial Sequence
<220> FEATURE:
<223> OTHER INFORMATION: Antisense Compound

<400> SEQUENCE: 89
caatagttct attctgaaaa                                                20

<210> SEQ ID NO 90
<211> LENGTH: 20
<212> TYPE: DNA
<213> ORGANISM: Artificial Sequence
<220> FEATURE:
<223> OTHER INFORMATION: Antisense Compound

<400> SEQUENCE: 90
tcaccccaat agttctattc                                                20

<210> SEQ ID NO 91
<211> LENGTH: 20
<212> TYPE: DNA
<213> ORGANISM: Artificial Sequence
<220> FEATURE:
<223> OTHER INFORMATION: Antisense Compound

<400> SEQUENCE: 91

```
tatcctcacc ccaatagttc                                              20

<210> SEQ ID NO 92
<211> LENGTH: 20
<212> TYPE: DNA
<213> ORGANISM: Artificial Sequence
<220> FEATURE:
<223> OTHER INFORMATION: Antisense Compound

<400> SEQUENCE: 92
agaggaactt ttattctgtt                                              20

<210> SEQ ID NO 93
<211> LENGTH: 20
<212> TYPE: DNA
<213> ORGANISM: Artificial Sequence
<220> FEATURE:
<223> OTHER INFORMATION: Antisense Compound

<400> SEQUENCE: 93
aagggagagg aactttaatt                                              20

<210> SEQ ID NO 94
<211> LENGTH: 20
<212> TYPE: DNA
<213> ORGANISM: Artificial Sequence
<220> FEATURE:
<223> OTHER INFORMATION: Antisense Compound

<400> SEQUENCE: 94
atccaaggca aacagtggat                                              20

<210> SEQ ID NO 95
<211> LENGTH: 20
<212> TYPE: DNA
<213> ORGANISM: Artificial Sequence
<220> FEATURE:
<223> OTHER INFORMATION: Antisense Compound

<400> SEQUENCE: 95
gtccaggccc catctatcat                                              20

<210> SEQ ID NO 96
<211> LENGTH: 20
<212> TYPE: DNA
<213> ORGANISM: Artificial Sequence
<220> FEATURE:
<223> OTHER INFORMATION: Antisense Compound

<400> SEQUENCE: 96
tgaaaatctt tgctacatgt                                              20

<210> SEQ ID NO 97
<211> LENGTH: 20
<212> TYPE: DNA
<213> ORGANISM: Artificial Sequence
<220> FEATURE:
<223> OTHER INFORMATION: Antisense Compound

<400> SEQUENCE: 97
ccaggtggtc acatctggtc                                              20

<210> SEQ ID NO 98
<211> LENGTH: 20
<212> TYPE: DNA
```

<213> ORGANISM: Artificial Sequence
<220> FEATURE:
<223> OTHER INFORMATION: Antisense Compound

<400> SEQUENCE: 98
tgagtccaag atcaggcggg                                                    20

<210> SEQ ID NO 99
<211> LENGTH: 65001
<212> TYPE: DNA
<213> ORGANISM: M. musculus
<220> FEATURE:
<221> NAME/KEY: misc_feature
<222> LOCATION: 14965, 14966, 14967, 14968, 14969, 14970, 14971, 14972,
      14973, 14974, 14975, 14976, 14977, 14978, 14979, 14980, 14981,
      14982, 14983, 14984, 14985, 14986, 14987, 14988, 14989,
      14990, 14991, 14992, 14993, 14994, 14995, 14996, 14997
<223> OTHER INFORMATION: n = A,T,C or G
<220> FEATURE:
<221> NAME/KEY: misc_feature
<222> LOCATION: 14998, 14999, 15000, 15001, 15002, 15003, 15004, 15005,
      15006, 15007, 15008, 15009, 15010, 15011, 15012, 15013, 15014,
      15015, 15016, 15017, 15018, 15019, 15020, 15021, 15022,
      15023, 15024, 15025, 15026, 15027, 15028, 15029, 15030
<223> OTHER INFORMATION: n = A,T,C or G
<220> FEATURE:
<221> NAME/KEY: misc_feature
<222> LOCATION: 15031, 15032, 15033, 15034, 15035, 15036, 15037, 15038,
      15039, 15040, 15041, 15042, 15043, 15044, 15045, 15046, 15047,
      15048, 15049, 15050, 15051, 15052, 15053, 15054, 15055,
      15056, 15057, 15058, 15059, 15060, 15061, 15062, 15063
<223> OTHER INFORMATION: n = A,T,C or G
<220> FEATURE:
<221> NAME/KEY: misc_feature
<222> LOCATION: 15064
<223> OTHER INFORMATION: n = A,T,C or G
<220> FEATURE:
<221> NAME/KEY: misc_feature
<222> LOCATION: 14965, 14966, 14967, 14968, 14969, 14970, 14971, 14972,
      14973, 14974, 14975, 14976, 14977, 14978, 14979, 14980, 14981,
      14982, 14983, 14984, 14985, 14986, 14987, 14988, 14989,
      14990, 14991, 14992, 14993, 14994, 14995, 14996, 14997
<223> OTHER INFORMATION: n = A,T,C or G
<220> FEATURE:
<221> NAME/KEY: misc_feature
<222> LOCATION: 14998, 14999, 15000, 15001, 15002, 15003, 15004, 15005,
      15006, 15007, 15008, 15009, 15010, 15011, 15012, 15013, 15014,
      15015, 15016, 15017, 15018, 15019, 15020, 15021, 15022,
      15023, 15024, 15025, 15026, 15027, 15028, 15029, 15030
<223> OTHER INFORMATION: n = A,T,C or G

<400> SEQUENCE: 99
agataagggt cactggtgag ccttccaatt ccggattgta gttcattcca aatattgtca    60
agttgacaac caggaatagc cactacacat ggcttttttt actacatgat tataggtgta   120
atcaacatgt ctattatata ctaaaaaaaa aagtttttta accatgactt tttgtttggt   180
ttttcaacac atagtttctt tgtgttaatc atcctggctg ctttagatct taatttgtag   240
acctggctgg catccaactc aaagagatcc attggcctct acctcccaag tactgggatt   300
aaaagcatgt aatgccagtg aactacaatt tcttatatta aagtgtgcca tatagatgtc   360
atgttttgtt ttgttttgtt ttgttttttgt aaatttgaca caagctaaga tcatctgaga   420
ggaggaaaag ccattaaggc aatgcctcca tcttggcata gtggtgcccc cctttaatgc   480
cagcaaatga aagtgtgaaa gcaggtggat ttctatctgt tcacaactgt ttgaaactcc   540
aggttaatgg gatctttctt gtctgtctaa ttgtgttcca atactcaggt gtactgactt   600
aaatgcagac acattcacat aattaaaaat aaaactattc aaaacccaa gaaaatgtct    660 aaacaaacca accaaaccaa ccaaataacc taaagcaagc aagcaaccaa caaacgagaa   720

```
gccagcatga tgtcactgcg cctctcactg cacctctttt tagtgaatgg gagttagttc    780
tctcctcgaa ccattgtgtg gcttttggag aatccaactt caagtacctt tagctcttga    840
gccatcttgt cagttctact tctaaatgtt tttaaaattt ttgtgtatgt gtgagtgcac    900
atgttttggt gtgaggaaag ttgaagataa tttgcaggag tcctctcctt gtgtaagttc    960
agagcattgg atcttgggat gttaggtgta gctgtgtagt ggagtcgtct ttatggctaa   1020
ttaaaaaaat ttttttttggt gaatcagact gacaacaagc caaagagtag tgccatatgc   1080
ttatagttct aacattggaa ggagagggtg aattcaagac cattttcatc ctcatagtga   1140
atttggggtc agtctaggct acatgagacc ttgtttcaaa gaacaaaatt accctcctcc   1200
ccccagtcca catatacatg gtgatgaata taatagactt tgggtgttag tttcattcac   1260
tttgcttctc actactggat taatttgcaa ggtggccttt gtttcatgtc tttggttttt   1320
gtttgttttt gagatagtgt ctttctatat atagctcctg ctgtcttaga actcactatg   1380
tagaccaggc tggcattgaa ctcagagaaa ttggccagtc tctgcctcct gagtactagg   1440
attaaaggca tgcatcacta tgcctggatc tgtttgtagt tctttttttt ttttaaatat   1500
atatttttaa gatttattta tttatttat gtatatgagt acactgtagc tgtacagatg   1560
gctgtgagcc ttcatgtggt tattgggtat tgactttagg acctctgctt gctccaatca   1620
acctcgccca ctccagttgg tcggctcact cagttcctgc tttctctggc ccaaagattt   1680
atttattatt ctaaataagt acactgtaat tgtcttcaaa cacaccagac gagggcgtta   1740
gatctcatta ggggtggttg tgggccacca tgtggttgct gggatttgaa cgcaggacct   1800
ctgaaagagc agtcagtgct cttacccgct gagccatctc tccagcccct gcttgtagtt   1860
cttgatttgt aaaattatag aatttatctc acagtgtttt gagtcgacat tgtctgttct   1920
gaattgctca gttcttataa ttagacatta cgtctgtgtg tttactacct tgtcatttta   1980
aaaaaacttg tgacatagga cacctcactt ttggagggca gagaaaggga ctagtttcat   2040
tttgtagtac agactggtct ttgcattctg agttctggaa tacttgttta ataaaaattc   2100
tttgttcgtt gtctccattt caaatgttgg catctttggt accacgtaat cacccagctt   2160
tttcctacca gcttcagagc caactcttaa gaattagtta tcggacttttt actagtgaca   2220 aaagttcata aagaaaaaac aacctagaat ggattagtga tccctgtgtt agaacctata   2280
aagagggttt gcataacaaa tcgtctgtag gaagcatatg ctgatgagcc cactaagaaa   2340
gaaaacattt tagtaaaatg ctcgttttct ttgcatttca ctgacgtcaa tttggttatg   2400
aatctctgac gccgagaagg ccggattagg gaaacagctg gttggcttcc tagctcaggc   2460
ttcctagcac tcctcgggtc accggactca ctggccgagt cactagcccg gcctctatgg   2520
cgacttactg tttctattgg ccagttctcc caggaggct gtctggagac tgaccgcgcc   2580
catagtttgg ggcgtgtctt ctgcccagga tggggagggg ggtgggcgtc cgccatcttg   2640
gattccgcgg tagcggtggc ggcggtaagg tgcctaatct gcggagtggc tcttccctcc   2700
cctcccccag ctcggtggcg gctgcccctc ccaccgaggg tggcgcaggg acggtgccat   2760
ctcgaccatg cgggcgacta cagctaaccc aggtgaggcg gcagaaagga ctgacaagtg   2820
cggagagcca gagcagagca gcagggccgt ggcgttcggg tgttggggga gggtgtcga   2880 ggaggcgccc tgcccggagg acctgggaa cgggtgacgg tgtttgggg gctccgtgcc   2940 ccaacttctg gagtagtggt ggcgcttggc cagcgtctcc actctgcctg cggtgttagg   3000
gagtgttgtg gtcttttaac cctctgccag ctgatgttcc cctgatgcct agtaagtaac   3060
tgggcaaact gacttggtgt aactgcgagc gtaaactggg ctatagacgg ggccacgttg   3120
```

-continued

```
acgttttgca aagtcttgct tgattctaca cttggtttac atttaaatgg aaaacttagt    3180
tctttgagaa tctgctcaga ttcttgtaac tcctatactt tgaaatttag ggttttagcg    3240
tagttattag tgtcttgctg ctgaaggcag aggtttgggt aatggtaata gttcaggaca    3300
ggtctttagt ccagaaccca ggtttaaatc ttgttaggtc gaggtggagc aactcctgtt    3360
ctttcagaaa aatgtcccgc gccatttgtc tgtggacgtc ctcttgcttg tttgtctgtc    3420
tgtctctgtc tctcgttcat cttattttga gtcttgtctc attccagccc ccggttgact    3480
ttggatcact gcagtctccc tctcagtcct ttctactgta ttcagttaca tcttaggaag    3540
tatttcattt tagttgggct aatttacctt gttattttcc aacaaagtaa atccatcatt    3600
tcccagaagt ctgtatcatc gaagagtttg gagggagggt tgtgtaatat tggtctctgc    3660
tatttcacat tgaactttta aattttatct tgttaatgta ctatattaca gtaacagggt    3720
acacacacgt atgtatatac atacacacaa tagctgaaac actgggaaat gtattgtttt    3780
cccattattt ttggaaacag ccttttttttt taagagagag agagagagag agagagagag    3840
agtcctagaa cttatatgta gcccaggttg cttcaaatt catgtgtcaa tatcaacttt    3900
aaaaaaaata ttttttaagct ttagaaatta tgtatatgat aatgtctact tgtgagtgca    3960
ggaatgggag gagtccagaa tagggtgttg gatcccctgc agcaagagtt tcaggcagtt    4020
gaaagccccg tgatgtggat gctaggaact gacattaggt cctagaagag taacacatac    4080
tcacaactac tgaaccttcc tttcagcccc tgaatatcag tttttttaaat cctaaattat    4140 tatttttttt acatgaagat gaagtaaatt gtcaggaaac tattggaata tttgatgaat    4200
tatagaataa aactatacaa ctgaaaaatg ttagagaaaa tcagaccttg tagcaaaata    4260
gcccatgtct gattagagta aacaagattt caaactgatc ccatgttgca aaatccttat    4320
ataactcttc agactgcaaa gtgtctctct tgttaaggcc gtagagacac gttagtaagt    4380
cagaagcttt tctagctgcc ctgttctgat tttaaaccaa ttactaaaac aacactttct    4440
tgaccaaata gtcatttcct tatcaatatt agcttaagtc tgtaagcagg aaatagtaat    4500 tttttctat ttttttttct gagtggggaa ttttgagagg ctggcctgca gtgttctgtg    4560
aagatcaggc tggccttgaa cttgcagtgg tcttcttgct tctatcttca agtgctggaa    4620
tcactcgcat gtgccatcct atataaacta tcaaaacttt ttaaaaagta cgatttaaga    4680 atcttttta atgaaacagt tgtttgtttg tttgtttgtt tgttttgact ttggttttc    4740 aaggcagggc ttctatatgt atccctggct gtcatgaaac tcactctgta gaccaggatg    4800
gcctccaact caagatctgc ttgctcctgc ctcctgagtg ctggattaaa gctgtgagtg    4860
tcatcaccag tagaaataat tgatttatt tattgttatt tgattgcttg cttcttcaat    4920
tttgaggtgg gcagagtcat cataggtact taccaaacag agggagaata ggctggaatt    4980
cctttaatct ttgcagaagc agggggatat cttagttcat ggccatcttg gtctacaaag    5040
tcagttccat gctacatagt gagaccttgt ttcaaaatca aaagccagac caaaccaagc    5100
aaaaacctca aaaggtgagg tgtaggttct tagcaaacct ttgaaaatta acctgagaat    5160
gtaagagttt tcttaaattc tagtctgctg ttagttatgg catagcaccc agtggttcct    5220
gctgtagctg acatccctgc gtagcctcag cctcttatga gatgggatgg taggtctgag    5280
cggagaacag agaacgacag acccagtgag actaaccccc tgctctcttt accatctgcc    5340
ttaacttcct tttccgggggg ctacattcct agctcaagat ttctttttc catgtggaga    5400 attcttccat gtcttctaat ttattgatcc catgttcagt acatgcatga tacttaagtc    5460
```

```
ataaaataga gccttttgtt gttgctttt  cctccttcct ttttgtgtca aacaggatat    5520
gttttggcct gttgaatttt ggaaaattag attcaccact ggaggtatat acagtgggaa    5580
attactatgt tcagtgtgca cttgtacaca ggccagaaga caccggatat ccacctctgt    5640
aactttctgt cttattcctt tgaggcagaa tttcttctta actgtgggca tcttactgtg    5700
tcactctgcc ttatttcttc caggtcaggt gtctccctta acctgaggct tgtgtgtttt    5760
gctcggctga cagtcagcaa ggcctagcag tcttcctgcc ttggatcctc agagtgcatg    5820
gattcctggt ggatgcagga tgatgccaga cttgttatgt gggttctggg atccaaactc    5880
aggtctccag attgtgtagc aagtgctctt aaccactgga tcatgtcttc attccacatc    5940
ccacctccgc tttttgagac aggatctgtt actggcctgg agtgggccaa agaggataaa    6000
cttctggtta gagagcccca agctcactgg gtttcggctt taccaatgct ggaaatacaa    6060
gtaaacgcta ccatgccttg tcttttcatg tgggttctgg agattaactc aggaccttat    6120
tgcttgattg gcaattcttt tttgattgag ctaccaagcc ctttattatt aattagtcag    6180
tgttcttaat tgctggtcat atctccagcc ccactttccc cccaccccc cccaaaaaaa    6240
gattttaatt aaattatgca cattggtgta gtagttactt ttctgtggcc atgaagagac    6300
accatgacca tgggaactta gagaagcatc gctttattag acttgagttt tccagaggtg    6360
agtccatgat cactgtgact ggaagcatgg cagcagctgt attacttcca acaaagccat    6420
acctcttaat tcttcccaag acactaacac caactgtgga ccaagaatta aaatatagga    6480
gcctgtgggg accattctca ttcaaaagac cgtaattact gcatgtatgt ttgttcatgt    6540
gagtgcaggt gcagaagagt gtgttgattc tcttgtagtg caattacagg tggttgtgag    6600
ccatctaatg tgggttctca gaactgagct catgtgttat gcaggaatgc caagttgtct    6660
taacaactga gccatctctc cagccccca atcaatcaa tttatctctt tttttttct      6720
ttctttttaa aggaattgaa ccattttact aactcagcag ttaaaataca ataaactttt    6780
tgttttgag gcaagtctca tttagactag gctaggttga aactcactat gtctctgagg    6840
gtgaccttga atttcttttt ttcattttt aagatttctt tcttttttg ttttttgtt      6900
tttcgagaca gggtttctct gtatagctct ggctgtcctg gaactcactc tgtagaccag    6960
gctggcctcg aacttagaaa tccgcttgcc tcttatttct tgatattgag tacactgtag    7020
ctgttttcag agacaccaga agagggcatc agatcccatt acagatggtt gtgagccacc    7080
atgtggttgg tgggaattaa acccaggacc tctagaagag cagtcaatac tcttaaccgc    7140
tgaactatca tctctccagc cctgatctta aatttctgat ccagtgcta tgatcttata     7200
gttacaacca tgcctgtctt accatgtgct atggatggag ccagggcttg gtgcatgcct    7260
ggcaagcatt ctaccaactg aactgcatac tcagtggata acagttttgg aacgaaactt    7320
cagttggtgt acttttatgc agtagacttg tggtaccaag tttgactcta ttttcctaga    7380
atttaagaag taaagactta cgttgagaat ggtagccgtg tatcagtaaa caaaaatggc    7440
tggagagtgg ttctgccatt agaagcaagc actggctgct cttggagttg actgaggttt    7500
ggttccagca catactggtg ctactaccca cagctataat tccagtagat ctattgccac    7560
cttctggcct ccatggacaa caagcctgca tgtgttgcat atatacacac aggcaaaaca    7620
tacacataaa gtcgtttaaa atacaaaata gagaaaagtt ctctgatgtt acaatattat    7680
aaagaatctt gaaaatgtt tccattattt gtccagtgtt ttgtcagcta tataactgat     7740
ttcatccaga tgttgtaata ataaaagaat gtctttaaca cccctttgaa aatgtaggct    7800
tgaactcagc agagtctgag ccaactcccc aaccctcagg tagtaggcac tgcttgtata   7860
```

```
acctggttga attgcttgac ttgctgtttt gacagggtct gggtgtgtgg ttcaggctgg    7920
acttaggctc tccatctctc ctgagtgttt aagagatgga catgagaacc tcagctgggt    7980
agtgagttca aggccacttc tgggctacat gagactgcct cagcttcccc agtactagga    8040
ttataggcat gacctaccat gccttgctaa atccatctat ttttaggatt gctgtcctat    8100
tttccatgat gacttcagta ggtaaatatc agggagtgag tccattgtaa ataaaacagc    8160
actgtcctaa agggcttcag tgccagcaaa gatctgtgaa ttctgagggc agacaaaact    8220
atacagcaag agagaccatg tctcaaacaa ataaaaacaa aggatgataa ctctttgatt    8280
ttatagcaag gaaacaaacc tagagaaaga aatgaacata tttattaagt atttattatt    8340
tttctctgtg tccaggctat actttagtat tttgttggtt actcattata ttatttattt    8400
ttaaaatatt tatttgcttt atgtgtatat gcgtgcctga gtgtatgtct gtaccacatg    8460
ggtttagaag acttcagagg tcaaaagagg aggactttt aagtcccctg gaactggagt    8520
tacagatgtt tgtgagccac catgtgggtg ctgggaattg aacctgggtc tctgcaagaa    8580
cagtcagttt cttaacccct gagatatctc tgtagttctt attctctgta tcataaagtc    8640
tcttctattt actccctcca caattttta aactttatac cttccttcta agcatggcgg    8700
tgcacaccat taatccgagc acttgggagg caaaggcggg tggatcagtg cgagttcaag    8760
gctagcctgg tctacaaatc cagtctagga cagccagggc tgttacacag agaaaccctg    8820
actccaaaaa caaaattata ctttaacttt tatatttctc cttttcattt ttacagtagt    8880
tgggtgacca cagtaagttt ttcctgagac aggctctcaa ataccatgct ggccttaatc    8940
ttactatcct aagctagggc ttgaacttcc agaccctact gcttatacct ctgtagtggt    9000
gggattagag ttaggtgcca tcactccagg gctattgggc tcaagatagg gcttcatgc    9060
ctgccaggca aatacctagc tgagctacat gggttccagg tcagtcagaa ctagggtgag    9120
gtcctgtctt aaaaaaaaat aataataata aaattgggcc agggatgcag cttagttaga    9180
agaacccttg tgtgtcagat acaagatcct aagtctcatt cctagtacat gcaaaccccc    9240
acctccctcc aaacaccaaa gggtttctaa gctggataag gtggtggcct atatctgttt    9300
tttctttgtt ttttccttg agaacgagtg taatttagct ggcctaaaat ttcatgtgaa    9360
cttcctgtga ttctcctacc gtctcctcag tgctggaatt acaggctaca ctactgacaa    9420
agcaagtccg ttctgtcaga agattccttc agttgactgc ttttttcata tatatttagt    9480
ttttcatttc ccatgaaggg ggagtcagta ttttccattt ttttccatgt gagttgatat    9540
cagtaaacct taagttcaga tatgtaaatg catatatatg tgtgtagaca aacaactcca    9600
tcaactttgg tgtctgtttt tgagacaggg tcttaccatg tagctttagc tatcctcgat    9660
cttgctatgt ggaccaggct ggtctagaac ttaaattaac ctgcttttgc ctcccatgtg    9720
ctgatattaa aggtatccac caccctatct agtaattttg ttttttagac ttattttta    9780
attgtatata tgtatatgtg agttcaggtg cccttgaagg tcagaagagg tgttgggtcc    9840
tctggtgctg gagttccaga ttgagcttcc aggtgtaggg aacagaggaa gtcctgagta    9900
actgcattgt tgacatgcac gtggccatat tgaggtctcc aaggccacag acccatggga    9960
gattgacaaa gccattaccc atatggccag gctaaagaga gtgacaaagc tcttctgaat   10020
tctagtatga gtgtgttagt gtgtgcttac atgtgtataa atgtatgtgt gtgtatgtgc   10080
gcatatgtgc gcgtgtggag tctggctttc cctcatccgt ctacctctct tacccaagtc   10140
tggggtttta tatgtgtgcc actataccttg ccttgtagat gactaactcc tatttggtaa   10200
```

```
tcttttgtaa agtatttttag tatcagttttt cagaaagaat attggtttat aattggcata    10260
tttttttactg tttgttttgt tgtgatatca gattaatact agaatcatca gtaaaatgag    10320
gccaggagag gatatcacat ccaaatattt tcttgaagag actatgtaga actcatagta    10380
aagtaatttg aacctggata tttctttttg gagtacagtt gtagaactat tattattatt    10440
attattatta ttgagacagg gtttctcttt gtagccctgg ctgtcctaga aattactctg    10500
tagaccaggc tggtcttgaa ttcaagagat ccacctatct ctgcctctgg gcttaaagtc    10560
gtgcaccact gctgcatggc tattacattt gtttatttat ttttatattt agtcagttat    10620
aattgtatgg gcttttccta gtgttgttgg tcttgaagta aaagcttaat gattgatttt    10680
gttttgtttt ttaagatgta tgtgtgtgtg tgtgtctgtg tgtgtctgtg ttattatata    10740
tatgtgccct tggaggccag aagagaaact ctggaactag agtttcaggt gactggatta    10800
tctgccgtgg tgctagggat agaactttgg gcttttggaa gggagccatc ttgctaaccc    10860
tttgctttgt tgcttttttgt tttctgtgat acagcagtgt tgtaaattgc ttaccagta    10920
gagtttaat tgtctcccgt aattttaatt ttgctatatt gtatttaaat tttttgttta    10980
ttgttgttat tattcctcct cctctccctc ctcttcttct tctctctctc tctctctctc    11040
tctctcttgc tctctcgctc tctcgctctc tctgtatgcg tgtgacacat ttttctaagt    11100
cagttttctc ctactgtggg ttcaagggca gaactttgat cagatttgca tggctggtac    11160
tttttctctc tgagtcacac tgtcagctct ctagtatatt tttgttttat gcacttgtgc    11220
atatctgtgt atgtgcttgg agtgcagtgc ccttagagac caaacaagga tgtaggatcc    11280
tctagagcaa gaggtacctg tgtttgtgag cagcccaaca tggtgccttg aagaactctg    11340
caagagcaga gcttgtgcct cacttacatt tagttaagct tgtgacagtt ttcttttgag    11400
actttgactc attcattaat tgtattgtat ttttttcatg tttgtagaga ttttcctatc    11460
tttttccttc cttctttcct tccttccttc cttccttcct tccttccttc cttcctttct    11520
ttctttcttt ctttttttga gacagggttt ctctgtgtag ccctggctgt tctgaaactc    11580
actctgtaga ccaggctggc ctcaaaactca gaaattcacc tgcctctgcc tcccaagtgc    11640
taggattaaa ggcgtgcgcc accatgcccg gctttttttt tttttttttt aagatttatt    11700
tatttatttt atgtatttga gtcagatgat cgtgatccat catgtggttg ctgggaattg    11760
aactcagacc tctgctcgct ctaacccaaa gattatttta ttgttatatg taagtacact    11820
gtagctgact tcagacactc cagaagaggg caccagattc cattacggat ggtggtgaga    11880
caccatgtgg ttgctgggaa ttgaactcag gacctctgga agagcagtta tatctccaga    11940
tataatgttt ttcttttagt tgtgtcagat tttacaacac attttgccct gtcttgttta    12000
gtatatgtgc attgctgtgt tactggtggt ggattctcac tctgtaattt cttcaggtaa    12060
attttatttg ctgttttttt ggtttttttg tttttttttgg ttttttcgaaa cagggtttct    12120
ctgtatagcc ctggctgtcc tggagctcac tctgtacacc aggcaggcct cgaactcaga    12180
aatctgcctg cctctgcctc ctgagtgctg ggattaaagg cgtgcgccac cacgcccagc    12240
ttatttgctg ttttatcggg tttatttgta tatataacaa ttcctataac cacagcttta    12300
ggaaaaaaag cttggtctct ctgtgtcccc tggctaggct cagtcaccta acccaattaa    12360
ttgacaacta atgatgaaat acagagattt actcattgtg gtcacattgt cctaggaaca    12420
gatagaaggg tccagtgacc cctaagtccc tttaactata ttgacttcag ctttaggttt    12480
aagtagaaca gttagggcag caggccggag gtttagccag tcctgaacac agtgtctcat    12540
tgtctcgggt cctgctaggt ggatgaatta aattgttgct gacaggacca ctgtggctcc    12600
```

```
tacaagatag tgcattctgg gtgtagcctc ttcatcacag gtaattgttc tcactgtctc    12660
agccgaggca tagcttcagt tctttatctt gtttctgctg gaatccaagg tgacaagaag    12720
acagattaaa gacagtgacc tagctctgtg tctccagaag taaaggagac agacagacaa    12780
aacggaggcg gagatgccag cctttcatct tactttagta aagcaaaggc tcacattggt    12840
ctttgcaaga gtaacttctg tcttagttag gttttctggt gctttgatga aaactttata    12900
tgtgaccaaa acatgttggg gaggaaggat ttatttcagc ttatacttcc acatacacat    12960
cacagtccat cacttaagag agtccaggca ggaactcagc agggcaggat ttggggacag    13020
gaactcaagc agaaatgact tggtttactg gcttcgtctc ccatggcttg ctcaacctgc    13080
cttcttatag cacccaggac caccagccca gggatggcat tacctacagt gaactgggcc    13140
ctcccatatc aatcactaat taagaaaact ttccacaggc ttgcctgcat accaatctag    13200
tggggcattt tctcagttga tgtccctgtt ttcagtgact cctttgtcca gttgacatga    13260
agcatagcct ctaaggctgt tgcagtccca cttaactttg gttaatgtgt gcatgatgtt    13320
cctttccttt cccctttctt tctttttttt tttttaaag atttatttat taatatatgt    13380
aagtacactg tagctgtctt tagacactcc agaagaggga gtcagatctt gttgcggatg    13440
gttgtgagcc accatgtggt tgccgggatt tgaactctgg accttcggaa gagcattcgg    13500
gtgctcttac ccactgagcc atctcaccag ccctcctttc cctttccttt tccctcctt    13560 tcctttcctt tcctgaggtg gagcaccgag gatgactttg accccccagc ccgagtgct    13620 ggagttatac acccagagcc tctagcatgc taggcccata ttctactggc tgagccatac    13680
tccaagcccc atgctgtgac acagggtggg tccctttagc aagttcttga tctcatggat    13740
aaaagattga agaggctaga gagatggctc agtggtaag agcctgcatg actcgtccag    13800
aggatctgag cttggtttca agtgcccatt atcagggcaa ctcccagctg actgtgcagt    13860
gccctctttg gcatccgtag gcagcagcac tcacatgtgc acacatcctc ctcactactc    13920
cccaccacaa taaaaataaa tccttttaaa aaaatgtgct ttgaagggta tattttacta    13980
gagtcagtaa gaaaaggcag ggcaggcaag ctagagatct cagcattgtc atgaggaagg    14040
aaatgtaaag aagacaaaaa ggaaaaagtc acatccttaa atagaacagg aggaaaacga    14100
cctcttgggg gacaggtgac tcacggaaga actggggtat tcagagccca tcaccaaact    14160
gccctccttg gtagacgtac tttatggggc ggtctcactg cagcccaggt ggcctgggat    14220
tagcagccat cctgaacgct gcttttatag accagaagct ctacacttgg atggaaatag    14280
taatactact tggtttaggt ttgtaatcag tcaagagttg ctctatgtgg cctaggactc    14340
agatgtgttt aagattagaa agaataataa ctgtatgtag tgttgttagc ttagtgtcta    14400
gttttattag ctttggatca ggaagggatg aataacagtt ttgaactatg tcaatttacc    14460
tttaaaatgg tttacaaatt tgtttatggg agttcttaca tgtgtgtgca cacatacatc    14520
agaggacaac ctcaaatatt gttccttaga gtagttcacc ttgttatttg agacagtctc    14580
tcattggcct tgaacgtata acaagatggc cagcttgtct acttgttttt acctcccagc    14640
ttctacatca gtgctgggca tctgacctca ggtccttatg ctattatggt aaacactttg    14700
ctgtctgaga catgtctctc taatcccagt ttacctgttg gcaaaggcta gttttggact    14760
aatttgaagc tcctgtcatt ggctcatttt aaatttttcct tagttttgt tttgttttgt    14820 tttgagagtg tgtatgtgcc catcttgatg aaggtacaga ggtcagagga cagcttgcct    14880
gagttaggtg atcagggtcc tgctcagtct tggcaggaag ctcccgcatc tgttaagcca    14940
```

```
ttttcctagc cctcaaaacc tgagnnnnnn nnnnnnnnnn nnnnnnnnnn nnnnnnnnnn    15000
nnnnnnnnnn nnnnnnnnnn nnnnnnnnnn nnnnnnnnnn nnnnnnnnnn nnnnnnnnnn    15060
nnnntcttgc ttctctggtg ctctggttca ttctcattga tgcccatgat ctattgataa    15120
gatcatatga cattttttatt tgaattatac atatttctat acaatacagt ccctactttc    15180
ttccctccca tccacacttg ttttccccat cctgttaaga tggtcttgct atgctggcct    15240
taaactaggt agctagcata ggttgacctc aaacatgcag gccctttgcc agtctcccga    15300
gtgtcaacat tatagggatg caccgttatg cctggttcac ttacagcttt tattcccaaa    15360
gttcccattt ttcccccata ttctatgttt ttatttgcta agactgttta acatttgttt    15420
caaatgttct tctaaatact tgctgaagaa ttttatcag gctacttgc aaaactttg    15480 ttagataatt ctaacatctg tattgtctta gtgttggcat ctattagctg atgctccccc    15540
acccccgccc acagctctct tgagacctgc ctgattcttt gtatgaccag tgattttctt    15600
ttaaattaaa aaccttgata attttgtatt taaatgacc tgttctgaat atgtaattct    15660
tctaatacat acatgattaa gccatagctt aaacatttct ttctttcttt ttctttcttc    15720
aagacagggt ttctctgtat agtccctctg gctgtcctgg aacttgatct aaagaccagg    15780
ctagcctgga actcagggat ctgcctctct ttgtccccaa gtactaaaag gcgtgcagta    15840
ccactcttgg cttttgtgg gggttttgag tcaatttcat gtggcctgga tagtgtggct    15900
ccaaatccac tttgtataat aagatgactt tgaactttgt tttgttttgt atttttgag    15960 acaggatatc tctgtgaaat tctgactgtc ttggaactct atctgtagac cagactggcc    16020
ttgaactcag agatctgcct gcctttgact cctgaatgct gctgggatta aaggcataaa    16080
ccaccattcc tgattttcct ctttccagtc tttcaagtgg tggaatcaca gatgtttgcc    16140
accaggcttg gcttgagcca gactgccttc ctgcctgcct tatttccttt cttccttcct    16200
tcttttcata tttaaattgt atgtatttac ttgtgagcaa gtgcatgtct ggaggtatat    16260
gcctacctat gagtcagttc tctctttcca ccatgtgggt gtgaaggatt gaattaaggt    16320
catcagaatt ggcagcaagg ggttttgatg acccctggtg tgagtatttc ttttagccag    16380
catcatgaca ttgattgctg agaatatgga cgatattctt ttacgacaga aatgacatca    16440
gatgtaccat cgctgggtcc caccattgct tctggaaacc ctggacctgg gattcaaggt    16500
ggaggagctg ttgtacagag ggctattaag cgacggtcag ggtaagtttg aatgtttatc    16560
atccgtgtgt ttctcttgta ccatcaactt tgagttagt tgctgttggc tcttgtttat    16620
tcctgaccac acatctaatt gattacttac tatactgctg tcataact aaaactaact    16680 cttagtccct ggattattcc ttatccaggc tctctatttt aagtaaattt ctttaatttt    16740
ttttgtataa tttgaatata aatatagctg taaagaaaaa aatgaggact ggagagatgg    16800
ctcagtggtt aagagcactg aggtcctgag ttcaattccc agcacccaca tggtggctca    16860
caaccatctg taatagaatc ggatgccctc gtctggtatg tttgaagaca gctacagtgt    16920
gctcatacat aaataaatgt atcttaaagg aaagaaaagg atgaaacggt cacacctatt    16980
acttatcatc cgacctcact cacagtgcct gtatgtcacg tagggttttg gcttttatta    17040
cttacatcgt tttcacataa aaatttctat acaggttaaa aattgttttc tagtatcttt    17100
attgataagc ctgttttaaaa aaaaaaaaaa cgaagccaaa ccaaaccaaa attttctgaa    17160
aggtaaaggg actgtggcaa agaagagttt cactgttggt aaaaacaaac aaacaaaacc    17220
aaaccaaaaa aaaccccaaa aatctgttgg ctttccttaa gctctggtct gcattctcaa    17280
aatcattttg ttaagcttat ttcttttta atttattaat actttcttg acttggagtg    17340
```

```
cacagttcat ttagtttcaa aagtctttat tgaagtacca gatttgaatg tgccattgaa   17400
gtatgattgc tgtcttagtc aggatttcta ttcctgcaca acatcatga ccaagaagca   17460 agttagggag gaaagggttt attcggctta cacttccatg ctgctgttca tcaccaaagg   17520
aagtcaggac tggaactcaa acaggccatg gagggatgtt ctttactggc ttgtttcccc   17580
tggcttgctc agcctgctct tctatagaac ccaagactac cagccctgag atggtcccac   17640
ccacaagggg cctttccccc ttggtcacta attgagaaaa tgccttacag ctggatctca   17700
tggaggcatt tctccaactg aagctccttt ctctgtgata actccagctg tgtcaagttg   17760
acacaaaact agccagtaca attgctaata ggctctaaag atagatagga aaagttccta   17820
aagttctgat ggtcgttata tttatgtata aatatacaag acacagtatg acaaaagtct   17880
gcaatacctg aagttctagc agtcagtagg gctgagtcag gatggagact gagtccatcc   17940
tgagttacat agtgatactc ttatctcaaa acaaagcgaa aaacaaatta attttaaaat   18000 attattttt aaatatatag aaacactgct tttggacggt aaagattgag aaaagttttt   18060
aaaagaagtt tgctttaggg cagtggttct caactttctt aatcctgtga ccttttaata   18120
tagttcctca tgttgtggtg actacaacca taaagttatt attattttta tttttatttt   18180
tttggttttt cgagacaggg tttctatgta tagtcctggc tatcctggaa ctcatttgt   18240 agaccaggct ggtctcgagc tcagaaatcc gcctgcctct gcctcccaag tgccgggatt   18300
aaaggtgtgt gccaccacgc ccggcttcat aaaattattt tagttctact taataactgt   18360
aatcttgcta ctgttaataa ctgtaatgta ggatatcaga tatgcaactt ccaaagggt   18420 cgttgtgact cacaggttga gaacagctgc tttagggcct gtgaggtagc ttgttaaaag   18480
cctagttagt taccttttaat tgattcccag aacccacaca caagtagaag gagaaaacta   18540
actctaccaa attgccctct gacctctaca tgagtgtggt acctatatgc acacactact   18600
aaagcacaca aaaatattaa acttaaaaat gaatgaatga gcagcaacca catggtggct   18660
cccagccatt tgtaatgtga tatggtgccc tcttctggcc tgctgacata tttgcaagca   18720
gaacacttaa agcagtcaac actctcaatc tctgactttt ctccagccca aagagtgcac   18780
gctactcttc cagagaatct gaattcaggt cctagaaccc atgtcagtga ctcacatctg   18840
tgatctagtt ttggggttct gccacccctt ttctgggtac ctgtattcac atgggcatat   18900
atccctatac agacacatca taaaataaaa tcattttaaa aatcataaaa gatgctctct   18960
tcagtattaa aaacacattt caaatagtgt ttgctttttt tgttttttaa caaagtctgt   19020
ttaatttgat tttattattt tgacatagct ttcttgtaga ctcagctggc ctgcgttctt   19080
cctggttcca cttcccaagt gcttggaaac aaaaacatgt gaccaccaca cctagtttca   19140
gacagtcctg ctgtgtagcc atgttggtct ggaattcagt atgtacacaa agctggcctc   19200
ccactcatga ttctcctgcc ttagcttcct atgtcgcagg actacagtca agtgccacta   19260
catctgggtt ttgtggcacg tctttaaggc cagcccttga gagacaaagg cagtgtgggt   19320
gggagggcag cttggtgtac atggaggttt ctgggacagt cagagctatg tagagagatc   19380
ttgtctccaa acccaaaccc aacctcattc tcacttatta tatatattaa catgcattta   19440
tatgtttatt tactcactct gtgtttgtgt aggttagaaa acaagttgtg ggaaatcttt   19500
ctttaccatt tgggtcccag ggatccaatt tatgcctgta ggcttggtgg caggttttt   19560 aatttgctga gctgtctatc tctctggcct cttgctttat agttgctgtt gtctgggctg   19620
aaaagctccc tgagggtatt ttttttcttt taccacgggt cccacactat tttgtgtggc   19680
```

-continued

```
gtgtgatctt gctttcttgc tttcttcttt gacaggatct ggctatgtag cttaagctgg   19740
ccttggattt atcatccttt tgcttctact tgatgaatac tttgagctaa aggtacgtgc   19800
caccaaggct ggccacttag cacagtgatt tgaatatggt atatatttta tttttagact   19860 aacaacttt tgtgtcttct ttcctctatg taatattgct ttgaaagatg tttcagaaaa    19920
ctgacaaggc ttagattaga tcataaaaat gaaaactaga tctcagggat tttctgtttt   19980
tcaggcaggg tctcacgtag ctcaccctaa ccttgaactc agtggtatag ccaaggttga   20040
ccttgagctc ccgatcatcc tgctgccacg tcccttgtgg cagaattcca ggtgtgtagg   20100
tgtgtgccac catgtccagt tttacgctgt actggaattg aaccggggct tcctgactcc   20160
tcagctgagc tgcattctta gactctgggc gctatttata ctcgtatctc ttcctggtta   20220
tggtactggc ctcctgtatg gaatcctggg tggagggga gggggtcggt gctgctgctg    20280
ctgctccctc acttcttcat tttgcttttt gaaacagggt ctgattatgt agccaaggct   20340
agcttagaat tcattatgtg tctgaggata gccttgaact cccagaaccc accacaggct   20400
ctggacggtg ggttctatat aggcaccgct acggctgcct tttactgcct aacttctgcc   20460
cagttgtaat actatgaaaa gcatgtatta tagacatgtt tttgttttgc ttctgtccac   20520
ttttccttcc attaaggtga gtacataggc atcttttgtt aatatgtttt gctttcttat   20580
ggtgttatct ttactgtatt atcatcaata aacttagaat attgtttgtt gcctttcccc   20640
aggctggatt ttgatgatga agtagaagtg aacactaaat ttttgaggta agatttaaaa   20700
atatttttag agacttctta gtggggtgga gggctggtgg ctggctcagc aggtaacagc   20760
actcctgcca agcaggatgg tctgagtttg atacccaaag ttactgctga aggagagagc   20820
tgactgctgt aaacagccct ctgatctcca catgctggct gaggcgtgag cacccatcac   20880
cctcacagat aactaaatgt catcagatta ttttcagatc accagctggg aatgtagctt   20940
ggtgggatgc ttgcctccta tgcttcaggt tcaatccata gtaccaagaa ggttatttaa   21000
gtatgtttat actttgggca ttgtcctaaa gaatatgctt catcctaaaa ctatgttttc   21060
ctacatcata ggatagtttc aggcatttta ttatttttag agagaatact tcagggagga   21120
gggcacagaa aatataagcc agtcatgttg attcatggct taagagaagt aacacactag   21180
ggagattgct cagtggttaa gaccttggcg ttgcaaatct aaggctaata gttcagatca   21240
ccaaatctca cataaattct gagtgggcat agcagcctgc ttcctgtctt ggaaggtaga   21300
gacaggagag caagctggca ttgagaataa ttctatctgc aacctgtgaa tttgattgag   21360
aaattttgtc taattgaata aagtagtaga gtgatagagg aggattcctg acattaacct   21420
tggacctcta cctgtatgtc cactcacgtg taatgcaccc acacgtgtga gtgctgagtt   21480
tgttattatt ttgttcccat ctgtcccatg agccctgggt gagattaaat gaggctgcct   21540
catcaagtaa ggtagaagag agatgaaggg ttatatcaac tttgggcttc ttcatacttg   21600
ttcacccaca cacatgagca cccacacaga cctgtgccta tacccataca aacatgcgta   21660
tacatacaaa tggaaaataa aaaaaaaaag ttgattcgtt ttcacaggtc tataattgac   21720
taaatcttgc ttgggttcat ggtaagattg tgctcagcca cctggtctat taaaagttat   21780
actcaactgg cacagttgca cctctgtctg tctgtctgtc tgtctgtcta tctgtctctg   21840
tctgtctctc tctctcttgc tctctctctc tcatgttctc tctctctcac acacacactt   21900
gcactctcac ttaaactctt tctccatctc tccctcctta tttctcctat ccccattgtc   21960
ttgtcttcaa acagaggagt gtggtgatgg ttgtaacaca aagggcaagt ctccgtgtgc   22020
ttaacaagcc cctgcttctg tgcttttgtc cttcactgat gtctcctagg ccagagcgct   22080
```

```
tgtgtatccg tgtcctgagt cactgctgta gagggctaca gaaggacgta gatgttagag    22140
ggaataattt gataatgctc tactctgtca tgctgcagta cctgttggcc cctttttag    22200 gtagcaggaa ttagaggttc tgtatgtata aatggtgatg gttgggcagg gtctcatgta    22260
atccaggcct gcctcaaact ttatatagcc tgagatggga tggcggcttg aatgagaatg    22320
ctcacggtaa ggttgtgtgt ttgagtgctt gctccccagt tggtagacct ttttttgaag    22380
ggttaggtgt ggccttggtt ggttgtgtgg cccaagtgga tgtctctagg actacctgcg    22440
caggggaggt agtgagatag actttcctca tcaatcaata atcaaaataa tattacactg    22500
gcttgcccac aggccactct gatagagaca ttgtctcagt tgggattccc tcttctcaga    22560
tgtctaggtt tgtgtcaaat tgatagaaac gaaccagcac agcaattaaa cgtaattctt    22620
ctgatactta gtggatccta ataaatgtga agaagaaaaa agatttcact ttttgcccta    22680
ggcaagcttt cattgttact gctggattta tctatttta tcttaagtgt tttacctgta    22740
agtgtgtata tcgtgctggc agaggccaga agagggagtt gggtcctcta gtactaggag    22800
ttatagatga ttgtgagctg ccatatgggt gttggtgtta tggagtatcc accagaggat    22860
gcttggatat ggatttaatc caatagaaag ttactattag cctgccagca actacactgg    22920
tgtttgggat tccaatgcag cactcagcct ttctcagggt gagcttttaa acacgacagt    22980
atgttctgtg ttgttggcat acttcagtta acaagaacag ttagccagaa gcagaactgc    23040
agaagccaaa gagactttcc cagaactgca gactttgatg gattaggcct ttgttttagt    23100
tttggtaggt agtgctgtat acatactgaa tttcacaacc tgaatggttc ttctatcaag    23160
ggatcaattg tgttaaggtc tggagctatg ttagtactgt gaactgaacc caggtcctct    23220
gcaaaagcag caactgttct taataactga gccattttc cacccctaag atagcatttt    23280
cacacaggac tattgggaat gtcttcatta gagaattctt aattacagtc acatgatgtt    23340
actggaccta tgttgtatga atgctacagg ggtaactaga gtatttgtca ctgtcaaata    23400
gttttgacct tgagttattc cacaaaatca agtagtcata agttttgtaa cattttggtt    23460
cttatcagac tactatatga ccgtgggttc aaacaattat aatgggagtt ataaaagtct    23520
aattacatag gacatagcta ttataacttc agagtgcaaa gaattcatca ttcatgtttg    23580
tgatgatatt cacataataa tgttgacatg atggtgttgc tggttgtatt taaatgtagc    23640
acatatgtgt acagttaata acacttgagt ataaaaaaat cccttgggta tgtatttact    23700
atgttacaat gttcattcat gtttgcactg ttagtaatca ggcacaggga ttactgaatg    23760
ctggggaagc actgtgccac tgagtcagcc ctggccccta ttgttgttat tttagagctg    23820
cccctttctt actgaatgac aaagtttact ttaacacatt gtatcatgta attgccagtt    23880
tgtgaaactt acttaagtcc taatagttct ttttgcttgt cctgaagaag taaaatgtag    23940
aattgggaaa aaatacttgc aaatcatgga tcttagcagc agtcggtatc tagaatatgt    24000
aataaactac aattctgata caacctttga aaagtgattt aatatttaag atgaagaact    24060
gtgggaattg gagagatggc tcagctatta agagtgcttg ctgctctttg agagtactag    24120
agttttgtac ctggaaccca ctttaggcaa cttacaactg cctataacta cagcgccaaa    24180
ggatctagtg ccctcttctg gcttccacag tctcccaaac acatggcaaa gcacacactc    24240
acaaatagaa atagaaataa atgttatttt attttaagta gaatttggta caacttaatt    24300
cagtgcttgt ctagagtgca tgaagctctg ggttcccttc ccagcactgc ataagccagg    24360
catggtggga tacacagcct tggggagact taatcaggac gattataggt tcaagtttga    24420
```

```
ggtcaccctg cactgtatag ccagaccttg tctatacaag attaaaaaaa ccaaacaaaa    24480
caataatacc cccagccaag tatggtacct gtaattccag cactggggta atggcagcag    24540
cttagtgagt tctaccttaa tcaagttaca taggaaacag tttcaaaaag ataagacaga    24600
aatgacagca gctgtgctct tgatgctgca cagtggttaa ataggggcta cagtgtagct    24660
cagtggtgaa gcgtgtgctt agcgtgtgca cggcctgggc ttcattccca gcactactct    24720
gcgtgtgtgt actaagaagg aaattctgaa ttttattcat ccagttcagt tagtgtccat    24780
ggatagacag cgatagtaac tgtataggca tgcctttgtt gctagtgtag gggaagaaag    24840
accttccttt tcttctaagc attttgatga ccaagttgat aagacaaact gactggaggc    24900
aggtaaacag aagaggtaga tagactaata tgtggtctaa gagtagccta gctgcccaaa    24960
gggaaaacag taagtgtgca gtcagtgaaa ttggagaatt tatatggtct cataggaatg    25020
gcaacatagg caactcagta gaagattcac agatacgatg aatgggcatt tgagtaatgg    25080
gtgatagttg tggcacagtt tgccttgatc tatagttgtc tcttgacctc ctgtcctttg    25140
gttgagtact ctttccaggt tgataaatct tcctagaggg tatttgtggc tataagagaa    25200
cttaatgaat gtgtgtgtgt gtcattgtgt gttttaaaca ttttgcgtgt gtgtgtgtgt    25260
gtatcttgac acatgtgcta cacatgtatg aaggtcagag aaaacttgga ggaataggta    25320
tccgcgccct cccccttcac cgccccccc ccctcccatg taggttctgg gaactcagat    25380
cagcaggctt ggcagcaaat gttttatcta ttgaaacatc tcaccactta cctccatttt    25440
gtttgacaga atcccacttg gtaatccaat caagccttgt atagcccagg ctttacacaa    25500
atgtacggag agcctctttt ctcagaggct actgtaggct caagccacta caccctgctt    25560
agcacttgtt tttgttttgt tgtaaatagg tctgactctg tagctttggc tggcctgaaa    25620
cttccagagg tctgcctgtc tctgccttct aattctggga ataaagttgt gaccccctaac   25680 acagtattgt tttttcacat tcttttctaat ctgaataatc agtagactag agcattgagg   25740
tattttctga ctcctttgag ttaaagtcta tctcttcatg tgctgcgcct cttgtgggga    25800
ggacagtaat cagctagaca gatgagagca cttcaatagg acaggggtat tcacactact    25860
gctgtgtaac tgaggcccat attagactga agacctcaag actttggggg aggacacatt    25920
tcatctttag gctgacgtgg tgaaaaggaa gtgaaatggg atgttagcta gagaggcttc    25980
ctagaaaagg aaagggaagt acaaagaccg gaagcaagac gggaagaatg tagctgctgt    26040
tgggaacaca gagtccttgc ttgtaggcca cagttaggag ggaagtagga atccccagaa    26100
ggcagtagcc aggagcttta ccatcttgga gaacctttct cagaggaaga gttagggagt    26160
agtcttgttt caatttaatg cttttgtttg tttgttttac accaaacata gattactttc    26220
aaagttggta aaagcaaatt taaaaatgaa aggggggaaaa atgccaaaag acatggagag    26280
gcatttctcc aaagaaaaga tacaaatggc caagaagcat gtgaaaggtt gacattagta    26340
atcattcaga gatatttagg aggtatacaa gtcaaagata acatttatat ccaatccaga    26400
gaccactatc aaaaccaaaa caaaatcgga gctaagtctg gagactgata cccaccagcc    26460
tcccatgggg agagggaacc cagggctgca cagggagctc ctgtctcaaa aagacacaag    26520 taaccccca gaaaataaca aaattgctag agaagtggag gaatcggaac agttatacac    26580
tgtgatattg taaaatggta cagtcacaat ggaagagaat atggtgccac tttacaagtt    26640
acagctcagg gtcacttgcc tcacaagctt aaaagattcg attgctcata ctaaaacttt    26700 gtatattgc ttttttctga agactttaga aattttattt tttatatgtg tgttttgcct     26760
acatatgtat cttgcacagt atgtgtgcct ggttcctaga cctggagtta cagacaattg    26820
```

```
taagctgcca ggtgggttct gagaactgaa catgggctct ctgcatgaac aacaagtgct    26880
tgtaatcatt gagctctctc tctagcccct aaatgaatta gttttgagct aggtatgatg    26940
gcacatacat ataatcccaa cacttgaggc ttatgtaaaa ggatcgctgt gaattcaagt    27000
ctgagctgct ctcaataatt acacacagag acctaacgca tagagtgctt ttgaggtgac    27060
tgatctcgga acccacactg tgaaaggata gagttgttct tgaaagttgt tctccacctc    27120
catatctgcc ctgtggctgc aaacacaagt ttggttttga tggcctgaaa cttgctgtct    27180
agaccatgcc gacctccaac ttgaactgat cctctttgaa cttgcattct gcatgcaggg    27240
gttcagttgt gcacaattta tattttcata catatatata aggcattgta taccccaccc    27300
ctcaccctgg gacatcctct tctcgatagt ccccttcctt ttcccaacta gttcctcttc    27360
tactttcgtg accttttttt tttttctctt ttcttttgga gtgggatgtt tcattagggt    27420
tgcttaccag tagtatgtgt gagtgattac actttcctcg gggctacaac aatgaagaaa    27480
agctctccca gcaactaact gcttatagat cctcaagggg gtttgtggct ttgtgaactc    27540 ctccccctt ctatgctagg atgttgtgta gttttgtag tcacagctgt tgtgaattca    27600
agtatgcatt gctcatgtca tttcagaagg cagtgttcca caacagtctg ccctttctct    27660
taactcagag tgttaactct tatgcaatgg tccctgaccc ttggaggctt tggctatctc    27720
tttcccatcc cccattcctt gtggagtgtt gctgtgttgc tcagaccagc ctcctacacc    27780
tggctcaaat gttcttttct ctcagctgcc taagtaggcc taaagaactg caggcacatg    27840
ctaccacacc cagcttaaag cagggtcaaa atatgggtat tagatgaata cccatattta    27900
tgatcctgtt tttcacagaa gaatgaaaac atgaaaaata tacccacacg ctgttctatt    27960
ggttttttga tttttgtttt tgttttgttt ttttaaagc tacaattaaa aaacaaacaa    28020
actgagtcag gcttagtgat tgacacctgt aataagcaat tgggaggcag aggcaaaggg    28080
tctgtaagtt gagagtgaat gccagactag ccagtgctac atagctgtcc ccatctcaaa    28140
aaaacacccc ccccccggaa aaaaccaaa caaaaacccc aaatatattc ccaactttag    28200
agaaatcaca agacatttca tgttttcatc ataccatctt tctgtgtgtg gtcactgaga    28260
catgatagtc atcggctctc agtgttctct cagatgctat tagtgtctgc tgctttgtgg    28320
tgctggtcca ttatctttcc ctgttgagta gttttattta tttctagttt ttatttcaga    28380
gcggagtaga tataagtaca agggtttgaa ttaatccctg ccctttctttt tcagatgcga    28440 tgatgaccag atgtgtaatg acaaagagcg gtttgccagg taatgtacta gaattcttgt    28500
cctggttatg ggatcaagca gtctaaatgt tggatttaaa ttttatctag gtgagagtga    28560
atttctctgg ttagtctcct cctcttctga agtttgaaac agcctggaat ttatgcatgc    28620
tcattgactt gaagctaggt atatttaaca taatgtttct ctcatgcatg caagttttag    28680
taatgtgtat attgcatcta caggatcaca aactgtagac ttcttgggca tattatattt    28740
gtacaaatac agaagaatct tttatagaaa atggtttatt catttaaatg agttttatt    28800 ctggatacca aacttaaatt tgtttaagta actgtcagaa gattatgaaa tatactgatt    28860
ttactttttt tttctcctcc caccctgat tttacttttt attaaagagt aatcattctc    28920
aactcatata ctggttttac ttttagaaaa ttcttgctgt aagttactct tttaaaaaga    28980
ggggagggtg tcatggggct ggagagatgg ctctatgggt aaaagtgctt gttgctctga    29040
cagaggacct gaatttggtt tctagcatgc acaaccaggg agtctgacat cctcttttgg    29100
cttctgttga cgtctacatg tacatgatca tacatatata tagatgtaca cgtatacaca    29160
```

```
tacatacatg catgcataca tacatacata catacataca tgctttattt attatcatta  29220
agtgttcatg cttacttggg gagccaagat gttgggttcc aagtataagc ctgtgtccct  29280
gaccactctc cccagtatct tcaccccagc tgagtatctc tggagagaga cccagaaggc  29340
acaagtagaa ggtttgggca taagggtgaa gctcagcggg agtacttgct tcagtacagt  29400
ggccccaaac accaaatgca caataaagac cctgccttga ttcattgaac ttattcagga  29460
tcaacaaatg tttaatctaa tttcagaacc actcccaaga atttactcat tttttaggag  29520
ctctgctggt atttgggccc ctcatcttct ggtattatgt tttcaaaaca gatagggaca  29580
gaaaatatag gaaaattgaa ctgaacattt aacctctcat ttaatttggc aagggacttt  29640
tattgctata taaatagatc tactaattta aacactggaa ataaataagt aaataaatca  29700
atactttaag ctcaaatcct gaagttttt cccttacaca cacacacaca cacacacaca  29760
cacacacaca cacacacaca cacatataca cagtggtact catgtgcctg tacttatata  29820
tatacattgt atagacacac ttaatgataa taaataatta aaaatttaga agatactgaa  29880
tttttggctg gggagatgac tcaggattta aagtgcttaa ccccagaacc cacataaaat  29940
cttgatacag agtatcccaa gtctatgatc ctagtgagtc tttattgggc gatagaagac  30000
agagatggga atagccacaa actcatggct cagctaactt ggtgtgtgca gcagtgaaca  30060
ataagagtga ctctgggctg gagagatggc gcagtggtga agactgctct tctagaggtc  30120
ctgagttcaa ttaccagcga ccacatggtg gctcacaacc atctgaaatg ggatctgatg  30180
ccctcttctg gtgtgtctga agacagctat agtacagttg tatacataaa ataaatattt  30240
tttaaaaaac ttaaaaaaaa agagtgtctg tctcagacta agtggaaggc atcgaacaac  30300
atctgaggct gccttttaac tttcccttgc atttcatgca cacgcatgca cgtgcacgca  30360
cacacataaa attgagtttg tgatcctctc aaaaattagt aactttattt ttaaatttgt  30420
atgtaattga ttacttaaa aatgatctat ttcattttta attatgtgtt tgtatagatt  30480
atacagtttt tatagataaa tggttatata catatgaatt tggataccaa aagaagacat  30540
caggctccta gaaacgcagc aagcccattt acccaccaag ctgatcctat agcccaatga  30600
atacttactt aaggtttgat tacattgatt gattgattga gaaagtatgt gtgtttgtga  30660
catgccaaca tgctaagctc agaggacaac ttctaggagc agattcttgc ctttcacccg  30720
tgagtcccag tgttgaaact cagatttagc agcaagcacc tttacctatt aagcctgtct  30780
gctatgtctt ctgtgagtac tgatcaacag tgtttactca ttgctcagct gtctgaatgg  30840
gatctacttt gaggaccact gatcgagaga accaagaaat atcaggaaga atagttaact  30900
cttagacaca gtgttggcag tatatagagt tgactgaaaa gagcaggtag gtaggtaggt  30960
agtaggtaag taataggtag aaagagggag ggtagataga atctgctgaa gtattaggat  31020
agctatgaaa tcatgagtac ttgggcccag aaatgttgcc gtgacactag tgaaagaatg  31080
aatataggtt gtttttccaag agcagtgtat caaaacttct tgaaataaat gaaatctaaa  31140
ggatacagta atctttaaag tgaaagttaa ttattgattt tgggtaataa tctttcacat  31200
tctattaaaa agtctagcta taaaactgga ggtgatcctg taacacttgt aatggaggtg  31260
gaggtaagag attagaaatt ctaggttagg gactagagag atggctcagt agttaagagc  31320
actggctact ccctgtagtg gacctgagtt tgattcccag cacttactgg tggcgcacaa  31380
ccatgtatga ttcagttctt gggggagggt ggggagtcca atgccgcctt catacatata  31440
tacatacata catacataca tacatacaca catacataca tacgagtaaa atacttacac  31500
acctaaaaat aaaaataggt aaatctttat ttttttaggt tactgggcag cagggcagtg  31560
```

```
gtggcacatg actttaatcc cagcacttag gaggcagagg caggcaggat agccagcctg    31620
ttctatagag tgaattccag gacagccagg actagagaga gaaactgttt tgaaaaacag    31680
aacaaaagaa aagttatttg gctatgtagt tcaagaccag cgttggcttc atgtgatcct    31740
aaaaaccaaa ggtcagatca tcattagggc agctaataca ggtccagtcc tcagtctttg    31800
atcgacactc tggaaagcca taaaacacaa cctggagtat ctaatctgcc tatgtcctat    31860
tctgtttaga aatattggag tagagagggg gttgtgtgac tctactatta attttaaagg    31920
aattaattaa aggaatttta aatgattaac ctcaaacaaa aatgcatttc ttagagttac    31980
agtttgttat gatagtttac ctcatacacc accagaaatt cagtaggtga aaagctaaaa    32040
ataggtgaat ttacttatct tttgaaaatg aatgttttgt tgcttgttaa aaactatcta    32100
ggataaggaa caggcaggtg tgactactct gttatctgtc ttctcttcag catgtgtgca    32160 tacatttttat agtattcatg actatctgca gttctaactt tttttatttc ttatttttaa    32220
cattcaacaa ttttattcca gtttaaaaga agaacagaac aggtaagctg taaaatgtca    32280
gccagtggct ggaggaagag agtggaggaa agaggaagca aggccacgcc attttaagct    32340
ggcgtggaga tgagacattt gaggggcgct ttagggaaag agtagggaag cccaaaacgc    32400
tggtgagacg catgcttgga aaagacacag agagttgttt tgggtgatca aatgaccctc    32460 tcacagggt ctcatatcag acatcctgca tatcagatgt ttatattaca aaataatttt    32520
atgattgggg tcaccacagc atgagggctg ataaagggtt gcagcattag gaaggctgag    32580
aagaaccact gtgctagaga aaggagaaag gagaaggtga cagataatga tccttacatg    32640
gctgaggcct gttcaggttc tgctattaga cattagctga ttgtgtttat gtatgtgagt    32700
atgtgcatat gaaggcatat aggattttcc agttgaattt acaggcagct gtaagctatc    32760
cagcatggat gctggggatc agactccgat cctgtgccag aacagtgtgt gcttttaact    32820
cctgagccat ctttccttct cctttttttg agttaagatc tcaccaggcc aggctttcct    32880
ggaacctgca gaaaataatt ttacctttgt ttctgactgt tggtattaaa taaagttgag    32940
caccaccaca gccagttgtt ctttttctac tgatcatttg tgtatatatg tgcatggaga    33000
ggacagagga caactccagg tgtcatttct cagccccacc cccacccccg ccgagatgga    33060
gcccttctct gtcttggatt gcactaggtc gactaggatg ctgttcagtg agcccatagg    33120
atcctcctat ctctgccttt cctgtgccaa gattgtaagg attgtagttt ccactttatt    33180
tttacatata ttgataaaat tattattatt aagctcaagt tttactctgt tgcaaatccc    33240
taggctcaag cagttcttcc atttcatcat caccagtagc taggactaca aggtccctgc    33300
ttcctgctgt atccatttta aggcagagtc ttaggaagtt atttttatttg cgtgtctggc    33360 tttattattt tggtttatgt gagacagtct tggcctgtca cccatgctca tgctctcagg    33420
ggatgattga gattatgctc catggaggac aggagagggc gtcaggtctt ctagagttag    33480
agctagagac tgtcatgaat tgctggacat tgaacccagt ttctctggag gagtagccag    33540
tgttccttat ctactcacct catctctcca gccccatcat ctttaatagt gaagtctttt    33600
tggactatta atatacctta ctagataatt tatttgaggc ttatctctct taaaatgagc    33660
acttataata ctgagttagc tagtaccttg ttttggtttg tttgcgtttt tgtgtagcct    33720
ggctgtcctg gaactcactt tgtagaccag gctggcctca agctcagaaa tccacctgcc    33780
tctgcctccc aagtgctggg attaaaggcg tgcgccacca cacccagccc ttgtttttt    33840 tcagttgctt ctctctcccc ttttgtgcg gtgggtattg agccagtcct tccacattgc    33900
```

```
cctggttatc ctggaactct ctatctctgt gtgtaccaat ctggacttga actcctcaag    33960
tgctaggatc ggaggcacca ccaccatgcc tagcccctgc cacccattct taaagtgttt    34020 tgttttctg  gaagagttta atgaaaacct ttgtctttct tcgagggagg agggattgac    34080
atactggtta aaccatagaa gaaatgctaa ggtgcctaaa ccagagttca ttaaattagg    34140
agtgtgtcag tgatagagaa tatgcaggaa acctagctct tgattttat  catgtgatca    34200 tgtcaagcta cacggctcgg tgtatggctt tcactccaag cctgagaact caggttcttc    34260
ctcacagggt agaaggagag agccaactcc cgcagtcgcc ttctgacctg tggcacacag    34320
acacactaag tactacaatg ggaaaaataa atcttgtcat aatttgtgtg tgtgaatgtg    34380
tgtgtgtgag gaaattatat ttctaatccg ttgtttgaag ctgtgtaatc tagtcactag    34440
tagacaatag cgaatgtgaa taagtgtttc ttcccagatt ggcagcagtt tataagaatg    34500
ataattctga taattctgaa tttcctggtt ggttcttgtt cacactctgt atctttggtt    34560
tctgtagaga ttgtttgaca aagtgttttt tgtgttgaga ttatgttagt ttctaattgt    34620
ccttgacttt cgacttataa tttacttgtt acaaaaatac agttctatag gttctcaagg    34680
ttcttccttg tatggccttt cctcactttt tctgtatcca tttcatttct tccttctttt    34740 cctttcatt  ttgcatttca tttccctcc  ctcgcttca  tctgccttt  cttctttcct    34800 ttcttcctt  ttattttaat tttcgcttag ttcatcaatt ctgtttttag gtcggatgat    34860
gagcagagct ctgcggataa agagagactt gccaggtagg agctgtgctg tttagcatga    34920
agcacatact gccttcttac cctttgtcta acccatcttt ttttcccttt ctgtattttt    34980
ctcttacctg tggcaaagga ggacatgagg ttttacaagt tggggtacaa taagaacttt    35040
ggcttcccca acaggaagtg ggtgaattaa gccaggtatg gtggctcact cttttgatcc    35100
ctgcatttgg gaagcagagt ggagttctgt aagattgagg ccagcctggt ttacaaagaa    35160
attctaagac agagaaaccc tacctgaggg tgatggaaga ataaattata aattactgtt    35220
catctttaag atttttatt  tttctttact tcatcactaa gttccacaga taatgattta    35280
gaagtaatgt ggctgtgtcc acagatgctt aacaggcgc  atactctctc agaataccga    35340
taattaccat agttctatca gaataccgat aattaccata gctcccagaa tttaggccat    35400
agcacatact ctgacttccc tatgccgatt cacagtctag attactatga tggtagaact    35460
gattgaatcc ttataatttc tgaggaaagt tttagctact ttggtatgac tatttaaagg    35520
atggattttc tagggtggag agatagtctg taaaatactt gctctgcagg tatgattacc    35580
agagtttgat cctcagaacc cattgaatag aagggtgcgg gtttataact gcacatgttt    35640
atgattctag tacaataggg aagcaggggc agacctctca ctgggcagct gcactggctt    35700
aggagaagag ccctgggtcc ccatgagaga tgctgtctca gaaaacaacg tgggaagtgg    35760
atatcttaaa aatgacattt taaattgacc tttggatttg acatacatgc acatgcatgc    35820
tcacacagtg tgtatttgca cacatagttt tctggacttc agtctcagaa atttgtcaga    35880
tactaagaag atgggtactt caaaattaag agtagattt  tttaaatgtc tgagagtagc    35940 taaaatattaa cctataaagt aggttctttt tctttcgga  aagagaccac ttttcctttc    36000
cttcaggaca gggtctcatg tactttatgc aggccctaac gtcctgatcc tcctgccggg    36060
gtgctggatt gcaagggtgt gccgtcatgt ccagataaac atctccatag gcagatttcc    36120
ttctgaggga ctcccagctt tgtgtgttgt gggtgacact gtgacactca ctgagctaca    36180
ttcagggacc tgtttagtt  ctctttagag tgttgtccat gatacagaaa tagtgctttc    36240
ctgctctggc ctttgagttg gtgtacctgg atcattataa aaatactttt accactgtcc    36300
```

```
ccttgtgtta cttcttcaag ctaggccaca cattcattct gtgactgtta acccagggtt    36360
gctactgcga tgcttccagc cttcagagaa ctggaaggcc ttacactggg gaggagggca    36420
gctctgagaa agccagctaa ctcttgcttc atttggctca ttaaacacaa ggatgtcagt    36480
gttagggttt gtggttttgt ttttctcttc agaagagatc cataagtggc gagagagata    36540
cataaagaca gtaaagccaa gctgttcctt cgaggcgtcc tcgtgggaga ccccaaagag    36600
tccatttgta aactcttagg ttattccttt tgacagttgt attgcaatcc tgcctcacgt    36660
ttgcggtctt tgttaccctg gtgagatgcg ggttctcttt cagtgctttt gatgttcatt    36720
tccccagcta ctcctcttcc cacaatacct tttgcccagg ctgggaaacc acatgataac    36780
cagcactctt ttaagttcag cgcactgcca aacccagaga agaattttgt gcattagtat    36840
aacaaataaa attccaacat accccaattc tgtatcttaa tgccataagc aactttgaca    36900
aggcagcatt taatatacta aaagaattta cactatcatg tcttcttttt ctttcctttt    36960
ttccttttgg gataagatct cactatgtag cgctggctgt tctagaactc agagattccc    37020
ctgcctccac ctctgagtac tgcaattaaa ggtgggcgcc accacccctgg cgcgcgctcg    37080 ctctctctct ctctctctct ctctctctct ctctctctct ctctctctct cacacacaca    37140
cacacacaca cacacacaca cacgctctcc attttaaagg cagtcttatg tattccagga    37200
ggtgagaagg aattatccac tcaagtgctg gactcacagg ttctcctgac tgctagcgat    37260
cagacccaga gccttggcct tgctagacaa gcactccaac acctgagcta aattaccagg    37320
ccaaggtggc tgctgctttt cttcttcctt aaaaaggagg cattgggtag ttttgagatc    37380
catcttgctt catagcccag gctggcttca aactcacctt gaagttgatg gtgattctct    37440
tgcctcagcc tcccagtagc agggattata gacaggcatg tgccagcatg cctggcctca    37500
tttggatatt tggaacaggg tatcactatg tagtccatgc tgccctgtat agcccaggct    37560
ggcctcaaac ccaaaactct tgtgctttat agtcttcgga gtgctgaatt gtagtatttg    37620
ctaccagctc tggcctttat actattattt cttcataag ctactggttc atttacttaa    37680
cttttcaaaa gttggtcatt ttattttata gccttcaaat gttttaacta gaaaacatgt    37740
ggtcagtgaa gctgagattt atccccttag gaacttaaat gagtgaaatc aacatttaaa    37800
aaaacactca ctctcaacct tacccctgag acaggatttc tgtgtgttgc ccttgctgtt    37860
actttgtaga ccaggctggc ttagaactca gtgatccatc tgcctgcctc tgcctcatga    37920
gtgctgggat taaaggcatg caccaccaac accttgtttt aattatttct taaactattc    37980
actctgaagt ggtgatttaa tggaagtggt tgactggaga ggcgatatgt acttgttctt    38040
tgtctagact ttgttagttt gtttcattct tactctgcat gaggttggcc tgcttggctt    38100
ctgagatttg aacatcatca gacctaagtt actgcatcct tcagcagctg accaggtatc    38160
catatcactc tcctgatacc aaaggaacag atgtgaccac ctagaatgga gcctcttcct    38220
ctttttttat gcagggaaaa tcatagtgaa atagaacggc ggcgacggaa caagatgaca    38280
gcttacatca cagaactgtc agacatggta cctacatgta gtgccctggc tcgaaaacca    38340
gacaagctaa ccatcttacg catggccgtt tctcacatga agtccttgag gggaactggc    38400
aacacatcta ctgatggctc ctacaagcca tctttcctca ctgatcaggt ctctggatct    38460
taaaactgac tctgggtata tctgttgaaa gttttggact aatttaatgg ttttgtttgg    38520
ttgcttgctt ggttttttt gggagggtct catgtagccc aggctgacat ccaactcagt    38580
atattgccaa catgtgccac catgtccagc ttcaggagag tgattcttca ggagacatca    38640
```

```
gatgtagaaa agtgaattca gcccttagct ataagtgatc aagtattggg ggagtgagaa    38700
tagataaatt tagttgtgag aacttattta gcaaggtgtc aggtatttta gaacttggct    38760
catacaaatg acctgtgaag tgaaagaagg gtgtgtcccc agagaggttg ccacactcat    38820
ggatcagtgt tccttgggtt atatttctag agcatggaag aaatctgcct caccccttgaa   38880
gcaacttta gtcttaacga tgagagacgt gtagtaaaca accctgttg ctccatgata     38940
tgttttgtta cacttgatat atcatgagga aaacagaaag ggcagaaata cttgccatca    39000
ttcaggagcc ccatctaaga gttatctcac tattgccagg agagagaact aaatgtgagt    39060
agagtaaacg ggtgagtagt aagatgccta agtgaaaaac gatgggaaga ggcatgcgga    39120
aaagagccgg tgtctttgtt aatagtttgt gtgtgataga tatacaatgg tggcatgtct    39180
aactttatt agtctctcta gacttgactg agaatgacta ggaaagacaa gttacatttc    39240
acttaaaaat ccacgattgg gtagggcata gtggtgaatg cctttaatcc cagtactcag    39300
gaagctaagg ccagcttgtt ctacagaggt ccaggccagc cagagctaca tagcaagacc    39360
ctgttcaaa aataaaaga catatgattg ttcatacta gcctatgcaa agccctgaat      39420
ttggtcccaa cactatatgc agttgtgtat ggtaactgga tatggctgct cataacccgt    39480
cttcagcac tgaggcacaa gtaggaggtt gagggttaga gttattctca aggccagcct     39540
gttaacatag gagactgtct aaaatagata catacacaca taagatggtc atataggaga    39600
ctgtctaaaa tagatacata cacacataag atggtcatat aggagactgt ctaaaataga   39660
tacatacaca cataagatgg taatatagga gactgtctaa aatagataca cataagat     39720
ggtaatatag gagactgtct aaaatagata aatacacaca taagatggta acataggaga   39780
ctgtctaaaa tagatacata cacacataag atggtaacat aggagactgt ctaaaataga   39840
tacatacaca cataagatgg taatatagga gactgtctaa aatagataca tacacacata   39900
agatggtaat ataggagact gtctaaaata gatacacaca taagatggta ataaggaga    39960
ctgtctaaaa tagatacata cacacataag atggtcatat aggagactgt ctaaaataga   40020
tacatacaca cataagatgg tcatatagga gactgtctaa aatagataca tacacacata   40080
agatggtcat ataggagact gtctaaaata gatacataca cataagat ggtaatatag    40140
gagactgtct aaaatagata catacacaca taagatggtc ataggaga ctgtctaaaa    40200
tagatacata cacacataag atggtaatat aggagactgt ctaaaataga tacacacata   40260
agatggtaat ataggagact gtctaaaata gataaataca cataagat ggtaacatag   40320
gagactgtct aaaatagata catacacaca taagatggta ataggaga ctgtctaaaa    40380
tagatacata cacacataag atggtaatat aggagactgt ctaaaataga tacatacaca   40440
cataagatgg taatataga gactgtctaa aatagataca cataagat ggtaatatag    40500
gagactgtct aaaatagata catacacaca taagatggta ataggaga ctgtctaaaa    40560
tagatacata cacacataag atggtcatat aggagactgt ctaaaataga tacatacaca   40620
cataagatgg tcataragga ctgtctaa aatagataca tacacacata agatggtaat    40680
ataggagact gtctaaaata gatacataca cataagat ggtaatatag gagactgtct    40740
aaaatagata catacacaca taagatggta acataggaga ctgtctaaaa tagatacata   40800
cacacataag atggtaacat aggagactgt ctaaaataga tacatacaca tataagatgg   40860
taatataga gactgtctaa aatagataca tacatata agatggtaat ataggagact     40920
gtctaaagta agtgtcaaca tataaaatgt gtgagtagtg tgggaagttt tagaaaatac   40980
aggaaatgac acttaatgta atgtcaccat tgctgtctga gaattatagg aatacttctt   41040
```

-continued

```
gagagaaagg gataaatttt ccaaataggg cagtctgttt gctagccatg gagtacattt  41100
aatagctatg tacatagaaa tagtcaattc atgtcctcag aatacgtcag gtatttatta  41160
aactccagtc atgctccttt tgtggcaaac caggtacttg cgctatgaga aatccaaaga  41220
atttaaaaag gaaataaagg tcactggtgg aatcagataa tataaattga taactaataa  41280
tacgaaacta gagttgtaac aggaacagta acaaggctaa tagagtatag gtatagaaga  41340
ggaactaggt gctggccatg gtgacccact actgtagtcc cagcagtcaa ggtatctgag  41400
ttacattgca attcagtgat acgtggaagt gggggaggag tgtggtggta tggagggtaa  41460
gtacagggta tacttggatt ttattttatg atgtggaagc atgtgtatgg tttctaagaa  41520
gagaggatga ataggatcta ggaagtgttt acatgtaaca tacgaacaaa gggaagagta  41580
tctgggcaga aaataaagca gaaatgaatg gaatttcaga agatactaag caaaaatgaa  41640
atttctaggg ttccatgggc agtattaaca ggttgtgtag agagattgaa tttaaaaaat  41700
gatgagaatc caggagaagg gacttgaatc atcaattagg aggatgtaat tgaatcctca  41760
attacagaag tagtgggtta cagtgaagat ggagggataa ttgaaaagca agagagtgta  41820
aaatatggtc tcacccatct taccatcttt tatctaccct caaaatgaca gtgatctaat  41880
taggttttg tagtgctgac ttagttaaac ctttggctcc tggtgagcat ccgctcaaga  41940
gctctctgga tttgtggatg aaagacgtgt gccagcttaa ttttgatatg ccttgactag  42000
ttcaatggct gggcagttct aaaactccca aagccagcaa acactcccct tgggtattcc  42060
tgggttaata tcttttaaaa tctgtatttt cttttgcttcc ctggctcctt tggggcagcc  42120
ctttctttt ccccctttgt tttccccag ggaacctaga agtcccgcct ctttcatcct  42180
gcccatcctg gctctttatt gatcaatcaa aaaccagttt gggtgaccaa aattagcatt  42240
ataacacaag cagcattaga ccaaacccac ttcatgtttt tatggttact tcctaagcat  42300
taaaacctag atcctttaat aacatattct gaacaagttg agggaggcta tgtttgtgtt  42360
tataagttgg agtggaaagg gggaaagtga gaggctccta accctaaccc ctgcccctc  42420
cagaagtctt atcatttaat gtaagccttt ttattttcct ttgagtgcta agaggcaaat  42480
agcaacttag agaaattgca ggaatactta ctgtaaaaag tttgccagtg gatatttagg  42540
gtaggaaccc atggcttata tcgtggtata agcctgtgat tcctagtgga gcagtgcata  42600
tgtacccaag gatcttgctg cttcccatga tcagttgtgt atgttttttc agagttcact  42660
attaactttg gttatttttc ttgaccagga actgaaacat ttgatcttgg aggcagcaga  42720
tggctttctg tttattgtct cctgtgagac tggacgggtg gtgtatgtct ctgactcagt  42780
gactcccgtt ttgaaccagc cacagtctga atggttcggg agcacactgt atgatcaggt  42840
gcacccagat gatgtggata aacttcgaga gcagctctct acatcagaaa atgccctaac  42900
aggtgagagc tggctggaca gcagatatgt gggggaaaag tctttatttc actcaagtag  42960
ttaagatatt taagcccgaa aaaccaaaaa aaaaaaaaa aaaaaaaga tatttaagcc  43020
tgtacattgg ttggttgaat ctagcaaagc ttctaaaatt ttttttcctta atgactataa  43080
ttgttttaa ttcacgtgca aaatatccac tctgtagctt attcttagaa aatatttcat  43140
cagtgcttgt gttcttataa aagctcattt ctatcttaat aatatcttaa aataggatgg  43200
agaggctgtt ggttagtgta taagggactt gtttgttgtc actgtatctc tattaggtca  43260
tttcccctcc accagtaggt gagactcagt cctttaccat cgtttggaga ataagtgcca  43320
cctgttctca gcaactgtac aggaagtaac aaaatggaaa caaataacta ggagttaaaa  43380
```

```
taggagaaac tagggctgga gaggtggctt agtggttaag agcactgact gcttttcag    43440
aggtcttgag ttcaattctc agcatggtga gatggtggcc cacaaccatc tgtaatgaga    43500
tctgatgcct tcctctggtg tgtctgaaga tactacaatg tactcataaa catgaaataa    43560
ataaataagt ctaaaaaatt taaaagaaaa agaaactcca atatctttgc agtgggaatg    43620
ttcatattaa tgttgtttgt ttgtttgttt gtttgttttc ccctcttttt gtgattttgt    43680
acatttcatt tctataattt tccttttccc caaatgttac ttacattttt aaaaaaataa    43740
ataaaggaga gagactgttt tgttttggga cacatgcatg tttcttagca tgtaaaatta    43800
cttgttttta aaccagacac tgtccctacc cgaagcgtga cgatagttag tgactggcct    43860
aatggctcgg tggtgaagga gcatgccacg taagcccagc agtctacgct cagtctgcag    43920
actgcataac agtggaagca gtgacagctc acatagttg  tcttctgacc tccacataca    43980
ggagtgggct cacatgcaca atagttctag tagtttccac tcctgcttta ctcagttctt    44040
gtgccgtttt ggagctaata gtgagattcc tagatgagga cgcaagtagt ttaggcttca    44100
agaataaagc atctctgtca taaacacgga atctggaagg cttggctgga cccaagcttt    44160
gccgcggtgt ctccttcctt tcccatccac aagaagtaac ttgagattgc tctctacctc    44220
cttgaccagg gcgggtcctg gatctgaaga ctggaacagt gaaaaaggaa ggccagcagt    44280
cttccatgag gatgtgcatg ggctcacgaa ggtcgttcat ctgccgcatg aggtgtggtg    44340
cttgggattg tgttgggtgg gaataagagc agctaaggct tccatttctg tcagaggcat    44400
tagttagtat ctagtatcta gagctacgtt ccttgccaca gttggattac atttaacttt    44460
caagaaccag ttgttttacc atacttataa tatgtaagag aataacagtg aattacagtt    44520
aaggcacagt tggtaggtcc tttgtgttga cttcttactt ctgtcttagc ttcactactg    44580
ttcatagggt aagagtcaac gttcattatt ttgttcaggg gctagagaga tggctcagca    44640
gttaagagca ccttttgctc ttccagacga cctcagtttg aattccaaca ccacatggca    44700
gctcacaaca tctgtaactc cagttccagg ggaatctgat ttctctcttc tcgattctgt    44760
gggcatcagg catgcatgtg gtgcacagtc atgcaggcaa aaacccatac gcattaaaaa    44820
tgttttaact ggatttaaga tgtgggagag ttgtcttact agttaagagc acttgttttg    44880
ttcgtctaaa ggacttaggt ttcttttgta gtacccatgt ggtggctcac agccacttgt    44940
ggctccagtt ctaaggggtc tgatatcctc ttgggccagc aggccatata catggtgcat    45000
atatttgcat gcaggcaaaa cattcataca cataaaataa aataaatct ttttttcctt     45060
tttaaagtga atgcagaaat tggagagata gcccagtact aagtgtgtga tgcacaaaca    45120
tgaagaacct gagctcaatc cccagcacct atggaaagtt agatagtccc atttctggag    45180
aggcctagcc aaattaatga gcctcaggtc ctagtgagag accctgtctc aaaattcagg    45240
gtaggagggg ctggagagat ggctcagcag ttaagaataa tagctgctct tccagaggac    45300
tggctcaatt cccagcatct gcatggttgc tcacagccat ctatgacccc agttccaggg    45360
catcggatac cttttctgg  ttcctgtgta tccaggcgtg cacgtaatgc acttagagac    45420
aggtagagca ttaatacaca tttcaaaaga attacgatgg agagctcttg aggaactaca    45480
tgtgaggctt gtctctggcc tccgcatgcc tgtgcgtgta cagcatgaac atatacatac    45540
atatacatgt atcaagaaac cggctgcaga gatggctatg cagggataag agattatatt    45600
gctcttgcag aggactagct ggggttagtt tcccagcatt cttatcagat agcttgtaac    45660
catctgtgct tctagctgca aggagattca aagcctccag cctccacagg tagctcaaca    45720
tgcacatact cccctccttt tccatgcata cagctaaata aaataaatct tacaaaacag    45780
```

```
aacagatgtg ctagaaagat ggctcatcag ttaagggccc taactgctct tctagaagtc    45840
ctgggttcaa atcccatcac ctaatggcag ctcgaaactg taactacaag atctgacgct    45900
ttgacactga catacatgca ggcaaaacac caatgcatat aaagtaaaaa caatagacaa    45960
accgagtgtg acattgcttg tcttaaatca tagtgctcag gaggcagagg ccggcatatg    46020
tgagtgaagc attaggttct cgagatcacg agactgatag agaatcttgt tttagttcat    46080
agcagcagaa ctccaccatt gatgtgtatt cagacttaaa actcaagact gacctgcttc    46140
atcatccaag tgctgagatt ataggcggtt tttgtttgtt ttgtttttca gattaaaaaa    46200
aattatgtgt gcatgatata tgtggatgtg gactcgtgtg tggtgtttgg ggtgcaagtt    46260
gttggttctt tcctacaaca ctgtgggttg aggtaatcaa atttaggtca tgaggcttgt    46320
cacaagcacc tttacctgat ggccaatctc cctggctacg ttaaaaaaaa aaaaaaaaa     46380 aaagagtttc tggcagaggt acaaaattga ctattccata gtttaatagt ttagaggagc    46440
cgctggaatc aggctactct ggtttatttt gaggggtgg ggtcttatta tgttgtccag     46500
gctcatttaa agatcctcgg ctcaagttat cctccatttg agtttcctaa gtagcttggg    46560
tctacagaag gtatatcact gtagttgact gaatgttggt atttgtttag ggatggggtc    46620
tcactgtgta cccctggctg ttctagaatt ggctatgtag gacaggctga ccttgaaatc    46680
acagagacct gtctgactgc ctcccaagta agttgtttga atccatagta ttccctggat    46740
ttgaattcta atttgatact ataagacttg tgttgctttg atgtcatcat ccactattgg    46800
aggtgagact gtcaaacgta aaacattgtt atcaggatta gctcgattga tagtatgaaa    46860
atactttaaa aagaacgttg aggcaggagg attcctacaa ggccagtatg cctatatag     46920 caagttctgg atctcctggg ctatatagtg aaaccttgtc tcaaacaatc aatctagatt    46980
tggtggtgca tgcctgtaat cccagaacct tggaggctaa ggtaggaaga tcatgaattc    47040
caggctagaa tgaactacat agtaagacct tatctctaaa aaaaaaaaaa aaatagaaa     47100 agaatagaag taggattgga gggcgtatct tgtggacatg gtaagcctgg agtaaggtga    47160
ataataatga aatatagcac acagagatga tatgcttaga gcagaagtca gagaacagaa    47220
gttcttattt gtgactaaag cttcattgca ccatagctct tcctgtgtga acacttgtca    47280
tctttggctg cttttatgct tgattgctca gaattgtcta gttaaagac tgtgtgacca     47340 tcagactaaa accacttact gtctagtcat tcacagaaaa cagtaaaaca gtcaccaact    47400
cctgatgtaa aaagatggca tttgaagagt gtatgcaatt gttttagttg gagttttagg    47460
ccaattaaaa gttttaaagg agtccaaacc tttcatcttt gctcctcttg aggctaagga    47520
aagaggatct caatcaagat caaggccagt gtgggcaact tggtgagctc cagtccaaag    47580
ttagggaaat aaaacataaa aggaggactt actgctcgga ggccagaggc tcgcctggca    47640
agcacagaaa cagctcaata ctcagttttt aagtaatcta ctaactctgt tggcctggtg    47700
gtactttcta tatctcatta cttgggactt aaaggcaagc agacagtttg tgttcattct    47760
gtgttgtatg agatcctgtt tcaaaaagtg gtctgggttg gaaaccagag atagatagct    47820
tagtgtaagg aaacttggca gaaagcctga taatacacgg ttgattactg gaacctacat    47880
agggcatgca cagagacaga gacagagaga gagaccgaca gacagacaga cagacagaca    47940
gacagacaga cagacagaca gacacacaat cagccagggt cgggaatata atatggcttg    48000
gttggtagag tgcttgtcta aaatgcatgg agtcatgggt tcaatcccta acaccgactg    48060
gtatgttgat acctgcctgt agtgccatca ctcaggtgct gttgatcaaa gggtcagaag    48120
```

```
ttcaaggtct ccctggcca catagaaagt ttcaaaccag cctaagcctg aaggtgctgc    48180
ctcaaattaa acaaaacaac aagcaaacaa aataatagaa ggttttttcca tctcagcctg   48240
acttttcttg ttacttacta gttttcagtg tgtagttgga tcttcttatt ctgttgttac   48300
tgtttcccat agcccagcaa tttgcatctt ctgtttgttg acaggtgtgg tactagctcc   48360
gtggaccctg tttccatgaa tagactgagc tttttgagga acagatgcag gtaagatctt   48420
aggcagtgga gatcaagaga tgggattttt accttctcta ctggctctca ccttctttta   48480
cctcacggtc acttaccgtc tcacaatgtg tttctgaact tactgaatag atcaatccat   48540
ccatcaattg attgactgat tggttttct gtgacagggt ttctctgtgt agccctggct    48600
gtcctgaaac ttaatctgta gaccaggctg gtcttgaact cagagatctt gagtgctggg   48660
atcaaaggca tgcaccaccc tgcctgtatt gtttctgaac tttaaaagct tctcttgttc   48720
aaggaagttg cttactatgt tacctatttt tcttgtgtgt tttatttcaa caagggctgg   48780
tgcagcatcc acacacgtac cagtaataaa tggataaata aataaataaa taaataaata   48840
aatgctttta aaacacaggt ttcctttgta gaatttcacc ccggattcct atacctttc    48900
taggaatggg cttggctctg tgaaggaagg agaacctcac tttgtggtag tccactgcac   48960
aggctacatc aaggcctggc caccagcagg tagggaaaat atacagtaat ttctctctgg   49020
tatatttggt tacataaaca attggcaata tgttactaac agttagcaat actatgtacc   49080
cctttatgaa atgtgcttaa gaataattca aaagatagat agacaaataa aacagactcc   49140
ctctcatctg ttaccaatgt tatagtctat ttgagcatat ggattactaa aacataaaaa   49200
tgactcaata ttagctttat tacaaaatgc tgtaggtttg ttttcgaagc aggtttctct   49260
gtagccctgg ctgctttgga gctgactttg tagaccaagc tcatttcca ctgcctctgt    49320
ctccccagag ctggattaac taaagcctac accacaactg ctcaaccttt tttttttt    49380
tttttttt aaatgttta ttgggagctg gaaagagggc tcagcagcag ttaagaacac    49440
ttactgctct tgcagaaaat ctgggttcag ttctcagaac ccacatgttg gcttaaaact   49500
gcctataact ccagtttctt gtgatctgtc actctcttct ggcctctgca ggttcctgta   49560
cttatattgt gtccataaat tcacacaggc aaatacacaa aaacaaatgt attactgatg   49620
cttatcccta tatttatagt agataatatc atatgtaaag tagatacttt tcatctctgg   49680
cctggaactc ctatttcag caattttctc ttcaatacct tctctgggaa ttgcaagcat    49740
gagctgctgt agttggtgta gaattcagtt attagtgcta agaatatagc tcagtaatag   49800
agtacttgcc aggtttatgt caggaccaaa acaacagaac aaaacaagcc agtgtgtggt   49860
ttaaaataat tctcaagtat aatagtagta tacactgaat actgtgtctt taagtagctg   49920
tggcaaaaca aacaaacaaa aaaaaacca ctggagtttt attttatttt ttgggtctta    49980
gtgtattcct ggctgccctg gagctggcct cagattcaca gagatccacc tgcctttatc   50040
gtgctaaggg ctaggataga aggtgtgtgc cactatgccc agcttgaaac attggtattt   50100
aatgcaatta atttgggcaa gctgaaatgg aagagaaact ttaagcaatg aatgcaatgg   50160
ctttcttgca gtaactttaa aagggaggtt tctcttgaaa tgttagtcgt gagtagagta   50220
gctttatttt aatttgagat taactaaggg atgtagcaaa agaggtaggc tgtggggtca   50280
gacttggttt ttagatcatg gccatgaact ccttacctca gtctaacaaa ttctgaatta   50340
cgggctggtt ctccatgccc agcaaggcca gcttttaaa ctgactgtca actttccaga    50400
tctcacccta ttactttcct actataaaag gattgctggg aaatgggat ttacagaaga    50460
cagaaatgca gagaaaagag agacaggttt ttaatactta gttgttttgt gtgtggtagt   50520
```

```
gtttcgtctg catatatgta tgtctgtgca ccacttgttt gtctggcgcc cacagaggtc    50580
agaagaggat gttgaatccc ctggaactgg aattacaggc ggttgtgagc tgccatgtgg    50640
gtaatgggat ttgagcctag tctggaagag cagccagtgc tcttaaccac tgagcctttt    50700
ctcagcttcc tttctcagc tgatatattt aaaaggaaa ttaacattga tttgtgtctt    50760
agggtttcta ttcgtgcaca aacatatgac caagaagcaa gttggggagg aaagggttta    50820
ttcagcgtat actttccaca ttgctgttta tcacggaagt caggcctgga actcaagcag    50880
gtcaggaagc aggagctgat gtagaggcca tggagggatg ttccttactg gcttgcttcc    50940
cctggcttgc tcagcctgct ctcttataga accaagacta ccagcccaga gatggtccca    51000
cccaccaggg gcctttcccc cttgatcact aattgagaaa atgccttaca gctggatctc    51060
atggaggcat ttccccaact gaagctcctt tctctgtgat aactccagct gtgtcaagtt    51120
gacacaaaac tagccagtac gatttgggaa aaacttaata tttgctctct ggcatttgtg    51180
aatagtttaa cctatggcaa gtttcttgac ctttacatgt ttttccttat ctgcagtcca    51240
ggtcatacat cctgtatatc atcatcgtga gttagattta gtgtaaggaa agaacacccc    51300
agtgcctggc acatgctcta tagccaagaa atgggaatta ataattgagg aaatattatg    51360
tatagtggca catgaactgt tgagttaact tcctatgtaa atcataccttt tactgtatgt    51420 atgatctttg atacttctgc atagctgtcc tagataagaa tgagagataa agacattgtg    51480
agggatgaac tcttattccc tttttctgtg gaaatgaata tcttttggtg ttgggacaat    51540 ttaattttc tttactttaa aaatcactgg ttaggcagga atatttactt ctctgtgtat    51600
gatatagtca catagcataa gtaaagttta tatttttaga ctcctttgat tgggacttgc    51660
attttcaaat ttcttaaaat ggttaaagcc aggtgtgctc atatgcctga aatcctgcat    51720
tgaaaagatg aagagtccag gttacacaca cacacacaca cacacacgca cacactcaca    51780
cgtgtgtcac atgaaacagt aactggttat tttattaaat cttagcatct tcataggaa    51840 atagtgagtc ttcagtgact tgcccttaaa gggatttgaa tttgtgatct ctctgagtca    51900 ttctccttt tcttcatgaa ggtgtctccc tcccagatga tgacccagag gctggccagg    51960
ggagcaaatt ctgcctagtg gccattggca ggctgcaggc aagtatgagt cttcacatct    52020
atgtcctttc agtttaggga aaaaaaactt ttcagatttt atttgtggta attatctttt    52080
gctctgtgaa tacatagaaa aattccataa aactcaagat ctaaaataat gtgatatta    52140 taataaacat tgctattctc agacttagct aaaatcaaaa gcatgagaga gggtggtaat    52200
cttgttgttg ttgatcttgg taatgactcg tccctgttac ctaggcctcg agctccttgg    52260
ttcaagggat cctcccccta aagcctcctg catgttggga gagaggcagg cgtccgtcac    52320
catgccaggc tcccctggac attgttagtt ttagctttac agtacttact tttctatttc    52380
caattaattt cttttgttcc tatgcaaagt aagaacaatc attttattta tgtcattaca    52440
ttctttataa tagatctaaa atatcttaaa attttattt tatgtgtatg ggtgttttgc    52500
tttcatgtgt gtctgtgcac ttgcatgcct ggtacccgag gaggctagaa gaggttattg    52560
aatcccctgg aactggagtt ccagaaagtt gtgacttgac gtatgggttc tgggaatgga    52620
acgcgggttc tctggaaagc agtcagtgct cttaacactg agccgtctct ccagcccttg    52680
attttgatta ttttcatgaa ccctgttcag tttctcagaa acttgaatca ctctgaataa    52740
tgaatacggg ctaaccaaat aaaaagtagg tggtttaggg taacattcac tattttctta    52800
ctttaccaac ttggtaagag aacttacata ggagtagagt tagagtttat gcctgtcgtt    52860
```

```
aggattgaca ttttttgcatt tctgggtaaa acttctaaga agtttctaaa tctggtagtt    52920
tcatatctac acagatactc atgaaatatt aaaagtattt atgtaagtaa tggtgttatt    52980
tgggctcatt ttatctctcc tttcttaggt aactagttct cccaactgta cagacatgag    53040
taacatttgt cagccaacag agttcatctc ccgacacaac attgaaggga tattcacttt    53100
tgtagaccat cgttgtgtgg ctactgttgg ctaccagcca caggtgagga gcgtagcttc    53160
tgcattagta acacgtaggc ctctgttttc tgttaccagt gttgaggtta catggctaat    53220
tccagagatg accaaaatat agcagtccag ttcagaaaaa gagatgctcc tattttgcga    53280
gtagcaaaat atagtctcaa cttcctttca agactatcac tccatataga gaaatgtagt    53340
tggtaaaacc atatggaaat agtaggtata aatatatagt ttttattact aatgtcaata    53400
cagatcattt aaaactcctt atttttaatta ttctagtata actagaattt atataattac    53460
tatattttag taatttatat aattactagt agaataagcc tataataatt ataagtgtag    53520
cactgcttat taaaattctc atacagtagt atatcagtta actaccctg acttacatgg     53580 acatggtctc tgttatttat gagcgtggct atgagtgtgt gaagtggtca gtcaagatgt    53640
catcttgggg gctggagaga tggcttagtg gttaagagtt caaatcccag caaccacatg    53700
gtggcttata accatctgta atagatctaa tgccctcttc tggtgcgtct gaagacagct    53760
acagtgtacg tatattaaat aaataaataa ataaataaat cttaaaaaa aaaaagaagt    53820 tgccttgaaa atgaagaagg tcgggcagtg gtggtgtatg cctttaatcc cagcacttgg    53880
gaggcagagg caagccgatt tctgagttca aggccagcct agtctataga gtgagttcca    53940
ggacagccag ggctatacag agaaaccctg tgtcaacccc cccccccaaa aaaaaaaaa     54000 gaaaatgaag aagaaagttg gagaatttac ttacacccag atccaacact ccctgtaaag    54060
gtgctgttat taaggctgtg tggtgttaat gtactgatct attctcatga gtaagctaaa    54120
gagtcttttt tgcattggta attggatttt cagcaaagat gcttagacat ttcaagggga    54180
ttctatatag accacagcca ccaccccctaa aaatcatcat accatagaca aaaatcgact    54240
caaagcccta aatgtataag tactaattgg aaacacctttt tagaagaaaa tctttatgct    54300
cataggtgag caggccgcgg cacaccttgg gagggtggga ctcaccgggt gctattcatc    54360
tttttgtttt gaggcaagat ctcccattgg actagaactt gcccagtagt atagacttgc    54420
tggccactga gctcccataa tccactgctc taagattatg agaatatcct acacttgact    54480
ttttgttttt tggaaacagt gtctcactcc attgctttgg gtactggagc tctttataga    54540
gaccaggctg gcctcaattt cagaggtctg cctgcctctg cctcctaagt gctgagatta    54600
aaaggcctgg ctatttttta ttttttatttt atgtatatat gtgagtgcct aagtatatga    54660
atgtgtgcca tgtgttact tagtaccaga aagaccagaa aaatgcgttg gttctcctga    54720
aactggattc taggtggtta taacattctt gataacaact gctctacagg aagtgttggg    54780
tcagggattg taaattttttc aacttagttc ttcatttttta acgtctggtg tgtgatcttt    54840
gcaaatgcag gaagtgcttt taagggatga gccatctctt ctgctctgcc ataccccctac    54900 ctttttctat ggttttttgaa aatgtattct aaggaccaca ctcagctcct ctaatgttat    54960
ctacaggctt agctcttttcc atccctccgt ccctcctaac tcccatcttt ttctaggcta    55020
gcctcaaact ggaaatcttt ctgtcctagc ctgtgatgct gagattagag tatgccacta    55080
tgcctggcaa aaattttctc taaaatgata tcattaaaag agctggtaaa gtgattttgt    55140
gagaaaggcc tctttgtttc tagttgttcc attacattct tcaagcacac acgtgaccca    55200
tagagtccaa gtgtgttttg gaggacactg agcaggagtc agctccccga gttgggttcc    55260
```

```
agagatggac tcactgaacc atctactggc cctgcttctc cacacaccta tttatagtag    55320
gataaagaga agaagtaaca tccatatctc taacagatgg aaggcgggt ttattttacg     55380 tctctccttc ccttctagga gctcttaggg aagaatattg tagaattttg tcatcctgaa    55440
gaccaacaac ttctaagaga cagctttcag caggtaacat ttttcctggt ttgatctgag    55500
tacatatttt gatcaattct tcaagtttat tctagatact tactgataag tgttcagttg    55560
agcactgtgg tggatactat ctacctatct taatttctaa aaatataaa atgataatac     55620 tttgaaacta gacaaagtcc aaggtatttc tgctttggtt ttatccaata aattctcttc    55680
aaagcattta aaatattatc tgcttaacta ctttatttta gattatagca gaaaaattgt    55740
ctcagaattc ttttctctat aattgaaagt taactcacta gtaactcact ggtaacttgc    55800
tgtagttctc aggcacgagc tcttgaaaac actcggagac gataaatggc cttggcttta    55860
gataacaggt cttatatttt tgtaagttaa ttaagtcttg atactgtgct tcctgataca    55920
atggctatag taatacttaa ggtagaagct tgtgggagag tcaagtatgg taaagccata    55980
ggcacatata tacatatggc ccagcctttg acacatgttc attgctaata tcttattgt      56040 tagagatgga taactaagag attgtcttct gttccataag acagaaacta aaacattaac    56100
atagtacttc tcttaggggc tttgtggaaa ccaaaattgt taagttttga gttgaagagc    56160
tgggattgct aagtaaggtg taaagtgtat ttagtgtcac ccacctgggg ttcctggtat    56220
taacctagaa agccagtttg ttgagaatgt ctgcatcaaa cttcaaggaa acatggagac    56280
actcgcttct gtgttccctc ttcactgtac agtcatacag gctgcagctc tgggaagata    56340
cctgatagat agatgccccc cttaatttcc tcttcctcgt ttgaacgttg aaaaagactg    56400
gtgcttcagg ggcaacaaca cgagtcctaa ggctgtaaac atggcaagat tattacttaa    56460 ttttctttt ttttaagtcc actgatggat gaaacccctt tcaggtggtg aaattaaaag      56520
gtcaggtgct gtccgtcatg ttccgattcc gatctaagac ccgagaatgg ctgtggatga    56580
gaacgagctc ctttaccttc caaaaccctt attcagatga aattgagtat attatctgca    56640
ccaacaccaa tgtgaagtat gtaccttca gtctgcccct gtgttgggtt cttcatcctg      56700
tagccactcc tagggtgggg tggggtgca gcagggcaag tcttagcttt atcatgctgt      56760
cttctcttca gcttgaactt actaaataac atcagtttga gattcctcat ttaacattta    56820
aatttaacat taattgaaat tccttctat aggagttgat gtagttgagg tagagaacaa      56880
ggtgggtttt agttgctgtt ggtatctact ttctaatttg tgtatgttga atgggcccgt    56940
aatagcatgt gtgaacatca gagcacagct tgcagtagtg ggtccccctt tatcaagtag    57000
gtcgcaggca tggaattcaa gttgtcagct gttggctggc acttttccta ccaggccatc    57060
tcattggctc acggtggaat aagtgttaat aagcagcagt agttggtgct gtgagcagag    57120
ctttcactgc tgcccagcct tgttgcccac tgcagtgtgc tcagccaact tgttttctaa    57180
aaggctgcaa gtaaaatttc caaagattag attttttgt tttttcttct ttttggtttt     57240
acgagacagg gttctctgt gtagccttgg ctgtcctgga actcactttg tagaccaggc      57300
tggcctccaa ctcagagatc cccctgcctc tgcctcctga gttctgggat taaaggcatg    57360
gaccagcact gcctttcttg ttgtaaattt ttatataata tattctgatc acactttccc    57420
cttctagctc cttccagatc ctcccaccta ctaaactcca tgacctacac acacccgaga    57480
gagacagaga cacagagaga gacagacaga cagacagaga gaccaaaata tataacaaa     57540 agacccaata agacaaaaaa aatgcctgaa cagagcaaga tgagataaaa accctgtaaa    57600
```

```
aatatcactg aataca tagg ttacctatgg gactggacta agatgttagt aattgttcac    57660
ctttagtcaa tatatggagt ttattgtatt gagtaattcc ttgtttcccc tttgtgttc      57720
ttgtctactc tattttccta ggaactctag ccaggaacca cggcctacac tgtccaacac    57780
catcccaagg tcacagctag gtccgacagc caatttatcc ctagagatgg gtacagggca    57840
gctgccatcc aggtaagaaa tggtgaaata gttagctttt caagtaaaaa ctagctgggt    57900
gtagtgatgt gcaatcacat attttgttg ttgctgcatg tggtttattt tttaaagtct     57960
ttttctccaa attctttgtt aaagtctaa ttttccccta tcgctttcca cactgatgtt     58020
tgacgtatag gcagcagcag cagcagcaca cagaactgga tatggtacca ggaagagatg    58080
ggctggccag ctataatcat tcccaggtga gtgtacctt ttcctataag gagacaatga     58140
acatttctt aaaatgtata ttgaagctac cagaatggtt tagtggttaa gagagtactg     58200
ctcttggaga aagcccaaat tcaattccta gtaaccatag tgggtggctc acaatcacct    58260
gtagacacta tgttcatata cacagacaca gacacaacaa tttaaaacaa aaatgaatct    58320
taaaaacaat atttatcagt gccagtgaga atgttctata taaaattgaa cattattgat    58380
tgttttcact attttattcc ataggttct gtccagcctg tggcaagtgc aggatcagaa     58440
cacagcaagc cccttgagaa gtcagaaggt ctctttgcac aggacagaga tccaaggttt    58500
ccagaaatct atcccagcat cactgcaggt atgggtttct tccgcaggct ccttttacag    58560
gctgagtttc attattactg atgggactgc ccagtcagca tacttctact tcagttacag    58620
tacttcatga ataagtagga attgattaaa ctatgtgcta cagcccttg atggccctcc     58680
cccaactcct tttggtctgc agatcagagt aaaggcatct cctccagcac tgtccctgcc    58740
acccaacagc tgttctccca gggcagctca ttccctccta accccggcc ggcagagaat    58800
ttcaggtgag ccccatatgt gtgtgctgct tgacagggct ctgcagggtt cagttgctgg    58860
atccgtgtgt catcttccct tgctttctct ggtcacctca gacaaagcag tagaacttac    58920
tggacctagg gtgagacaac gaagctgctt ttcctcctgt ttttgcacct attctattgc    58980
cttgctctag gttccaaacg tctctgtgtg gtcagtgtgt gacagtcagt ctttcttgtg    59040
tttttaaatt tatcaggttt tccttaactc caagaaatca gaggaatcta gggatagaat    59100
gtgtccttg attcatagct tctgtgatgg agtcaacctt ttaaccttca ctttctattt     59160
gttccttcct aggaatagtg gtcttacccc tcctgtaacc attgtccagc catcatcttc    59220
tgcagggcag atactggccc agatttcacg tcactccaac cctgcccagg gatcagcgcc    59280
gacctggacc tctagctccc gcccaggctt tgccgcccag gtagcgcctc ttacctgtct    59340
gaccctgtgt gttgttgttt gtgggatctt tttttttcc tccaggtaaa tttattattg     59400
tcagatacct ccttttcagt tcctgttctt catcttttaa ttttcatctt ttttgcgagg    59460
agctagataa ttaaaatacc agagataaca tccagaagtc tctttagaac ctatgttttc    59520
atatgctcac cttaagacag aactgctcat tcacagcagt ttgaacagct ttggtctcag    59580
gcttgtttgg agtaaattca aagagtttgt ctttgtttag gactatgtaa tatagtacca    59640
aagtagaaaa ttagtaatta tattcattta tttatgaaaa tatagtatcc atctatataa    59700
tatatagtaa atatgttaaa tttatttatt actatgtatt tctcttgtct atataataat    59760
ttagaaaagt ttaaaaaaaa atgaaaactc aaacttgact ccagaattgt tctctatagc    59820
tttttgtgt atgtgtaaaa atactcagga atgttgccca tgactcttgg tcaggatgtg    59880
ccgtgatgtt gatgacagct gctaccatgg ttttcatact ggtgacataa tcaagcatgc    59940
atatattatc tcccttggag ttactttta aattgtggat ttaaaacggt ctctagaaat     60000
```

```
tattgtatct cacaaaaaat gttagaggca ataactagtt tcttaatcaa tatacagtaa   60060
atgggtgtga gaaaggacag ctttaatttc aacaaagaga ctgaggcagg agcatgggcc   60120
tgggccacat agtgagagat aaactgtctc ataaagaaa  gaacagaaca aaaccaaaat   60180
agcataatgg aaaataaaag aggacattgt ccactgtgcc aagtaacagt ctcttctggt   60240
ggggttaaca gtgaggtttc atttctagtt tattttttcc aatttttttc tattcttttt   60300
gaggcagatt tagaatttat attaaacaac cctttgcaga tttacactta aagtcaagag   60360
caaaagagaa gcactcagaa ctgagtgtgg gtgtgaactc cctaagatgc caccaaattc   60420
ctctgtaaca catagggatt ccagtaaaaa agaaaatggt tgtgccttta ggaaaaggat   60480
ctagaaacgg gtgcagtgtg gagtgagtgg tttctctttt ataacactct accattggga   60540
cccgagagat gacgccattg ggaaagtgtt ttgtcacttg agcctgacct gatgacctga   60600
gtttaatccc caatctcctt gggggaagaa gagaaccaat tcctgcatgt tgtcctctaa   60660
catgcgtgcc agagcatgca tgtgttctca tgtgcataca tactcatgca cactaaaaat   60720
aaggtggaaa cctttaatac caccacttgg gaggccaatt caggtagatt tctgagtttg   60780
agttcagcct ggtcttcaga gtgagttcca tgacctcaga gaaatcctga ctccaaagac   60840
aatagaaaaa agaaataata ataataatgt ggaaaataat aaaggaaaac acccagtgtt   60900
attgacatct gtgtgtacat gcaaccatta tacagagaca tgcacatgaa cacacacaaa   60960
tgaagtgaag acatgttgat ctctggttcc cattaatttg tgcacaatag cctgtacatg   61020
tatgttgaac ttgacacac  atggatgtta tgctttctat taattgccat aatttatgag   61080
ctgattatat ataggaatag ttttttttt  taagatttat ttacttatta tatgtaagta   61140
cactgtagct gtcctcagac acaccagacg agggcgtcag atctcatttc gggtggttgt   61200
gagccaccat gtggttgctg ggatttgaac tctggacctt tcggaagagc agtcgggtgc   61260
tcttacccac tgagccatct caccagcccc aggaatgggt ttttaataat gttttcatgt   61320
atttatatag tgttgttttg ggtttttgg  tcttttgaa  atagagtttc tctgtataac   61380
agagtcctgg ctgtccttaa cctgacttaa tagaccaggc tgaccttgaa ctcacaagag   61440
gtctatctgc cttcatctct ccttcccgag tgctggctgg gattaaaggc atgtgccacc   61500
acactgaccc gtatacagtg tattttgatc ataacgtgtt ctactccaga ccagtgatgc   61560
ctctccctct taccaaccag tccctcttgt atgtcagtgt ctctttccca tttcatgatc   61620
cagtgagctt aattatacaca atttgtaatt cttttgttttt ttcttttttca cttttatttt   61680 agtttcctaa aacatttagt tttaggaaga attgggagtt aatcagaagt atacattaga   61740
agcaggtaat gggttgggtt tggaagaagg tagtggttga tgagtatcga cttacaggaa   61800
tgcagtacac gattaacaat cctttgttct gtaccccctt cctttagcag gtgcccaccc   61860
aggctacagc caagactcgt tcttcccaat ttggtgtgaa caactttcag acttcttcct   61920
ccttcagtgc tatgtctctt ccgggtgctc ccactgcctc atctggtact gctgcctacc   61980
ctgctctccc caaccgtggc tccaactttc gtaagtgcag acaagggaga taacaggaaa   62040
atcaaactac taagaagga  ggacttggca gttatgattg ttttccctgc gtcctgcatg   62100
tgctgaccga attataagga aatgcatggt ccaggtctgt ttgattttaa acagccttgc   62160
atagggcctg ttgaaatggc tcattgtgca aagtgctcga cacacaaacc gggtaacctg   62220
agttcatatc caggagagag ctgacgccac catgagctca catgcaccat acacaagaca   62280
gtaagaatct taagaatcat tataaaaaca tggtatagga aaaccattta actcctgtag   62340
```

```
ttaaagacca tgtgaatcat tttaatatgt ataacaatct tacttaatag actgcatatg    62400
taaatgaaca aggaattctt cagaaatgct atctaggaaa tgaaacttac tgtgagactg    62460
agttttgaaa atagaagcag ccctgaccag cagagagaag agcagaaggt agcatatgga    62520
gactactgac ttacacgtag ttgtgtgctg gtttctcctc tccattacaa ctataaatgc    62580
ttattcttat ttctagctcc tgagactgga cagaccacag gacagttcca ggcccggaca    62640
gcagagggcg tgggtgtctg gccacagtgg cagggccagc agccccatca tcggtctagt    62700
tccagtgagc agcatgttca gcagacacaa gcacaagcac ctagccagcc tgaggtcttt    62760
caagtgagtg ggtaaagact tcagagagag atcggtcagg gaagagagga agaaagaagc    62820
acatggtatt ggttagggct gaacggaatg agacagagga tgcatgtcag cagttgaagc    62880
aattataaac atagcctgta accagaccag gcagaggtac tgatgggaag caacatgcaa    62940
agatgctaaa gaaaggtatt ttaatttat acagagattt acatctcaaa gtagtagtta     63000
tggatttaaa tagaagaata cgaaaatata tggagtagaa catactgatc atagctataa    63060
gtatctgttt cctttgaggg gcctgcaaga ttgaatgtgg tcatctcaga gaagccagtc    63120
agaaagacca aaggaaggca atatagggtt tgattgagaa cagatgtgat taggcacatt    63180
tcagatgtgc ctgtaggagt taaatgaaat gttggcatgc atatttcttc agttaaaaat    63240
attgagtaca agaaaagagg aaaataaatg atctcagagg aagatagaac agagaatgag    63300
gaaagagttc tcagaagagg gaggttgaga gaactcgcca tgcagacttg tgcggctcag    63360
gaatggtggt ggtgtgggtg ggggaagggg gtcctggaag ggaactcact aaaataaggg    63420
tatgtgaccc aagtctaccc tttttctcat taggaaatgc tgtccatgct gggagaccaa    63480
agcaacacct acaacaatga agaatttcct gatctaacta tgtttccccc cttttccgaa    63540
tagaactatt ggggtgagga taagggtggg gggaaatcac tgtttgtttt taaaagcaaa    63600
tcttttgtaa acagaataaa agttcctctc ccttcccttc cctcacccct gatatgtacc    63660 cttttccaccc cttgacttgc tgaagaaacg ttatagaaga aattaaatga atttcccagg    63720
cttttaggat cctctgaaat tttgaggata ggtgaggcct gaattcctgt ccttatttct    63780
tctgaccaga agttgcacag acatgatttg tgctggagtc aaggggcaga acagaagaat    63840
ctgacaggca ctaattggat actgtggctt gtttggatag aaattctgaa tggagtggag    63900
gaaaggagaa atgccctcat cactgaggat catgaaacac agtagggtg tgtggagcct     63960 tgggacgtga gcagtctcca gaaagaggcc tgagagagag catgaacact tatctttgtg    64020
agtgagtgag tgagtgagtg agtgagtgtg tgtgtgtgtg tgtgtgtgtg tgagagagag    64080
agagagagag taagacacag agacagatgg ggtgagggg gcatttgagc tcctatgttt      64140
tgttccctat tatagagtat atgcaaaatt tgtcccagat cttctttgac tttgtgcttg    64200
ctctttaaag tgtcctaaga aaattaattt tttcaggtat ttttctattt agtgttgcag    64260
ccaaagagta tttaaattaa gtctttgctg cacttaaatt catacccagc caaatggaa     64320 cttttaggcca acccccagcc ttctgttgct agggttggtc tcctacagac acagtgatca    64380
agctggatga ctcctgctct ttggtgcttt caactcattg ggaagagctg cagatattac    64440 caaaatggc tggctacatg aacactgtca gaaatcccag acttgcccac aaggataatg     64500
ctgcattttt ctgtcagagt cacacatgtt tttctggaga ggttatttct gcatggaaac    64560
tcaacttctt ggattagcta tcttgagtga aagtcctcac tgacgagtat gcaaaccaaa    64620
tagcctcctg cacagtagcc tctccttcct gtcaccaaaa cagttttagg tctgctgaag    64680
tctggtgttc tttgctcctt ctgcaatctt gaaattgggg tttgctttag agcacaaaca    64740
```

```
taagtctgtg ttaggtggac ttaaatccca acagggtcac ttgataatta tagccataga    64800
aatgcagatg caggtaactg cttttaccct ttaccgtcct caggtgagtc tcctagatca    64860 acagccttt tttttttttt tttccttaaa ctggctcctg tcaaagatta agttaatatg    64920
gaaaagacct cttatgtgta ttgatggggc atgaggagcc caggcaagga gaggctcgtg    64980
gagaggctga gggaatgtta c                                              65001

<210> SEQ ID NO 100
<211> LENGTH: 2557
<212> TYPE: DNA
<213> ORGANISM: M. musculus
<220> FEATURE:
<220> FEATURE:
<221> NAME/KEY: CDS
<222> LOCATION: (150)...(2174)

<400> SEQUENCE: 100
ggggggggcg tccgccatct tggattccgc ggtagcggtg gcggcggtaa ggtgcctaat     60
ctgcggagtg gctcttccct cccctccccc agctcggtgg cggctgcccc tcccaccgag    120
ggtggcgcag ggacggtgcc atctcgacc atg gcg gcg act aca gct aac cca      173
                                 Met Ala Ala Thr Thr Ala Asn Pro
                                  1               5 gaa atg aca tca gat gta cca tcg ctg ggt ccc acc att gct tct gga      221
Glu Met Thr Ser Asp Val Pro Ser Leu Gly Pro Thr Ile Ala Ser Gly
         10                  15                  20 aac cct gga cct ggg att caa ggt gga gga gct gtt gta cag agg gct      269
Asn Pro Gly Pro Gly Ile Gln Gly Gly Gly Ala Val Val Gln Arg Ala
 25                  30                  35                  40 att aag cga cgg tca ggg ctg gat ttt gat gat gaa gta gaa gtg aac      317
Ile Lys Arg Arg Ser Gly Leu Asp Phe Asp Asp Glu Val Glu Val Asn
                 45                  50                  55 act aaa ttt ttg aga tgc gat gat gac cag atg tgt aat gac aaa gag      365
Thr Lys Phe Leu Arg Cys Asp Asp Asp Gln Met Cys Asn Asp Lys Glu
             60                  65                  70 cgg ttt gcc agg tcg gat gat gag cag agc tct gcg gat aaa gag aga      413
Arg Phe Ala Arg Ser Asp Asp Glu Gln Ser Ser Ala Asp Lys Glu Arg
         75                  80                  85 ctt gcc agg gaa aat cat agt gaa ata gaa cgg cgg cga cgg aac aag      461
Leu Ala Arg Glu Asn His Ser Glu Ile Glu Arg Arg Arg Arg Asn Lys
     90                  95                 100 atg aca gct tac atc aca gaa ctg tca gac atg gta cct aca tgt agt      509
Met Thr Ala Tyr Ile Thr Glu Leu Ser Asp Met Val Pro Thr Cys Ser
105                 110                 115                 120 gcc ctg gct cga aaa cca gac aag cta acc atc tta cgc atg gcc gtt      557
Ala Leu Ala Arg Lys Pro Asp Lys Leu Thr Ile Leu Arg Met Ala Val
                125                 130                 135 tct cac atg aag tcc ttg agg gga act ggc aac aca tct act gat ggc      605
Ser His Met Lys Ser Leu Arg Gly Thr Gly Asn Thr Ser Thr Asp Gly
            140                 145                 150 tcc tac aag cca tct ttc ctc act gat cag gaa ctg aaa cat ttg atc      653
Ser Tyr Lys Pro Ser Phe Leu Thr Asp Gln Glu Leu Lys His Leu Ile
        155                 160                 165 ttg gag gca gca gat ggc ttt ctg ttt att gtc tcc tgt gag act gga      701
Leu Glu Ala Ala Asp Gly Phe Leu Phe Ile Val Ser Cys Glu Thr Gly
    170                 175                 180 cgg gtg gtg tat gtc tct gac tca gtg act ccc gtt ttg aac cag cca      749
Arg Val Val Tyr Val Ser Asp Ser Val Thr Pro Val Leu Asn Gln Pro
185                 190                 195                 200
```

-continued

| | | |
|---|---|---|
| cag tct gaa tgg ttc ggg agc aca ctg tat gat cag gtg cac cca gat<br>Gln Ser Glu Trp Phe Gly Ser Thr Leu Tyr Asp Gln Val His Pro Asp<br>205 210 215 | 797 | |
| gat gtg gat aaa ctt cga gag cag ctc tct aca tca gaa aat gcc cta<br>Asp Val Asp Lys Leu Arg Glu Gln Leu Ser Thr Ser Glu Asn Ala Leu<br>220 225 230 | 845 | |
| aca ggg cgg gtc ctg gat ctg aag act gga aca gtg aaa aag gaa ggc<br>Thr Gly Arg Val Leu Asp Leu Lys Thr Gly Thr Val Lys Lys Glu Gly<br>235 240 245 | 893 | |
| cag cag tct tcc atg agg atg tgc atg ggc tca cga agg tcg ttc atc<br>Gln Gln Ser Ser Met Arg Met Cys Met Gly Ser Arg Arg Ser Phe Ile<br>250 255 260 | 941 | |
| tgc cgc atg agg tgt ggt act agc tcc gtg gac cct gtt tcc atg aat<br>Cys Arg Met Arg Cys Gly Thr Ser Ser Val Asp Pro Val Ser Met Asn<br>265 270 275 280 | 989 | |
| aga ctg agc ttt ttg agg aac aga tgc agg aat ggg ctt ggc tct gtg<br>Arg Leu Ser Phe Leu Arg Asn Arg Cys Arg Asn Gly Leu Gly Ser Val<br>285 290 295 | 1037 | |
| aag gaa gga gaa cct cac ttt gtg gta gtc cac tgc aca ggc tac atc<br>Lys Glu Gly Glu Pro His Phe Val Val Val His Cys Thr Gly Tyr Ile<br>300 305 310 | 1085 | |
| aag gcc tgg cca cca gca ggt gtc tcc ctc cca gat gat gac cca gag<br>Lys Ala Trp Pro Pro Ala Gly Val Ser Leu Pro Asp Asp Asp Pro Glu<br>315 320 325 | 1133 | |
| gct ggc cag ggg agc aaa ttc tgc cta gtg gcc att ggc agg ctg cag<br>Ala Gly Gln Gly Ser Lys Phe Cys Leu Val Ala Ile Gly Arg Leu Gln<br>330 335 340 | 1181 | |
| gta act agt tct ccc aac tgt aca gac atg agt aac att tgt cag cca<br>Val Thr Ser Ser Pro Asn Cys Thr Asp Met Ser Asn Ile Cys Gln Pro<br>345 350 355 360 | 1229 | |
| aca gag ttc atc tcc cga cac aac att gaa ggg ata ttc act ttt gta<br>Thr Glu Phe Ile Ser Arg His Asn Ile Glu Gly Ile Phe Thr Phe Val<br>365 370 375 | 1277 | |
| gac cat cgt tgt gtg gct act gtt ggc tac cag cca cag gag ctc tta<br>Asp His Arg Cys Val Ala Thr Val Gly Tyr Gln Pro Gln Glu Leu Leu<br>380 385 390 | 1325 | |
| ggg aag aat att gta gaa ttt tgt cat cct gaa gac caa caa ctt cta<br>Gly Lys Asn Ile Val Glu Phe Cys His Pro Glu Asp Gln Gln Leu Leu<br>395 400 405 | 1373 | |
| aga gac agc ttt cag cag gtg gtg aaa tta aaa ggt cag gtg ctg tcc<br>Arg Asp Ser Phe Gln Gln Val Val Lys Leu Lys Gly Gln Val Leu Ser<br>410 415 420 | 1421 | |
| gtc atg ttc cga ttc cga tct aag acc cga gaa tgg ctg tgg atg aga<br>Val Met Phe Arg Phe Arg Ser Lys Thr Arg Glu Trp Leu Trp Met Arg<br>425 430 435 440 | 1469 | |
| acg agc tcc ttt acc ttc caa aac cct tat tca gat gaa att gag tat<br>Thr Ser Ser Phe Thr Phe Gln Asn Pro Tyr Ser Asp Glu Ile Glu Tyr<br>445 450 455 | 1517 | |
| att atc tgc acc aac acc aat gtg aag aac tct agc cag gaa cca cgg<br>Ile Ile Cys Thr Asn Thr Asn Val Lys Asn Ser Ser Gln Glu Pro Arg<br>460 465 470 | 1565 | |
| cct aca ctg tcc aac acc atc cca agg tca cag cta ggt ccg aca gcc<br>Pro Thr Leu Ser Asn Thr Ile Pro Arg Ser Gln Leu Gly Pro Thr Ala<br>475 480 485 | 1613 | |
| aat tta tcc cta gag atg ggt aca ggg cag ctg cca tcc agg cag cag<br>Asn Leu Ser Leu Glu Met Gly Thr Gly Gln Leu Pro Ser Arg Gln Gln<br>490 495 500 | 1661 | |
| cag cag cag cac aca gaa ctg gat atg gta cca gga aga gat ggg ctg<br>Gln Gln Gln His Thr Glu Leu Asp Met Val Pro Gly Arg Asp Gly Leu<br>505 510 515 520 | 1709 | |

| | | | |
|---|---|---|---|
| gcc agc tat aat cat tcc cag gtt tct gtc cag cct gtg gca agt gca | 1757 |
| Ala Ser Tyr Asn His Ser Gln Val Ser Val Gln Pro Val Ala Ser Ala | |
| 525 530 535 | |

```
gcc agc tat aat cat tcc cag gtt tct gtc cag cct gtg gca agt gca      1757
Ala Ser Tyr Asn His Ser Gln Val Ser Val Gln Pro Val Ala Ser Ala
            525                 530                 535 gga tca gaa cac agc aag ccc ctt gag aag tca gaa ggt ctc ttt gca      1805
Gly Ser Glu His Ser Lys Pro Leu Glu Lys Ser Glu Gly Leu Phe Ala
            540                 545                 550 cag gac aga gat cca agg ttt cca gaa atc tat ccc agc atc act gca      1853
Gln Asp Arg Asp Pro Arg Phe Pro Glu Ile Tyr Pro Ser Ile Thr Ala
            555                 560                 565 gat cag agt aaa ggc atc tcc tcc agc act gtc cct gcc acc caa cag      1901
Asp Gln Ser Lys Gly Ile Ser Ser Ser Thr Val Pro Ala Thr Gln Gln
        570                 575                 580 ctg ttc tcc cag ggc agc tca ttc cct cct aac ccc cgg ccg gca gag      1949
Leu Phe Ser Gln Gly Ser Ser Phe Pro Pro Asn Pro Arg Pro Ala Glu
585                 590                 595                 600 aat ttc agg aat agt ggt ctt acc cct cct gta acc att gtc cag cca      1997
Asn Phe Arg Asn Ser Gly Leu Thr Pro Pro Val Thr Ile Val Gln Pro
            605                 610                 615 tca tct tct gca ggg cag ata ctg gcc cag att tca cgt cac tcc aac      2045
Ser Ser Ser Ala Gly Gln Ile Leu Ala Gln Ile Ser Arg His Ser Asn
            620                 625                 630 cct gcc cag gga tca gcg ccg acc tgg acc tct agc tcc cgc cca ggc      2093
Pro Ala Gln Gly Ser Ala Pro Thr Trp Thr Ser Ser Arg Pro Gly
            635                 640                 645 ttt gcc gcc cag gta gcg cct ctt acc tgt ctg acc ctg tgt gtt gtt      2141
Phe Ala Ala Gln Val Ala Pro Leu Thr Cys Leu Thr Leu Cys Val Val
            650                 655                 660 gtt tgt ggg atc ttt ttt ttt tcc tcc agg taa atttattatt gtcagatacc    2194
Val Cys Gly Ile Phe Phe Phe Ser Ser Arg
665                 670 tccttttcag ttcctgttct tcatctttta attttcatct tttttgcgag gagctagata    2254
attaaaatac cagagataac atccagaagt ctctttagaa cctatgtttt catatgctca    2314
ccttaagaca gaactgctca ttcacagcag tttgaacagc tttggtctca ggcttgtttg    2374
gagtaaattc aaagagtttg tctttgttta ggactatgta atatagtacc aaagtagaaa    2434
attagtaatt atattcattt atttatgaaa atatagtatc catctatata atatatagta    2494
aatatgttaa atttatttat tactatgtat ttctcttgtc tatataataa tttagaaaag    2554
ttt                                                                  2557

<210> SEQ ID NO 101
<211> LENGTH: 4259
<212> TYPE: DNA
<213> ORGANISM: M. musculus
<220> FEATURE:
<220> FEATURE:
<221> NAME/KEY: CDS
<222> LOCATION: (135)...(2417)

<400> SEQUENCE: 101
gatcttggat tccgcggtag cggtggcggc ggtaaggtgc ctaatctgcg gagtggctct     60
tccctcccct ccccagctc ggtggcggct gccctccca ccgagggtgg cgcagggacg      120
gtgccatctc gacc atg gcg gcg act aca gct aac cca gaa atg aca tca      170
                 Met Ala Ala Thr Thr Ala Asn Pro Glu Met Thr Ser
                  1               5                  10 gat gta cca tcg ctg ggt ccc acc att gct tct gga aac cct gga cct      218
Asp Val Pro Ser Leu Gly Pro Thr Ile Ala Ser Gly Asn Pro Gly Pro
        15                  20                  25
```

| | | |
|---|---|---|
| ggg att caa ggt gga gga gct gtt gta cag agg gct att aag cga cgg<br>Gly Ile Gln Gly Gly Gly Ala Val Val Gln Arg Ala Ile Lys Arg Arg<br>30                          35                    40 | 266 |
| tca ggg ctg gat ttt gat gat gaa gta gaa gtg aac act aaa ttt ttg<br>Ser Gly Leu Asp Phe Asp Asp Glu Val Glu Val Asn Thr Lys Phe Leu<br>45                        50                    55                    60 | 314 |
| aga tgc gat gat gac cag atg tgt aat gac aaa gag cgg ttt gcc agg<br>Arg Cys Asp Asp Asp Gln Met Cys Asn Asp Lys Glu Arg Phe Ala Arg<br>                    65                    70                    75 | 362 |
| gaa aat cat agt gaa ata gaa cgg cgg cga cgg aac aag atg aca gct<br>Glu Asn His Ser Glu Ile Glu Arg Arg Arg Arg Asn Lys Met Thr Ala<br>                80                    85                    90 | 410 |
| tac atc aca gaa ctg tca gac atg gta cct aca tgt agt gcc ctg gct<br>Tyr Ile Thr Glu Leu Ser Asp Met Val Pro Thr Cys Ser Ala Leu Ala<br>          95                    100                   105 | 458 |
| cga aaa cca gac aag cta acc atc tta cgc atg gcc gtt tct cac atg<br>Arg Lys Pro Asp Lys Leu Thr Ile Leu Arg Met Ala Val Ser His Met<br>110                       115                   120 | 506 |
| aag tcc ttg agg gga act ggc aac aca tct act gat ggc tcc tac aag<br>Lys Ser Leu Arg Gly Thr Gly Asn Thr Ser Thr Asp Gly Ser Tyr Lys<br>125                      130                   135                   140 | 554 |
| cca tct ttc ctc act gat cag gaa ctg aaa cat ttg atc ttg gag gca<br>Pro Ser Phe Leu Thr Asp Gln Glu Leu Lys His Leu Ile Leu Glu Ala<br>                    145                   150                   155 | 602 |
| gca gat ggc ttt ctg ttt att gtc tcc tgt gag act gga cgg gtg gtg<br>Ala Asp Gly Phe Leu Phe Ile Val Ser Cys Glu Thr Gly Arg Val Val<br>                    160                   165                   170 | 650 |
| tat gtc tct gac tca gtg act ccc gtt ttg aac cag cca cag tct gaa<br>Tyr Val Ser Asp Ser Val Thr Pro Val Leu Asn Gln Pro Gln Ser Glu<br>              175                   180                   185 | 698 |
| tgg ttc ggg agc aca ctg tat gat cag gtg cac cca gat gat gtg gat<br>Trp Phe Gly Ser Thr Leu Tyr Asp Gln Val His Pro Asp Asp Val Asp<br>          190                   195                   200 | 746 |
| aaa ctt cga gag cag ctc tct aca tca gaa aat gcc cta aca ggg cgg<br>Lys Leu Arg Glu Gln Leu Ser Thr Ser Glu Asn Ala Leu Thr Gly Arg<br>205                       210                   215                   220 | 794 |
| gtc ctg gat ctg aag act gga aca gtg aaa aag gaa ggc cag cag tct<br>Val Leu Asp Leu Lys Thr Gly Thr Val Lys Lys Glu Gly Gln Gln Ser<br>                    225                   230                   235 | 842 |
| tcc atg agg atg tgc atg ggc tca cga agg tcg ttc atc tgc cgc atg<br>Ser Met Arg Met Cys Met Gly Ser Arg Arg Ser Phe Ile Cys Arg Met<br>                    240                   245                   250 | 890 |
| agg tgt ggt act agc tcc gtg gac cct gtt tcc atg aat aga ctg agc<br>Arg Cys Gly Thr Ser Ser Val Asp Pro Val Ser Met Asn Arg Leu Ser<br>              255                   260                   265 | 938 |
| ttt ttg agg aac aga tgc agg aat ggg ctt ggc tct gtg aag gaa gga<br>Phe Leu Arg Asn Arg Cys Arg Asn Gly Leu Gly Ser Val Lys Glu Gly<br>270                       275                   280 | 986 |
| gaa cct cac ttt gtg gta gtc cac tgc aca ggc tac atc aag gcc tgg<br>Glu Pro His Phe Val Val Val His Cys Thr Gly Tyr Ile Lys Ala Trp<br>285                       290                   295                   300 | 1034 |
| cca cca gca ggt gtc tcc ctc cca gat gat gac cca gag gct ggc cag<br>Pro Pro Ala Gly Val Ser Leu Pro Asp Asp Asp Pro Glu Ala Gly Gln<br>                    305                   310                   315 | 1082 |
| ggg agc aaa ttc tgc cta gtg gcc att ggc agg ctg cag gta act agt<br>Gly Ser Lys Phe Cys Leu Val Ala Ile Gly Arg Leu Gln Val Thr Ser<br>                    320                   325                   330 | 1130 |
| tct ccc aac tgt aca gac atg agt aac att tgt cag cca aca gag ttc<br>Ser Pro Asn Cys Thr Asp Met Ser Asn Ile Cys Gln Pro Thr Glu Phe<br>335                       340                   345 | 1178 |

```
atc tcc cga cac aac att gaa ggg ata ttc act ttt gta gac cat cgt      1226
Ile Ser Arg His Asn Ile Glu Gly Ile Phe Thr Phe Val Asp His Arg
350                 355                 360 tgt gtg gct act gtt ggc tac cag cca cag gag ctc tta ggg aag aat      1274
Cys Val Ala Thr Val Gly Tyr Gln Pro Gln Glu Leu Leu Gly Lys Asn
365                 370                 375                 380 att gta gaa ttt tgt cat cct gaa gac caa caa ctt cta aga gac agc      1322
Ile Val Glu Phe Cys His Pro Glu Asp Gln Gln Leu Leu Arg Asp Ser
            385                 390                 395 ttt cag cag gtg gtg aaa tta aaa ggt cag gtg ctg tcc gtc atg ttc      1370
Phe Gln Gln Val Val Lys Leu Lys Gly Gln Val Leu Ser Val Met Phe
400                 405                 410 cga ttc cga tct aag acc cga gaa tgg ctg tgg atg aga acg agc tcc      1418
Arg Phe Arg Ser Lys Thr Arg Glu Trp Leu Trp Met Arg Thr Ser Ser
            415                 420                 425 ttt acc ttc caa aac cct tat tca gat gaa att gag tat att atc tgc      1466
Phe Thr Phe Gln Asn Pro Tyr Ser Asp Glu Ile Glu Tyr Ile Ile Cys
430                 435                 440 acc aac acc aat gtg aag aac tct agc cag gaa cca cgg cct aca ctg      1514
Thr Asn Thr Asn Val Lys Asn Ser Ser Gln Glu Pro Arg Pro Thr Leu
445                 450                 455                 460 tcc aac acc atc cca agg tca cag cta ggt ccg aca gcc aat tta tcc      1562
Ser Asn Thr Ile Pro Arg Ser Gln Leu Gly Pro Thr Ala Asn Leu Ser
            465                 470                 475 cta gag atg ggt aca ggg cag ctg cca tcc agg cag cag cag cag cag      1610
Leu Glu Met Gly Thr Gly Gln Leu Pro Ser Arg Gln Gln Gln Gln Gln
            480                 485                 490 cac aca gaa ctg gat atg gta cca gga aga gat ggg ctg gcc agc tat      1658
His Thr Glu Leu Asp Met Val Pro Gly Arg Asp Gly Leu Ala Ser Tyr
            495                 500                 505 aat cat tcc cag gtt tct gtc cag cct gtg gca agt gca gga tca gaa      1706
Asn His Ser Gln Val Ser Val Gln Pro Val Ala Ser Ala Gly Ser Glu
510                 515                 520 cac agc aag ccc ctt gag aag tca gaa ggt ctc ttt gca cag gac aga      1754
His Ser Lys Pro Leu Glu Lys Ser Glu Gly Leu Phe Ala Gln Asp Arg
525                 530                 535                 540 gat cca agg ttt cca gaa atc tat ccc agc atc act gca gat cag agt      1802
Asp Pro Arg Phe Pro Glu Ile Tyr Pro Ser Ile Thr Ala Asp Gln Ser
            545                 550                 555 aaa ggc atc tcc tcc agc act gtc cct gcc acc caa cag ctg ttc tcc      1850
Lys Gly Ile Ser Ser Ser Thr Val Pro Ala Thr Gln Gln Leu Phe Ser
            560                 565                 570 cag ggc agc tca ttc cct cct aac ccc cgg ccg gca gag aat ttc agg      1898
Gln Gly Ser Ser Phe Pro Pro Asn Pro Arg Pro Ala Glu Asn Phe Arg
            575                 580                 585 aat agt ggt ctt acc cct cct gta acc att gtc cag cca tca tct tct      1946
Asn Ser Gly Leu Thr Pro Pro Val Thr Ile Val Gln Pro Ser Ser Ser
590                 595                 600 gca ggg cag ata ctg gcc cag att tca cgt cac tcc aac cct gcc cag      1994
Ala Gly Gln Ile Leu Ala Gln Ile Ser Arg His Ser Asn Pro Ala Gln
605                 610                 615                 620 gga tca gcg ccg acc tgg acc tct agc tcc cgc cca ggc ttt gcc gcc      2042
Gly Ser Ala Pro Thr Trp Thr Ser Ser Ser Arg Pro Gly Phe Ala Ala
            625                 630                 635 cag gtg ccc acc cag gct aca gcc aag act cgt tct tcc caa ttt ggt      2090
Gln Val Pro Thr Gln Ala Thr Ala Lys Thr Arg Ser Ser Gln Phe Gly
            640                 645                 650 gtg aac aac ttt cag act tct tcc tcc ttc agt gct atg tct ctt ccg      2138
Val Asn Asn Phe Gln Thr Ser Ser Ser Phe Ser Ala Met Ser Leu Pro
```

-continued

|   |   |   |   |   |   |   |   |   |   |   |   |   |   |   |   |   |
|---|---|---|---|---|---|---|---|---|---|---|---|---|---|---|---|---|
| | | 655 | | | | | 660 | | | | | 665 | | | | |
| ggt | gct | ccc | act | gcc | tca | tct | gct | cct | gag | act | gga | cag | acc | aca | gga | 2186 |
| Gly | Ala | Pro | Thr | Ala | Ser | Ser | Ala | Pro | Glu | Thr | Gly | Gln | Thr | Thr | Gly | |
| | 670 | | | | | 675 | | | | | 680 | | | | | |
| cag | ttc | cag | gcc | cgg | aca | gca | gag | ggc | gtg | ggt | gtc | tgg | cca | cag | tgg | 2234 |
| Gln | Phe | Gln | Ala | Arg | Thr | Ala | Glu | Gly | Val | Gly | Val | Trp | Pro | Gln | Trp | |
| 685 | | | | | 690 | | | | | 695 | | | | | 700 | |
| cag | ggc | cag | cag | ccc | cat | cat | cgg | tct | agt | tcc | agt | gag | cag | cat | gtt | 2282 |
| Gln | Gly | Gln | Gln | Pro | His | His | Arg | Ser | Ser | Ser | Ser | Glu | Gln | His | Val | |
| | | | | 705 | | | | | 710 | | | | | 715 | | |
| cag | cag | aca | caa | gca | caa | gca | cct | agc | cag | cct | gag | gtc | ttt | caa | gaa | 2330 |
| Gln | Gln | Thr | Gln | Ala | Gln | Ala | Pro | Ser | Gln | Pro | Glu | Val | Phe | Gln | Glu | |
| | | 720 | | | | | 725 | | | | | 730 | | | | |
| atg | ctg | tcc | atg | ctg | gga | gac | caa | agc | aac | acc | tac | aac | aat | gaa | gaa | 2378 |
| Met | Leu | Ser | Met | Leu | Gly | Asp | Gln | Ser | Asn | Thr | Tyr | Asn | Asn | Glu | Glu | |
| | 735 | | | | | 740 | | | | | 745 | | | | | |
| ttt | cct | gat | cta | act | atg | ttt | ccc | ccc | ttt | tcc | gaa | tag | aactattggg | | | 2427 |
| Phe | Pro | Asp | Leu | Thr | Met | Phe | Pro | Pro | Phe | Ser | Glu | | | | | |
| 750 | | | | | 755 | | | | | 760 | | | | | | |

```
gtgagaataa gggtgggggg aaatcactgt ttgtttttaa aagcaaatct tttgtaaaca    2487
gaataaaagt tcctctccct tcccttccct caccccctgat atgtacccctt tccaccccctt    2547
gacttgctga agaaacgtta tagaagaaat taaatgaatt tcccaggctt ttaggatcct    2607
ctgaaatttt gaggataggt gaggcctgaa ttcctgtcct tatttcttct gaccagaagt    2667
tgcacagaca tgatttgtgc tggagtcaag gggcagaaca gaagaatctg acaggcacta    2727
attggatact gtggcttgtt tggatagaaa ttctgaatgg agtggaggaa aggagaaatg    2787
ccctcatcac tgaggatcat gaaacacagt aggggtgtgt ggagccttgg gacgtgagca    2847
gtctccagaa agaggcctga gagagagcat gaacacttat ctttgtgagt gagtgagtga    2907
gtgagtgagt gagtgtgtgt gtgtgtgtgt gtgtgagaa gagagagaga gagagtaaga    2967
gacagagaca gatgggggtga gggggggcatt tgagctccta tgttttgttc cctattatag    3027
agtatatgca aaatttgtcc cagatcttct ttgactttgt gcttgctctt taaagtgtcc    3087
taagaaaatt aatttttttca ggtattttttc tatttagtgt tgcagccaaa gagtatttaa    3147
attaagtctt tgctgcactt aaattcatac ccagccaaaa tggaacttta ggccaacccc    3207
cagccttctg ttgctagggt tggtctccta cagacacagt gatcaagctg gatgactcct    3267
gctctttggt gctttcaact cattgggaag agctgcagat attaccaaaa taggctggct    3327
acatgaacac tgtcagaaat cccagacttg cccacaagga taatgctgca ttttttctgtc    3387
agagtcacac atgttttttct ggagaggtta tttctgcatg gaaactcaac ttcttggatt    3447
agctatcttg agtgaaagtc ctcactgacg agtatgcaaa ccaaatagcc tcctgcacag    3507
tagcctctcc ttcctgtcac caaaacagtt ttaggtctgc tgaagtctgg tgttctttgc    3567
tccttctgca atcttgaaat tggggttttgc tttagagcac aaacataagt ctgtgttagg    3627
tggacttaaa tcccaacagg gtcacttgat aattatagcc atagaaatgc agatgcaggt    3687
aactgctttt acccttttacc gtcctcaggt gagtctccta gatcaacagc cttttttttt    3747
tttttttcct taaactggct cctgtcaaag attaagttaa tatggaaaag acctcttatg    3807
tgtattgatg gggcatgagg agcccaggca aggagaggct cgtggagagg ctgagggaat    3867
gttactaagt ttccctccgt ttgtctccag tctggtgcca ggcagtagag tggaaaagga    3927
ggctattttt ttattctatg tgcacacata cagtatacat atatatttat atcacatttt    3987
actgaaccaa aaagtgtggg tttccaataa aatacttgtt ttttaataac cgacttgttt    4047
```

```
ttaactgtga tctgaactat aacgtacagt tattacaggg cttctgaaga aggggggggcg    4107 gggagaagct tctctgaggg gctcgctctg cttttccttc acggttttat ttttgattgt    4167
tttttcttgt tgcccatctg tgctaagcct taactgtggc aaaaataatg acatgtagca    4227
aagattttaa aacaaagtat tttttctttt at                                  4259

<210> SEQ ID NO 102
<211> LENGTH: 701
<212> TYPE: DNA
<213> ORGANISM: M. musculus
<220> FEATURE:
<221> NAME/KEY: unsure
<222> LOCATION: 670
<223> OTHER INFORMATION: unknown

<400> SEQUENCE: 102
ggaaaccctg gacctgggat tcaaggtgga ggagctgttg tacagagggc tattaagcga     60
cggtcagggc tggattttga tgatgaagta gaagtgaaca ctaaattttt gagatgcgat    120
gatgaccaga tgttttatga caaagagcgg tttgccaggg aaaatcatag tgaaatagaa    180
cggcggcgac ggaacaagat gacagcttac atcacagaac tgtcagacat ggtacctaca    240
tgtagtgccc tggctcgaaa accagacaag ctaaccatct tacgcatggc cgtttctcac    300
atgaagtcct tgagggaac tggcaacaca tctactgatg gctcctacaa gccatctttc    360
ctcactgatc aggaactgaa acatttgatc ttggaggcag cagatggctt tctgtttatt    420
gtctcctgtg agactggacg ggtggtgtat gtctctgact cagtgactcc cgttttgaac    480
cagccacagt ctgaatggtt cgggagcaca ctgtatgatc aggtgcaccc agatgatgtg    540
gataaacttc gagagcagct ctctacatca gaaaatgccc taacaggtga gagctggctg    600
gacagcagat atgtggggga aaagtcttta tttcactcaa gtagttaaga tattttaagc    660
ccgaaaccan aaaaaaaaaa aaaaaaaaaa agggcggccg c                        701

<210> SEQ ID NO 103
<211> LENGTH: 2412
<212> TYPE: DNA
<213> ORGANISM: M. musculus
<220> FEATURE:
<220> FEATURE:
<221> NAME/KEY: CDS
<222> LOCATION: (120)...(551)

<400> SEQUENCE: 103
aaaaaaaatg cctgaacaga gcaagatgag ataaaaaccc tgtaaaaata tcactgaata     60
cataggttac ctatgggact ggactaagat gttagtaatt gttcaccttt agtcaatat    119 atg gag ttt att gta ttg agt aat tcc ttg ttt ccc ctt ttg tgt tct    167
Met Glu Phe Ile Val Leu Ser Asn Ser Leu Phe Pro Leu Leu Cys Ser
  1               5                  10                  15 tgt cta ctc tat ttt cct agg aac tct agc cag gaa cca cgg cct aca    215
Cys Leu Leu Tyr Phe Pro Arg Asn Ser Ser Gln Glu Pro Arg Pro Thr
             20                  25                  30 ctg tcc aac acc atc cca agg tca cag cta ggt ccg aca gcc aat tta    263
Leu Ser Asn Thr Ile Pro Arg Ser Gln Leu Gly Pro Thr Ala Asn Leu
         35                  40                  45 tcc cta gag atg ggt aca ggg cag ctg cca tcc agg cag cag cag cag    311
Ser Leu Glu Met Gly Thr Gly Gln Leu Pro Ser Arg Gln Gln Gln Gln
     50                  55                  60 cag cac aca gaa ctg gat atg gta cca aga aga gat ggg ctg gcc agc    359
Gln His Thr Glu Leu Asp Met Val Pro Arg Arg Asp Gly Leu Ala Ser
```

```
              65                  70                  75                  80
tat aat cat tcc cag gtt tct gtc cag cct gtg gca agt gca gga tca        407
Tyr Asn His Ser Gln Val Ser Val Gln Pro Val Ala Ser Ala Gly Ser
                    85                  90                  95 gaa cac agc aag ccc ctt gag aag tca gaa ggt ctc ttt gca cag gac        455
Glu His Ser Lys Pro Leu Glu Lys Ser Glu Gly Leu Phe Ala Gln Asp
                100                 105                 110 aga gat cca agg ttt cca gaa atc tat ccc agc atc act gca ggt atg        503
Arg Asp Pro Arg Phe Pro Glu Ile Tyr Pro Ser Ile Thr Ala Gly Met
            115                 120                 125 ggt ttc ttc cgc agg ctc ctt tta cag gct gag ttt cat tat tac tga        551
Gly Phe Phe Arg Arg Leu Leu Leu Gln Ala Glu Phe His Tyr Tyr
        130                 135                 140 tgggactgcc cagtcagcat acttctactt cagttacagt acttcatgaa taagtaggaa     611
ttgattaaac tatgtgctac agcccttga tggccctccc ccaactcctt ttggtctgca      671
gatcagagta aaggcatctc ctccagcact gtccctgcca cccaacagct gttctcccag     731
ggcagctcat tccctcctaa ccccggccg gcagagaatt tcaggtgagc cccatatgtg      791
tgtgctgctt gacagggctc tgcagggttc agttgctgga tccgtgtgtc atcttccctt     851
gctttctctg gtcacctcag acaaagcagt agaacttact ggacctaggg tgagacaacg     911
aagctgcttt tcctcctgtt tttgcaccta ttctattgcc ttgctctagg ttccaaacgt     971
ctctgtgtgg tcagtgtgtg acagtcagtc tttcttgtgt ttttaaattt atcaggtttt   1031
ccttaactcc aagaaatcag aggaatctag ggatagaatg tgtcctttga ttcatagctt   1091
ctgtgatgga gtcaacctttt taaccttcac tttctatttg ttccttccta ggaatagtgg  1151
tcttacccct cctgtaacca ttgtccagcc atcatcttct gcagggcaga tactggccca   1211
gatttcacgt cactccaacc ctgcccaggg atcagcgccg acctggacct ctagctcccg   1271
cccaggcttt gccgcccagg tagcgcctct tacctgtctg accctgtgtg ttgttgtttg   1331
tgggatcttt ttttttttcct ccaggtaaat ttattattgt cagataccct cttttcagtt  1391
cctgttcttc atcttttaat tttcatcttt tttgcgagga gctagataat taaaatacca    1451
gagataacat ccagaagtct ctttagaacc tatgttttca tatgctcacc ttaagacaga    1511
actgctcatt cacagcagtt tgaacagctt tggtctcagg cttgtttgga gtaaattcaa    1571
agagtttgtc tttgtttagg actatgtaat atagtaccaa agtagaaaat tagtaattat    1631
attcatttat ttatgaaaat atagtatcca tctatataat atatagtaaa tatgttaaat    1691
ttatttatta ctatgtattt ctcttgtcta tataataatt tagaaaagtt taaaaaaaaa    1751
tgaaaactca aacttgactc cagaattgtt ctctatagct tttttgtgta tgtgtaaaaa    1811
tactcaggaa tgttgcccat gactcttggt caggatgtgc cgtgatgttg atgacagctg    1871
ctaccatggt tttcatactg gtgacataat caagcatgca tatattatct cccttggagt    1931
tactttttaa attgtggatt taaaacggtc tctagaaatt attgtatctc acaaaaaatg    1991
ttagaggcaa taactagttt cttaatcaat atacagtaaa tgggtgtgag aaaggacagc    2051
tttaatttca acaagagac tgaggcagga gcatgggcct gggccacata gtgagagata     2111
aactgtctca taaagaaag aacagaacaa accaaaata gcataatgga aaataaaaga      2171
ggacattgtc cactgtgcca agtaacagtc tcttctggtg gggttaacag tgaggtttca    2231
tttctagttt attttttcca atttttttct attcttttg aggcagattt agaatttata     2291
ttaaacaacc ctttgcagat ttacacttaa agtcaagagc aaaagagaag cactcagaac    2351
tgagtgtggg tgtgaactcc ctaagatgcc accaaattcc tctgtaacac atagggattc    2411
```

|  |  |
|---|---|
| c | 2412 |

<210> SEQ ID NO 104
<211> LENGTH: 20
<212> TYPE: DNA
<213> ORGANISM: Artificial Sequence
<220> FEATURE:
<223> OTHER INFORMATION: Antisense Compound

<400> SEQUENCE: 104

|  |  |
|---|---|
| gattccagca gaaacaagat | 20 |

<210> SEQ ID NO 105
<211> LENGTH: 20
<212> TYPE: DNA
<213> ORGANISM: Artificial Sequence
<220> FEATURE:
<223> OTHER INFORMATION: Antisense Compound

<400> SEQUENCE: 105

|  |  |
|---|---|
| agtaccataa ccaggaagag | 20 |

<210> SEQ ID NO 106
<211> LENGTH: 20
<212> TYPE: DNA
<213> ORGANISM: Artificial Sequence
<220> FEATURE:
<223> OTHER INFORMATION: Antisense Compound

<400> SEQUENCE: 106

|  |  |
|---|---|
| atcatcgcat ctgaaaagaa | 20 |

<210> SEQ ID NO 107
<211> LENGTH: 20
<212> TYPE: DNA
<213> ORGANISM: Artificial Sequence
<220> FEATURE:
<223> OTHER INFORMATION: Antisense Compound

<400> SEQUENCE: 107

|  |  |
|---|---|
| tcatacttgc ctgcagcctg | 20 |

<210> SEQ ID NO 108
<211> LENGTH: 20
<212> TYPE: DNA
<213> ORGANISM: Artificial Sequence
<220> FEATURE:
<223> OTHER INFORMATION: Antisense Compound

<400> SEQUENCE: 108

|  |  |
|---|---|
| agattaggca ccttaccgcc | 20 |

<210> SEQ ID NO 109
<211> LENGTH: 20
<212> TYPE: DNA
<213> ORGANISM: Artificial Sequence
<220> FEATURE:
<223> OTHER INFORMATION: Antisense Compound

<400> SEQUENCE: 109

|  |  |
|---|---|
| gccgccatgg tcgagatggc | 20 |

<210> SEQ ID NO 110
<211> LENGTH: 20
<212> TYPE: DNA

-continued

```
<213> ORGANISM: Artificial Sequence
<220> FEATURE:
<223> OTHER INFORMATION: Antisense Compound

<400> SEQUENCE: 110
gttagctgta gtcgccgcca                                              20

<210> SEQ ID NO 111
<211> LENGTH: 20
<212> TYPE: DNA
<213> ORGANISM: Artificial Sequence
<220> FEATURE:
<223> OTHER INFORMATION: Antisense Compound

<400> SEQUENCE: 111
tcatttctgg gttagctgta                                              20

<210> SEQ ID NO 112
<211> LENGTH: 20
<212> TYPE: DNA
<213> ORGANISM: Artificial Sequence
<220> FEATURE:
<223> OTHER INFORMATION: Antisense Compound

<400> SEQUENCE: 112
acatctgatg tcatttctgg                                              20

<210> SEQ ID NO 113
<211> LENGTH: 20
<212> TYPE: DNA
<213> ORGANISM: Artificial Sequence
<220> FEATURE:
<223> OTHER INFORMATION: Antisense Compound

<400> SEQUENCE: 113
ttccagaagc aatggtggga                                              20

<210> SEQ ID NO 114
<211> LENGTH: 20
<212> TYPE: DNA
<213> ORGANISM: Artificial Sequence
<220> FEATURE:
<223> OTHER INFORMATION: Antisense Compound

<400> SEQUENCE: 114
agctcctcca ccttgaatcc                                              20

<210> SEQ ID NO 115
<211> LENGTH: 20
<212> TYPE: DNA
<213> ORGANISM: Artificial Sequence
<220> FEATURE:
<223> OTHER INFORMATION: Antisense Compound

<400> SEQUENCE: 115
cgtcgcttaa tagccctctg                                              20

<210> SEQ ID NO 116
<211> LENGTH: 20
<212> TYPE: DNA
<213> ORGANISM: Artificial Sequence
<220> FEATURE:
<223> OTHER INFORMATION: Antisense Compound

<400> SEQUENCE: 116
cagccctgac cgtcgcttaa                                              20
```

```
<210> SEQ ID NO 117
<211> LENGTH: 20
<212> TYPE: DNA
<213> ORGANISM: Artificial Sequence
<220> FEATURE:
<223> OTHER INFORMATION: Antisense Compound

<400> SEQUENCE: 117
catcaaaatc cagccctgac                                          20

<210> SEQ ID NO 118
<211> LENGTH: 20
<212> TYPE: DNA
<213> ORGANISM: Artificial Sequence
<220> FEATURE:
<223> OTHER INFORMATION: Antisense Compound

<400> SEQUENCE: 118
ctggcaaacc gctctttgtc                                          20

<210> SEQ ID NO 119
<211> LENGTH: 20
<212> TYPE: DNA
<213> ORGANISM: Artificial Sequence
<220> FEATURE:
<223> OTHER INFORMATION: Antisense Compound

<400> SEQUENCE: 119
atcatccgac ctggcaaacc                                          20

<210> SEQ ID NO 120
<211> LENGTH: 20
<212> TYPE: DNA
<213> ORGANISM: Artificial Sequence
<220> FEATURE:
<223> OTHER INFORMATION: Antisense Compound

<400> SEQUENCE: 120
agctctgctc atcatccgac                                          20

<210> SEQ ID NO 121
<211> LENGTH: 20
<212> TYPE: DNA
<213> ORGANISM: Artificial Sequence
<220> FEATURE:
<223> OTHER INFORMATION: Antisense Compound

<400> SEQUENCE: 121
gtctctcttt atccgcagag                                          20

<210> SEQ ID NO 122
<211> LENGTH: 20
<212> TYPE: DNA
<213> ORGANISM: Artificial Sequence
<220> FEATURE:
<223> OTHER INFORMATION: Antisense Compound

<400> SEQUENCE: 122
ctggcaagtc tctctttatc                                          20

<210> SEQ ID NO 123
<211> LENGTH: 20
<212> TYPE: DNA
<213> ORGANISM: Artificial Sequence
<220> FEATURE:
```

<223> OTHER INFORMATION: Antisense Compound

<400> SEQUENCE: 123
tttccctggc aagtctctct                                                     20

<210> SEQ ID NO 124
<211> LENGTH: 20
<212> TYPE: DNA
<213> ORGANISM: Artificial Sequence
<220> FEATURE:
<223> OTHER INFORMATION: Antisense Compound

<400> SEQUENCE: 124
atgattttcc ctggcaagtc                                                     20

<210> SEQ ID NO 125
<211> LENGTH: 20
<212> TYPE: DNA
<213> ORGANISM: Artificial Sequence
<220> FEATURE:
<223> OTHER INFORMATION: Antisense Compound

<400> SEQUENCE: 125
gtaagctgtc atcttgttcc                                                     20

<210> SEQ ID NO 126
<211> LENGTH: 20
<212> TYPE: DNA
<213> ORGANISM: Artificial Sequence
<220> FEATURE:
<223> OTHER INFORMATION: Antisense Compound

<400> SEQUENCE: 126
gttctgtgat gtaagctgtc                                                     20

<210> SEQ ID NO 127
<211> LENGTH: 20
<212> TYPE: DNA
<213> ORGANISM: Artificial Sequence
<220> FEATURE:
<223> OTHER INFORMATION: Antisense Compound

<400> SEQUENCE: 127
tagcttgtct ggttttcgag                                                     20

<210> SEQ ID NO 128
<211> LENGTH: 20
<212> TYPE: DNA
<213> ORGANISM: Artificial Sequence
<220> FEATURE:
<223> OTHER INFORMATION: Antisense Compound

<400> SEQUENCE: 128
caaatgtttc agttcctgat                                                     20

<210> SEQ ID NO 129
<211> LENGTH: 20
<212> TYPE: DNA
<213> ORGANISM: Artificial Sequence
<220> FEATURE:
<223> OTHER INFORMATION: Antisense Compound

<400> SEQUENCE: 129
taaacagaaa gccatctgct                                                     20

```
<210> SEQ ID NO 130
<211> LENGTH: 20
<212> TYPE: DNA
<213> ORGANISM: Artificial Sequence
<220> FEATURE:
<223> OTHER INFORMATION: Antisense Compound

<400> SEQUENCE: 130
tggttcaaaa cgggagtcac                                                20

<210> SEQ ID NO 131
<211> LENGTH: 20
<212> TYPE: DNA
<213> ORGANISM: Artificial Sequence
<220> FEATURE:
<223> OTHER INFORMATION: Antisense Compound

<400> SEQUENCE: 131
gctgctctcg aagtttatcc                                                20

<210> SEQ ID NO 132
<211> LENGTH: 20
<212> TYPE: DNA
<213> ORGANISM: Artificial Sequence
<220> FEATURE:
<223> OTHER INFORMATION: Antisense Compound

<400> SEQUENCE: 132
gcacatcctc atggaagact                                                20

<210> SEQ ID NO 133
<211> LENGTH: 20
<212> TYPE: DNA
<213> ORGANISM: Artificial Sequence
<220> FEATURE:
<223> OTHER INFORMATION: Antisense Compound

<400> SEQUENCE: 133
ttcatggaaa cagggtccac                                                20

<210> SEQ ID NO 134
<211> LENGTH: 20
<212> TYPE: DNA
<213> ORGANISM: Artificial Sequence
<220> FEATURE:
<223> OTHER INFORMATION: Antisense Compound

<400> SEQUENCE: 134
gctcagtcta ttcatggaaa                                                20

<210> SEQ ID NO 135
<211> LENGTH: 20
<212> TYPE: DNA
<213> ORGANISM: Artificial Sequence
<220> FEATURE:
<223> OTHER INFORMATION: Antisense Compound

<400> SEQUENCE: 135
tcctcaaaaa gctcagtcta                                                20

<210> SEQ ID NO 136
<211> LENGTH: 20
<212> TYPE: DNA
<213> ORGANISM: Artificial Sequence
<220> FEATURE:
<223> OTHER INFORMATION: Antisense Compound
```

<400> SEQUENCE: 136
ctgcatctgt tcctcaaaaa                                            20

<210> SEQ ID NO 137
<211> LENGTH: 20
<212> TYPE: DNA
<213> ORGANISM: Artificial Sequence
<220> FEATURE:
<223> OTHER INFORMATION: Antisense Compound

<400> SEQUENCE: 137
tgcagtggac taccacaaag                                            20

<210> SEQ ID NO 138
<211> LENGTH: 20
<212> TYPE: DNA
<213> ORGANISM: Artificial Sequence
<220> FEATURE:
<223> OTHER INFORMATION: Antisense Compound

<400> SEQUENCE: 138
ggccagcctc tgggtcatca                                            20

<210> SEQ ID NO 139
<211> LENGTH: 20
<212> TYPE: DNA
<213> ORGANISM: Artificial Sequence
<220> FEATURE:
<223> OTHER INFORMATION: Antisense Compound

<400> SEQUENCE: 139
cagaatttgc tccctggcc                                             20

<210> SEQ ID NO 140
<211> LENGTH: 20
<212> TYPE: DNA
<213> ORGANISM: Artificial Sequence
<220> FEATURE:
<223> OTHER INFORMATION: Antisense Compound

<400> SEQUENCE: 140
ggccactagg cagaatttgc                                            20

<210> SEQ ID NO 141
<211> LENGTH: 20
<212> TYPE: DNA
<213> ORGANISM: Artificial Sequence
<220> FEATURE:
<223> OTHER INFORMATION: Antisense Compound

<400> SEQUENCE: 141
cagcctgcca atggccacta                                            20

<210> SEQ ID NO 142
<211> LENGTH: 20
<212> TYPE: DNA
<213> ORGANISM: Artificial Sequence
<220> FEATURE:
<223> OTHER INFORMATION: Antisense Compound

<400> SEQUENCE: 142
gtgaatatcc cttcaatgtt                                            20

<210> SEQ ID NO 143
<211> LENGTH: 20

```
<212> TYPE: DNA
<213> ORGANISM: Artificial Sequence
<220> FEATURE:
<223> OTHER INFORMATION: Antisense Compound

<400> SEQUENCE: 143
acagtagcca cacaacgatg                                            20

<210> SEQ ID NO 144
<211> LENGTH: 20
<212> TYPE: DNA
<213> ORGANISM: Artificial Sequence
<220> FEATURE:
<223> OTHER INFORMATION: Antisense Compound

<400> SEQUENCE: 144
gacaaaattc tacaatattc                                            20

<210> SEQ ID NO 145
<211> LENGTH: 20
<212> TYPE: DNA
<213> ORGANISM: Artificial Sequence
<220> FEATURE:
<223> OTHER INFORMATION: Antisense Compound

<400> SEQUENCE: 145
gtcttcagga tgacaaaatt                                            20

<210> SEQ ID NO 146
<211> LENGTH: 20
<212> TYPE: DNA
<213> ORGANISM: Artificial Sequence
<220> FEATURE:
<223> OTHER INFORMATION: Antisense Compound

<400> SEQUENCE: 146
gaagttgttg gtcttcagga                                            20

<210> SEQ ID NO 147
<211> LENGTH: 20
<212> TYPE: DNA
<213> ORGANISM: Artificial Sequence
<220> FEATURE:
<223> OTHER INFORMATION: Antisense Compound

<400> SEQUENCE: 147
gctgtctctt agaagttgtt                                            20

<210> SEQ ID NO 148
<211> LENGTH: 20
<212> TYPE: DNA
<213> ORGANISM: Artificial Sequence
<220> FEATURE:
<223> OTHER INFORMATION: Antisense Compound

<400> SEQUENCE: 148
cctgctgaaa gctgtctctt                                            20

<210> SEQ ID NO 149
<211> LENGTH: 20
<212> TYPE: DNA
<213> ORGANISM: Artificial Sequence
<220> FEATURE:
<223> OTHER INFORMATION: Antisense Compound

<400> SEQUENCE: 149
```

-continued

```
aatttcacca cctgctgaaa                                                20
```

<210> SEQ ID NO 150
<211> LENGTH: 20
<212> TYPE: DNA
<213> ORGANISM: Artificial Sequence
<220> FEATURE:
<223> OTHER INFORMATION: Antisense Compound

<400> SEQUENCE: 150

```
tcatccacag ccattctcgg                                                20
```

<210> SEQ ID NO 151
<211> LENGTH: 20
<212> TYPE: DNA
<213> ORGANISM: Artificial Sequence
<220> FEATURE:
<223> OTHER INFORMATION: Antisense Compound

<400> SEQUENCE: 151

```
gtggttcctg gctagagttc                                                20
```

<210> SEQ ID NO 152
<211> LENGTH: 20
<212> TYPE: DNA
<213> ORGANISM: Artificial Sequence
<220> FEATURE:
<223> OTHER INFORMATION: Antisense Compound

<400> SEQUENCE: 152

```
gtcggaccta gctgtgacct                                                20
```

<210> SEQ ID NO 153
<211> LENGTH: 20
<212> TYPE: DNA
<213> ORGANISM: Artificial Sequence
<220> FEATURE:
<223> OTHER INFORMATION: Antisense Compound

<400> SEQUENCE: 153

```
ctgtacccat ctctagggat                                                20
```

<210> SEQ ID NO 154
<211> LENGTH: 20
<212> TYPE: DNA
<213> ORGANISM: Artificial Sequence
<220> FEATURE:
<223> OTHER INFORMATION: Antisense Compound

<400> SEQUENCE: 154

```
ccagcccatc tcttcctggt                                                20
```

<210> SEQ ID NO 155
<211> LENGTH: 20
<212> TYPE: DNA
<213> ORGANISM: Artificial Sequence
<220> FEATURE:
<223> OTHER INFORMATION: Antisense Compound

<400> SEQUENCE: 155

```
ggacagaaac ctgggaatga                                                20
```

<210> SEQ ID NO 156
<211> LENGTH: 20
<212> TYPE: DNA
<213> ORGANISM: Artificial Sequence

```
<220> FEATURE:
<223> OTHER INFORMATION: Antisense Compound

<400> SEQUENCE: 156
gggcttgctg tgttctgatc                                               20

<210> SEQ ID NO 157
<211> LENGTH: 20
<212> TYPE: DNA
<213> ORGANISM: Artificial Sequence
<220> FEATURE:
<223> OTHER INFORMATION: Antisense Compound

<400> SEQUENCE: 157
aagagacctt ctgacttctc                                               20

<210> SEQ ID NO 158
<211> LENGTH: 20
<212> TYPE: DNA
<213> ORGANISM: Artificial Sequence
<220> FEATURE:
<223> OTHER INFORMATION: Antisense Compound

<400> SEQUENCE: 158
cctgggagaa cagctgttgg                                               20

<210> SEQ ID NO 159
<211> LENGTH: 20
<212> TYPE: DNA
<213> ORGANISM: Artificial Sequence
<220> FEATURE:
<223> OTHER INFORMATION: Antisense Compound

<400> SEQUENCE: 159
aatgagctgc cctgggagaa                                               20

<210> SEQ ID NO 160
<211> LENGTH: 20
<212> TYPE: DNA
<213> ORGANISM: Artificial Sequence
<220> FEATURE:
<223> OTHER INFORMATION: Antisense Compound

<400> SEQUENCE: 160
gttaggaggg aatgagctgc                                               20

<210> SEQ ID NO 161
<211> LENGTH: 20
<212> TYPE: DNA
<213> ORGANISM: Artificial Sequence
<220> FEATURE:
<223> OTHER INFORMATION: Antisense Compound

<400> SEQUENCE: 161
cactattcct gaaattctct                                               20

<210> SEQ ID NO 162
<211> LENGTH: 20
<212> TYPE: DNA
<213> ORGANISM: Artificial Sequence
<220> FEATURE:
<223> OTHER INFORMATION: Antisense Compound

<400> SEQUENCE: 162
atctgccctg cagaagatga                                               20
```

<210> SEQ ID NO 163
<211> LENGTH: 20
<212> TYPE: DNA
<213> ORGANISM: Artificial Sequence
<220> FEATURE:
<223> OTHER INFORMATION: Antisense Compound

<400> SEQUENCE: 163
aagaacgagt cttggctgta                                              20

<210> SEQ ID NO 164
<211> LENGTH: 20
<212> TYPE: DNA
<213> ORGANISM: Artificial Sequence
<220> FEATURE:
<223> OTHER INFORMATION: Antisense Compound

<400> SEQUENCE: 164
tctgaaagtt gttcacacca                                              20

<210> SEQ ID NO 165
<211> LENGTH: 20
<212> TYPE: DNA
<213> ORGANISM: Artificial Sequence
<220> FEATURE:
<223> OTHER INFORMATION: Antisense Compound

<400> SEQUENCE: 165
gtctcaggag gaaagttgga                                              20

<210> SEQ ID NO 166
<211> LENGTH: 20
<212> TYPE: DNA
<213> ORGANISM: Artificial Sequence
<220> FEATURE:
<223> OTHER INFORMATION: Antisense Compound

<400> SEQUENCE: 166
cctgccactg tggccagaca                                              20

<210> SEQ ID NO 167
<211> LENGTH: 20
<212> TYPE: DNA
<213> ORGANISM: Artificial Sequence
<220> FEATURE:
<223> OTHER INFORMATION: Antisense Compound

<400> SEQUENCE: 167
ttcttgaaag acctcaggct                                              20

<210> SEQ ID NO 168
<211> LENGTH: 20
<212> TYPE: DNA
<213> ORGANISM: Artificial Sequence
<220> FEATURE:
<223> OTHER INFORMATION: Antisense Compound

<400> SEQUENCE: 168
tctcccagca tggacagcat                                              20

<210> SEQ ID NO 169
<211> LENGTH: 20
<212> TYPE: DNA
<213> ORGANISM: Artificial Sequence
<220> FEATURE:
<223> OTHER INFORMATION: Antisense Compound

<400> SEQUENCE: 169
ccaatagttc tattcggaaa					20

<210> SEQ ID NO 170
<211> LENGTH: 20
<212> TYPE: DNA
<213> ORGANISM: Artificial Sequence
<220> FEATURE:
<223> OTHER INFORMATION: Antisense Compound

<400> SEQUENCE: 170
tctgtttaca aaagatttgc					20

<210> SEQ ID NO 171
<211> LENGTH: 20
<212> TYPE: DNA
<213> ORGANISM: Artificial Sequence
<220> FEATURE:
<223> OTHER INFORMATION: Antisense Compound

<400> SEQUENCE: 171
cggaatccaa gatggcggac					20

<210> SEQ ID NO 172
<211> LENGTH: 20
<212> TYPE: DNA
<213> ORGANISM: Artificial Sequence
<220> FEATURE:
<223> OTHER INFORMATION: Antisense Compound

<400> SEQUENCE: 172
ctccaaacaa gcctgagacc					20

<210> SEQ ID NO 173
<211> LENGTH: 20
<212> TYPE: DNA
<213> ORGANISM: Artificial Sequence
<220> FEATURE:
<223> OTHER INFORMATION: Antisense Compound

<400> SEQUENCE: 173
atgattttcc ctggcaaacc					20

<210> SEQ ID NO 174
<211> LENGTH: 20
<212> TYPE: DNA
<213> ORGANISM: Artificial Sequence
<220> FEATURE:
<223> OTHER INFORMATION: Antisense Compound

<400> SEQUENCE: 174
ggcacctggg cggcaaagcc					20

<210> SEQ ID NO 175
<211> LENGTH: 20
<212> TYPE: DNA
<213> ORGANISM: Artificial Sequence
<220> FEATURE:
<223> OTHER INFORMATION: Antisense Compound

<400> SEQUENCE: 175 agactttttcc cccacatatc					20

<210> SEQ ID NO 176

```
<211> LENGTH: 20
<212> TYPE: DNA
<213> ORGANISM: Artificial Sequence
<220> FEATURE:
<223> OTHER INFORMATION: Antisense Compound

<400> SEQUENCE: 176
taacctatgt attcagtgat                                                  20

<210> SEQ ID NO 177
<211> LENGTH: 20
<212> TYPE: DNA
<213> ORGANISM: Artificial Sequence
<220> FEATURE:
<223> OTHER INFORMATION: Antisense Compound

<400> SEQUENCE: 177
ttcgcggctg gacgattcag                                                  20

<210> SEQ ID NO 178
<211> LENGTH: 21
<212> TYPE: DNA
<213> ORGANISM: Artificial Sequence
<220> FEATURE:
<223> OTHER INFORMATION: Antisense Compound

<400> SEQUENCE: 178
cctggcaaca tctggggttg g                                                21

<210> SEQ ID NO 179
<211> LENGTH: 25
<212> TYPE: DNA
<213> ORGANISM: Artificial Sequence
<220> FEATURE:
<223> OTHER INFORMATION: Antisense Compound

<400> SEQUENCE: 179
caacaggctg gagtgactgg gctcc                                            25

<210> SEQ ID NO 180
<211> LENGTH: 26
<212> TYPE: DNA
<213> ORGANISM: Artificial Sequence
<220> FEATURE:
<223> OTHER INFORMATION: Antisense Compound

<400> SEQUENCE: 180
gtggagacag gactagtgca cgaatg                                           26

<210> SEQ ID NO 181
<211> LENGTH: 25
<212> TYPE: DNA
<213> ORGANISM: Artificial Sequence
<220> FEATURE:
<223> OTHER INFORMATION: Antisense Compound

<400> SEQUENCE: 181
ctgtggaggc atggactgag aatgg                                            25

<210> SEQ ID NO 182
<211> LENGTH: 24
<212> TYPE: DNA
<213> ORGANISM: Artificial Sequence
<220> FEATURE:
<223> OTHER INFORMATION: Antisense Compound

<400> SEQUENCE: 182
```

```
ctgggaacct ccaaatcccc tggc                                          24

<210> SEQ ID NO 183
<211> LENGTH: 26
<212> TYPE: DNA
<213> ORGANISM: Artificial Sequence
<220> FEATURE:
<223> OTHER INFORMATION: Antisense Compound

<400> SEQUENCE: 183
ctgggcaggg ttggcagctg ccttac                                        26

<210> SEQ ID NO 184
<211> LENGTH: 20
<212> TYPE: DNA
<213> ORGANISM: Artificial Sequence
<220> FEATURE:
<223> OTHER INFORMATION: Antisense Compound

<400> SEQUENCE: 184
tgagctgtct gtgatccagc                                               20

<210> SEQ ID NO 185
<211> LENGTH: 20
<212> TYPE: DNA
<213> ORGANISM: Artificial Sequence
<220> FEATURE:
<223> OTHER INFORMATION: Antisense Compound

<400> SEQUENCE: 185
gcgctgctcc caagaactct                                               20

<210> SEQ ID NO 186
<211> LENGTH: 20
<212> TYPE: DNA
<213> ORGANISM: Artificial Sequence
<220> FEATURE:
<223> OTHER INFORMATION: Antisense Compound

<400> SEQUENCE: 186
tcctcatggt cacatggatg                                               20

<210> SEQ ID NO 187
<211> LENGTH: 19
<212> TYPE: DNA
<213> ORGANISM: Artificial Sequence
<220> FEATURE:
<223> OTHER INFORMATION: Antisense Compound

<400> SEQUENCE: 187
cgagaggcgg acgggaccg                                                19

<210> SEQ ID NO 188
<211> LENGTH: 21
<212> TYPE: DNA
<213> ORGANISM: Artificial Sequence
<220> FEATURE:
<223> OTHER INFORMATION: Antisense Compound

<400> SEQUENCE: 188
cgagaggcgg acgggaccgt t                                             21

<210> SEQ ID NO 189
<211> LENGTH: 21
<212> TYPE: DNA
```

```
<213> ORGANISM: Artificial Sequence
<220> FEATURE:
<223> OTHER INFORMATION: Antisense Compound

<400> SEQUENCE: 189
ttgctctccg cctgccctgg c                                      21

<210> SEQ ID NO 190
<211> LENGTH: 19
<212> TYPE: DNA
<213> ORGANISM: Artificial Sequence
<220> FEATURE:
<223> OTHER INFORMATION: Antisense Compound

<400> SEQUENCE: 190
gctctccgcc tgccctggc                                         19
```